(12) United States Patent
Rachwal et al.

(10) Patent No.: US 10,005,787 B2
(45) Date of Patent: Jun. 26, 2018

(54) HIGHLY PHOTO-STABLE BIS-TRIAZOLE FLUOROPHORES

(71) Applicant: NITTO DENKO CORPORATION, Osaka (JP)

(72) Inventors: Stanislaw Rachwal, Oceanside, CA (US); Yufen Hu, San Diego, CA (US)

(73) Assignee: Nitto Denko Corporation, Osaka (JP)

( * ) Notice: Subject to any disclaimer, the term of this patent is extended or adjusted under 35 U.S.C. 154(b) by 0 days. days.

(21) Appl. No.: 15/541,457

(22) PCT Filed: Jan. 7, 2016

(86) PCT No.: PCT/US2016/012535
§ 371 (c)(1),
(2) Date: Jul. 3, 2017

(87) PCT Pub. No.: WO2016/112220
PCT Pub. Date: Jul. 14, 2016

(65) Prior Publication Data
US 2018/0002337 A1    Jan. 4, 2018

Related U.S. Application Data

(60) Provisional application No. 62/100,836, filed on Jan. 7, 2015.

(51) Int. Cl.
C07D 487/04    (2006.01)
C09K 11/06    (2006.01)
H01L 33/50    (2010.01)

(52) U.S. Cl.
CPC ............ *C07D 487/04* (2013.01); *C09K 11/06* (2013.01); *H01L 33/50* (2013.01)

(58) Field of Classification Search
CPC .................................................. C07D 487/04
See application file for complete search history.

(56) References Cited

FOREIGN PATENT DOCUMENTS

| WO | 2014/107606 A2 | | 7/2014 | |
|---|---|---|---|---|
| WO | WO-2014107606 A2 | * | 7/2014 | ............ C09K 11/06 |
| WO | 2014/120809 A1 | | 8/2014 | |
| WO | 2014/197393 A1 | | 12/2014 | |
| WO | 2015/168439 A1 | | 11/2015 | |

OTHER PUBLICATIONS

International Search Report of PCT/US2016/012535 dated May 4, 2016.

* cited by examiner

*Primary Examiner* — Matthew P Coughlin
(74) *Attorney, Agent, or Firm* — K&L Gates LLP; Louis C. Cullman; Robert W. Winn

(57) ABSTRACT

This disclosure is related to photo-stable chromophores which are useful in various applications. Chromophores disclosed herein include a bis-triazole core, two electron-donors at C-4 and C-8, and two groups derived from pentaerythritol ($R=OR^5$) or 1,1,1-tris(hydroxymethyl) methane ($R=H$) at N-2 and N-6. Such structures have been proven to have greater then five times higher photo-stability than their analogs with simpler alkyl groups at N-2 and N-6.

20 Claims, No Drawings

HIGHLY PHOTO-STABLE BIS-TRIAZOLE FLUOROPHORES

This application is a U.S. national phase of International Application No. PCT/US2016/012535, filed Jan. 7, 2016, which claims the benefit of U.S. Provisional Application No. 62/100,836, filed Jan. 7, 2015.

BACKGROUND

Field

This disclosure generally relates to photo-stable highly luminescent chromophores which are useful in various applications.

Description of the Related Art

In recent years, with the need for new optical light collection systems, fluorescence-based solar collectors, fluorescence-activated displays, and single-molecule spectroscopy, various approaches for preparing luminescent chromophores have been explored. However, many technical issues have yet to be overcome.

One of the useful properties of fluorescence (or photoluminescent) dyes is that they have the ability to absorb light of a particular wavelength and re-emit light of a different wavelength. This phenomenon also makes them useful in the photovoltaic industry. There has been very little work reported on the use of photo-luminescent organic mediums for efficiency improvements in photovoltaic devices. The use of anl organic medium, as opposed to an inorganic medium, is attractive in that organic materials are typically cheaper and easier to use, making them a better economical choice. However, most of the currently available organic luminescent dyes are typically not photo-stable for long periods of time, and therefore unusable in photovoltaic applications which require consistent performance for more than 20 years.

The use of luminescent dyes in greenhouse roofing materials to alter the incident solar spectrum plants are exposed to within a greenhouse has also been attempted. However, the disclosed systems lack efficiency and stability. For instance, current systems lose a large amount of the emitted light to the polymeric or glass matrix which encapsulates the dyes. Also, the stability of the dyes is poor and the dyes often degrade quickly, especially when exposed to UV light.

Because of high cost and low efficiency/stability, there remains an unmet need for dyes that improve plant growth, are photostable, and can be used to improve solar energy harvesting simultaneously.

SUMMARY

Novel compounds of bis-triazole fluorophores are disclosed. These compounds are highly photo-stable fluorophores that absorb green and emit red light.

Some embodiments include compound represented by Formula (I):

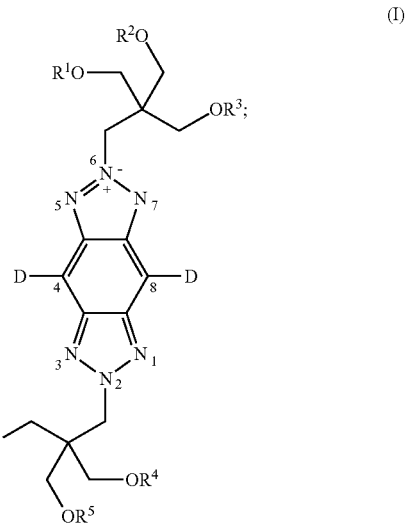

wherein: D is optionally substituted phenyl or optionally substituted heteroaryl; and $R^1$, $R^2$, $R^3$, $R^4$, $R^5$, and $R^6$ are independently optionally substituted phenyl, optionally substituted naphthyl, or optionally substituted heterocyclyl. These compounds may be used in wavelength conversion materials, films, or layers for use or conversion of solar energy, such as conversion of solar energy into electricity, or use in greenhouses or other buildings.

Further aspects, features and advantages of this disclosure will become apparent from the detailed description of the preferred embodiments which follow.

DETAILED DESCRIPTION

Bis-triazole chromophores having a unique combination of pentaerythritol and phenols photo-protective groups may have increased the photostability up to ten fold higher than without the photoprotective groups.

Chromophore structures of formula I have been shown to have up to ten times higher photo-stability than their analogs with simpler alkyl groups at N-2 and N-6. Spectral data (red shifts of the absorption and emission bands) and shifts of the NMR signals indicate that there may be strong interaction by p-p stacking between the chromophore core and aryloxy groups attached to the pentaerythrityl linker. This may allow shielding of the core against harmful radicals formed during exposure of the material to visible light. Depending on the environment and nature of the groups X, the equilibrium shown below may be shifted more or less to the right. For example, in glass encapsulated PVB matrix, some of these chromophores showed no degradation at all at up to 1000 h exposure time to light with intensity of 1 sun. This allows use of these chromophores in wavelength conversion films for numerous applications, including solar cell energy harvesting and agriculture (greenhouse roofing) materials, building and vehicle materials, etc.

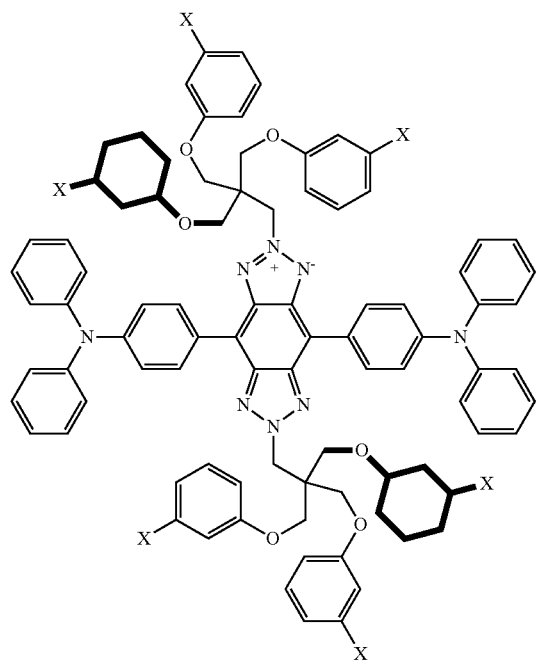 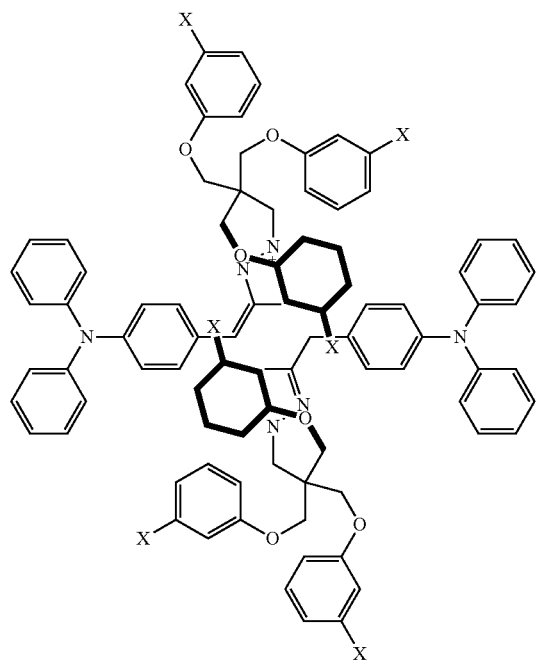

One of the useful properties of fluorescent (or photoluminescent) dyes is that they have the ability to absorb light of a particular wavelength, and re-emit light at a different wavelength. This phenomenon also makes them useful in several applications, including the photovoltaic industry and agriculture industry. In order for organic chromophores to be useful in these industries they require high quantum yield and good photostability. Surprisingly, the inventors have discovered chromophores comprising a benzotriazole system using unique combination of pentaerythritol and phenols that increase the photostability ten-fold higher than without the photoprotective groups. The fluorophores, as disclosed herein, can absorb green light at about 450 to about 600 nm and emit red light at about 600 to about 700 nm.

The chromophores represented by general formula I are useful for absorbing green light and emiting red light. These chromophores are useful as fluorescent dyes in various applications, including in wavelength conversion films.

The term "alkyl" refers to a branched or straight fully saturated acyclic aliphatic hydrocarbon group (i.e., composed of carbon and hydrogen containing no double or triple bonds). Alkyls include, but are not limited to, methyl, ethyl, propyl, isopropyl, butyl, isobutyl, tertiary butyl, pentyl, hexyl, and the like.

The term "aryl" used herein refers to homocyclic aromatic moiety whether one ring or multiple fused rings. Examples of aryl groups include, but are not limited to, phenyl, naphthyl, phenanthrenyl, naphthacenyl, fluorenyl, pyrenyl, and the like.

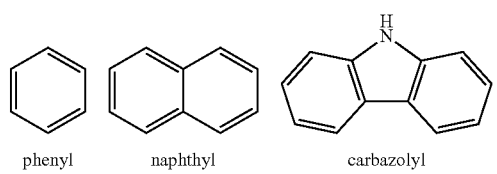

phenyl      naphthyl      carbazolyl

Further examples include:

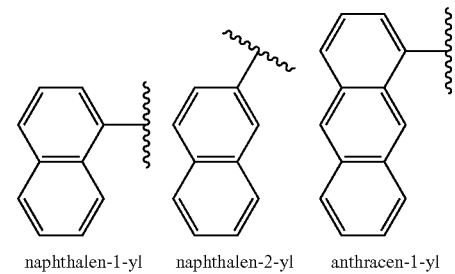

naphthalen-1-yl    naphthalen-2-yl    anthracen-1-yl

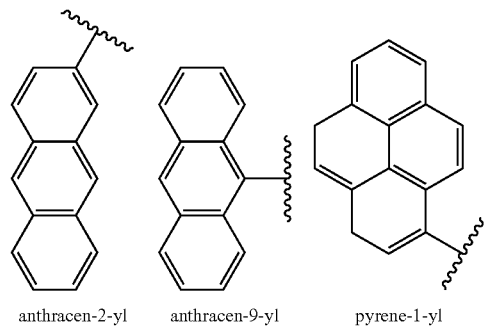

anthracen-2-yl    anthracen-9-yl    pyrene-1-yl

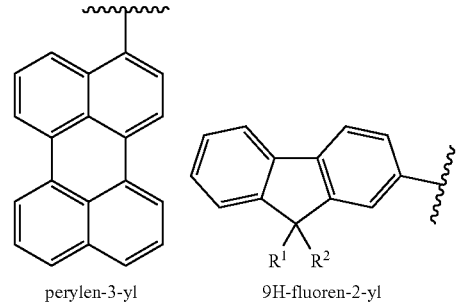

perylen-3-yl      9H-fluoren-2-yl

The term "heteroaryl" used herein refers to an aromatic group comprising one or more heteroatoms, whether one ring or multiple fused rings. When two or more heteroatoms are present, they may be the same or different. In fused ring systems, the one or more heteroatoms may be present in only one of the rings. Examples of heteroaryl groups include, but are not limited to, benzothiazyl, benzoxazyl, quinazolinyl, quinolinyl, isoquinolinyl, quinoxalinyl, pyridinyl, pyrrolyl, oxazolyl, indolyl, thiazyl and the like. Further examples of substituted and unsubstituted heteroaryl rings include:

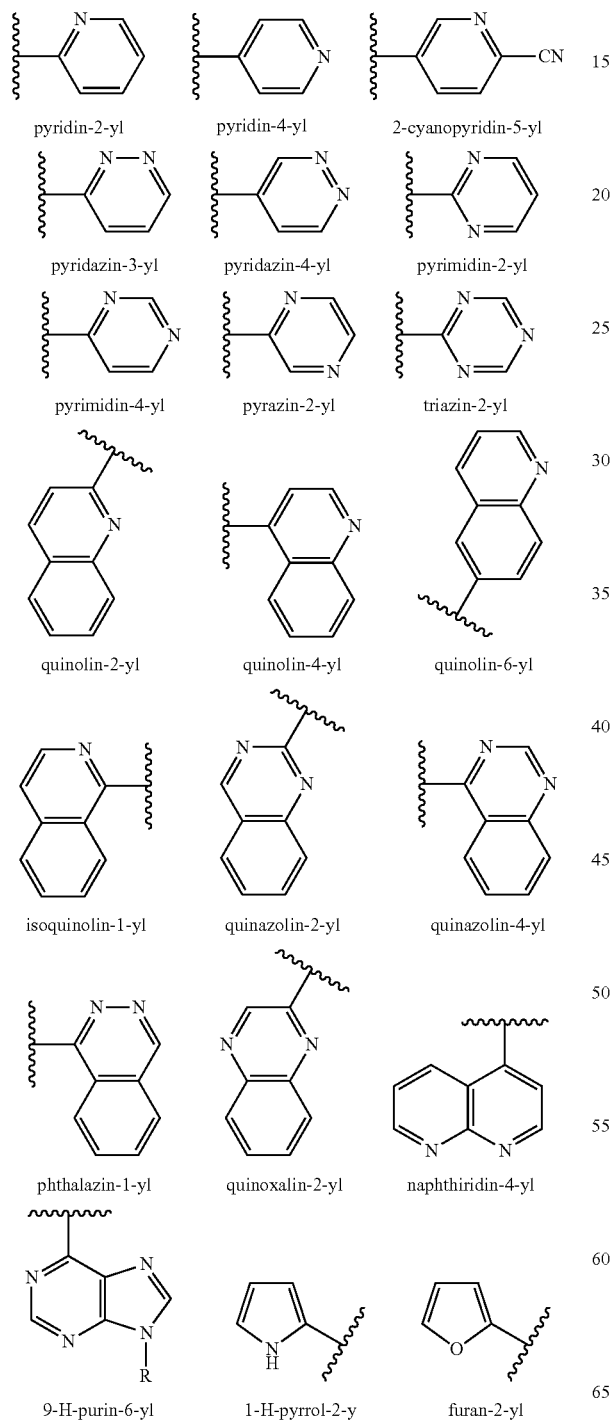

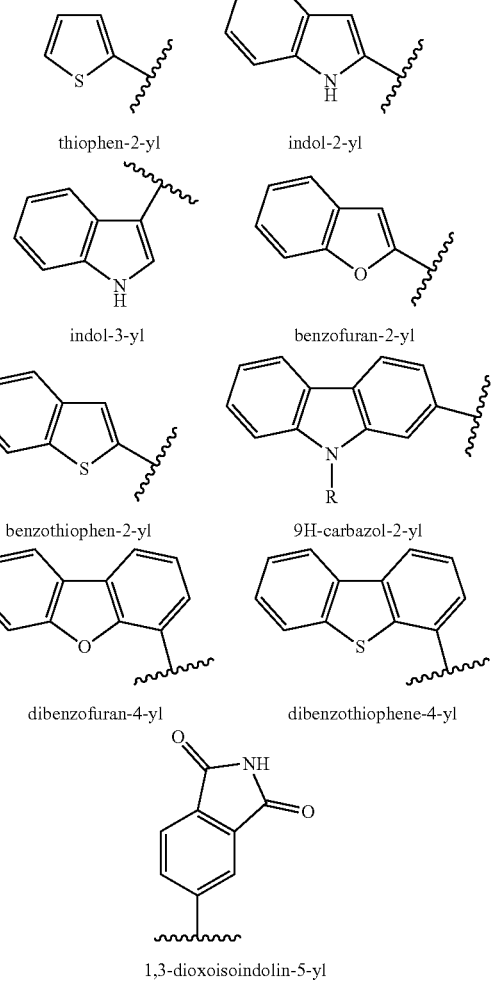

As used herein, a substituted group is related to an unsubstituted parent structure in that one or more position of the parent group that are normally occupied by one or more hydrogen atoms are instead occupied by a substituent. A substituent may be any organic group including organic groups having a molecular weight of about 15 to about 500 Da, about 15 to about 300 Da, about 15 to about 200 Da, about 15 to about 150 Da, about 15 to about 100 Da, about 15 to about 50 Da, or any other molecular weight bound by these values; and/or organic groups represented by a formula such as $C_{0-20}H_{0-41}N_{0-5}O_{0-10}S_{0-5}P_{0-3}F_{0-10}Cl_{0-5}Br_{0-3}$, $C_{0-18}H_{0-37}N_{0-2}O_{0-5}F_{0-5}Cl_{0-2}$, $C_{0-12}H_{0-25}N_{0-2}O_{0-5}F_{0-5}Cl_{0-2}$, $C_{0-12}H_{0-25}F_{0-10}$, $C_{0-12}H_{0-25}O_{0-2}F_{0-10}$, $C_{0-20}H_{0-41}N_{0-5}O_{0-5}$, $C_{0-20}H_{0-41}O_{0-5}$, or $C_{0-12}H_{0-25}O_{0-2}Cl_{0-3}$, provided that at least 1 non-hydrogen atom is present in each substituent.

In some embodiments, a substituent group is $C_1$-$C_{25}$ alkyl, $C_2$-$C_{25}$ alkenyl, $C_2$-$C_{25}$ alkynyl, $C_3$-$C_{25}$ cycloalkyl (optionally substituted with a moiety selected from the group consisting of halo, alkyl, alkoxy, alcohol, carboxyl, haloalkyl, CN, OH, —SO$_2$-alkyl, —CF$_3$, and —OCF$_3$), cycloalkyl geminally attached, $C_1$-$C_{25}$ heteroalkyl, $C_3$-$C_{25}$ heterocycloalkyl (e.g., tetrahydrofuryl) (optionally substituted with a moiety selected from the group consisting of halo, alkyl, alkoxy, alcohol, carboxyl, CN, —SO$_2$-alkyl, —CF$_3$, and —OCF$_3$), aryl (optionally substituted with a moiety selected from the group consisting of halo, alkyl, arylalkyl, alkoxy, alcohol, aryloxy, carboxyl, amino, imido, amido (carbamoyl), optionally substituted cyclic imido, cylic amido, CN, —NH—C(=O)-alkyl, —CF$_3$, —OCF$_3$, and aryl optionally substituted with C$_1$-C$_{25}$ alkyl), arylalkyl (optionally substituted with a moiety selected from the group consisting of halo, alkyl, alkoxy, alcohol, aryl, carboxyl, CN, —SO$_2$-alkyl, —CF$_3$, and —OCF$_3$), heteroaryl (optionally substituted with a moiety selected from the group consisting of halo, alkyl, alkoxy, alcohol, aryl, heteroaryl, aralkyl, carboxyl, CN, —SO$_2$-alkyl, —CF$_3$, and —OCF$_3$), halo (e.g., chloro, bromo, iodo and fluoro), cyano, hydroxy, optionally substituted cyclic imido, amino, imido, amido, —CF, C$_1$-C$_{25}$ alkoxy (optionally substituted with halo, alkyl, alkoxy, aryl, carboxyl, CN, OH, —SO$_2$-alkyl, —CF$_3$, and —OCF$_3$), aryloxy, acyloxy, sulfhydryl (mercapto), halo(C$_1$-C$_6$)alkyl, C$_1$-C$_6$ alkylthio, arylthio, mono- and di-(C$_1$-C$_6$)alkyl amino, quaternary ammonium salts, amino(C$_1$-C$_6$)alkoxy, hydroxy(C$_1$-C$_6$)alkylamino, amino (C$_1$-C$_6$)alkylthio, cyanoamino, nitro, carbamoyl, keto (oxy), carbonyl, carboxy, acyl, glycolyl, glycyl, hydrazino, guanyl, sulfamyl, sulfonyl, sulfinyl, thiocarbonyl, thiocarboxy, sulfonamide, ester, C-amide, N-amide, N-carbamate, O-carbamate, urea or a combination thereof. Wherever a substituent is described as "optionally substituted" that substituent can be substituted with the above substituents.

Formula (I)

Some compounds are represented by Formula (I):

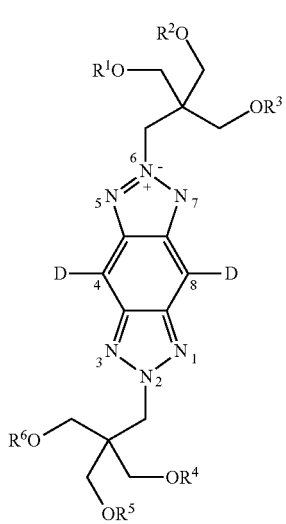

(I)

With respect to any relevant compound or structural representation herein, such as Formula (I), D may be hydrogen, optionally substituted alkoxy, optionally substituted aryloxy, optionally substituted acyloxy, optionally substituted alkyl, optionally substituted aryl, optionally substituted heteroaryl, optionally substituted amino, amido, cyclic amido, cyclic imido, -aryl-NR'R", -ary-aryl-NR'R", and -heteroaryl-heteroaryl-R'; wherein R' and R" are independently selected from the group consisting of optionally substituted alkyl, optionally substituted alkenyl, and optionally substituted aryl. In some embodiments, D is optionally substituted phenyl or optionally substituted heteroaryl (such as optionally substituted carbazolyl).

With respect to any relevant compound or structural representation herein, such as Formula (I), in some embodiments, D is optionally substituted phenyl, including optionally substituted 4-(diphenyl)amino phenyl, such as optionally substituted:

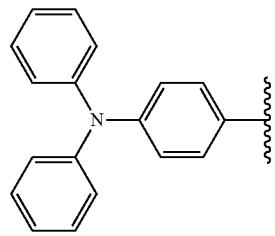 [SMILES: *c1ccc(N(c2ccccc2)c2ccccc2)cc1]

With respect to any relevant compound or structural representation herein, such as Formula (I), in some embodiments, D is optionally substituted carbazolyl, including optionally substituted 9H-carbazol-2-yl. In some embodiments, the carbazolyl, such as 9H-carbazol-2-yl, has 1, 2, or 3 substituents, wherein each substituent is independently C$_{1-6}$ alkyl (such as methyl, ethyl, C$_3$ alkyl such as propyl, C$_4$ alkyl, C$_5$ alkyl, or C$_6$ alkyl); C$_{1-6}$—O-alkyl (such as —O-methyl, —O-ethyl, —O—[C$_3$ alkyl] such as —O-propyl, —O—[C$_4$ alkyl], —O—[C$_5$ alkyl], or —O—[C$_6$ alkyl]); or phenyl optionally substituted with C$_{1-6}$ alkyl or C$_{1-6}$—O-alkyl. In some embodiments, D

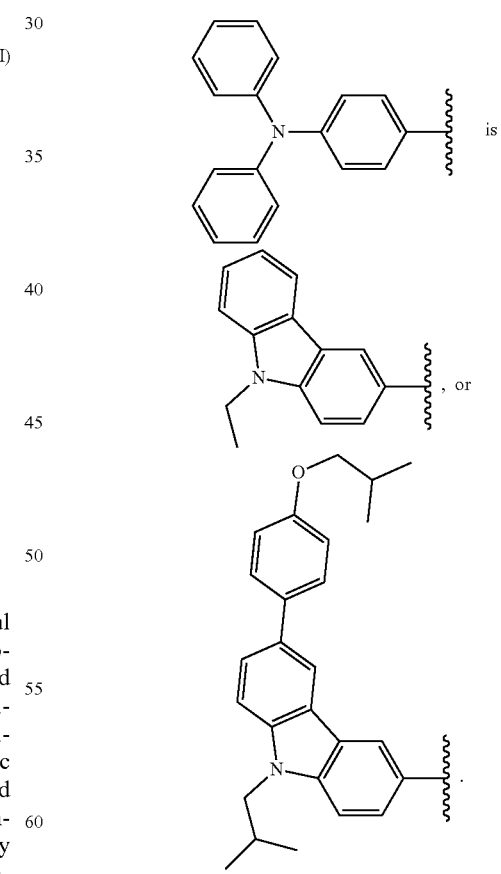

With respect to any relevant compound or structural representation herein, such as Formula (I), in some embodiments, R$^1$, R$^2$, R$^3$, R$^4$, R$^5$, and R$^6$ are independently selected from the group consisting of optionally substituted alkyl, optionally substituted alkenyl, optionally substituted cycloalkyl, optionally substituted heteroalkyl, optionally substituted aryl, optionally substituted heteroaryl, optionally substituted alkoxyalkyl, optionally substituted heteroalkenyl, optionally substituted arylalkyl, optionally substituted heteroaryl, optionally substituted cycloalkenyl, optionally substituted cycloheteroalkyl, optionally substituted cycloheteroalkenyl, optionally substituted amino, optionally substituted amido, optionally substituted cyclic amido, optionally substituted cyclic imido, optionally substituted alkoxy, and optionally substituted carboxy, optionally substituted carbonyl, optionally substituted ether, optionally substituted ketone, optionally substituted sulfone, and optionally substituted sulfonamide; or R is an optionally substituted polycyclic ring system, wherein each ring is independently cycloalkyl, aryl, heterocycloalkyl, or heteroaryl.

With respect to any relevant compound or structural representation herein, such as Formula (I), in some embodiments, $R^1$ and $R^4$; $R^2$ and $R^5$; $R^1$, $R^2$, $R^4$, and $R^5$; $R^3$ and $R^6$; or $R^1$, $R^2$, $R^3$, $R^4$, $R^5$, and $R^6$ are independently optionally substituted phenyl. In some embodiments, $R^1$ and $R^4$; $R^2$ and $R^5$; $R^1$, $R^2$, $R^4$, and $R^5$; $R^3$ and $R^6$; or $R^1$, $R^2$, $R^3$, $R^4$, $R^5$, and $R^6$ are independently 1,3-dioxoisoindolin-5-yl. For any of these embodiments, each phenyl or each 1,3-dioxoisoindolin-5-yl has 1, 2, or 3 substituents, wherein each substituent is independently $R^4$, —$OR^a$, —$CO_2$—$R^a$, —$CO_2$—$CH_2CH_2O$—$R^a$, F, $CF_3$, —CN, phenyl, -phenyl-$R^a$, -phenyl-$OR^a$, or -phenyl-$CO_2$—$R^a$, wherein $R^a$ is $C_{1-12}$ alkyl, such as methyl, ethyl, $C_3$ alkyl, $C_4$ alkyl, $C_5$ alkyl, $C_6$ alkyl, $C_7$ alkyl, $C_8$ alkyl, $C_9$ alkyl, $C_{10}$ alkyl, $C_{11}$ alkyl, $C_{12}$ alkyl, etc. In some embodiments, each 1,3-dioxoisoindolin-5-yl has 1, 2, or 3 substituents, wherein each substituent is independently $R^a$, —$OR^a$. In some embodiments, each phenyl has 1, 2, or 3 substituents, wherein each substituent is independently $R^a$, —$OR^a$, —$CO_2$—$R^a$, —$CO_2$—$CH_2CH_2O$—$R^a$, F, $CF_3$, —CN, phenyl, -phenyl-$R^a$, -phenyl-$OR^a$, or -phenyl-$CO_2$—$R^a$, wherein $R^a$ is $C_{1-12}$ alkyl.

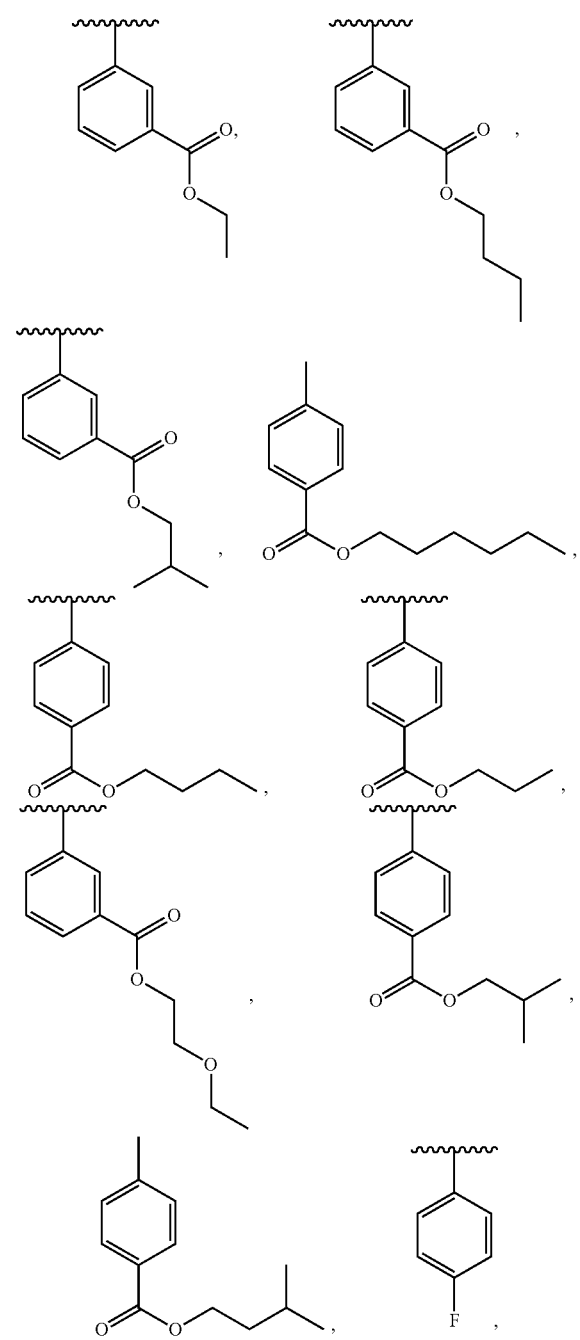

With respect to any relevant compound or structural representation herein, such as Formula (I), in some embodiments (for example when $R^3$ and $R^6$ are different from $R^1$, $R^2$, $R^4$, and $R^5$) $R^3$ and $R^6$ are independently phenyl having 1, 2, or 3 substituents, wherein each substituent is independently $R^a$, —$OR^a$, —$CO_2$—$R^a$, —$CO_2$—$C_2H_4O$—$R^a$, F, $CF_3$, —CN, or phenyl, wherein $R^a$ is $C_{1-12}$ alkyl such as methyl, ethyl, $C_3$ alkyl, $C_4$ alkyl, $C_5$ alkyl, $C_5$ alkyl, $C_6$ alkyl, $C_7$ alkyl, $C_8$ alkyl, $C_9$ alkyl, $C_{10}$ alkyl, $C_{11}$ alkyl, $C_{12}$ alkyl, etc. In some embodiments, $R^3$ and $R^6$ are independently phenyl having 1, 2, or 3 substituents, wherein each substituent is independently F or $CF_3$. In some embodiments, $R^3$ and $R^6$ are independently phenyl having 1, 2, or 3 substituents, wherein each substituent is independently F. In some embodiments, $R^3$ and $R^6$ are independently phenyl having 1, 2, or 3 substituents, wherein each substituent is independently F.

In some embodiments, D is optionally substituted phenyl or optionally substituted heteroaryl, and $R^1$, $R^2$, $R^3$, $R^4$, $R^5$, and $R^6$ are independently optionally substituted phenyl, optionally substituted naphthyl, or optionally substituted heterocyclyl.

In some embodiments, D is selected from furan, thiophene, pyrrole, benzofuran, benzothiophene, indole, carbazole, dibenzofuran, or dibenzothiophene.

In some embodiments, $R^1$, $R^2$, $R^3$, $R^4$, $R^5$, and $R^6$ are independently selected from

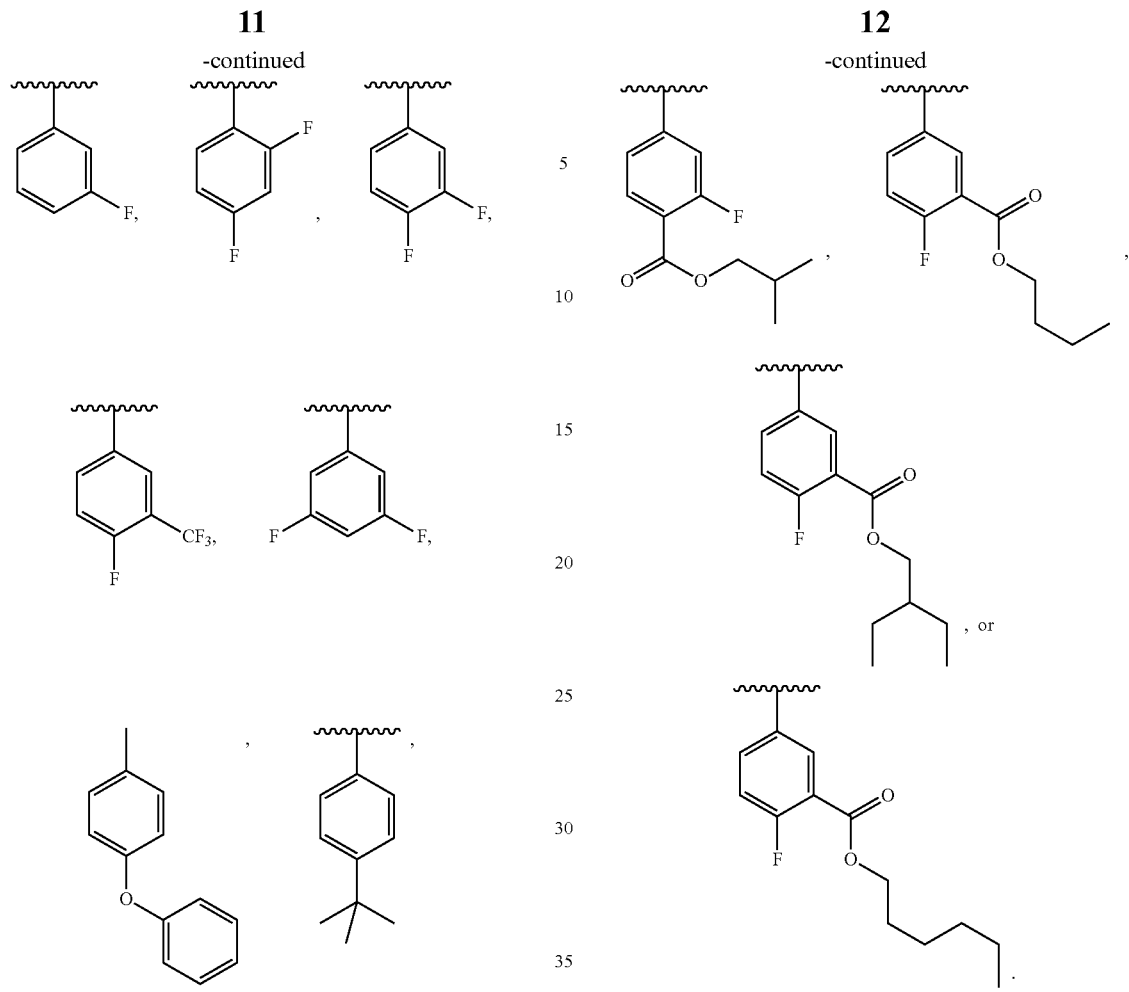
In some embodiments, the structure is any one of the following:
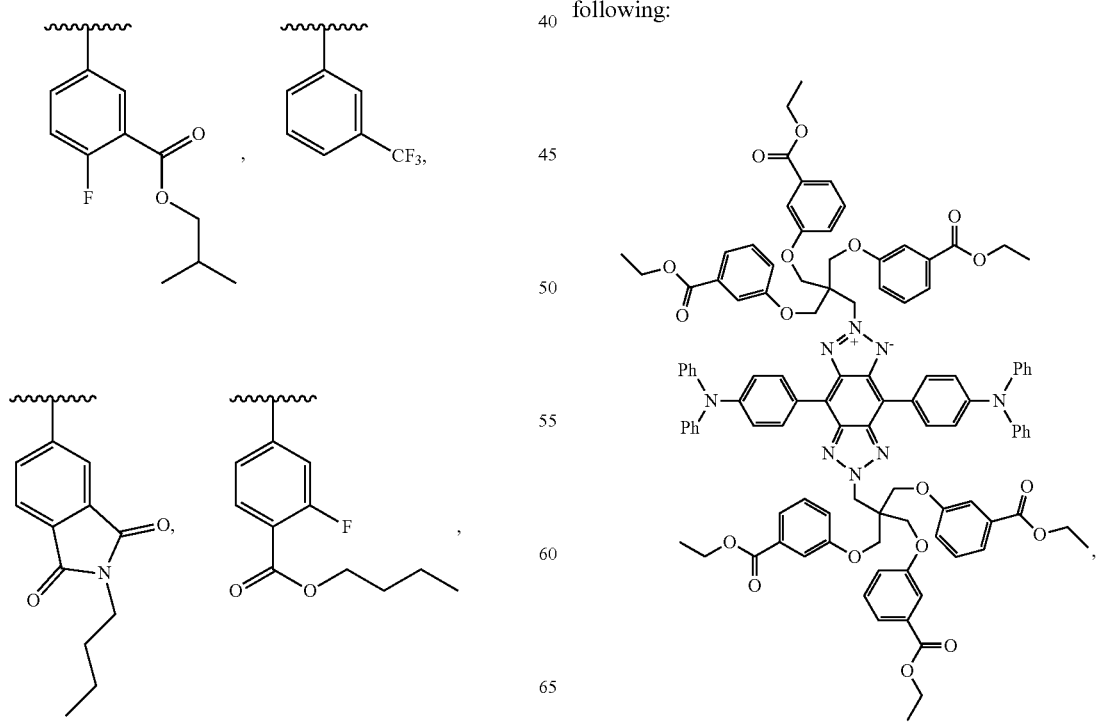

13
-continued
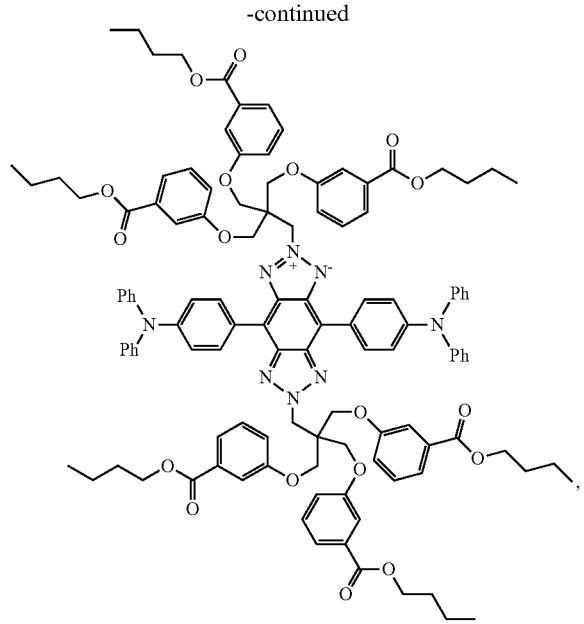
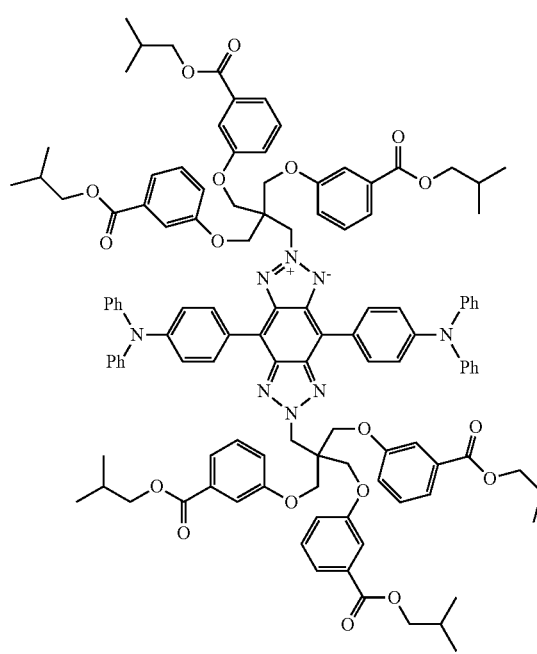
14
-continued
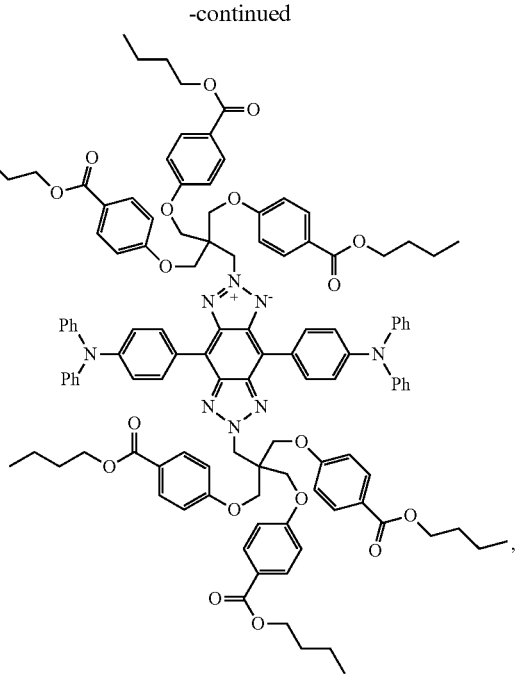
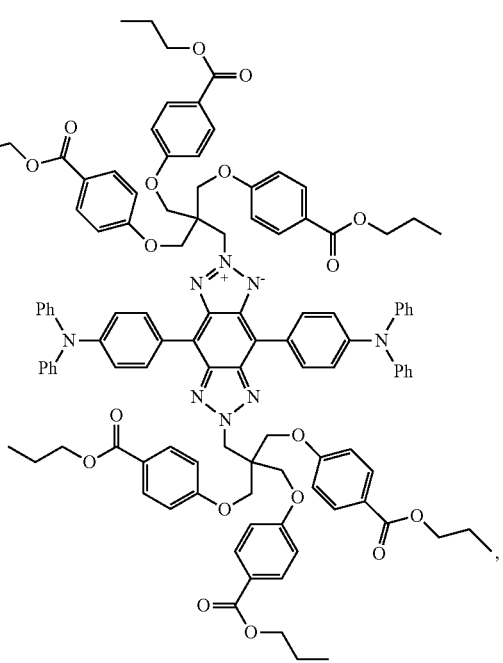

-continued
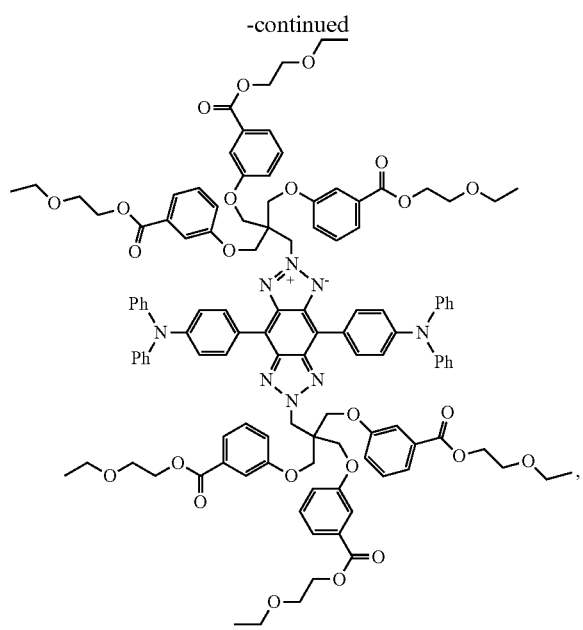
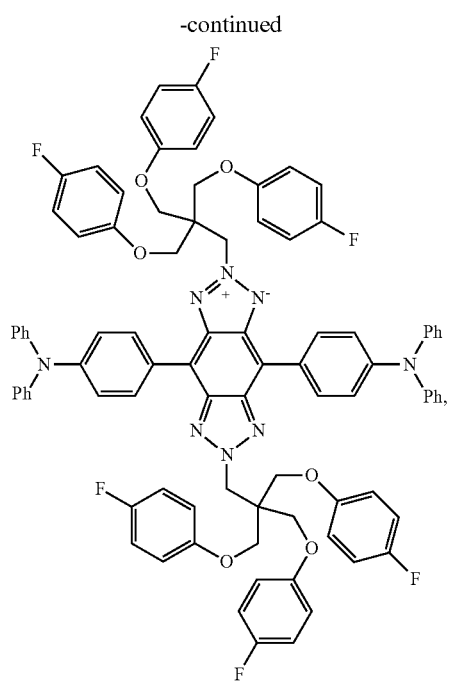
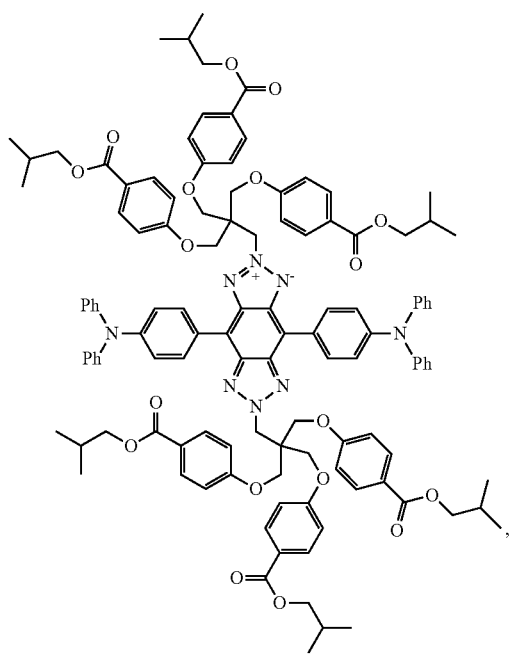
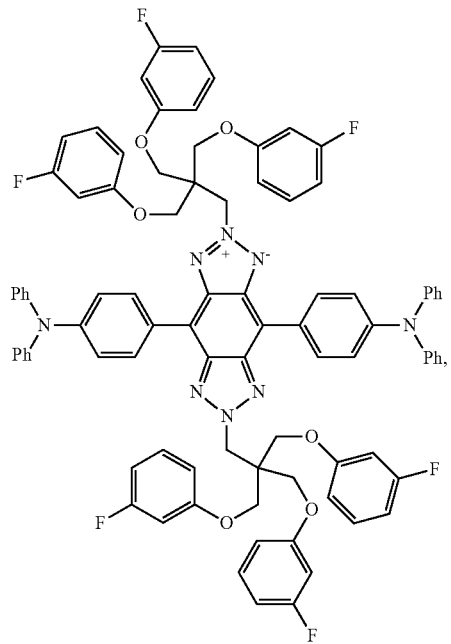

17
-continued
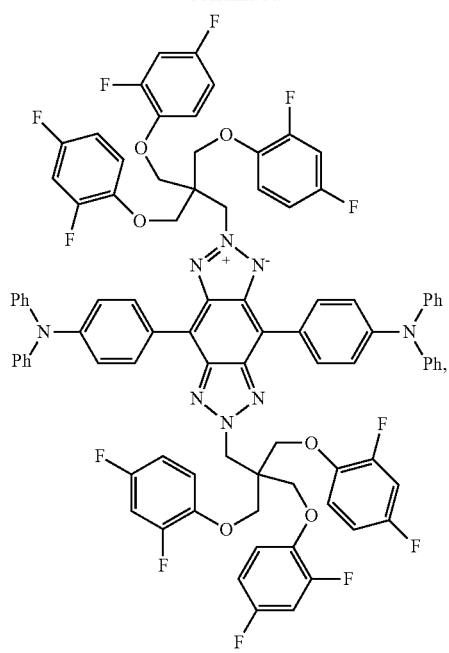
18
-continued
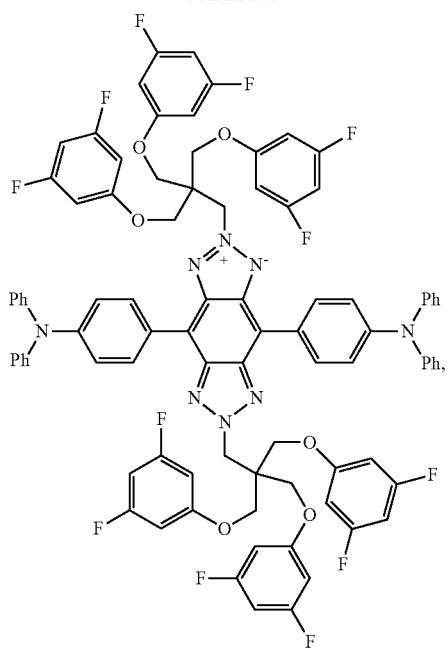
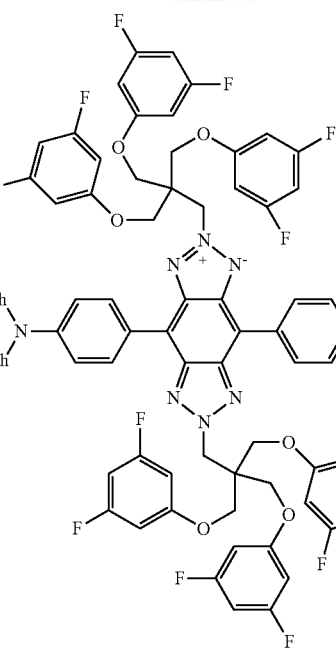
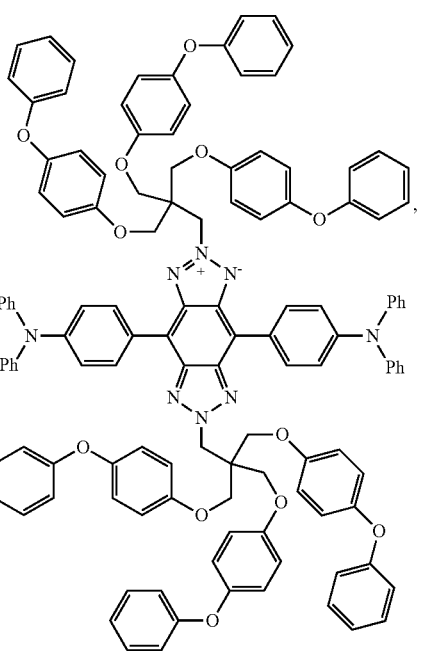

19
-continued
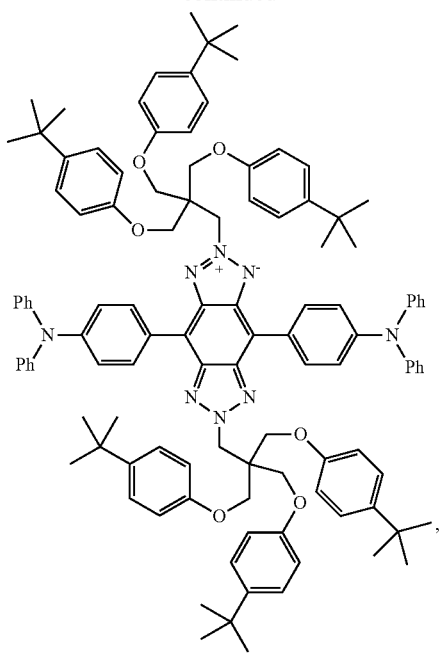
20
-continued
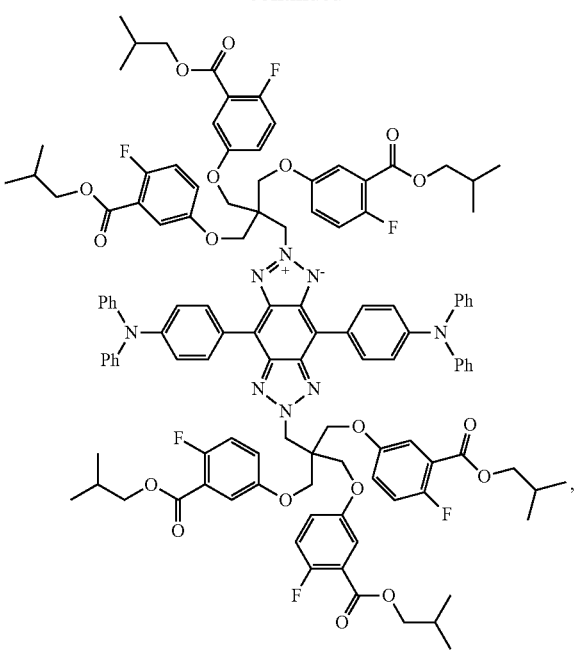
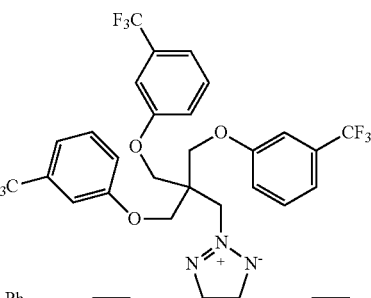
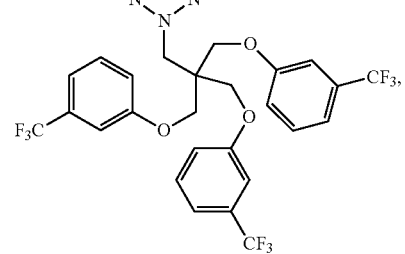

21
-continued
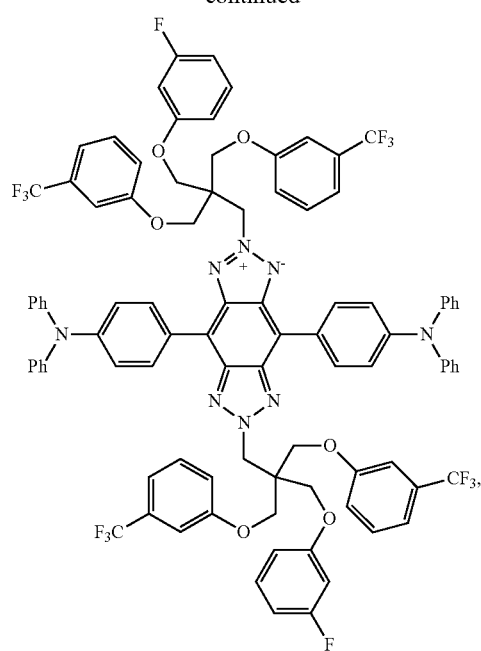
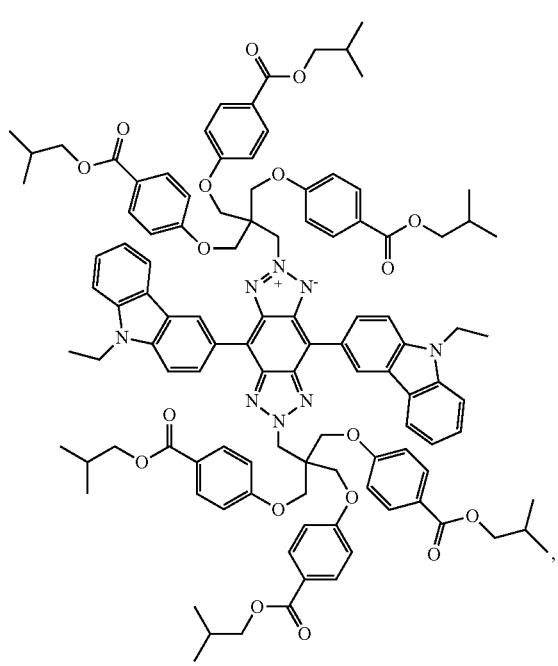
22
-continued
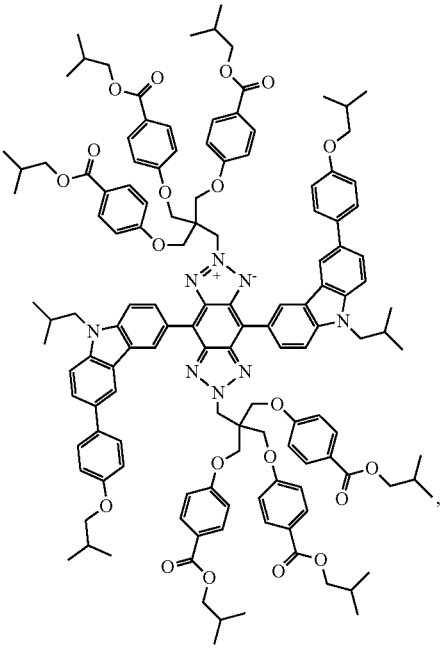
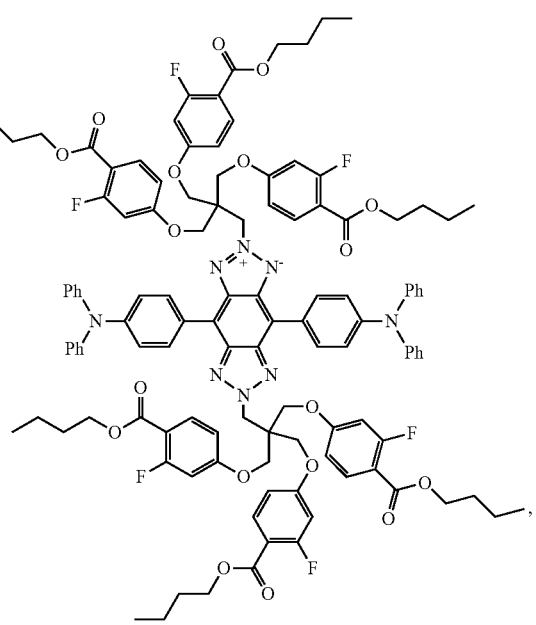

23
-continued
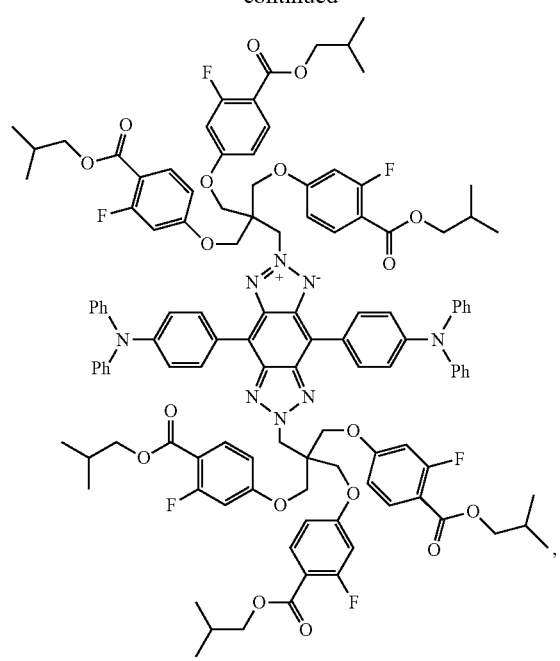
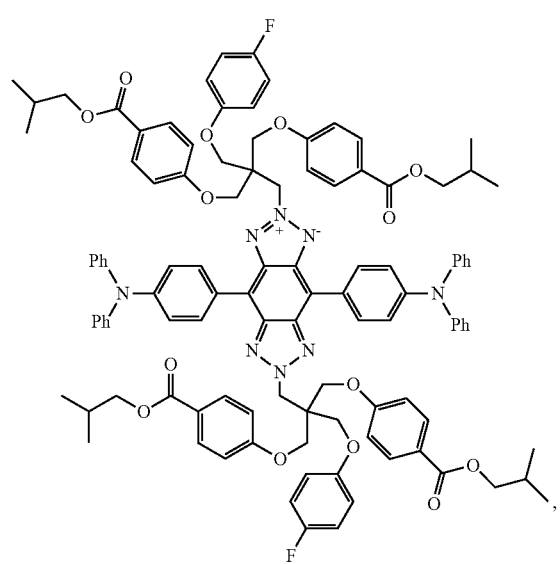
24
-continued
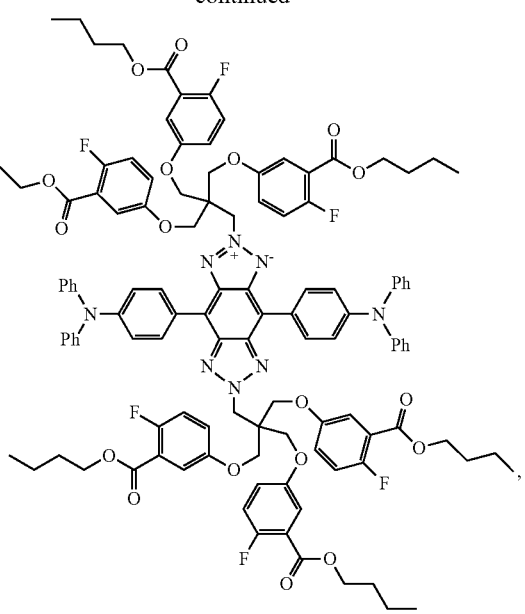
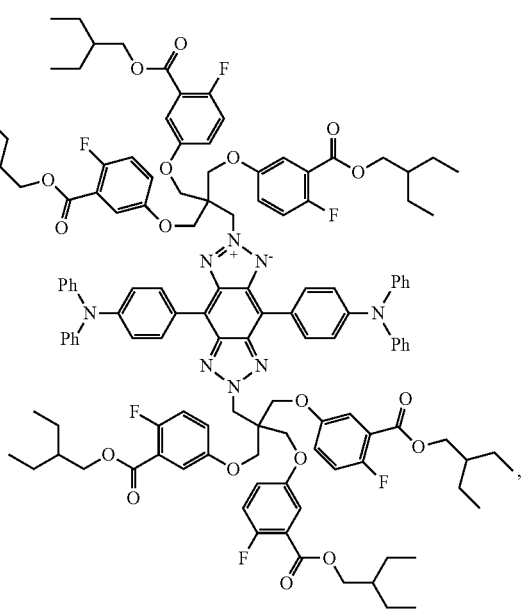

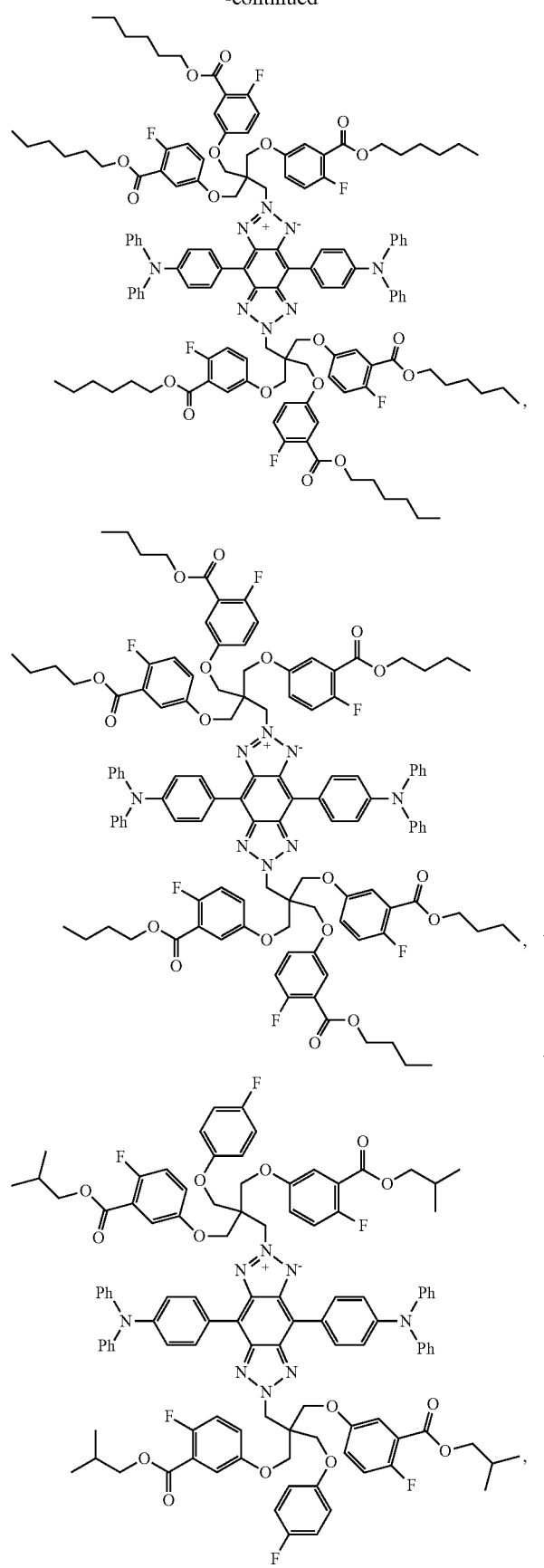
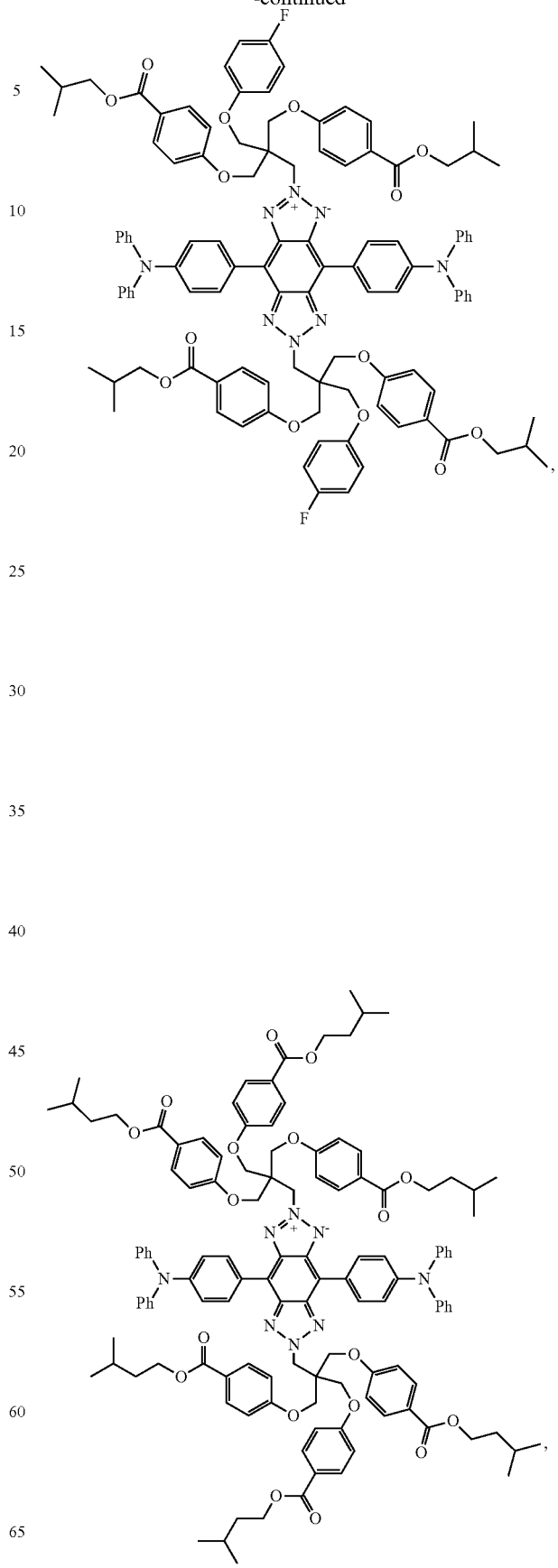

27
-continued
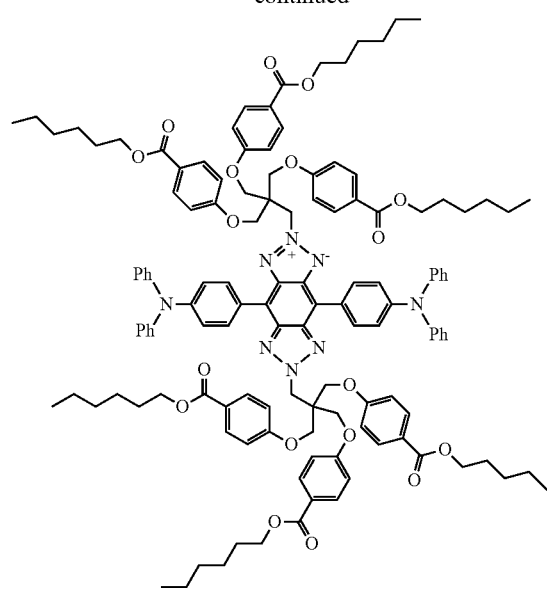
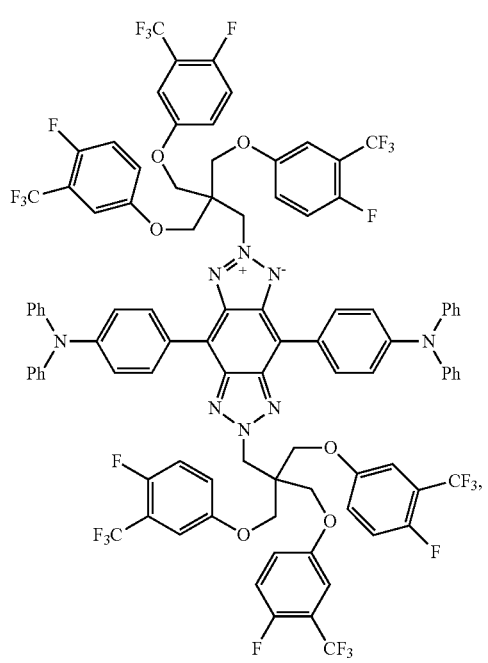
28
-continued
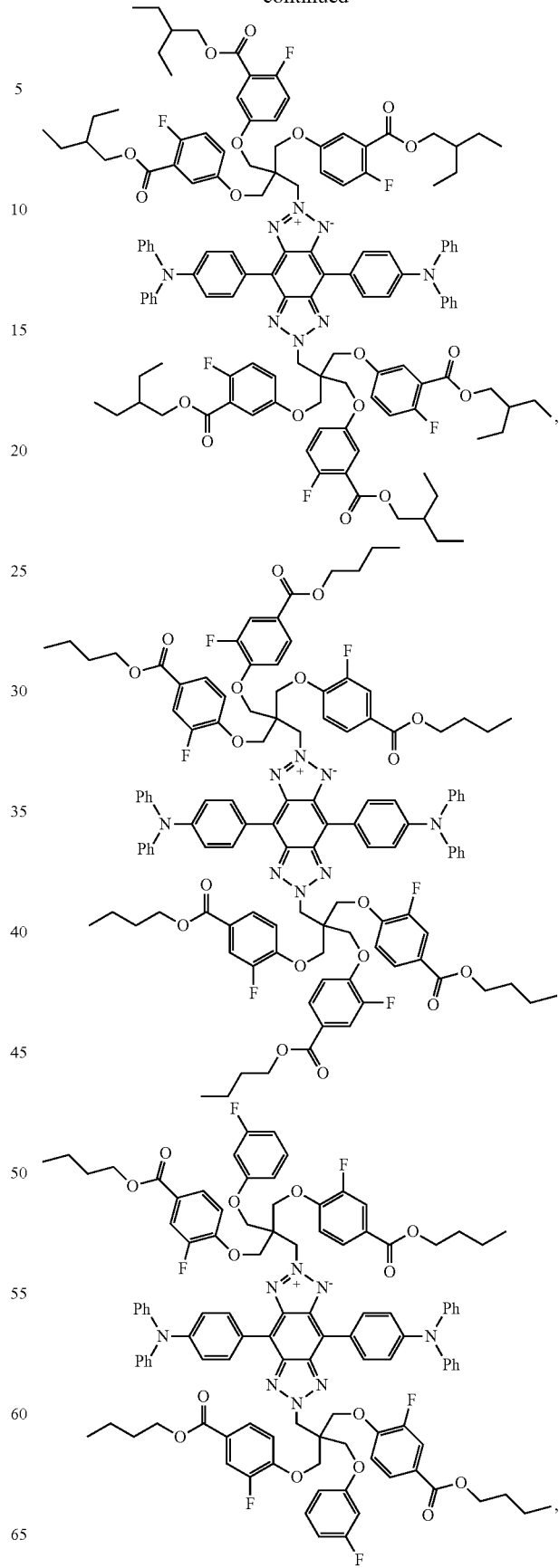

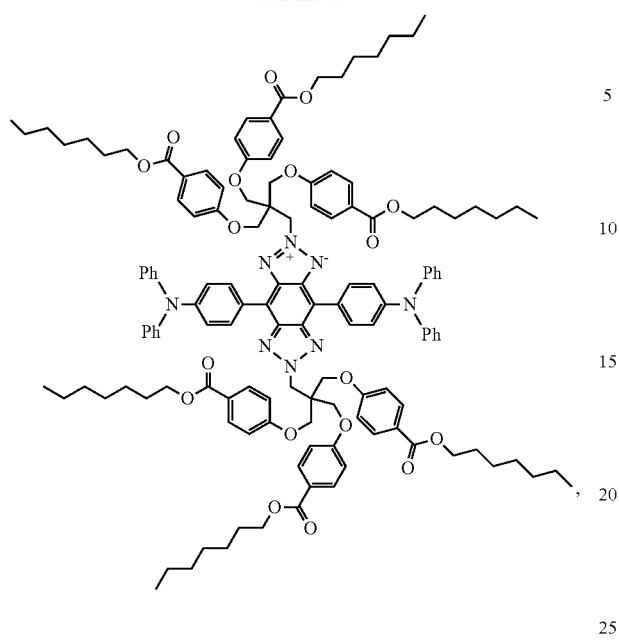

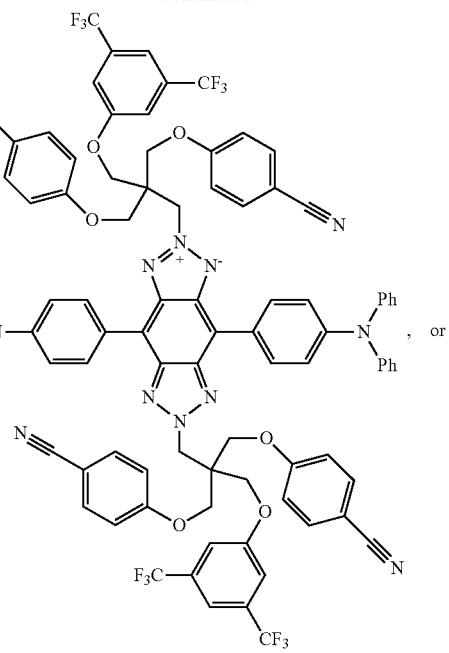

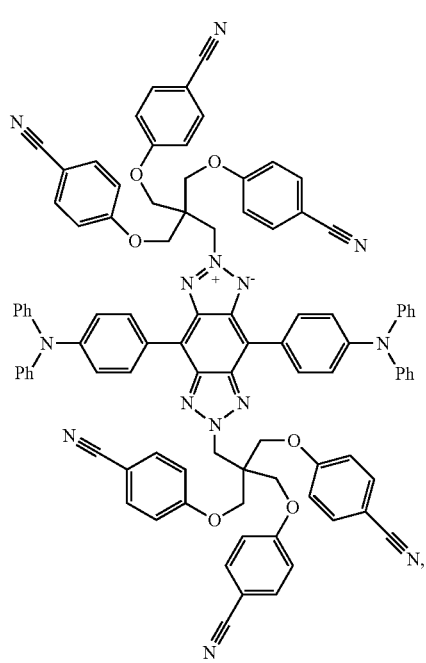

Some embodiments provide a chromophore having the structure of Formula (I), wherein D is optionally substituted phenyl or optionally substituted heteroaryl, and $R^1$, $R^2$, $R^3$, $R^4$, $R^5$, and $R^6$ are independently optionally substituted phenyl, optionally substituted naphthyl, or optionally substituted heterocyclyl, and wherein $R^1$, $R^2$, $R^3$, $R^4$, $R^5$, and $R^6$, do not comprise fluorine. In some embodiments, D is selected from furan, thiophene, pyrrole, benzofuran, benzothiophene, indole, carbazole, dibenzofuran, or dibenzothiophene. In some embodiments D is or

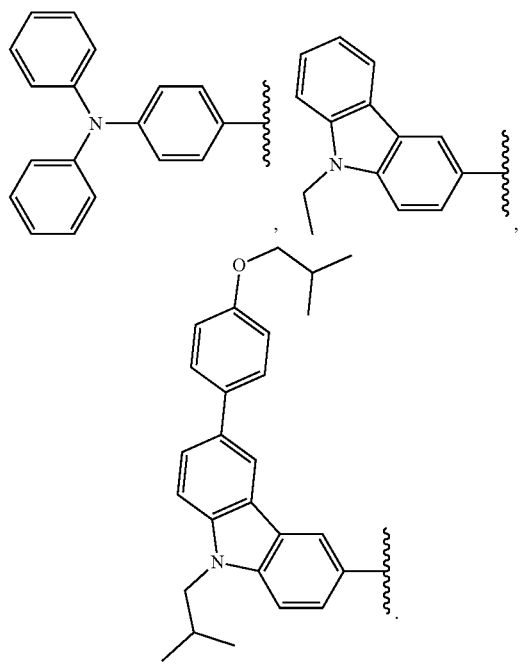
In some embodiments, R¹, R², R³, R⁴, R⁵, and R⁶ are independently selected from
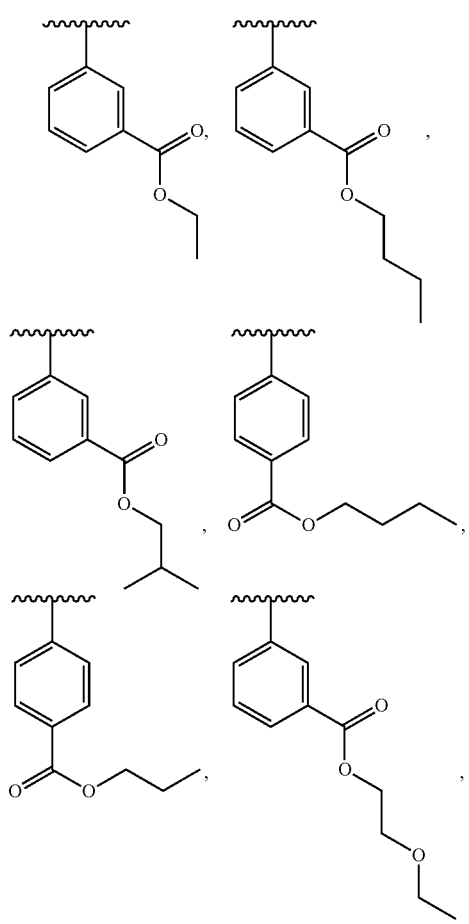
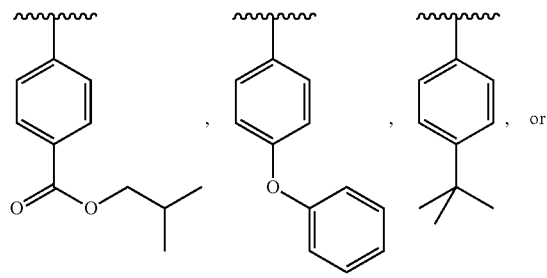
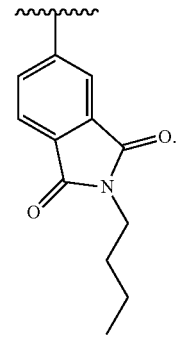
In some embodiments, the structure is any one of the following:
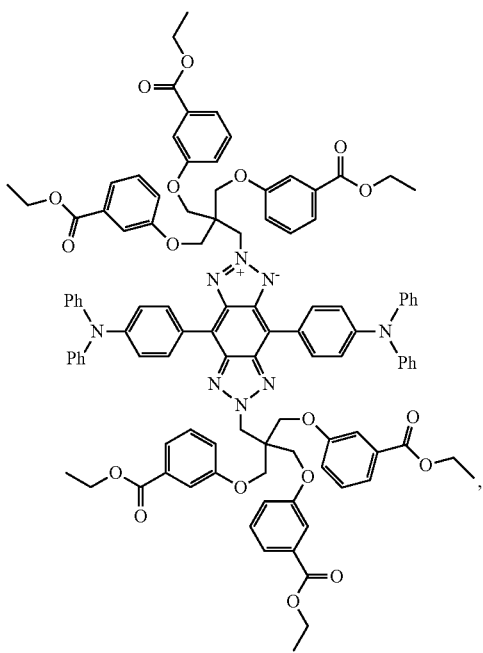

33
-continued
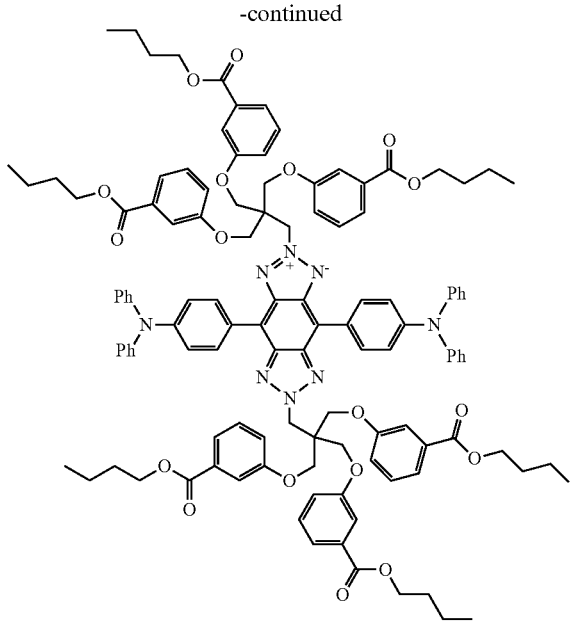
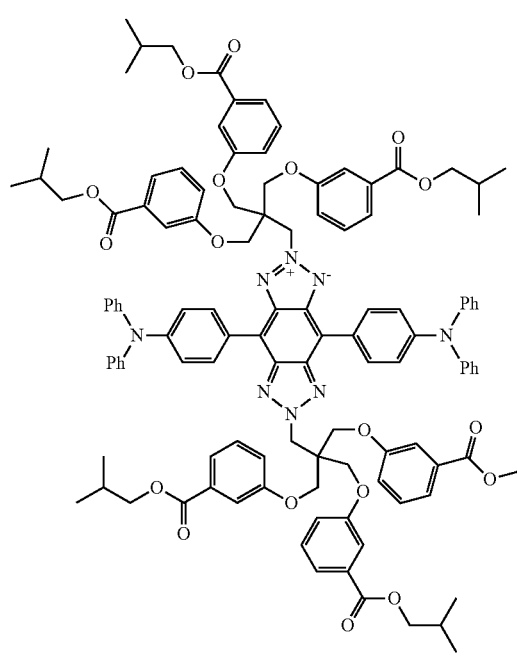
34
-continued
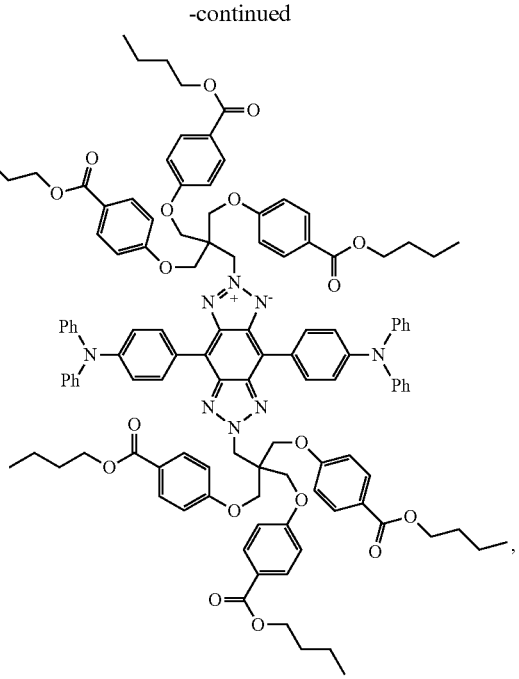
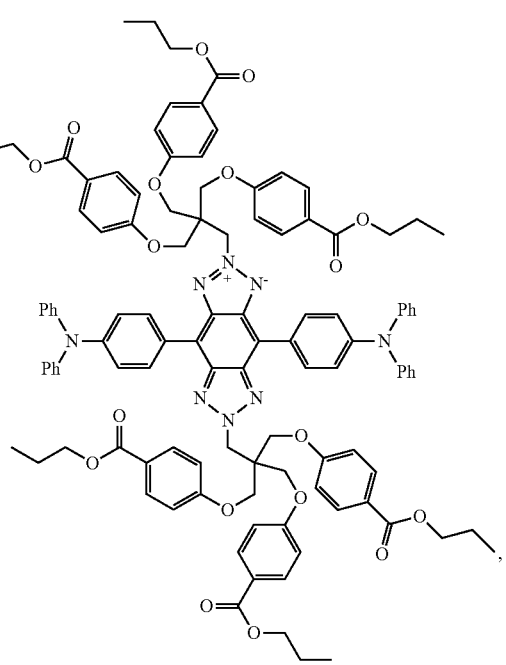

35
-continued
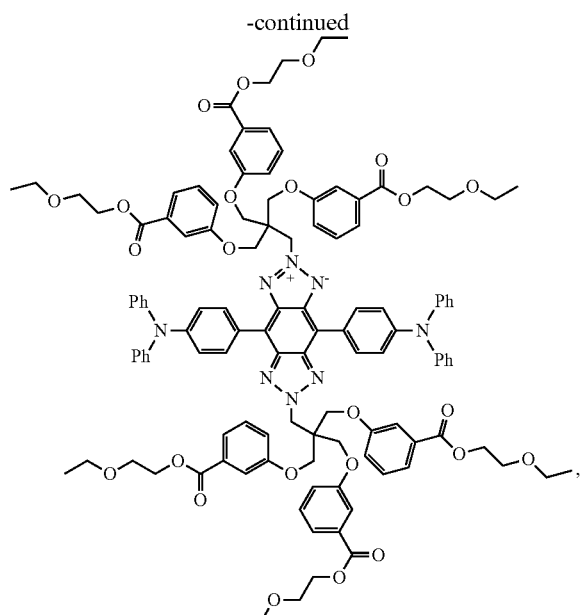
36
-continued
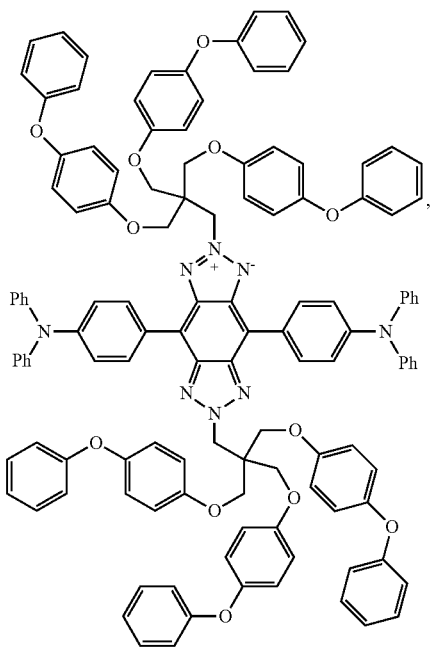
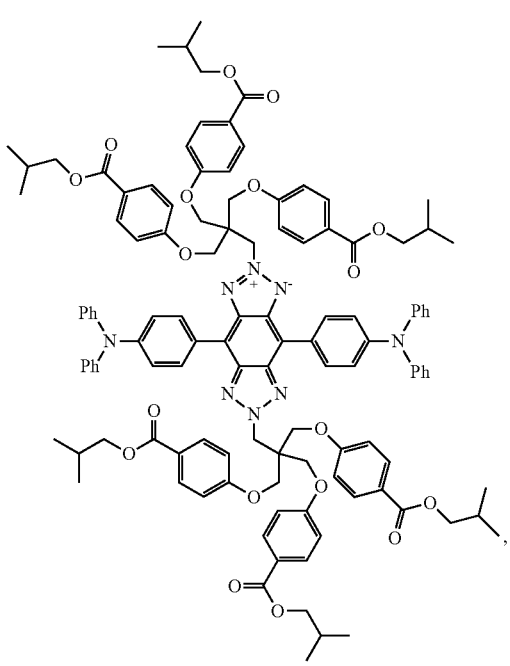
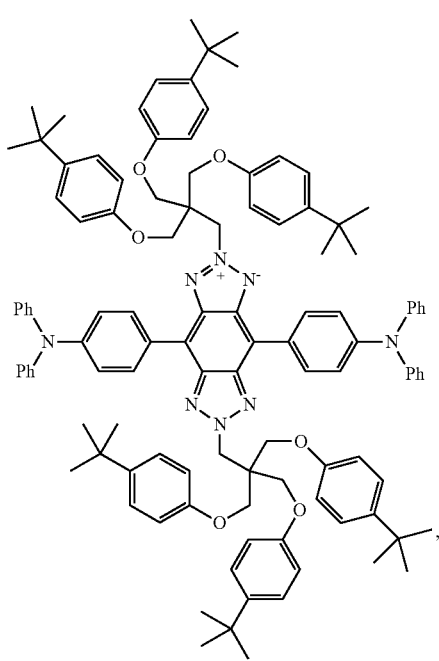

37
-continued
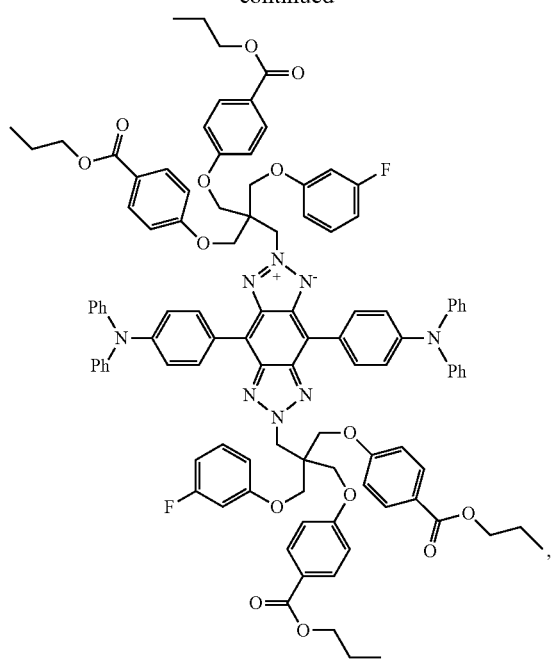
,
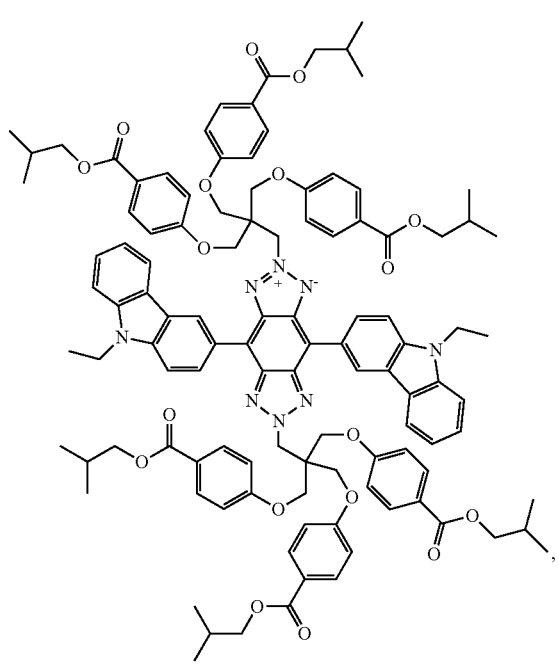
,
38
-continued
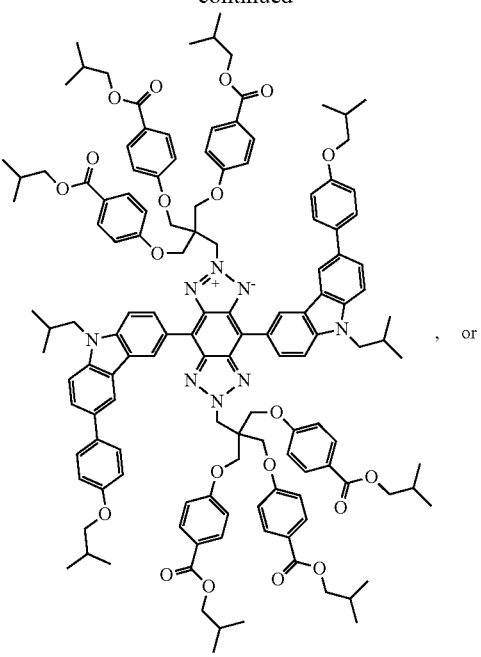
, or
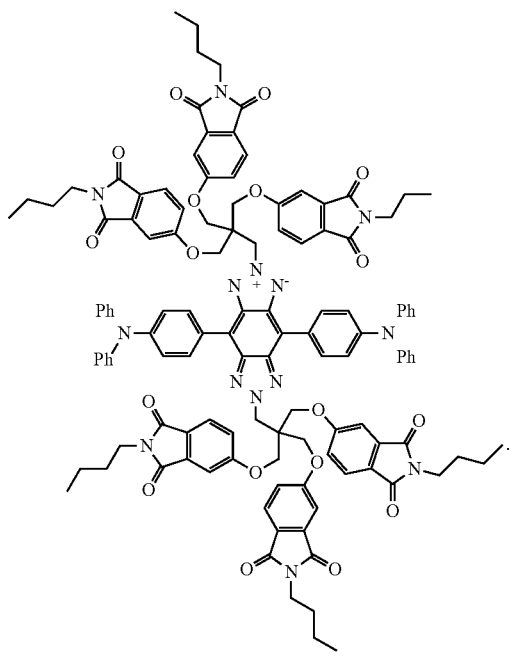
.
The following embodiments are specifically contemplated:

Embodiment 1

A compound represented by formula I:

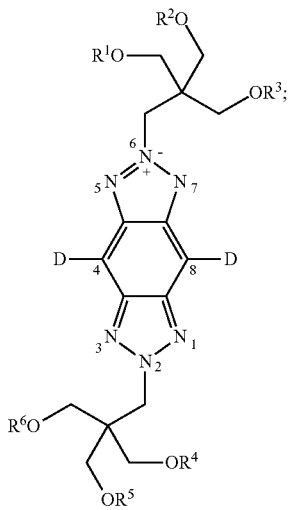

(I)

wherein:

D) is optionally substituted phenyl or optionally substituted heteroaryl; and $R^1$, $R^2$, $R^3$, $R^4$, $R^5$, and $R^6$ are independently optionally substituted phenyl, optionally substituted naphthyl, or optionally substituted heterocyclyl.

Embodiment 2

The compound of Embodiment 1, wherein each substituent of D, $R^1$, $R^2$, $R^3$, $R^4$, $R^5$, and $R^6$, if present, has a molecular weight of about 15 Da to about 500 Da and is represented by a formula $C_{0-20}H_{0-41}N_{0-5}O_{0-10}S_{0-5}P_{0-3}F_{0-10}Cl_{0-5}Br_{0-3}$, provided that at least 1 non-hydrogen atom is present in each substituent.

Embodiment 3

The compound of Embodiment 1 or 2, wherein D) is optionally substituted phenyl, optionally substituted furanyl, optionally substituted thiophenyl, optionally substituted pyrrolyl, optionally substituted benzofuranyl, optionally substituted benzothiophenyl, optionally substituted indolyl, optionally substituted carbazolyl, optionally substituted dibenzofuranyl, or optionally substituted dibenzothiophenyl.

Embodiment 4

The compound of Embodiment 3, wherein D is optionally substituted phenyl.

Embodiment 5

The compound of Embodiment 3, wherein the D is optionally substituted 4-(diphenylamino)phenyl.

Embodiment 6

The compound of embodiment 3, wherein D is

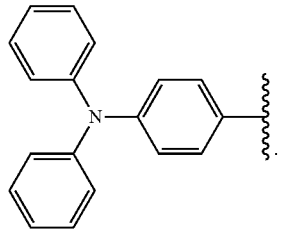 [SMILES: *c1ccc(N(c2ccccc2)c2ccccc2)cc1]

Embodiment 7

The compound of Embodiment 3, wherein D is optionally substituted carbazolyl.

Embodiment 8

The compound of Embodiment 3, wherein D is optionally substituted 9H-carbazol-2-yl.

Embodiment 9

The compound of Embodiment, 7 wherein the carbazolyl has 1, 2, or 3 substituents, wherein each substituent is independently $C_{1-6}$ alkyl, $C_{1-6}$—O-alkyl, or phenyl optionally substituted with $C_{1-6}$ alkyl or $C_{1-6}$—O-alkyl.

Embodiment 10

The compound of Embodiment 3, wherein D is

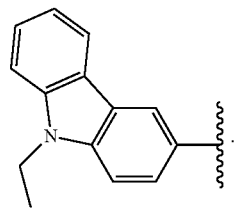 [SMILES: *c1ccc2c(c1)c1ccccc1n2CC]

Embodiment 11

The compound of Embodiment 3, wherein D is

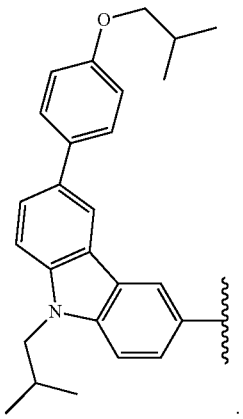 [SMILES: *c1ccc2c(c1)c1cc(-c3ccc(OCC(C)C)cc3)ccc1n2CC(C)C]

Embodiment 12

The compound of Embodiment 3, wherein D is

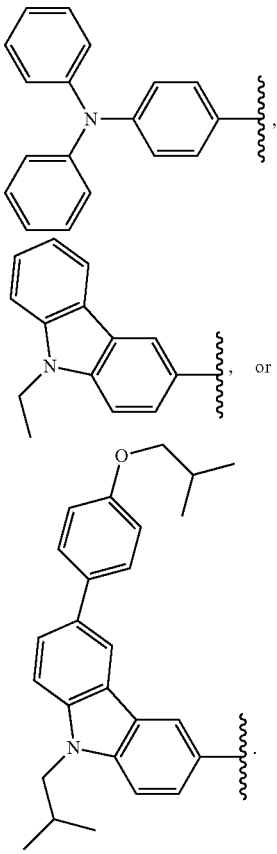

Embodiment 13

The compound of Embodiment 1, 2, 3, 4, 5, 6, 7, 8, 9, 10, 11, or 12, wherein $R^1$ and $R^4$ are independently optionally substituted phenyl.

Embodiment 14

The compound of Embodiment 13, wherein $R^2$ and $R^5$ are independently optionally substituted phenyl.

Embodiment 15

The compound of Embodiment 14, wherein $R^3$ and $R^6$ are independently optionally substituted phenyl.

Embodiment 16

The compound of Embodiment 1, 2, 3, 4, 5, 6, 7, 8, 9, 10, 11, or 12, wherein $R^1$ and $R^4$ are independently optionally substituted 1,3-dioxoisoindolin-5-yl.

Embodiment 17

The compound of Embodiment 16, wherein $R^2$ and $R^3$ are independently optionally substituted 1,3-dioxoisoindolin-5-yl.

Embodiment 18

The compound of Embodiment 17, wherein $R^3$ and $R^6$ are independently optionally substituted 1,3-dioxoisoindolin-5-yl.

Embodiment 19

The compound of Embodiment 13, 14, 16, or 17, wherein each phenyl or each 1,3-dioxoisoindolin-5-yl has 1, 2, or 3 substituents, wherein each substituent is independently $R^a$, —$OR^a$, —$CO_2$—$R^a$, —$CO_2$—$CH_2CH_2O$—$R^a$, F, $CF_3$, —CN, phenyl, -phenyl-$R^a$, -phenyl-$OR^a$, or -phenyl-$CO_2$—$R^a$, wherein $R^a$ is $C_{1-12}$ alkyl.

Embodiment 20

The compound of Embodiment 19, wherein each 1,3-dioxoisoindolin-5-yl has 1, 2, or 3 substituents, wherein each substituent is independently $R^a$, —$OR^a$.

Embodiment 21

The compound of Embodiment 19, wherein each phenyl has 1, 2, or 3 substituents, wherein each substituent is independently $R^a$, —$OR^a$, —$CO_2$—$R^a$, —$CO_2$—$CH_2CH_2O$—$R^a$, F, $CF_3$, —CN, phenyl, -phenyl-$R^a$, -phenyl-$OR^a$, or -phenyl-$CO_2$—$R^a$, wherein $R^a$ is $C_{1-12}$ alkyl.

Embodiment 22

The compound of Embodiment 15 or 21, wherein $R^3$ and $R^6$ are independently phenyl having 1, 2, or 3 substituents, wherein each substituent is independently $R^a$, —$OR^a$, —$CO_2$—$R^a$, —$CO_2$—$C_2H_4O$—$R^a$, F, $CF_3$, —CN, or phenyl, wherein $R^a$ is $C_{1-12}$ alkyl.

Embodiment 23

The compound of Embodiment 15 or 21, wherein $R^3$ and $R^6$ are independently phenyl having 1, 2, or 3 substituents, wherein each substituent is independently F or $CF_3$.

Embodiment 24

The compound of Embodiment 15 or 21, wherein $R^3$ and $R^6$ are independently phenyl having 1, 2, or 3 substituents, wherein each substituent is independently F.

Embodiment 25

The compound of Embodiment 15 or 21, wherein $R^3$ and $R^6$ are independently phenyl having 1, 2, or 3 substituents, wherein each substituent is independently $CF_3$.

Embodiment 26

The compound of Embodiment 14, wherein $R^1$, $R^2$, $R^4$, and $R^5$ are:

Embodiment 27

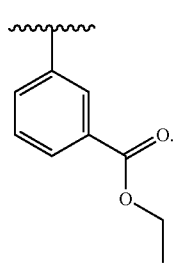 [SMILES: *c1cccc(C(=O)OCC)c1]

The compound of Embodiment 14, wherein $R^1$, $R^2$, $R^4$, and $R^5$ are:

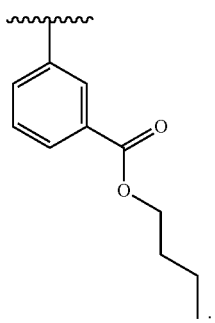 [SMILES: *c1cccc(C(=O)OCCCC)c1]

Embodiment 28

The compound of Embodiment 14, wherein $R^1$, $R^2$, $R^4$, and $R^5$ are:

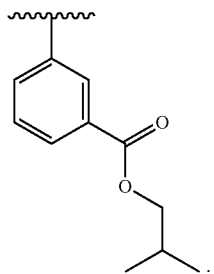 [SMILES: *c1cccc(C(=O)OCC(C)C)c1]

Embodiment 29

The compound of Embodiment 14, wherein $R^1$, $R^2$, $R^4$, and $R^5$ are:

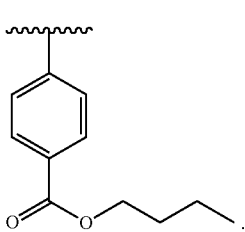 [SMILES: *c1ccc(C(=O)OCCCC)cc1]

Embodiment 30

The compound of Embodiment 14, wherein $R^1$, $R^2$, $R^4$, and $R^5$ are:

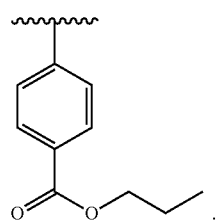 [SMILES: *c1ccc(C(=O)OCCC)cc1]

Embodiment 31

The compound of Embodiment 14, wherein $R^1$, $R^2$, $R^4$, and $R^5$ are:

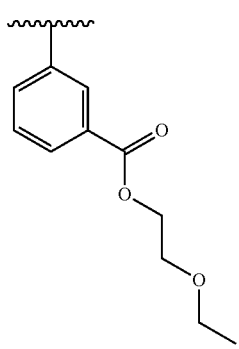

Embodiment 32

The compound of Embodiment 14, wherein $R^1$, $R^2$, $R^4$, and $R^5$ are:

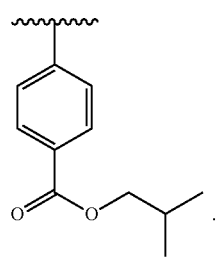 [SMILES: *c1ccc(C(=O)OCC(C)C)cc1]

Embodiment 33

The compound of Embodiment 14, wherein $R^1$, $R^2$, $R^4$, and $R^5$ are:

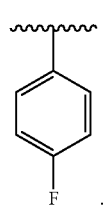 [SMILES: *c1ccc(F)cc1]

Embodiment 34

The compound of Embodiment 14, wherein $R^1$, $R^2$, $R^4$, and $R^5$ are:

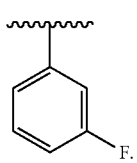 [SMILES: *c1cccc(F)c1]

Embodiment 35

The compound of Embodiment 14, wherein $R^1$, $R^2$, $R^4$, and $R^5$ are:

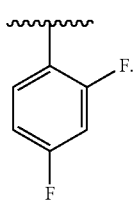 [SMILES: *c1ccc(F)cc1F]

Embodiment 36

The compound of Embodiment 14, wherein $R^1$, $R^2$, $R^4$, and $R^5$ are:

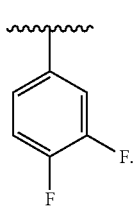 [SMILES: *c1ccc(F)c(F)c1]

Embodiment 37

The compound of Embodiment 14, wherein $R^1$, $R^2$, $R^4$, and $R^5$ are:

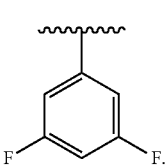

Embodiment 38

The compound of Embodiment 14, wherein $R^1$, $R^2$, $R^4$, and $R^5$ are:

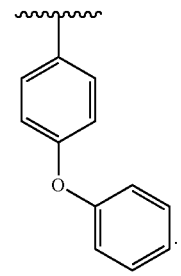 [SMILES: *c1ccc(Oc2ccccc2)cc1]

Embodiment 39

The compound of Embodiment 14, wherein $R^1$, $R^2$, $R^4$, and $R^5$ are:

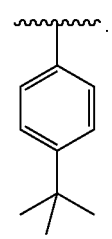

Embodiment 40

The compound of Embodiment 14, wherein $R^1$, $R^2$, $R^4$, and $R^5$ are:

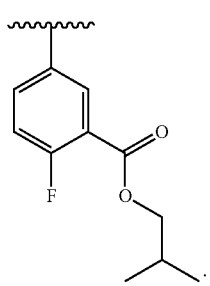 [SMILES: *c1ccc(F)c(C(=O)OCC(C)C)c1]

Embodiment 41

The compound of Embodiment 14, wherein $R^1$, $R^2$, $R^4$, and $R^5$ are:

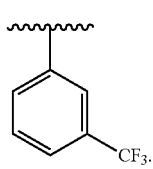

Embodiment 42

The compound of Embodiment 14, wherein $R^1$, $R^2$, $R^4$, and $R^5$ are:

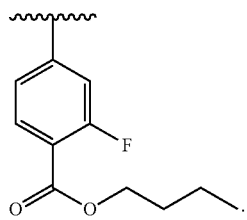 [SMILES: *c1ccc(C(=O)OCCCC)c(F)c1]

Embodiment 43

The compound of Embodiment 14, wherein $R^1$, $R^2$, $R^4$, and $R^5$ are:

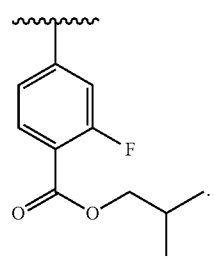 [SMILES: *c1ccc(C(=O)OCC(C)C)c(F)c1]

Embodiment 44

The compound of Embodiment 14, wherein $R^1$, $R^2$, $R^4$, and $R^5$ are:

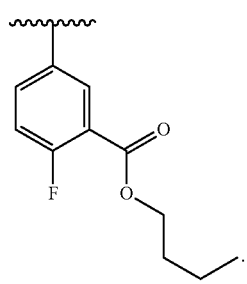 [SMILES: *c1ccc(F)c(C(=O)OCCCC)c1]

Embodiment 45

The compound of Embodiment 14, wherein $R^1$, $R^2$, $R^4$, and $R^5$ are:

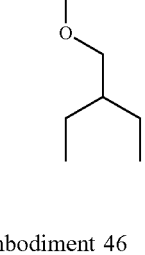

Embodiment 46

The compound of Embodiment 14, wherein $R^1$, $R^2$, $R^4$, and $R^5$ are:

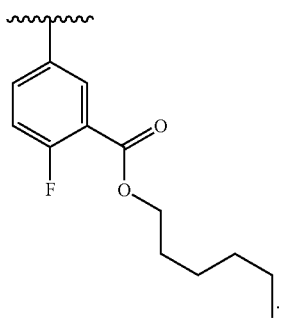 [SMILES: *c1ccc(F)c(C(=O)OCCCCCC)c1]

Embodiment 47

The compound of Embodiment 14, wherein $R^1$, $R^2$, $R^4$, and $R^5$ are:

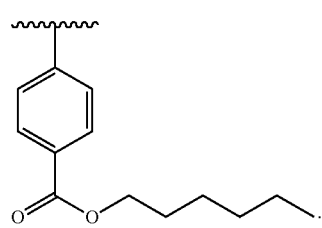 [SMILES: *c1ccc(C(=O)OCCCCCC)cc1]

Embodiment 48

The compound of Embodiment 14, wherein $R^1$, $R^2$, $R^4$, and $R^5$ are:

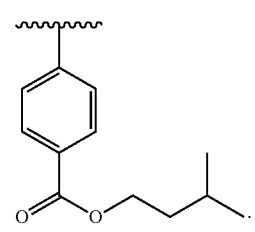 [SMILES: *c1ccc(C(=O)OCCC(C)C)cc1]

Embodiment 49
The compound of Embodiment 18, wherein $R^1$, $R^2$, $R^3$, $R^4$, $R^5$ and $R^6$ are:
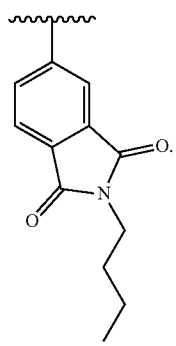 [SMILES: *c1ccc2c(c1)C(=O)N(CCCC)C2=O]
Embodiment 50
The compound of Embodiment 1, 2, 3, 4, 5, 6, 7, 8, 9, 10, 11, or 12, wherein $R^1$, $R^2$, $R^3$, $R^4$, $R^5$, and $R^6$ are independently:
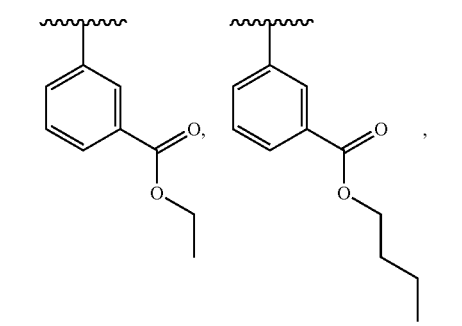
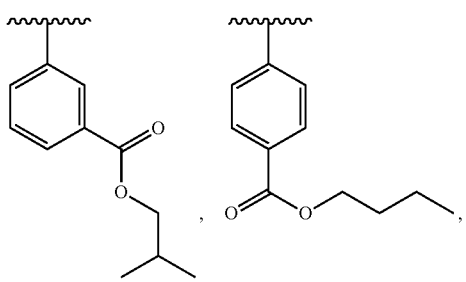
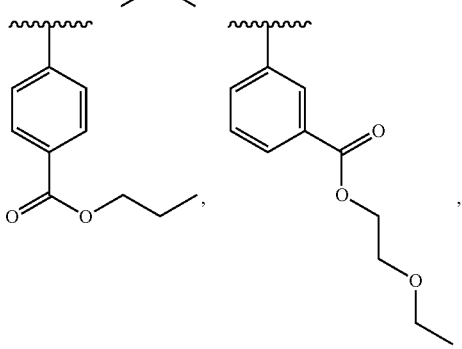
-continued
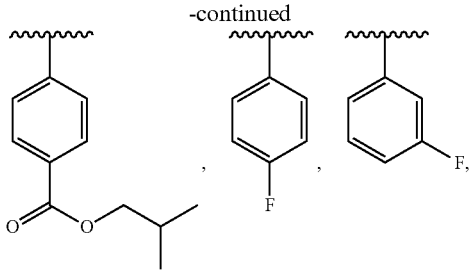
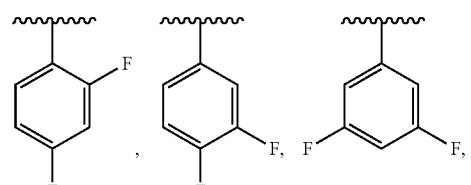
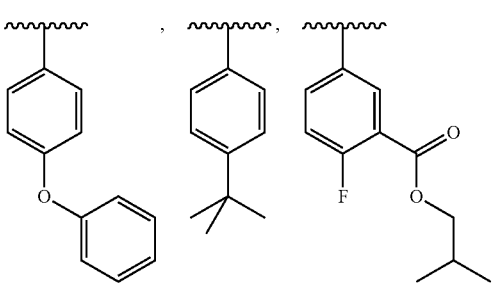
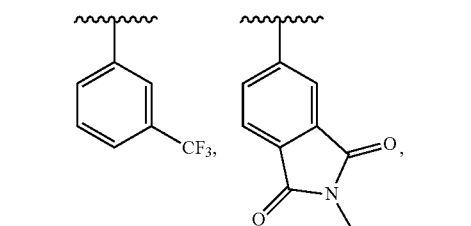
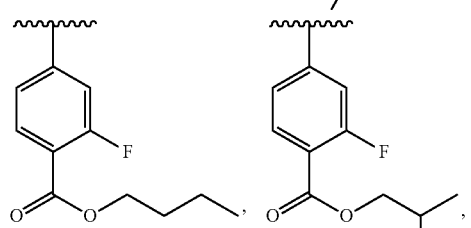
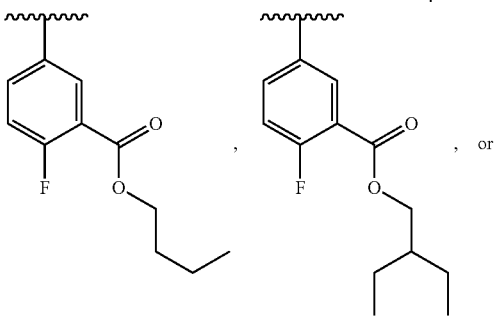, or 51
-continued
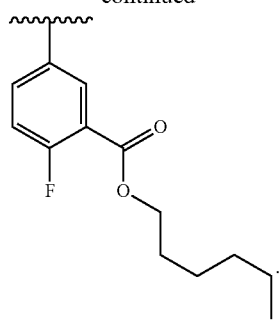
Embodiment 51
The compound of Embodiment 1, 2, 3, 4, 5, 6, 7, 8, 9, 10, 11, or 12, wherein $R^1$, $R^2$, $R^3$, $R^4$, $R^5$, and $R^6$ do not comprise fluorine.
Embodiment 52
The compound of Embodiment 1, 2, 3, 4, 5, 6, 7, 8, 9, 10, 11, or 12, wherein $R^1$, $R^2$, $R^3$, $R^4$, $R^5$, and $R^6$ are independently:
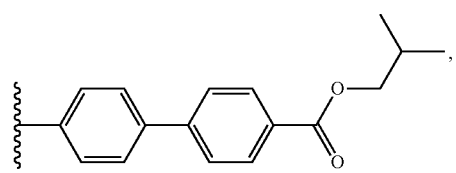
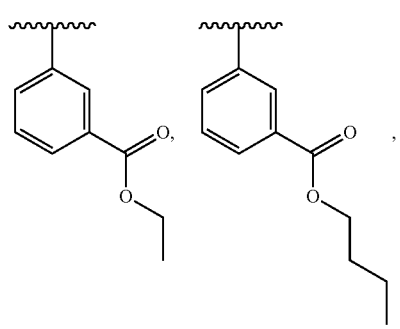
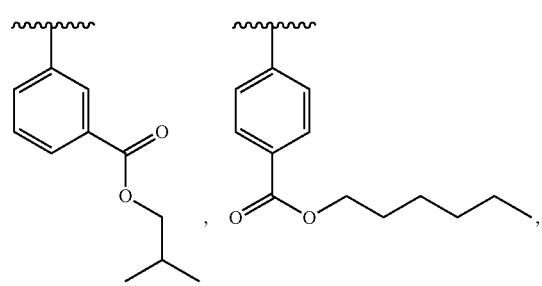
52
-continued
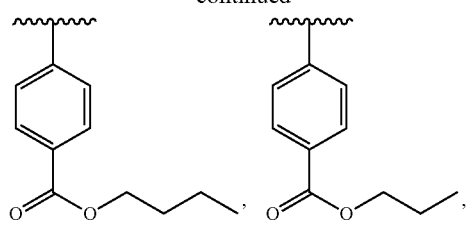
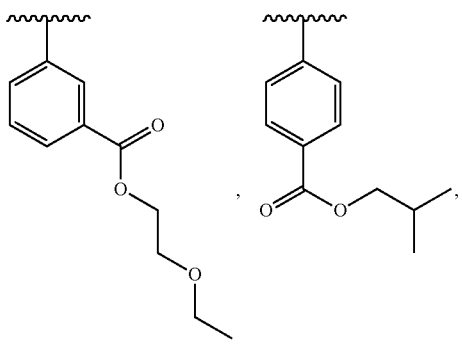
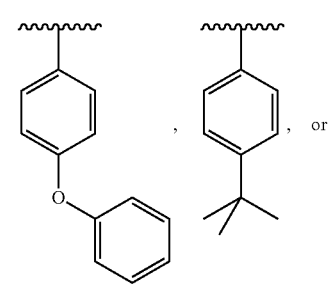, or
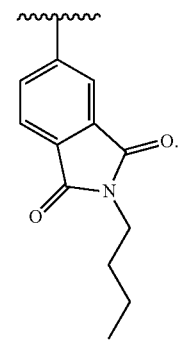 [SMILES: *c1ccc2c(c1)C(=O)N(CCCC)C2=O]

Embodiment 53
A compound represented by a formula:
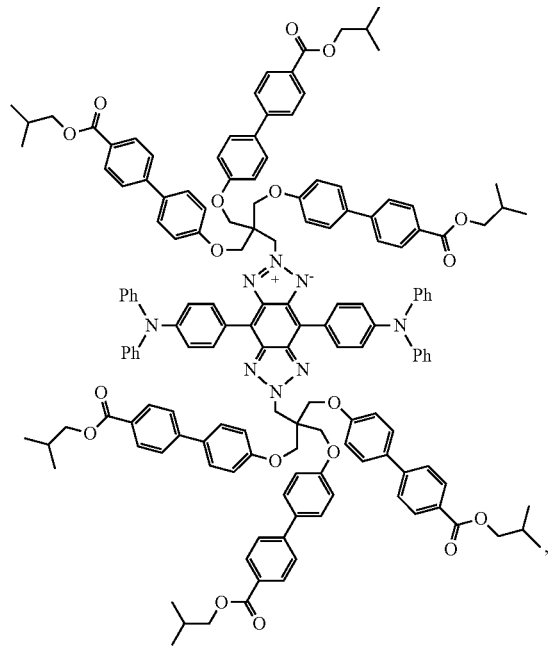
,
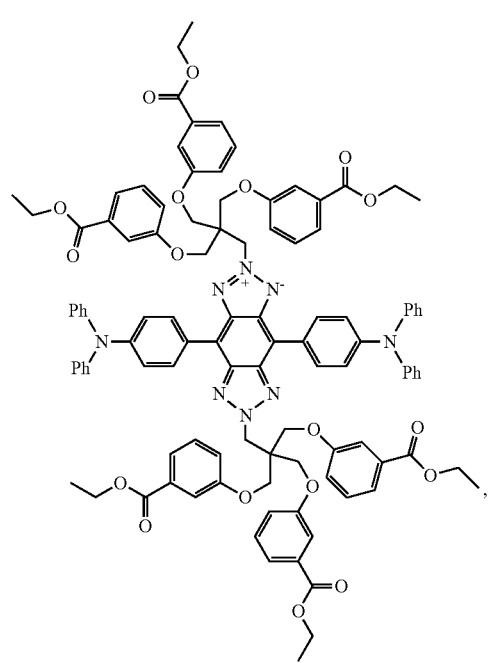
,
-continued
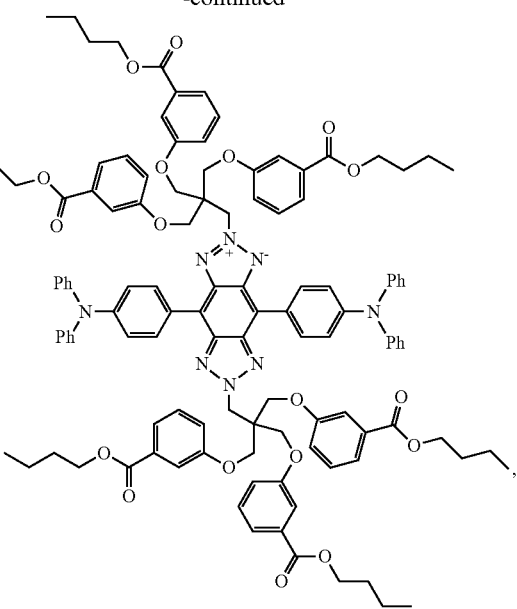
,
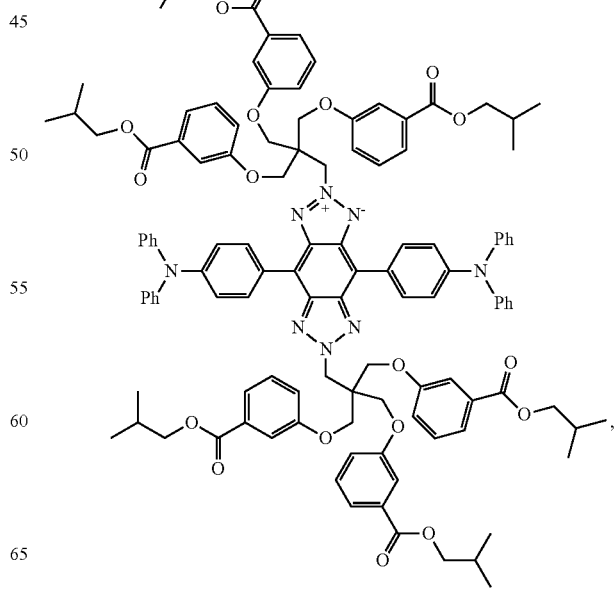
, 55
-continued
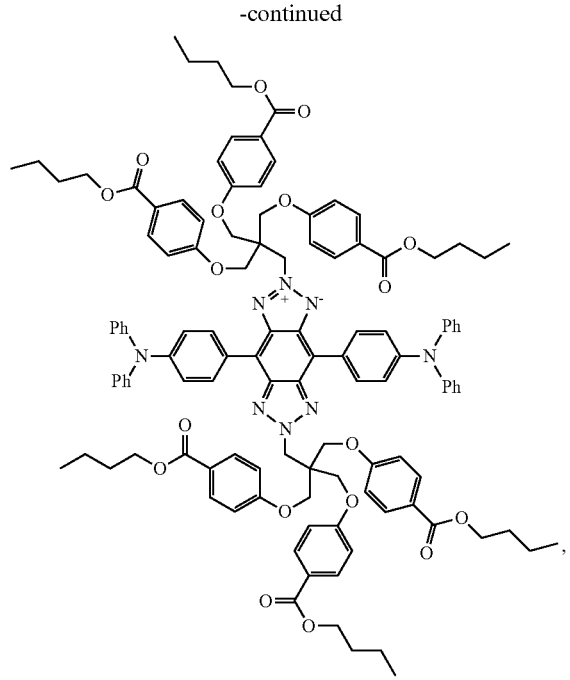
56
-continued
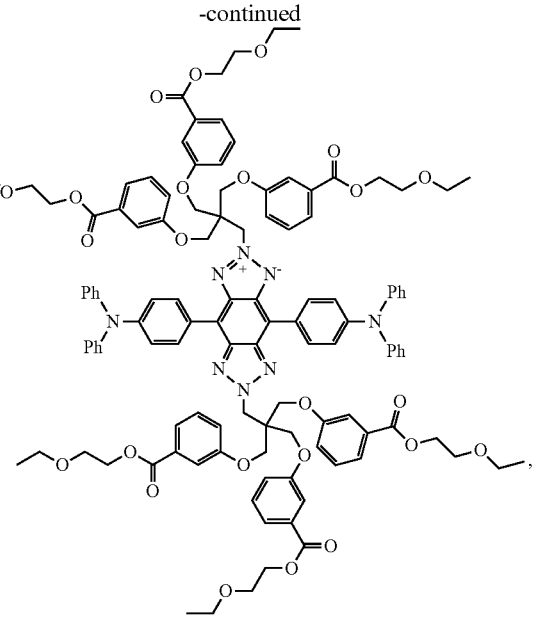
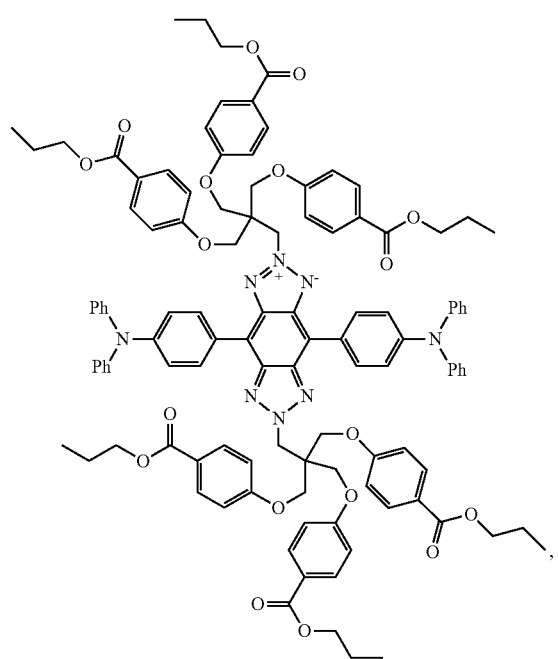
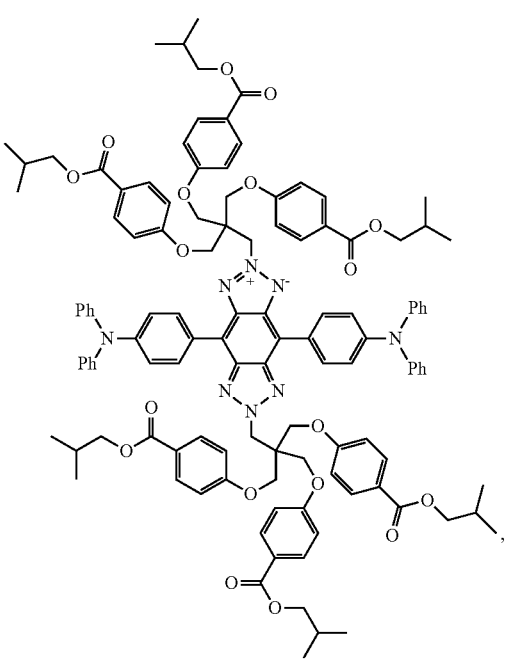

57
-continued
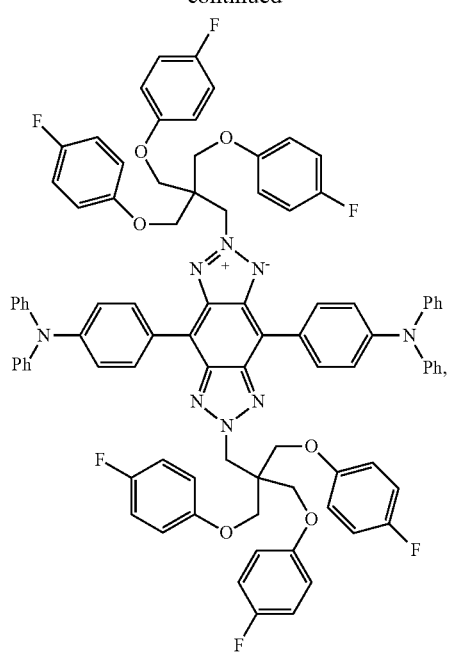
58
-continued
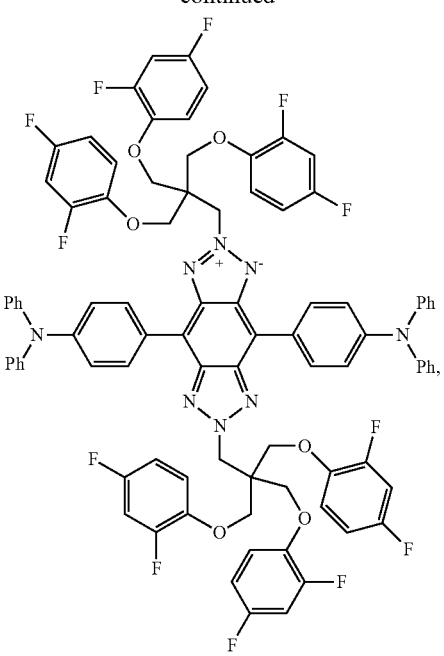
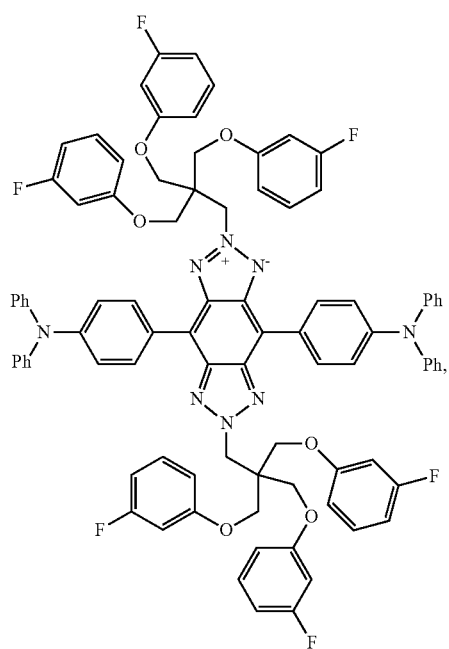
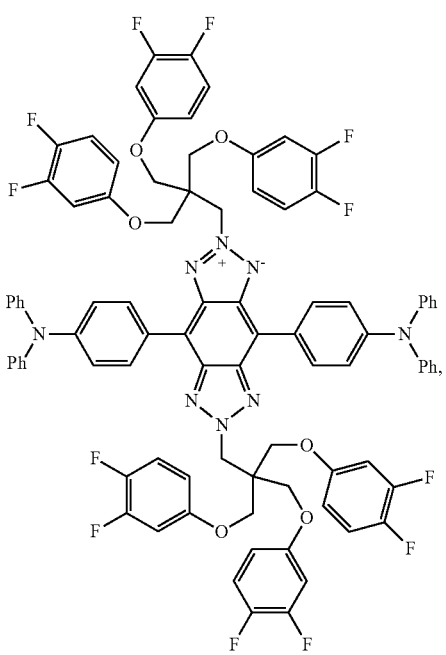

59
-continued
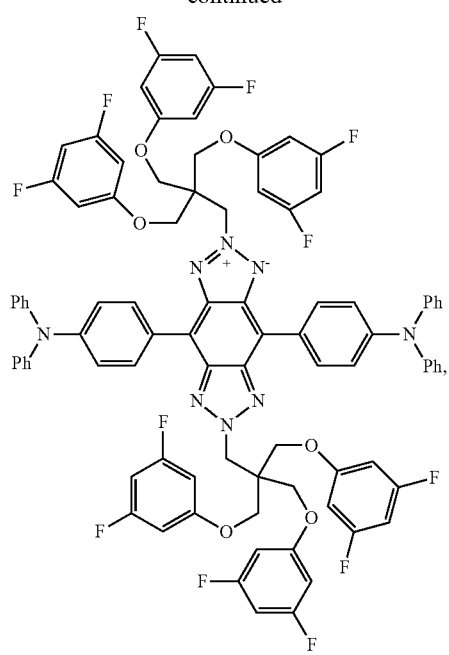
60
-continued
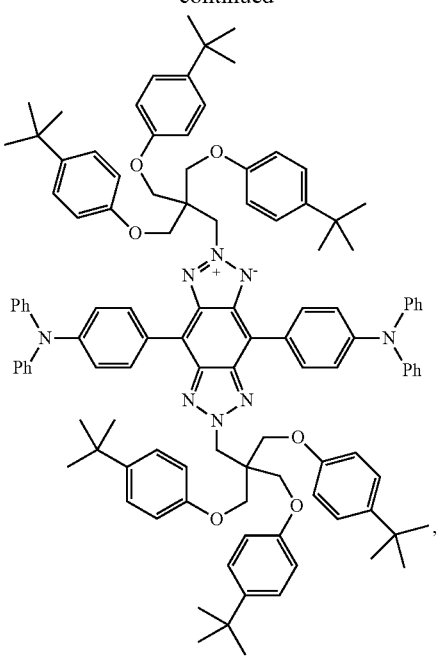
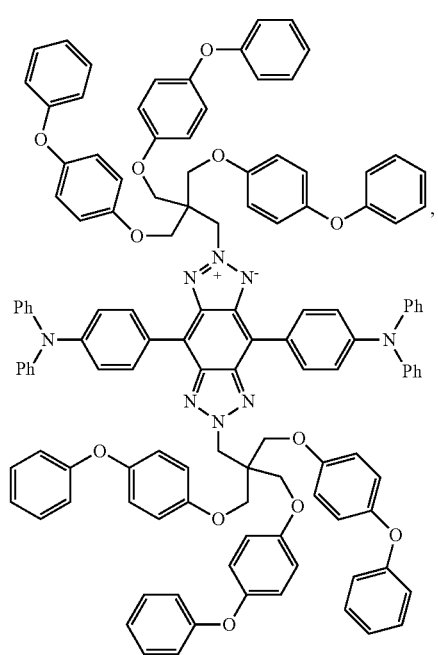
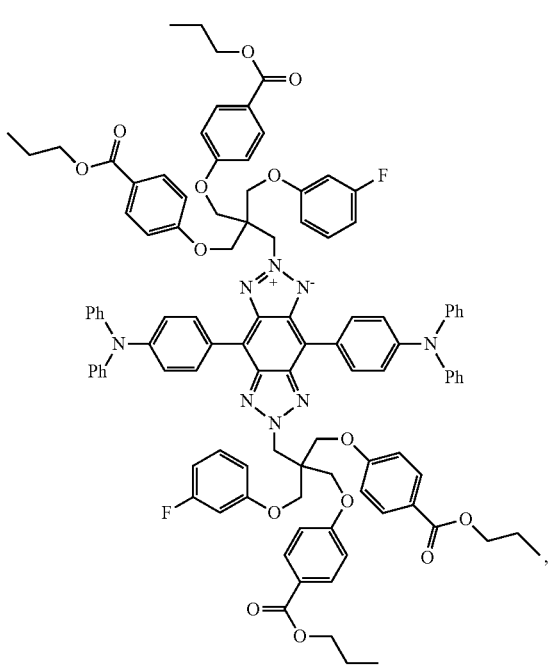

61
-continued
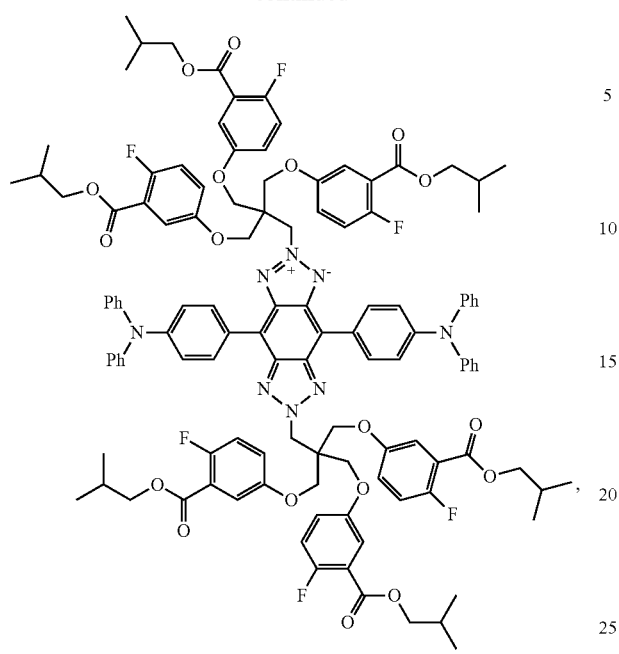
62
-continued
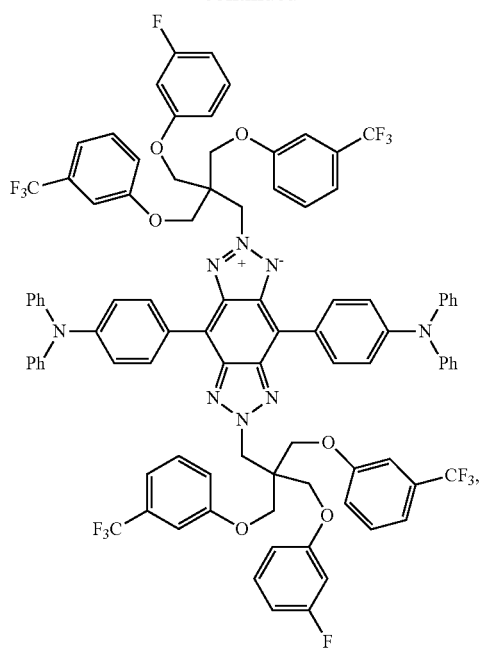
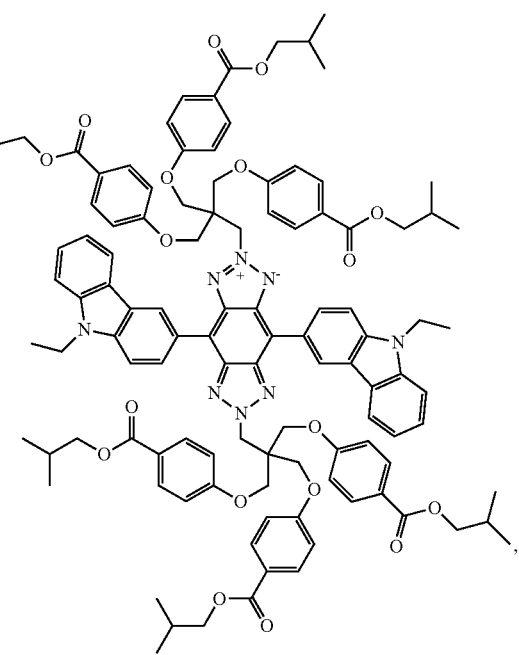

63
-continued
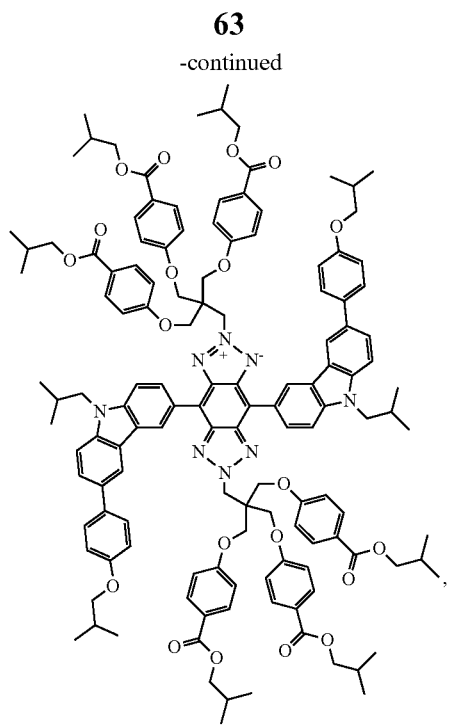
64
-continued
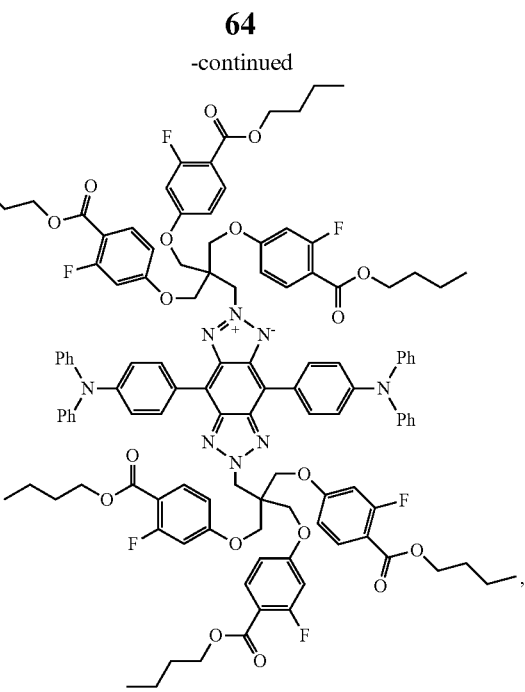

65
-continued
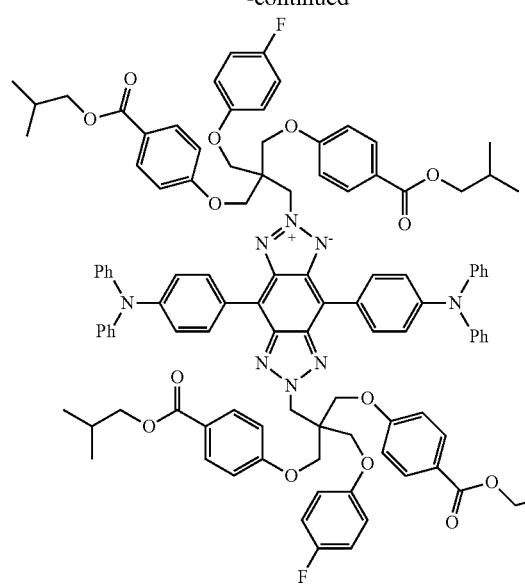
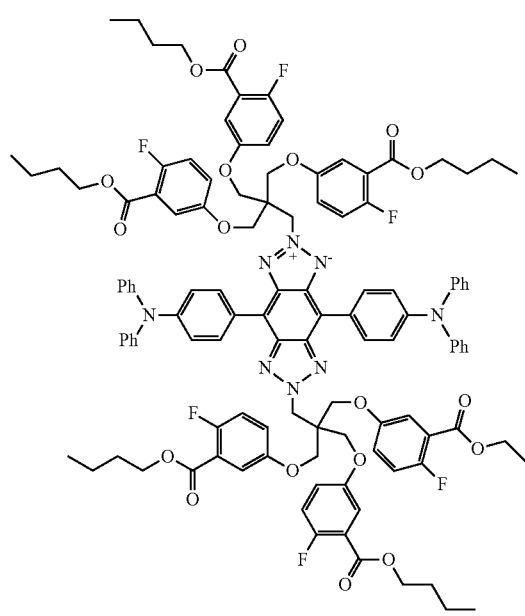
66
-continued
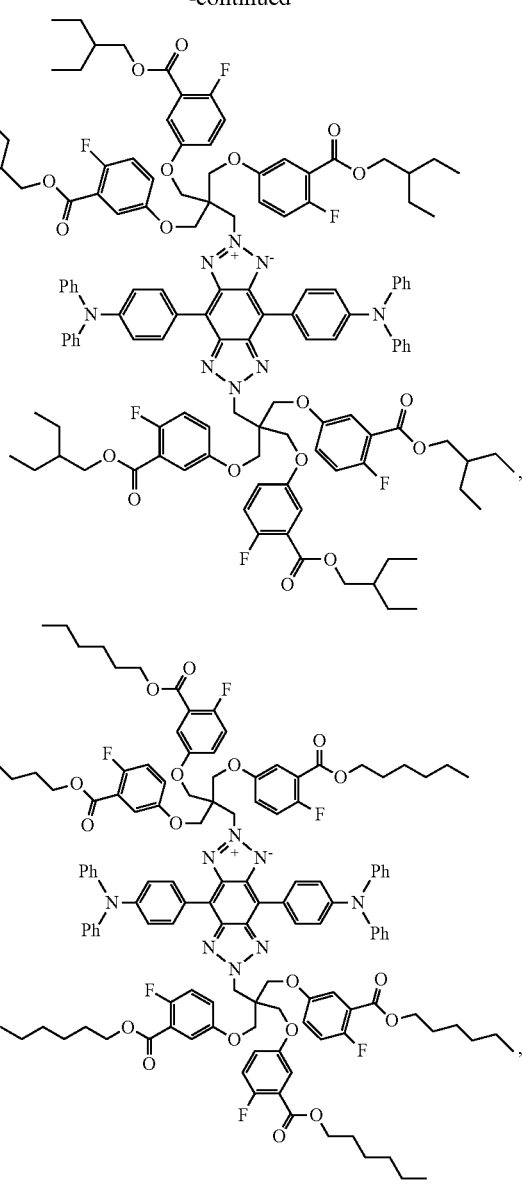
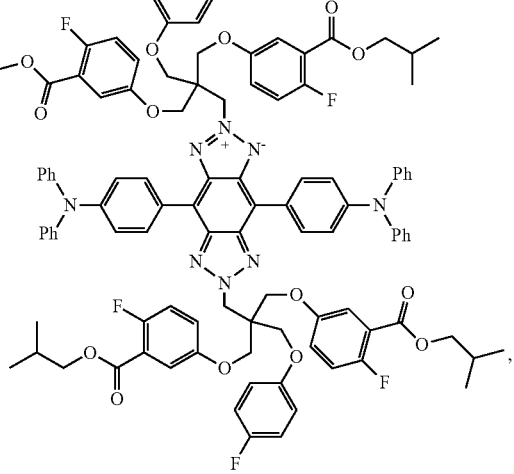

67
-continued
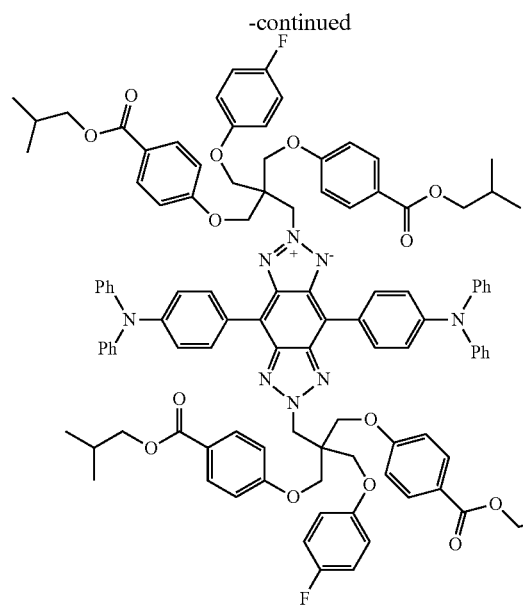
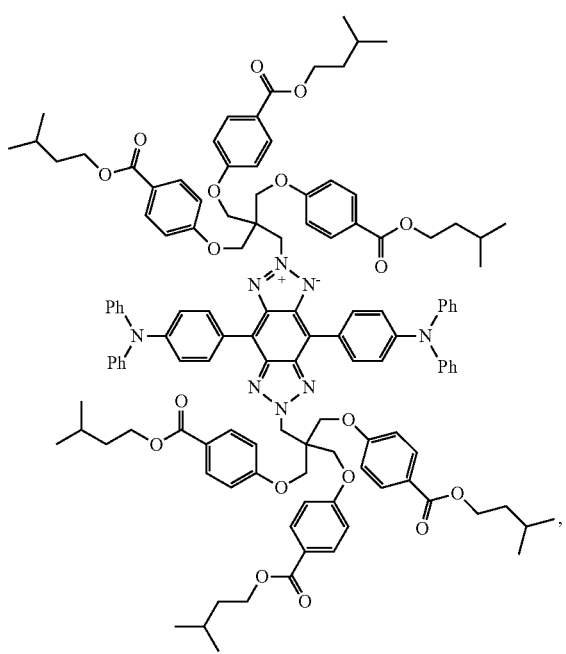
68
-continued
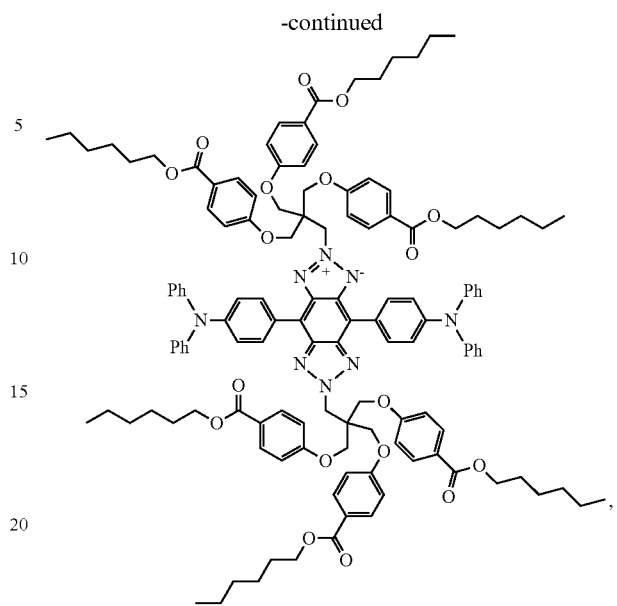
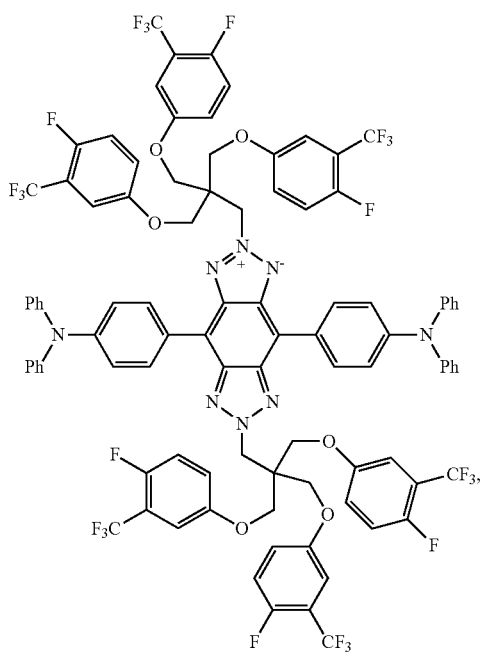

69
-continued
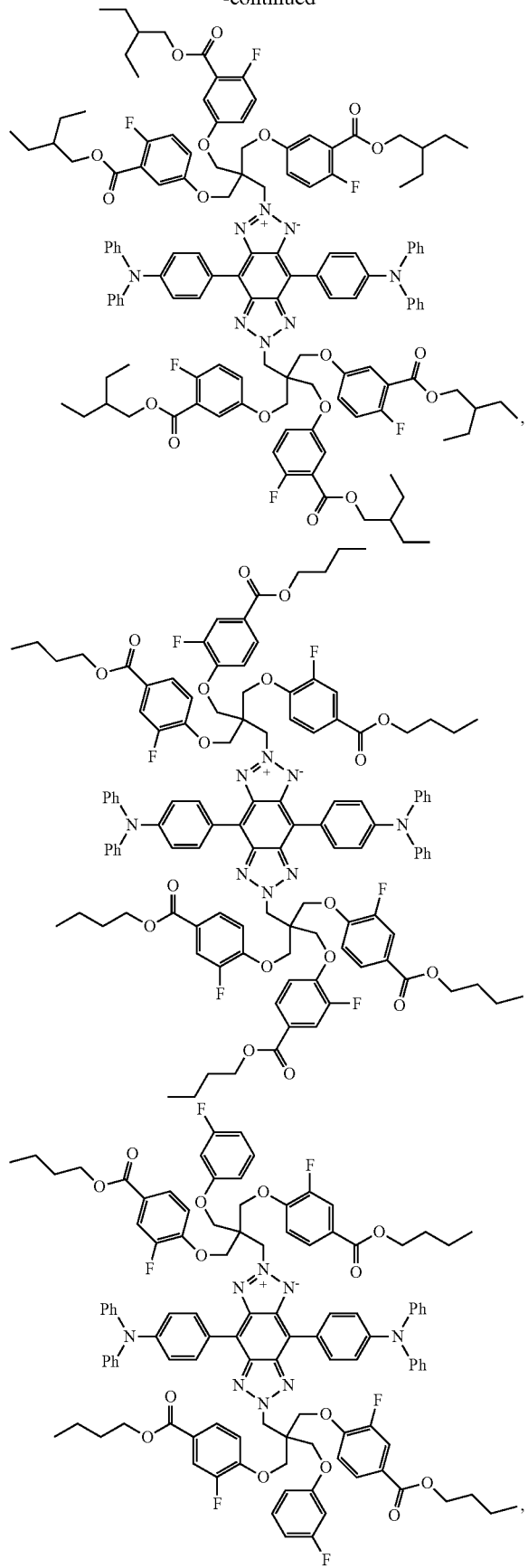
70
-continued
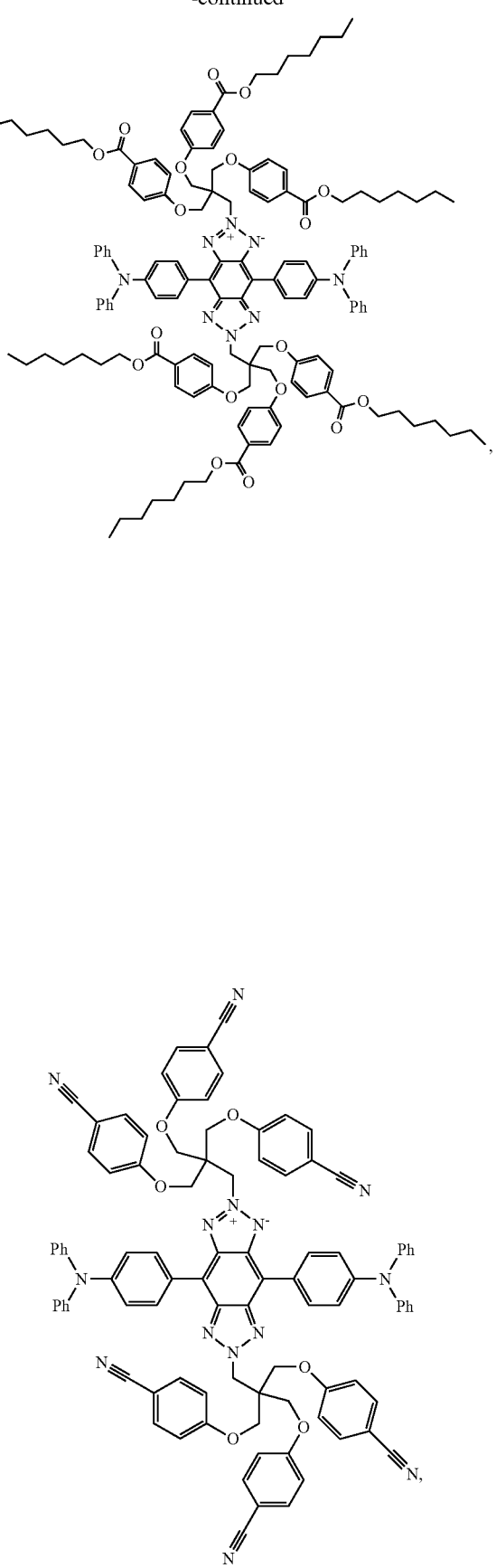

71
-continued
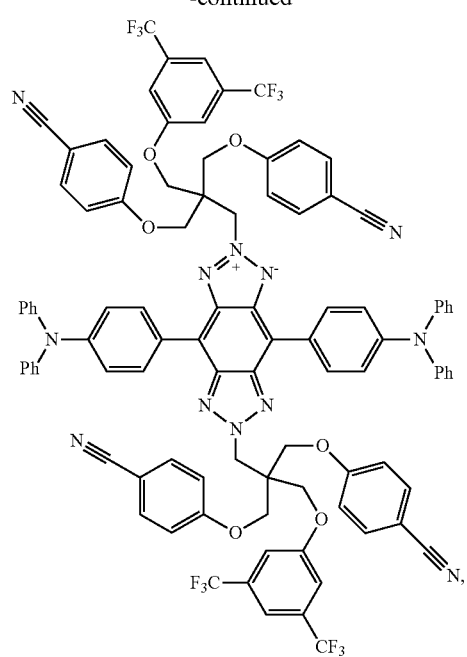
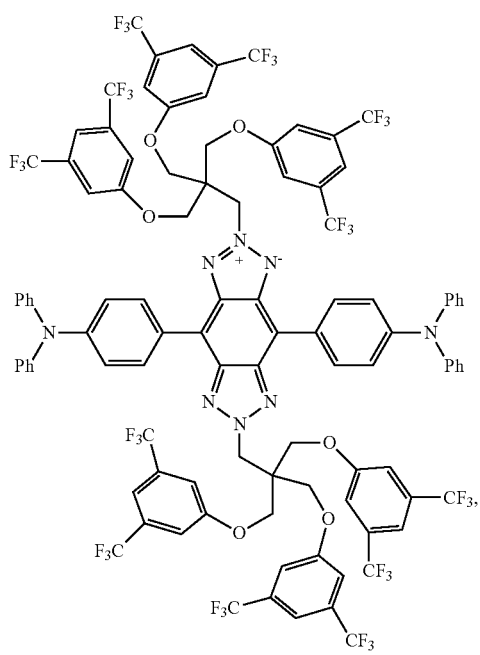
72
-continued
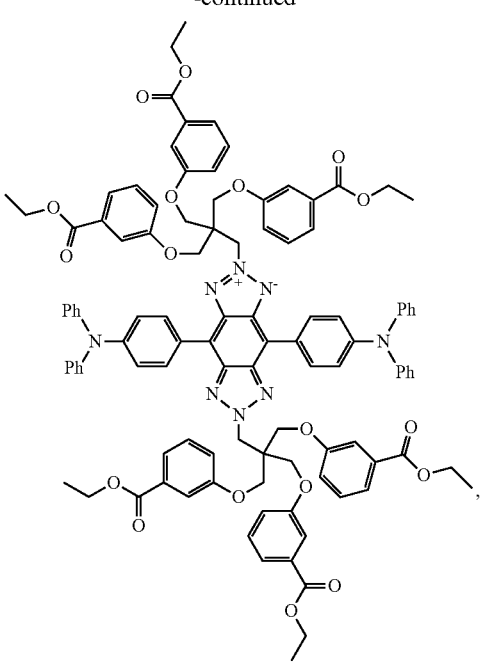
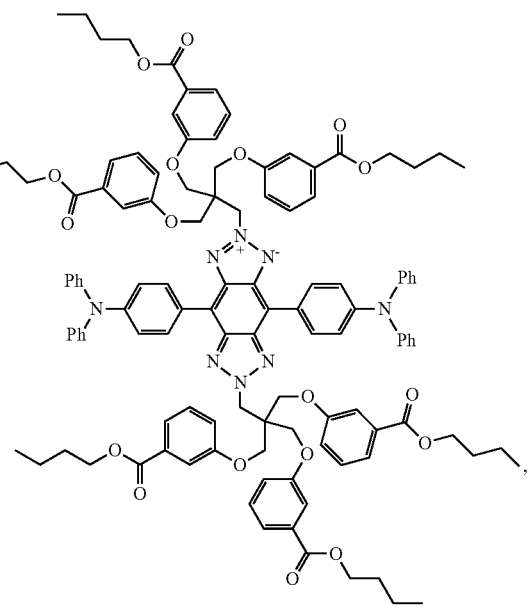

73
-continued
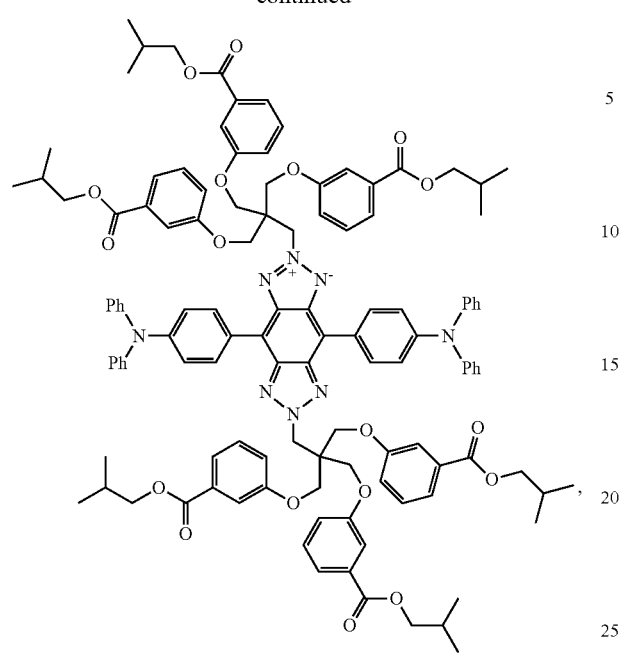
74
-continued
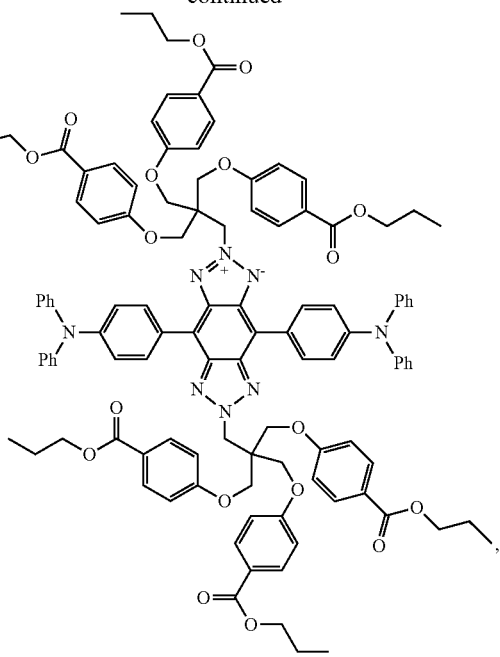
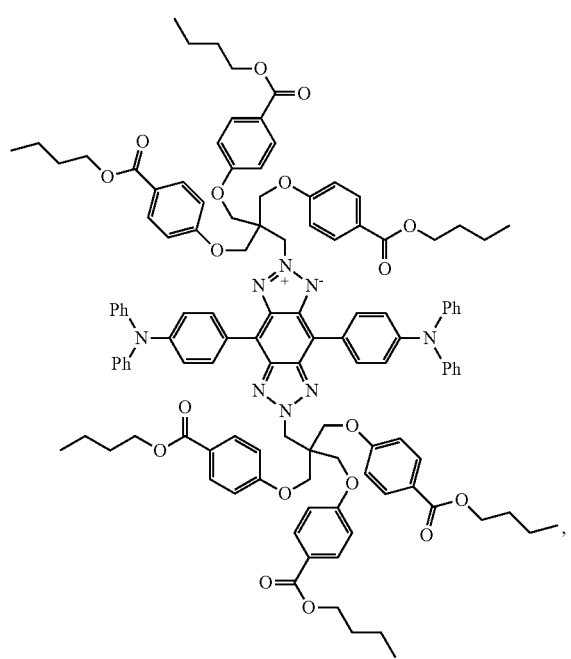
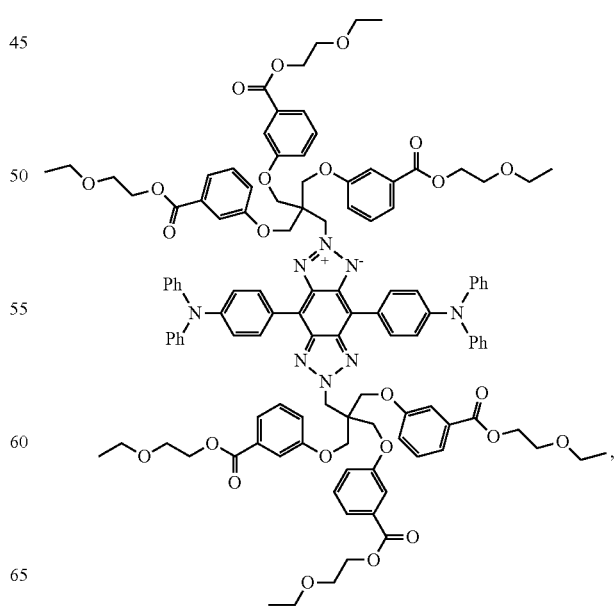

75
-continued
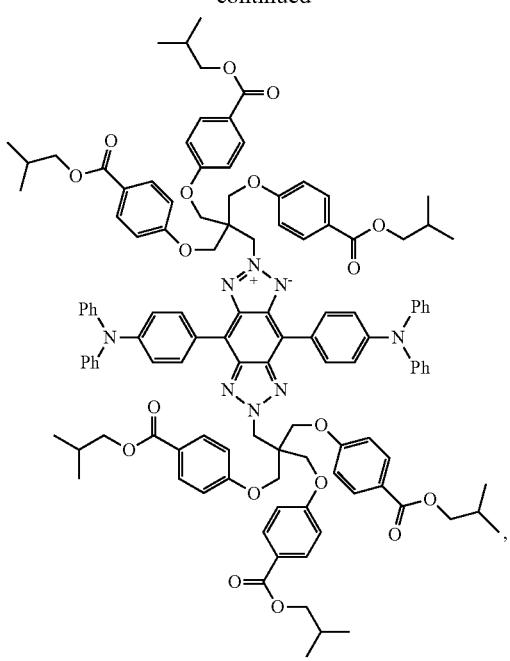
76
-continued
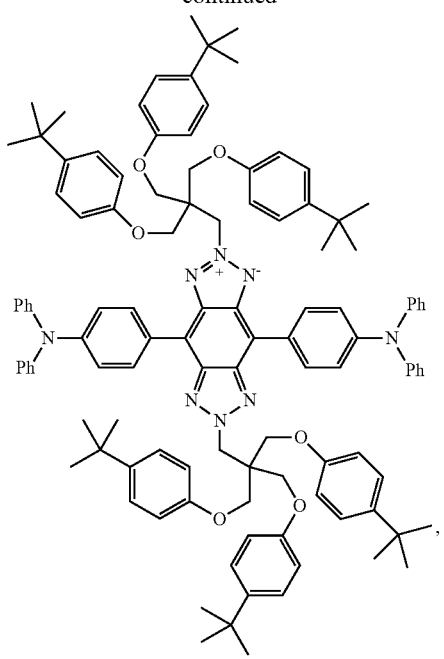
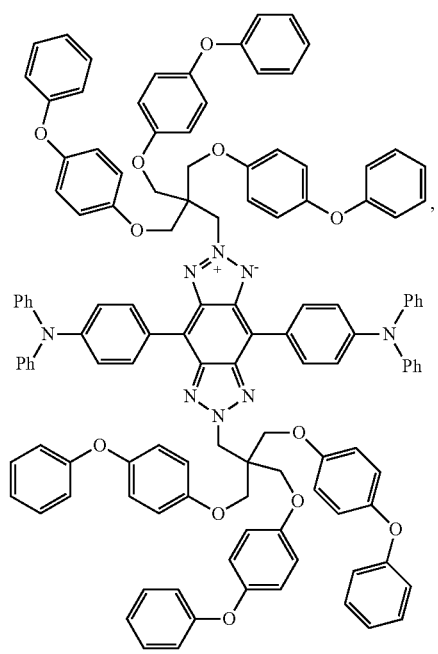
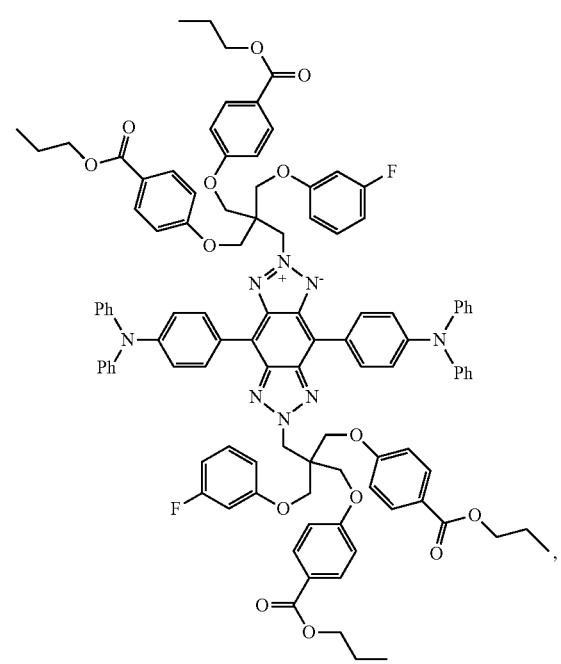

77
-continued
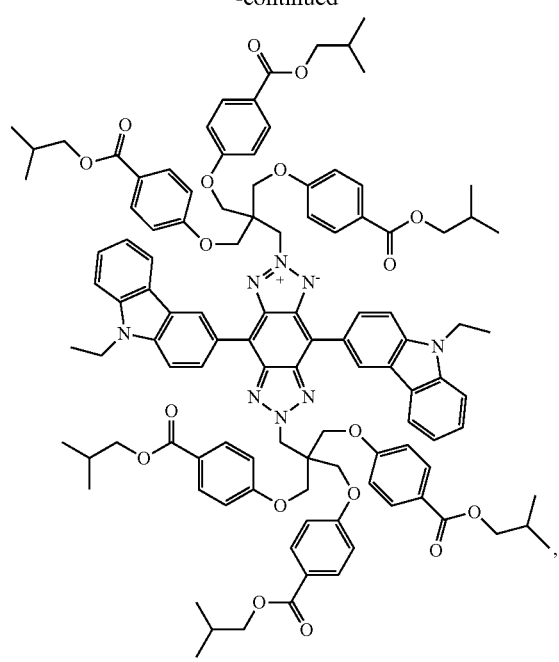
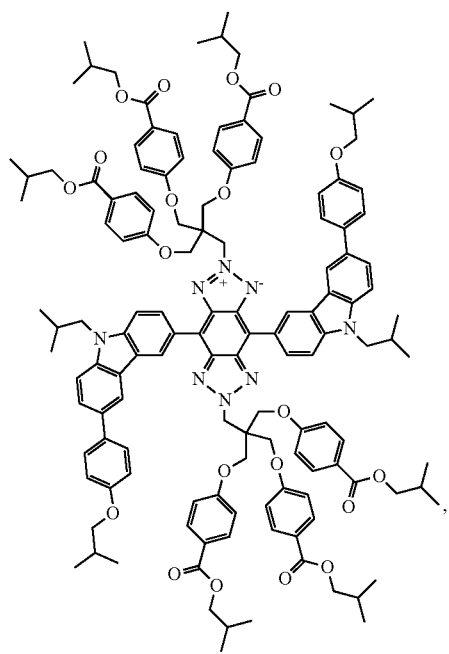
78
-continued
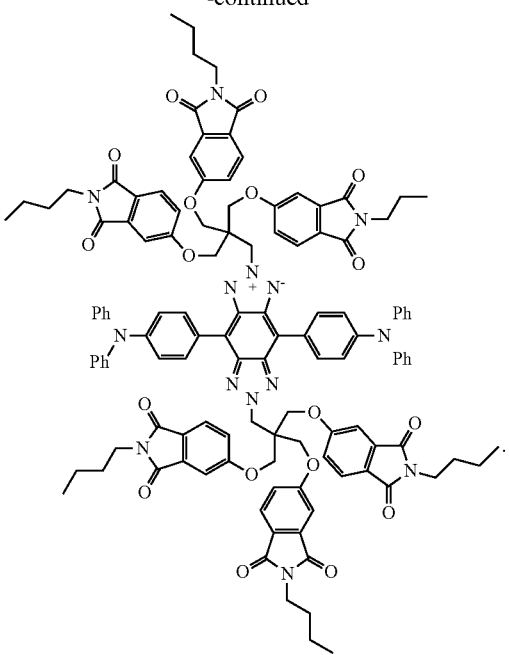
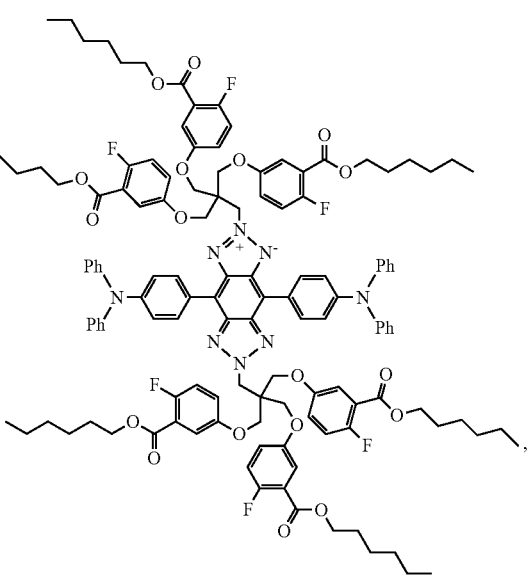

79
-continued
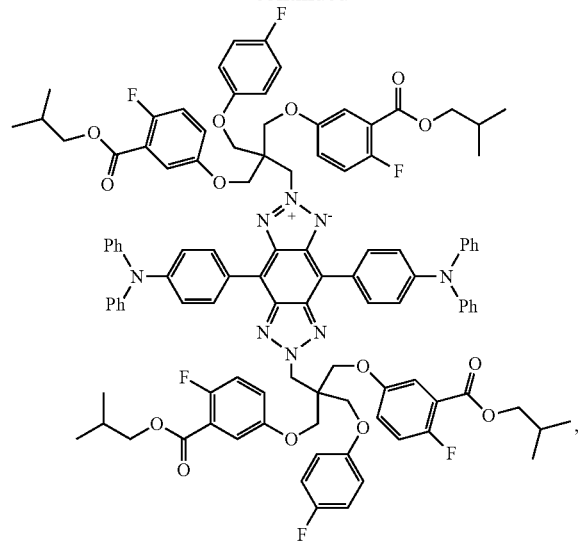
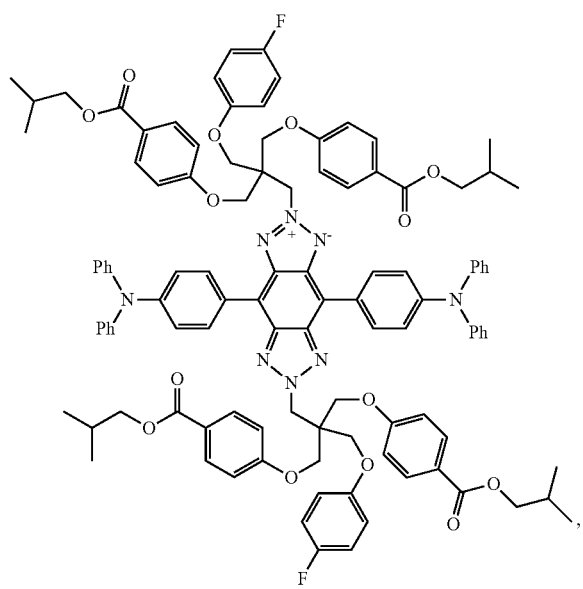
80
-continued
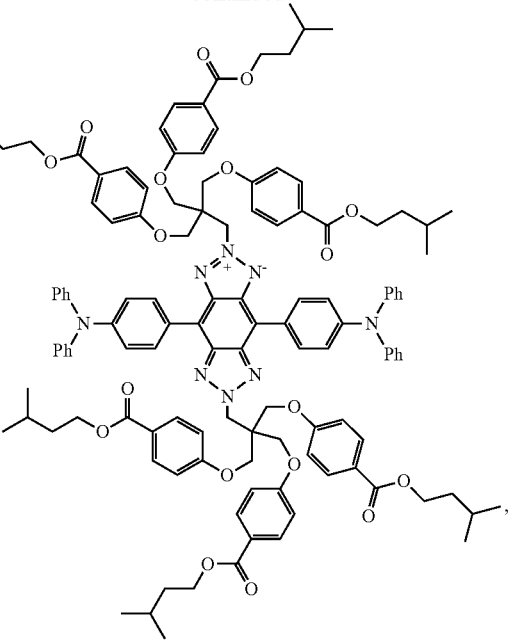
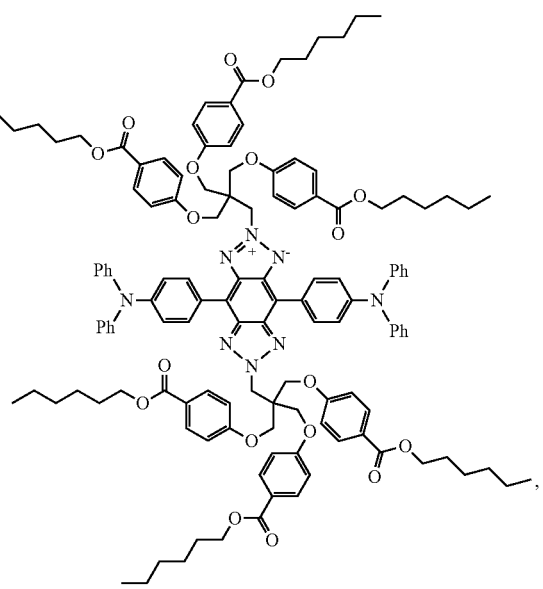

81
-continued
82
-continued
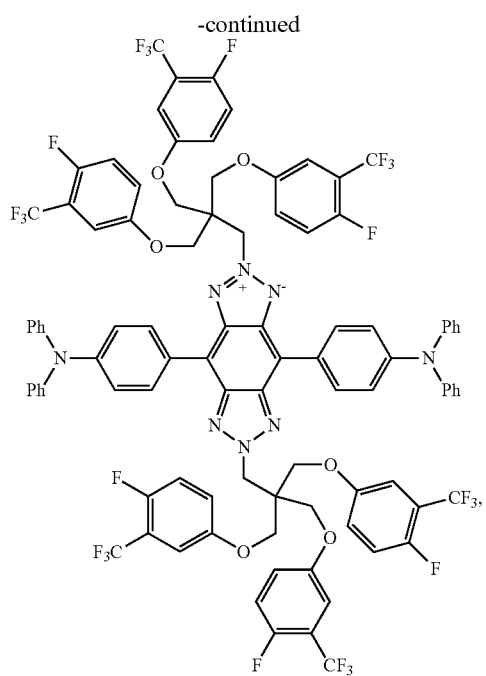
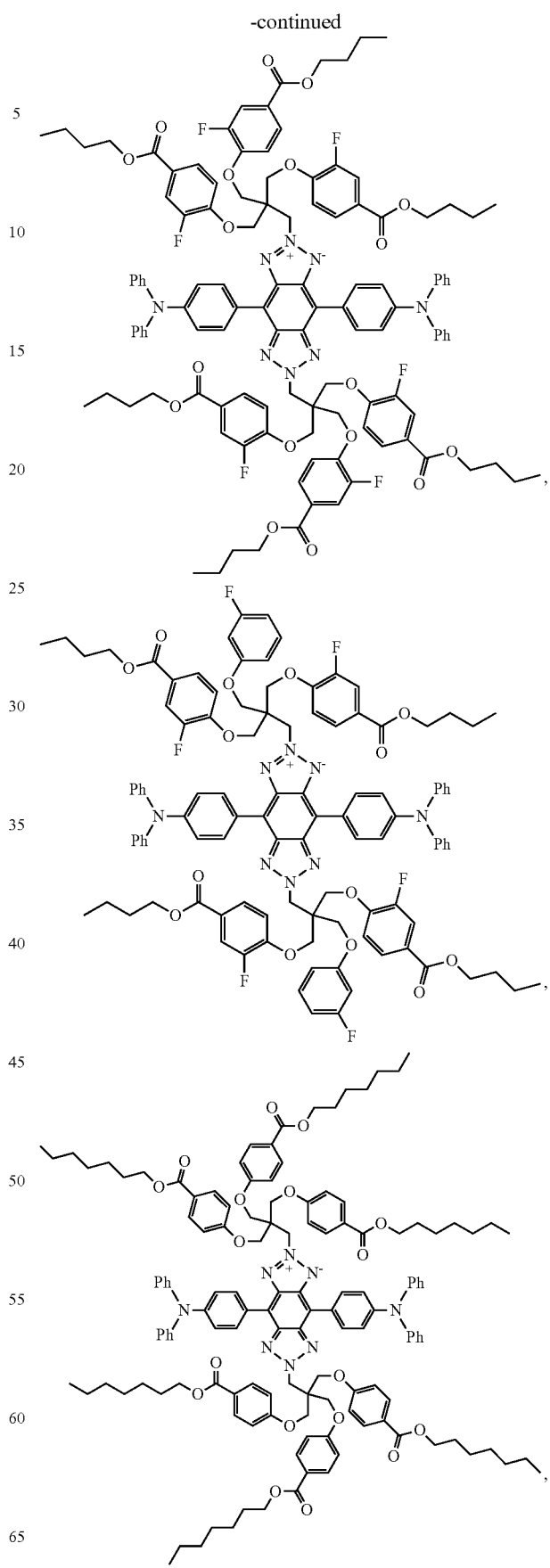

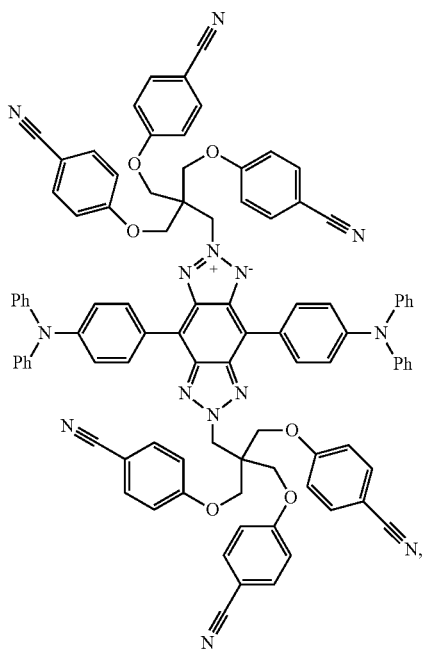

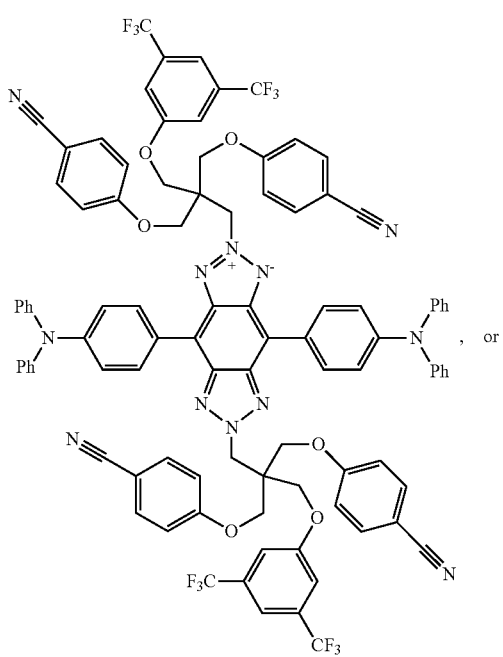
, or

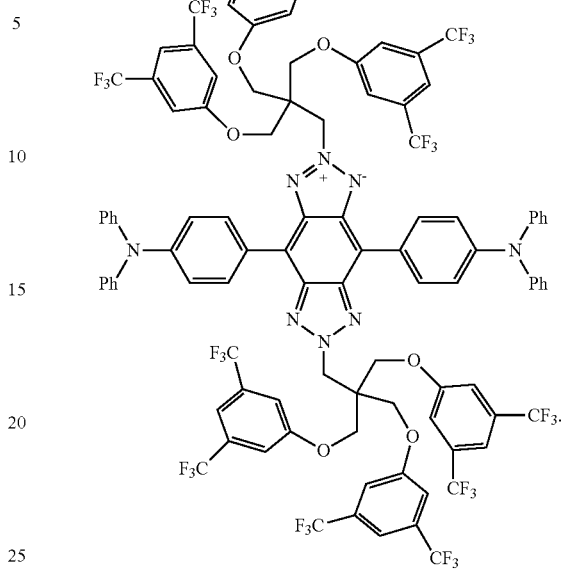

Embodiment 54

The compound of Embodiment 18, wherein $R^1$, $R^2$, $R^4$, and $R^5$ are:

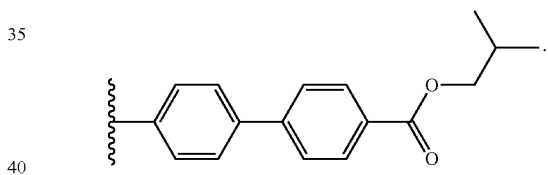

Wavelength Conversion Luminescent Medium

The chromophores disclosed herein are useful and may be suitable for providing a fluorescence film for use in improving wavelength conversion efficiency and provide high fluorescence quantum efficiency. The chromophores can provide a wavelength conversion luminescent medium that provides excellent light conversion effects. The wavelength conversion luminescent medium receives as input at least one photon having a first wavelength, and provides as output at least one photon having a second wavelength which is longer (higher) than the first wavelength.

The wavelength conversion luminescent medium comprises an optically transparent polymer matrix and at least one organic luminescent dye comprising a chromophore disclosed herein. In some embodiments, the polymer matrix is form from a substance selected from the group consisting of polyethylene terephthalate, polymethyl methacrylate, polyvinyl butyral, ethylene vinyl acetate, ethylene tetrafluoroethylene, polyimide, amorphous polycarbonate, polystyrene, siloxane sol-gel, polyurethane, polyacrylate, and combinations thereof.

In some embodiments, the luminescent dye is present in the polymer matrix in an amount in the range of about 0.01 wt % to about 3 wt %; about 0.03 wt % to about 2 wt %; about 0.05 wt % to about 1 wt %; about 0.1 wt % to about 0.9 wt %; or about 0.2 w t % to about 0.7 wt %. In some embodiments of the medium, the luminescent dye is present in the polymer matrix in an amount of about 0.3 wt %.

In some embodiments, the refractive index of the polymer matrix material is in the range of about 1.4 to about 1.7, about 1.45 to about 1.65, or about 1.45 to about 1.55. In some embodiments, the refractive index of the polymer matrix material is about 1.5.

In some embodiments, a wavelength conversion luminescent medium is fabricated into a thin film structure by (i) preparing a polymer solution with dissolved polymer powder in a solvent such as tetrachloroethylene (TCE), cyclopentanone, dioxane, etc., at a predetermined ratio; (ii) preparing a luminescent dye containing a polymer mixture by mixing the polymer solution with the luminescent dye at a predetermined weight ratio to obtain a dye-containing polymer solution; (iii) forming a dye/polymer thin film by directly casting the dye-containing polymer solution onto a glass substrate, then heat treating the substrate from room temperature up to 100° C. in 2 hours, completely removing the remaining solvent by further vacuum heating at 130° C. overnight; (iv) peeling off the dye/polymer thin film under the water and then drying out the free-standing polymer film before use; and (v) the film thickness can be controlled by varying the dye/polymer solution concentration and evaporation speed.

The luminescent thin film thickness may vary over a wide range. In some embodiments, the luminescent thin film thickness is between about 0.1 µm to about 1 mm, about 0.5 µm to about 1 mm, about 1 µm to about 0.8 mm, or any other thickness bound by these ranges. In some embodiments, the luminescent thin film thickness is between about 5 µm to about 0.5 mm.

Wavelength conversion mediums are useful in various applications, such as optical light collection systems, fluorescence-based solar collectors, fluorescence-activated display's, and single-molecule spectroscopy, to name a few. The use of the organic wavelength down-shifting luminescent medium as disclosed herein, significantly enhances the photoelectric conversion efficiency of photovoltaic devices or solar cells by greater than 0.5% when applied directly to the light incident surface of the device or encapsulated directly into the device during fabrication. The use of the wavelength conversion film as disclosed herein, may significantly enhance plant growth when applied as a greenhouse roofing film.

EXAMPLES

The embodiments will be explained with respect to preferred embodiments which are not intended to limit the any embodiment in general. In the present disclosure, the listed substituent groups include both further substituted and unsubstituted groups unless specified otherwise. Further, in the present disclosure where conditions and/or structures are not specified, the skilled artisan in the art can readily provide such conditions and/or structures, in view of the present disclosure, as a matter of routine experimentation guided by the present disclosure.

For each example compound, the maximum absorption and fluorescence emission wavelength were measured in an ethylene-vinyl acetate (EVA) film. For example, in a EVA film (having 0.3 wt % chromophore) comprising Compound 1 (4,8-bis(4-(diphenylamino)phenyl)-2,6-bis(3-(3-(ethoxycarbonyl)phenoxy)-2,2-bis((3-(ethoxycarbonyl)phenoxy)methyl)propyl)-2H-benzo[1,2-d:4,5-d']bis([1,2,3]triazole)-6-ium-5-ide), the maximum absorption of the chromophore was 553 nm and the maximum fluorescence emission was 634 nm upon 553 nm light illumination. The ability to absorb green wavelengths and convert into red wavelengths is an improved property that is useful for new optical light collection systems, particularly agriculture based applications (greenhouse roofing materials).

Example Synthesis and Spectral Data.

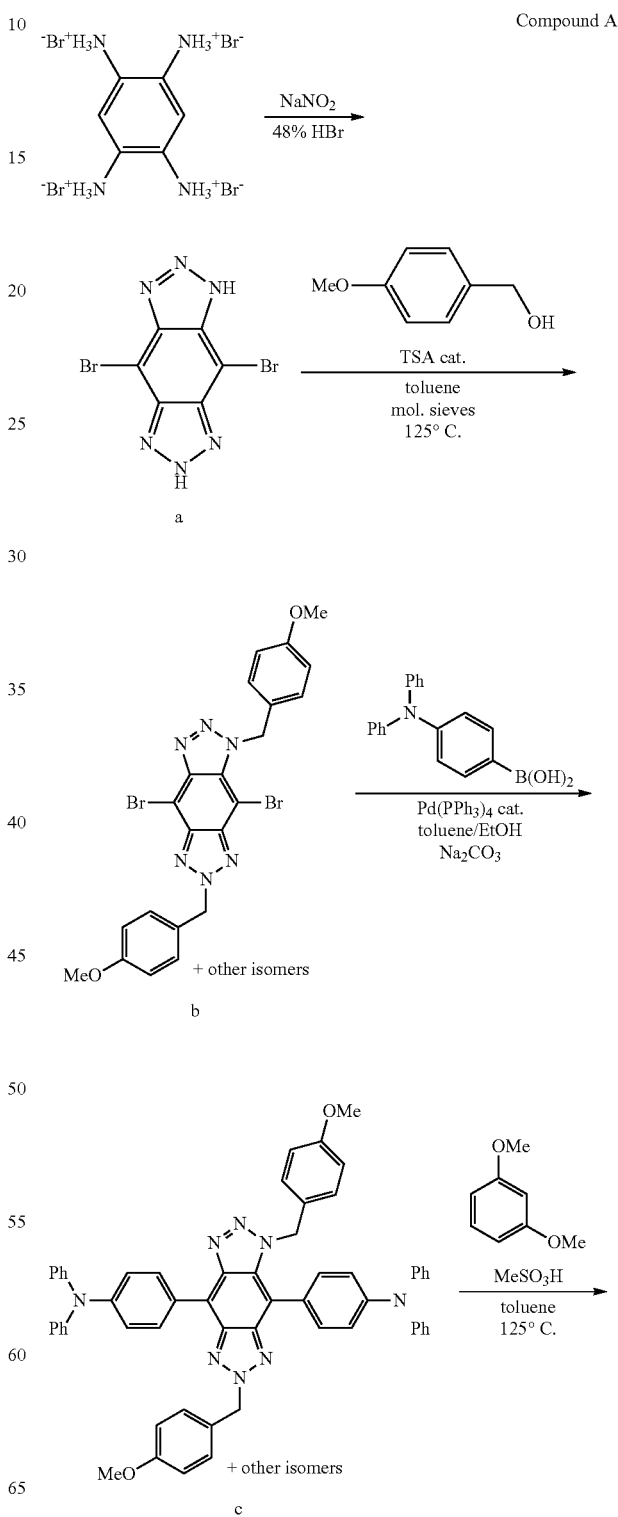

-continued

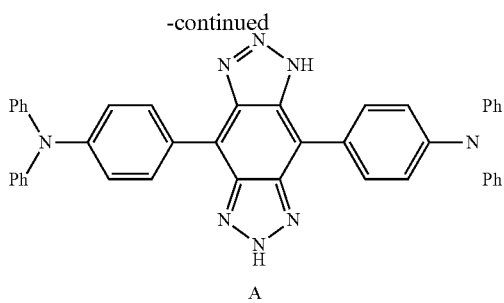

A

Step 1

A solution of 1,2,4,5-benzenetetraamine tetrahydrobromide (2.3 g, 5 mmol) in 50 mL of 48% HBr was placed in a 500 mL round bottomed flask, and it was stirred and cooled in an ice-water bath (approx. 0-5° C.). A solution of NaNO$_2$ (5.25 g in 100 mL of water) was added dropwise over a period of 2 h. After the addition, the reaction mixture was kept at 0° C. for an additional 1 h and then removed from the cooling bath and heated at 90-100° C. for 3 h. The mixture was set aside overnight for slow crystallization. The grayish-brown solid was separated, washed with water and dried to give Compound a, 4,8-dibromo-1,6-dihydrobenzo[1,2-d:4, 5-d']bis([1,2,3]triazole), (139 g, 86% yield).

Step 2

A mixture of Compound a (13.4 g, 42 mmol), 4-methoxybenzyl alcohol (17.5 g, 126 mmol, 3 eq.) and 4-toluenesulfonic acid (200 mg) in toluene was heated at reflux under Dean-Stark trap for 16 h. After cooling, the toluene solution was decanted from an oily layer formed on the flask bottom. The oily layer was triturated first with hexane and then with methanol to wash out an excess of benzyl alcohol. The brown solid obtained was separated, washed with methanol and dissolved in DCM (as little as possible to get clear solution). Diethyl ether was then added portion wise, while stirring, until crystals started to form, and the mixture was left for crystallization. The obtained yellow solid was separated, washed with ether and dried to give Compound b, 4,8-dibromo-1,6-bis(4-methoxybenzyl)-1,6-dihydrobenzo [1,2-d:4,5-d']bis([1,2,3]triazole) (20.50 g, 87% yield) as a mixture of Bt-2-Bt-2 and Bt-2-Bt-1 isomers.

Step 3

Compound b (6.7 g, 12 mmol) in a mixture of solvents (toluene/EtOH/2M-Na$_2$CO$_3$, 3:2:1 by volume, total volume 150 mL) was treated with 4-(diphenylamino)phenylboronic acid (10.4 g, 35 mmol) and tetrakis-triphenylphosphine-Pd (0) (2.00 g, 1.75 mmol) and heated with stirring at 100° C. Progress of the reaction was monitored by TLC. When all the starting material was consumed (about 2 h), the mixture was cooled down to room temperature and transferred to a separator funnel. The top organic layer was separated, dried over anhydrous Na$_2$SO$_4$ and subjected directly to fast column chromatography—"wash trough" 2 in of silica gel in a 3.5 in diameter column. DCM was used as solvent. The first few fractions with blue fluorescence have been discarded, and only red and orange colored fractions with strong fluorescence have been collected (approx. 1.5 L). After evaporation of the solvent, red solid (7.50 g, 70% yield) consisting of three isomers of Compound c, 4,4'-(1,6-bis(4-methoxybenzyl)-1,6-dihydrobenzo[1,2-d:4,5-d']bis([1,2,3] triazole)-4,8-diyl)bis(N,N-diphenylaniline), was obtained.

Step 4

A solution of Compound c (7.50 g, 8.4 mmol), 1,3-dimethoxybenzene (6.0 mL) and methanesulfonic acid (3.0 mL) in toluene (50 mL) was heated at 125° C. (temp. of oil bath) for 30 min. After cooling, the dark toluene layer was decanted, and the sticky oily residue was triturated with water. Soon brownish solid was formed. The solid was separated, stirred with methanol (20 mL), filtered off, washed with methanol, and dried to give Compound A, 4,4'-(1,6-Dihydrobenzo[1,2-d:4,5-d']bis([1,2,3]triazole)-4, 8-diyl)bis(N,N-diphenylaniline), as orange-brown solid (4.6 g, 83% yield) that was used for derivatization without further purification. $^1$H NMR (400 MHz, DMSO-d$_6$): δ 8.0-8.2 (bs, 2H), 7.93 (s, 4H), 7.26-7.30 (m, 8H), 7.17 (d, J 8.8 Hz, 4H), 7.13 (d, J=7.7 Hz, 8H), 7.04 (t, J=7.3 Hz, 4H).

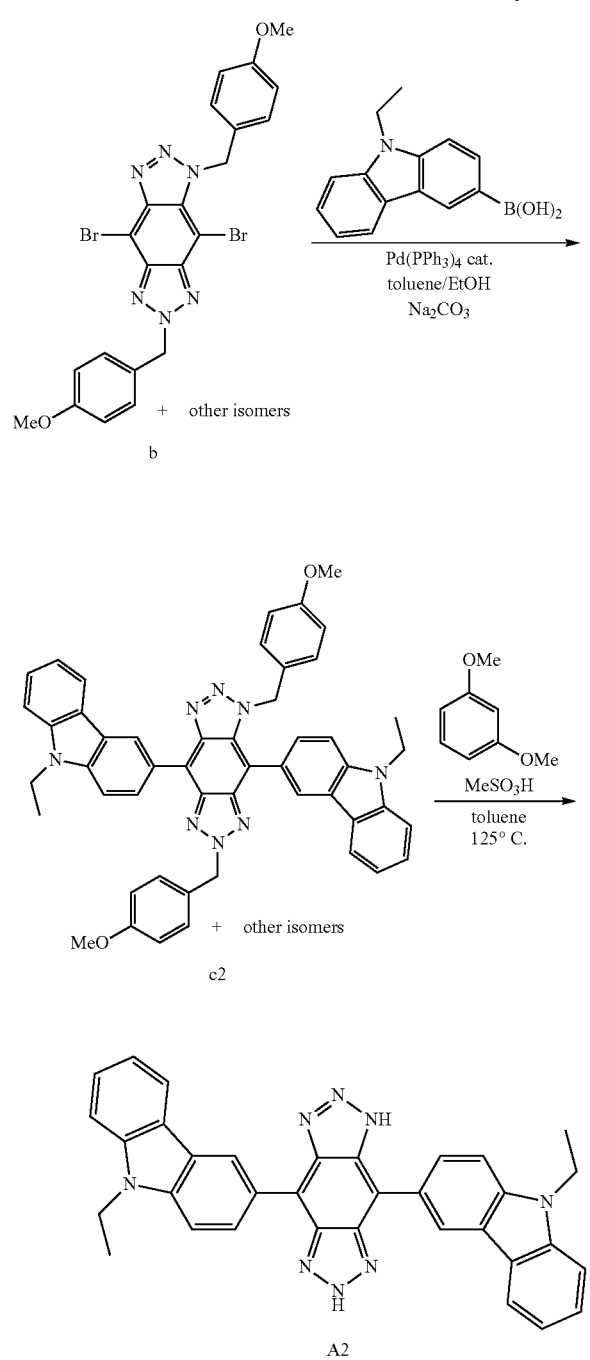

Step 1

A mixture of Compound b (2.23 g, 4.0 mmol), (9-ethyl-9H-carbazol-3-yl)boronic acid (2.4 g, 10 mmol), tetrakis(triphenylphosphine)palladium(0) catalyst (600 mg), 2M $Na_2CO_3$ (12 mL), toluene (36 mL), and ethanol (24 mL) was stirred under nitrogen at 110° C. for 5 h. After TLC confirmed that the starting material was consumed, the reaction mixture was cooled and extracted with ethyl acetate (100 mL). The extract was washed with water (100 mL), dried over anhydrous $MgSO_4$, and the solvent was removed under reduced pressure to give 40 g of a glassy orange material, which was purified by column chromatography to give Compound c2, 3,3'-(1,6-bis(4-methoxybenzyl)-1,6-dihydrobenzo[1,2-d:4,5-d']bis([1,2,3]triazole)-4,8-diyl)bis(9-ethyl-9H-carbazole), (2.10 g, 67% yield) as a mixture of two isomers (Bt-2-Bt-2 red color and Bt-2-Bt-1 orange color).

Step 2

Compound c2 (2.10 g, 2.7 mmol) was reacted with methanesulfonic acid (1.0 mL) in a mixture of toluene (20 mL) and 1,3-dimethoxybenzene (2.0 mL) at 125° C. for 30 min. After cooling, the reaction mixture was poured into saturated $NaHCO_3$ (100 mL) and stirred for 15 min. The obtained solid was separated by filtration, dried and purified by column chromatography (DCM→DCM-2.5% EA) to give pure Compound A2, 3,3'-(1,6-Dihydrobenzo[1,2-d:4,5-d']bis([1,2,3]triazole)-4,8-diyl)bis(9-ethyl-9H-carbazole), (420 mg, 30%).

Compound A3

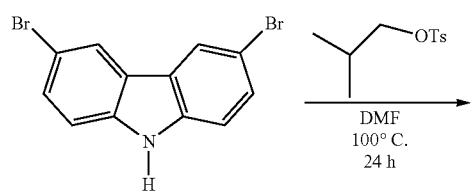

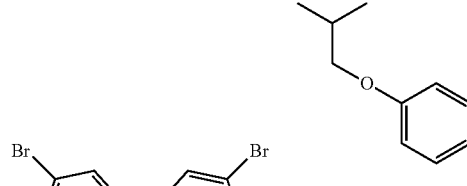

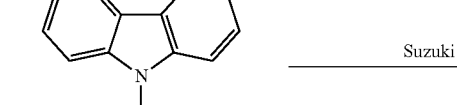

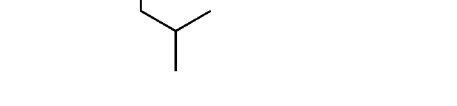

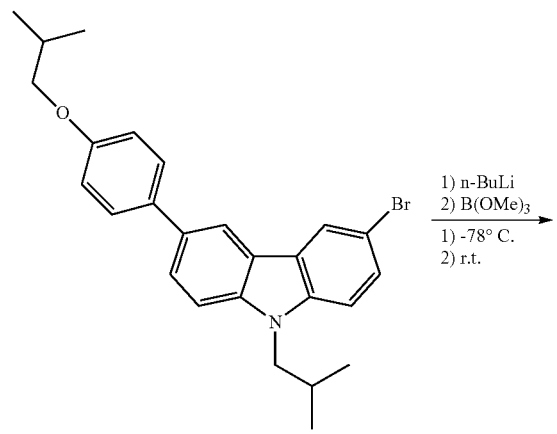

c3

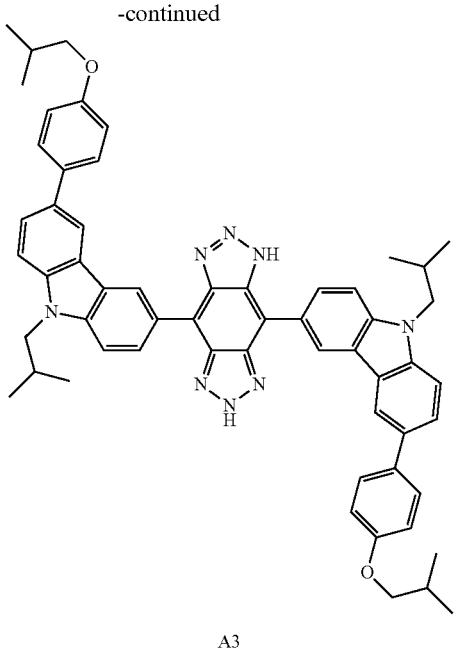

A3

Step 1

3,6-Dibromocarbazole (32.5 g, 100 mmol) was reacted with isobutyl tosylate (22.8 g, 100 mmol) in DMF (100 mL) in the presence of $K_2CO_3$ (27.6 g, 200 mmol) at 100° C. for 24 h. The reaction mixture was poured into water (500 mL) to give white precipitate. The solid was filtered off, washed with water (100 mL) and recrystallized from methanol to give pure 3,6-dibromo-9-isobutyl-9H-carbazole (32.5 g, 85% yield). $^1$H NMR (CDCl$_3$): δ 8.12 (d, J=1.8 Hz, 2H), 7.54 (dd, J=1.8 and 8.8 Hz, 2H), 7.25 (d, J=8.8 Hz, 2H), 4.02 d (J=7.3 Hz, 2H), 2.29 (m, 1H), 0.94 (d, J=6.6 Hz, 6H).

Step 2

3,6-Dibromo-9-isobutyl-9H-carbazole (7.6 g, 20 mmol) was reacted with 4-isobutoxy-phenylboronic acid (3.88 g, 20 mmol) in the presence of tetrakis(triphenylphosphine)-palladium(0) in a mixture of toluene, ethanol and 2M $Na_2CO_3$ (60-40-20 mL) at 110° C. for 16 h. After cooling, the reaction mixture was extracted with ethyl acetate (300 mL), washed with water (200 mL), dried ($Na_2SO_4$), and the solvent was removed under reduced pressure. Column chromatography of the residue with DCM/hexane (1:3) afforded 3-bromo-6-(4-isobutoxyphenyl)-9-isobutyl-9H-carbazole as white powder (1.8 g, 20% yield). $^1$H NMR (CDCl$_3$): δ 8.23 (d, J=1.8 Hz, 1H), 8.18 (d, J=1.8 Hz, 1H), 7.66 (dd, J=1.8 Hz and 8.4 Hz, 1H), 7.59 (d, J=8.4 Hz, 2H), 7.52 (dd, J=1.8 Hz and 8.4 Hz, 1H), 7.41 (d, J=8.4 Hz, 1H), 7.27 (d, J=8.4 Hz, 1H), 7.00 (d, J=8.8 Hz, 2H), 4.07 (d, J=7.7 Hz, 2H), 3.78 (d, J=6.6 Hz, 2H), 2.37 (m, 1H), 2.12 (m, 1H), 1.05 (d, J=6.6 Hz, 6H), 0.97 (d, J=6.6 Hz, 6H).

Step 3

The boronic acid was prepared under standard conditions: first lithiation of 3-bromo-6-(4-isobutoxyphenyl)-9-isobutyl-9H-carbazole in THF with n-BuLi (1.6 M solution in hexane, 1.05 eq) at −78° C. and then reaction with trimethyl borate (1.1 eq, also at −78° C.). The reaction mixture was left overnight to warm-up to room temperature, and then it was treated with 3M HCl, 1 ml/1 mmol and stirred for 30 min. Extraction with ethyl acetate, drying (MgSO$_4$) and removal of the solvent under reduce pressure gave a glassy product, 6-(4-Isobutoxyphenyl)-9-isobutyl-9H-carbazol-3-yl)boronic acid, that was used directly for the next step without purification.

Step 4

Reaction of 4,8-dibromo-1,6-bis(4-methoxybenzyl)-1,6-dihydrobenzo[1,2-d:4,5-d']bis([1,2,3]triazole) (Compound b, 560 mg, 1 mmol) was treated with (6-(4-isobutoxyphenyl)-9-isobutyl-9H-carbazol-3-yl)boronic acid (1.25 g, 3 mmol) and tetrakis(triphenyl-phosphine)palladium(0) (150 mg) under Suzuki coupling conditions at 110° C. for 4 h. Work-up with water and DCM. Column chromatography on silica gel using a mixture of DCM and hexane as a mobile phase (1:1→2:1→DCM) allowed to separate Bt-2-Bt-2 isomer as the first fraction, dark red color solid (50 mg). A mixture of other isomers was isolated as the second fraction, dark orange color solid Compound c3, 6,6'-(1,6-Bis(4-methoxybenzyl)-1,6-dihydrobenzo[1,2-d:4,5-d']bis([1,2,3]triazole)-4,8-diyl)bis(3-(4-isobutoxyphenyl)-9-isobutyl-9H-carbazole), (620 mg).

Step 5

Compound c3 (2.1 g, 2.6 mmol) was treated with methanesulfonic acid (1.0 mL) in a mixture of toluene (20 mL) and 1,3-dimethoxybenzene (2.0 mL) at 125° C. for 30 min. After cooling, the mixture was stirred with saturated NaHCO$_3$ (20 mL) to provide crude A3 as an orange solid (1.18 g), which was further purified by column chromatography (DCM, DCM-2.5% EA) to give pure Compound A3, 6,6'-(1,6-Dihydrobenzo[1,2-d:4,5-d']bis([1,2,3]triazole)-4,8-diyl)bis(3-(4-isobutoxyphenyl)-9-isobutyl-9H-carbazole), (420 mg, 30% yield).

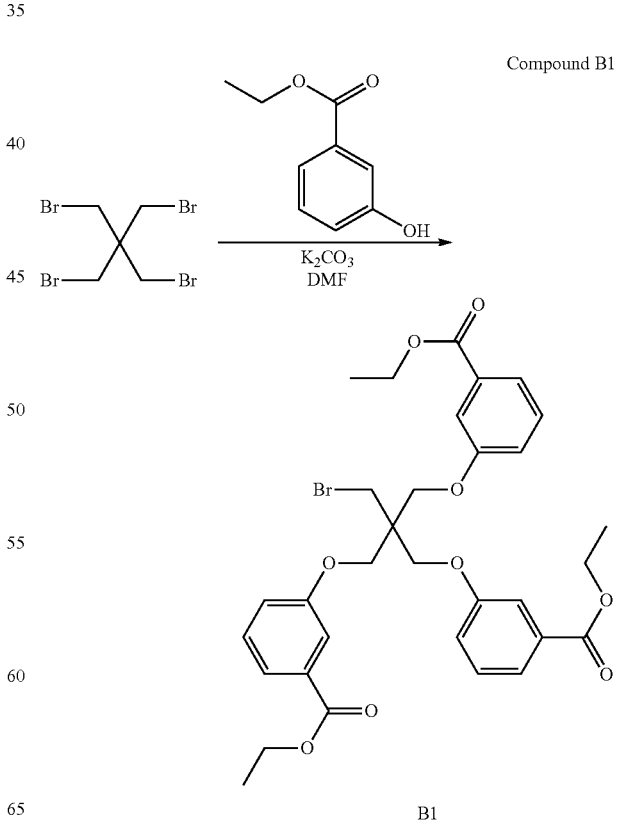

B1

A mixture of pentaerythrityl tetrabromide (7.75 g, 20.0 mmol), ethyl 3-hydroxybenzoate (10.80 g, 65 mmol), potassium carbonate (13.80 g, 100 mmol) and DMF (50 mL) was stirred under argon and heated at 110° C. for 20 h. After cooling to room temperature, the mixture was poured into ice/water (200 mL) and extracted with hexane/ethyl acetate (1:1, 400 mL). The extract was washed with water (200 mL), dried over magnesium sulfate, and the solvent was removed under reduced pressure. The crude product was purified by column chromatography using silica gel and hexane/ethyl acetate (9:1) as an eluent to give pure Compound B1, diethyl 3,3'-((2-(bromomethyl)-2-((3-(ethoxycarbonyl)phenoxy) methyl)propane-1,3-diyl)bis(oxy))dibenzoate, (5.22 g, 40% yield). $^1$H NMR (400 MHz, CCCl$_3$): δ 764 (d, J=8.0 Hz, 3H), 7.57 (dd, J=1.8 and 2.6 Hz, 3H), 7.32 (t, J=8.1 Hz, 3H), 7.10 (ddd, J=0.8, 2.6 and 8.1 Hz, 3H), 4.36 (q, J=7.4 Hz, 6H), 4.30 (s, 6H), 3.89 (s, 2H), 1.39 (t, J=7.3 Hz, 9H).

A mixture of pentaerythrityl tetrabromide (3.87 g, 10.0 mmol), propyl 3-hydroxybenzoate (6.30 g, 35 mmol), potassium carbonate (6.90 g, 50 mmol) and DMF (20 mL) was stirred under argon and heated at 100° C. for 4 h. After cooling to room temperature, the mixture was poured into ice/water (200 mL) and extracted with hexane/ethyl acetate (1:1, 200 mL). The extract was washed with water (2×200 mL), dried over magnesium sulfate, and the solvent was removed under reduced pressure. The crude product was purified by column chromatography using silica gel and hexane/DCM/ethyl acetate (48:50:2) as an eluent to give pure Compound B2, dipropyl 4,4'-((2-(bromomethyl)-2-((4-(propoxycarbonyl)phenoxy)methyl)propane-1,3-diyl)bis (oxy))dibenzoate, (1.59 g, 23% yield). $^1$H NMR (500 MHz, CCCl$_3$): δ 7.99 (d, J=9.0 Hz, 6H), 6.94 (d, J=9.0 Hz, 6H), 4.32 (s, 6H), 4.24 (t, J=6.5 Hz, 6H), 3.88 (s, 2H), 1.77 (sextet, J=7.5 Hz, 6H), 1.02 (t, J=7.5 Hz, 9H).

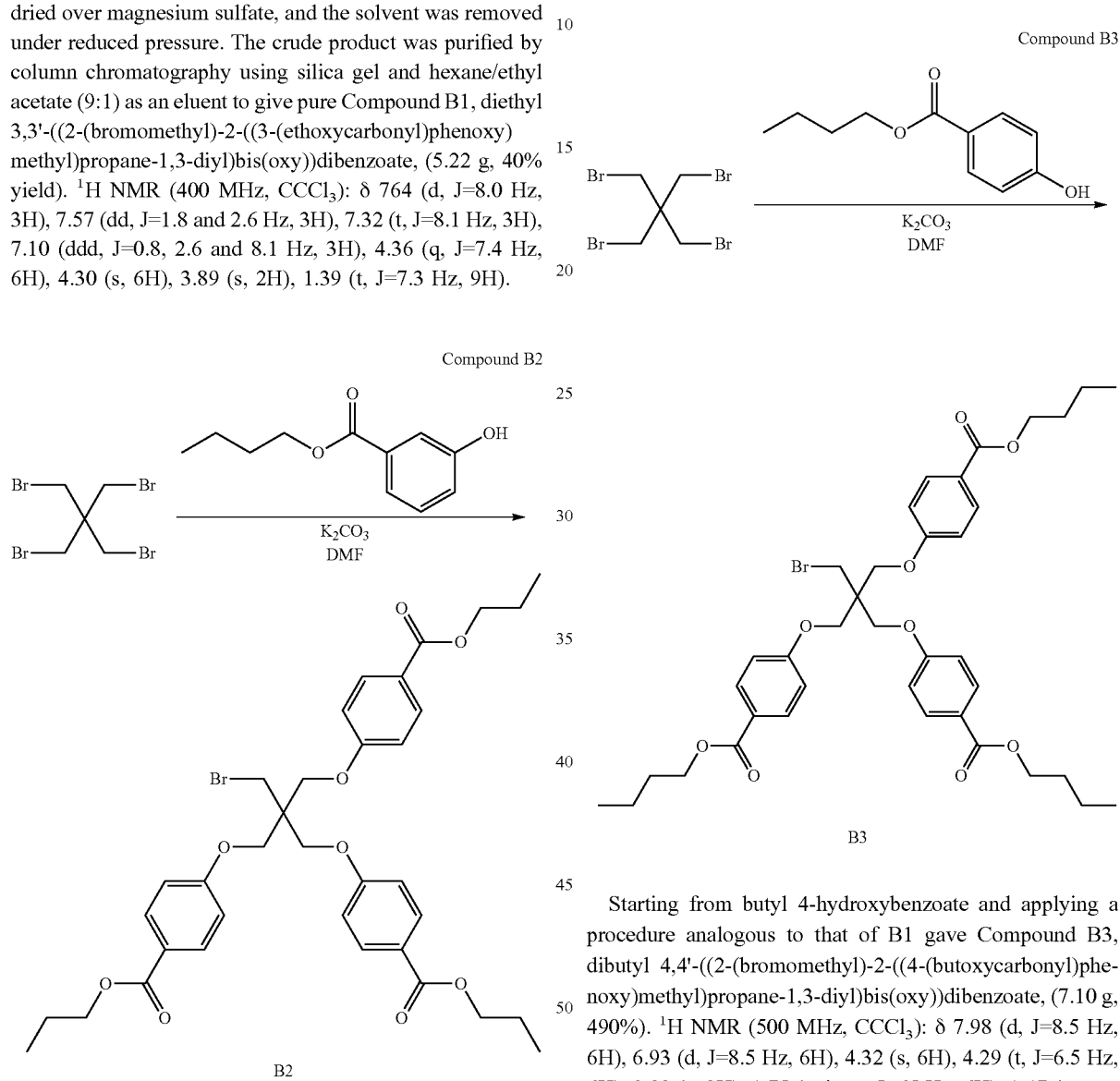

Starting from butyl 4-hydroxybenzoate and applying a procedure analogous to that of B1 gave Compound B3, dibutyl 4,4'-((2-(bromomethyl)-2-((4-(butoxycarbonyl)phenoxy)methyl)propane-1,3-diyl)bis(oxy))dibenzoate, (7.10 g, 490%). $^1$H NMR (500 MHz, CCCl$_3$): δ 7.98 (d, J=8.5 Hz, 6H), 6.93 (d, J=8.5 Hz, 6H), 4.32 (s, 6H), 4.29 (t, J=6.5 Hz, 6H), 3.88 (s, 2H), 1.75 (quintet, J=65 Hz, 6H), 1.47 (sextet, J=7.0 Hz, 6H), 0.97 (t, J=7.5 Hz, 9H).

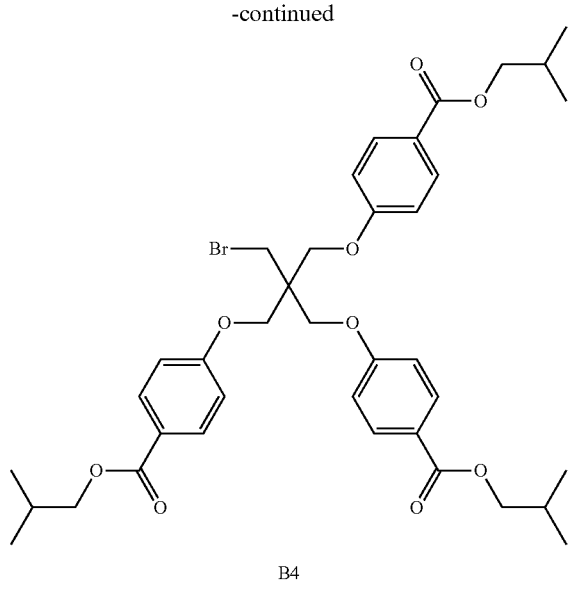

B4

Starting from isobutyl 4-hydroxybenzoate and applying a procedure analogous to that of Compound B1 gave Compound B4, diisobutyl 4,4'-((2-(bromomethyl)-2-((4-(isobutoxycarbonyl)phenoxy)methyl)propane-1,3-diyl)bis(oxy))dibenzoate, (6.74 g, 46% yield). $^1$H NMR (500 MHz, CCCl$_3$): δ 7.99 (d, J=8.5 Hz, 6H), 6.94 (d, J=8.5 Hz, 6H), 4.32 (s, 6H), 4.07 (d, J=7.0 Hz, 6H), 3.88 (s, 2H), 2.06 (m, 3H), 0.98 (d, J=7.0 Hz, 18H).

Compound B5

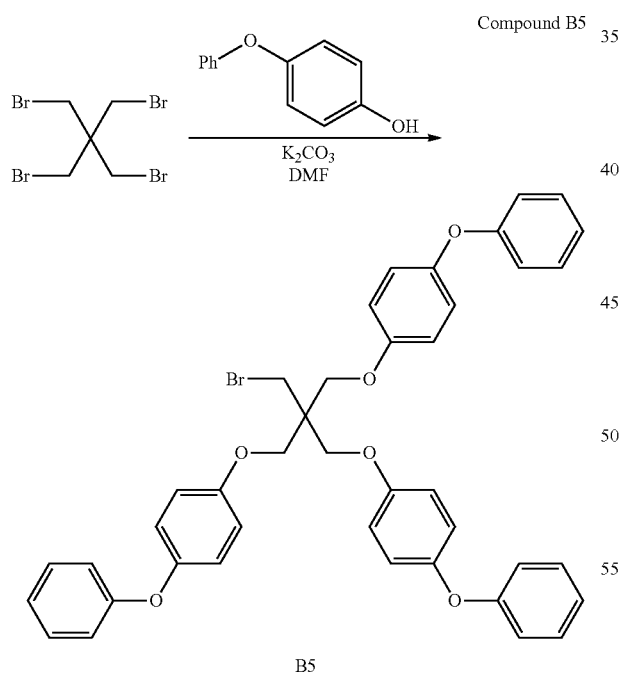

B5

A mixture of pentaerythrityl tetrabromide (3.87 g, 10 mmol), 4-phenoxyphenol (7.44 g, 40 mmol), potassium carbonate (8.28 g, 60 mmol), and DMF (15 mL) was stirred under argon and heated at 110° C. for 24 h. After cooling, the reaction mixture was poured into water (200 mL) and extracted with ethyl acetate/toluene (200+300 mL). The extract was washed with water (200 mL), and the volatiles were removed under reduced pressure. Column chromatography of the residue (silica gel, hexane/toluene, 1:1) afforded Compound B5, 4,4'-((2-(Bromomethyl)-2-((4-phenoxyphenoxy)methyl)propane-1,3-diyl)bis(oxy))bis(phenoxybenzene), (3.71 g, 53% yield). $^1$H NMR (400 MHz, CCCl$_3$): δ 7.29 (m, 6H), 7.04 (t, J=7.3 Hz, 3H), 6.9-7.0 (m, 18H), 4.24 (s, 6H), 3.90 (s, 2H).

Compound B6

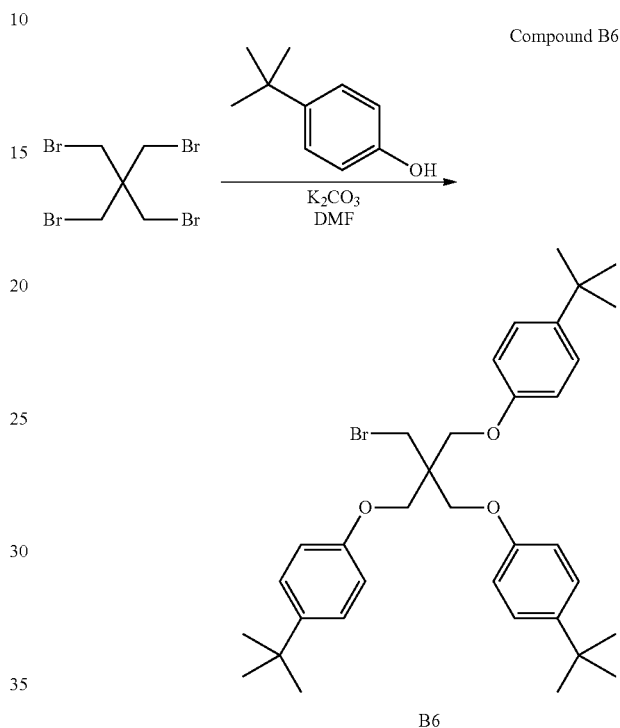

B6

A mixture of pentaerythrityl tetrabromide (3.88 mg, 10 mmol), 4-tert-butylphennol (6.00 g, 40 mmol), potassium carbonate (8.28 g, 60 mmol), and DMF (20 mL) was stirred under argon and heated at 90° C. for 16 h. Aqueous work-up like for Compound B5 and chromatography (silica gel, hexane/toluene, 4:1) afforded Compound B6, 4,4'-((2-(Bromomethyl)-2-((4-(tert-butyl)phenoxy)methyl)propane-1,3-diyl)bis(oxy))bis(tert-butylbenzene), (3.10 g, 52% yield).

Compound B11

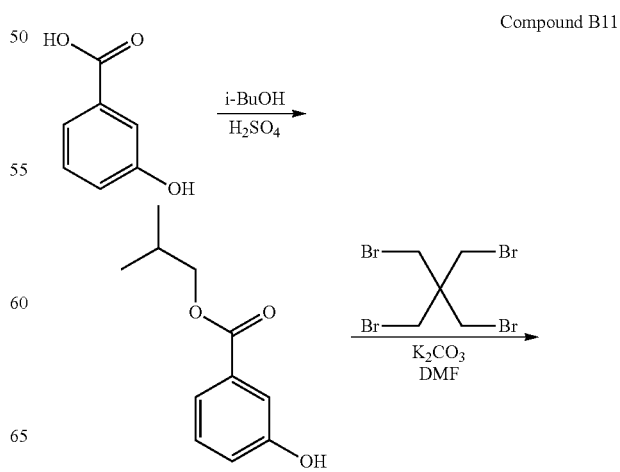

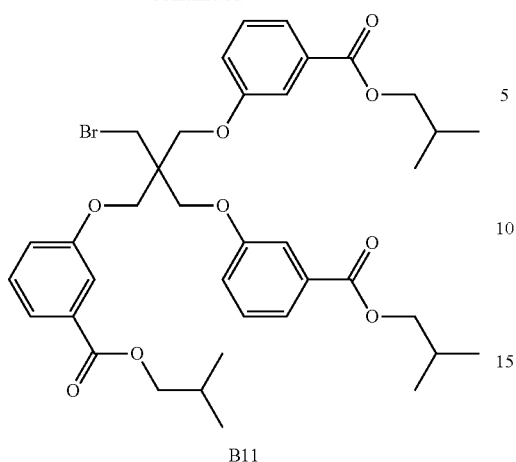

B11

A mixture of 3-hydroxybenzoic acid (6.90 g, 50 mmol), isobutanol (50 mL) and 20% oleum (0.5 mL) was heated at 110° C. for 20 h. The volatiles were removed under reduced pressure. A solution of the residue in ethyl acetate/hexane (1:1, 200 mL) was washed with brine (100 mL) and dried over anhydrous sodium sulfate. The solvent was removed under reduced pressure. Obtained isobutyl 3-hydroxybenzoate was directly used in the next step without purification.

A mixture of the obtained ester, pentaerythrityl tetrabromide (5.82 g, 15 mmol), potassium carbonate (10.35 g, 75 mmol), and DMF (40 mL) was stirred under argon and heated at 110° C. for 24 h. After cooling, the mixture was poured into ice/water (200 mL) and extracted with hexane/ethyl acetate (200+200 mL). The extract was washed with water (200 mL), dried over anhydrous magnesium sulfate, and the solvent was removed under reduced pressure. Column chromatography of the residue (silica gel—hexane/ethyl acetate, 9:1) gave Compound B11, diisobutyl 3,3'-((2-(bromomethyl)-2-((3-(isobutoxycarbonyl)phenoxy)methyl)propane-1,3-diyl)bis(oxy))dibenzoate, (4.27 g, 39% yield).
$^1$H NMR (500 MHz, CCCl$_3$): δ 7.65 (d, J=8.0 Hz, 3H), 7.59 (m, 3H), 7.33 (t, J=8.0 Hz, 3H) 7.11 (dd, J=2.0 and 7.5 Hz, 3H), 4.31 (s, 6H), 4.10 (d, J=6.5 Hz, 6H), 3.90 (s, 2H), 2.08 (m, 3H), 0.97 (d, J=6.5 Hz, 18H).

Compound B12

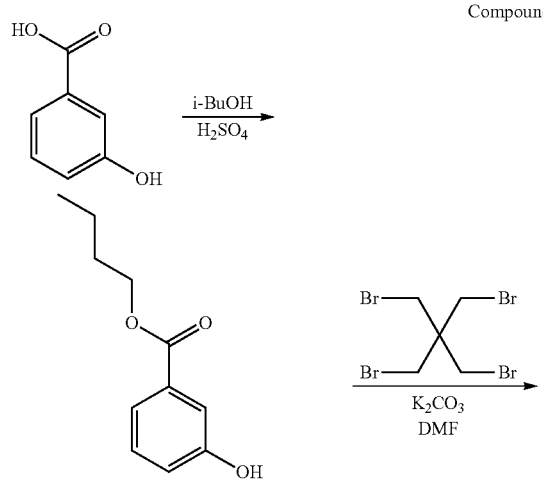

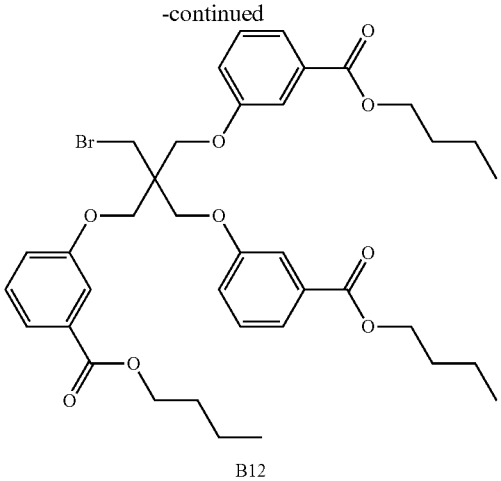

B12

Using n-butanol and following the procedure for Compound B11 gave Compound B12, dibutyl 3,3'-((2-(bromomethyl)-2-((3-(butoxycarbonyl)phenoxy)methyl)propane-1,3-diyl)bis(oxy))dibenzoate, (5.67 g, 52% yield).

Compound B13

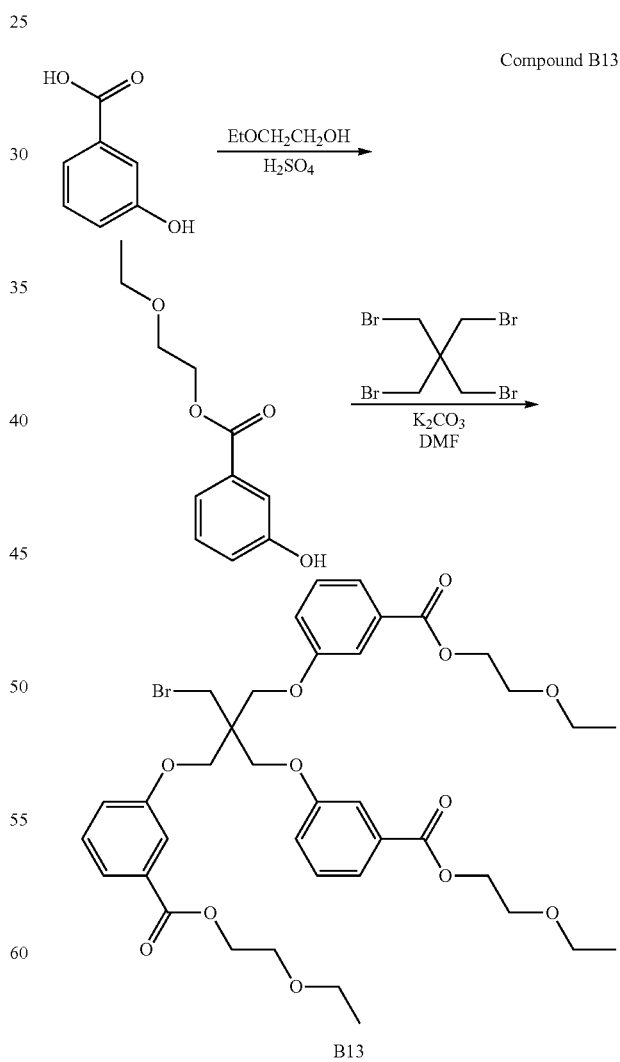

B13

Using 2-ethoxyethanol and following the procedure for Compound B11 gave Compound B13, bis(2-ethoxyethyl)

3,3'-((2-(bromomethyl)-2-((3-((2-ethoxyethoxy)carbonyl) phenoxy)methyl)propane-1,3-diyl)bis(oxy))dibenzoate, (3.82 g, 35% yield). $^1$H NMR (500 MHz, CCCl$_3$): δ 7.67 (d, J=7.5 Hz, 3H), 7.60 (dd, J=1.8 and 2.6 Hz, 3H), 7.33 (t, J=8.0 Hz, 3H), 7.11 (dd, J=2.0 and 8.0 Hz, 3H), 4.46 (t, J=5.0 Hz, 6H), 4.31 (s, 6H), 3.89 (s, 2H), 3.76 (t, J=5.0 Hz, 6H), 3.57 (q, J=7.0 Hz, 6H), 1.22 (t, J=7.0 Hz, 9H).

Compound B14

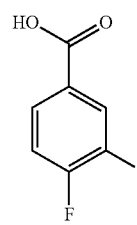

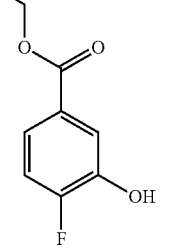

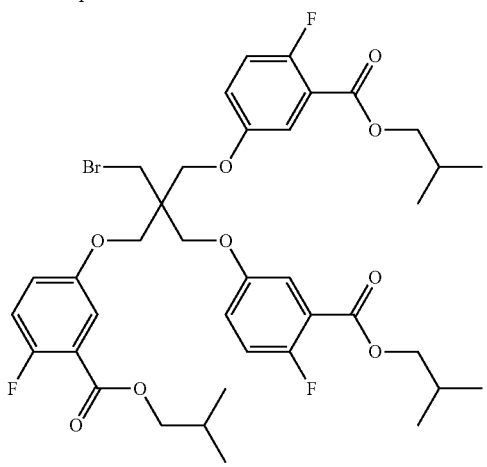

B14

By a procedure similar to that for Compound B11, 4-fluoro-3-hydroxybenzoic acid was converted to pentaerythrityl Compound B14, diisobutyl 5,5'-((2-(bromomethyl)-2-((4-fluoro-3-(isobutoxycarbonyl)phenoxy)methyl) propane-1,3-diyl)bis(oxy))bis(2-fluorobenzoate), with 24% yield. $^1$H NMR (400 MHz, CCCl$_3$): δ 7.42 (m, 3H), 7.03 (m, 6H), 4.22 (s, 6H), 4.11 (d, J=6.7 Hz, 12H), 3.83 (s, 2H), 2.06 (m, 3H), 0.98 (d, J=7.0 Hz, 18H).

Compound B15

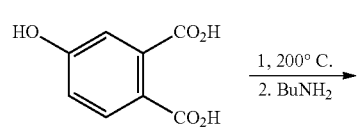

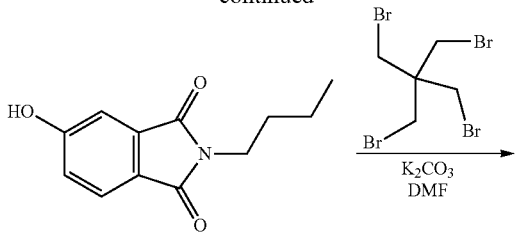

-continued

B15

Step 1.

4-Hydroxyphthalic acid (10.0 g, 55 mmol) was heated under argon at 200° C. for 16 h. After cooling, toluene (100 mL), butylamine (6.9 mL, 70 mmol) and molecular sieves 4A (30 g) were added, and the obtained mixture was heated at reflux for 24 h. The reaction mixture was poured into water (300 mL) and extracted with ethyl acetate (2×300 mL). The extract was washed with water (200 mL), dried over sodium sulfate, and the volatiles were removed under reduced pressure. The residue was crystallized from methanol/water (1:1) to give pure 2-butyl-5-hydroxyisoindoline-1,3-dione (7.24 g, 60% yield).

Step 2.

A mixture of 2-butyl-5-hydroxyisoindoline-1,3-dione (7.00 g 32 mmol), pentaerythrityl tetrabromide (3.87 g, 10 mmol), potassium carbonate (6.90 g, 50 mmol), and DMF (15 mL) was stirred under argon and healed at 110° C. for 24 h and poured onto crushed ice (200 g). When the ice melted, the obtained precipitate was filtered off, washed with water (200 mL) and dried. The crude product was purified by column chromatography (silica gel, DCM/ethyl acetate, 95:5) to give Compound B15, 5,5'-((2-(bromomethyl)-2-(((2-butyl-1,3-dioxoisoindolin-5-yl)oxy)methyl)propane-1, 3-diyl)bis(oxy))bis(2-butylisoindoline-1,3-dione), (1.96 g, 24% yield). $^1$H NMR (400 MHz, CCCl$_3$): δ 7.73 (d, J=8.5 Hz, 3H), 7.35 (d, J=2.2 Hz, 3H), 7.16 (dd, J=2.2 and 8.0 Hz, 3H), 4.38 (s, 6H), 3.86 (s, 2H), 3.64 (t, J=7.3 Hz, 6H), 1.60 (m, 61H), 1.33 (m, 6H), 0.92 (t, J=7.3 Hz, 9H).

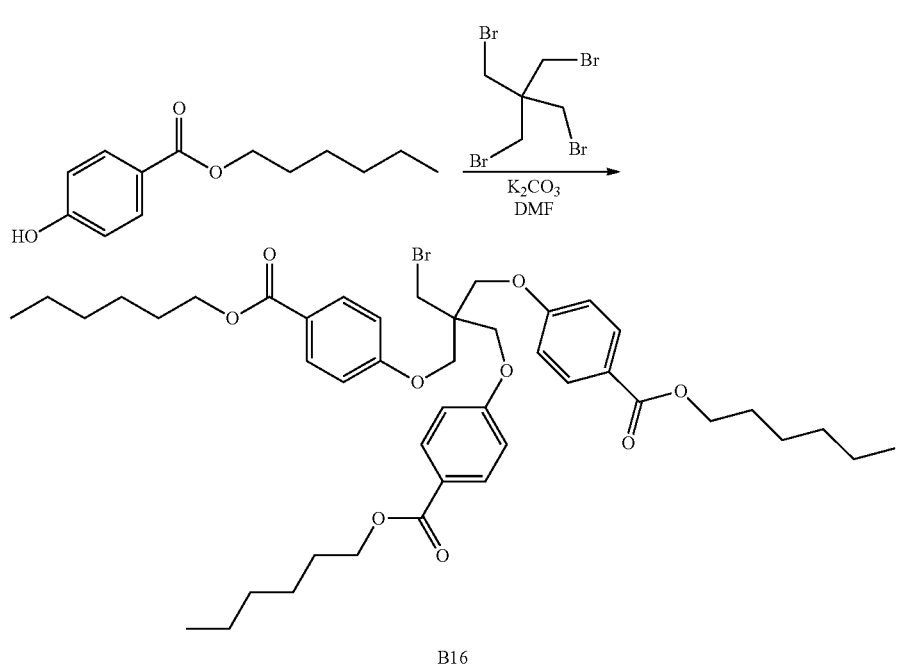

Compound B16

B16

Starting from hexyl 4-hydroxybenzoate and applying a procedure analogous to that of Compound B1 gave Compound B16, dihexyl 4,4'-((2-(bromomethyl)-2-((4-((hexyloxy)carbonyl)phenoxy)methyl)propane-1,3-diyl)bis(oxy)dibenzoate, (6.83 g, 50% yield). $^1$H NMR (400 MHz, CCCl3): δ 7.97 (d, J=8.5 Hz, 6H), 6.93 (d, J=8.5 Hz, 6H), 4.31 (s, 6H), 4.27 (t, J=6.5 Hz, 6H), 3.87 (s, 2H), 1.74 (quintet, J=6.5 Hz, 6H), 1.42 (m, 6H), 1.33 (m, 12H), 0.88 (t, J=7.0 Hz, 9H).

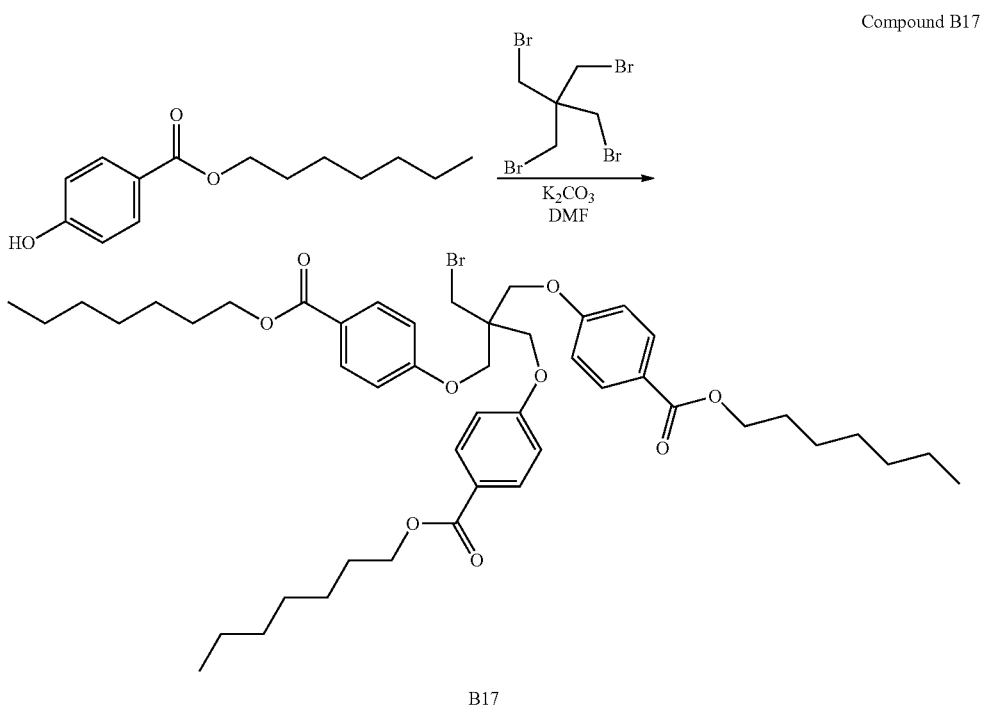

Compound B17

B17

Starting from hexyl 4-hydroxybenzoate and applying a procedure analogous to that of Compound B1 gave Compound B17, diheptyl 4,4'-((2-(bromomethyl)-2-((4-((heptyloxy)carbonyl)phenoxy)methyl)propane-1,3-diyl)bis(oxy)dibenzoate, (6.54 g, 46% yield). $^1$H NMR (400 MHz, CCCl3): δ 7.97 (d, J=8.5 Hz, 6H), 6.93 (d, J=8.5 Hz, 6H), 4.31 (s, 6H), 4.27 (t, J=6.5 Hz, 6H), 3.87 (s, 2H), 1.74 (quintet, J=6.5 Hz, 6H), 1.40 (m, 6H), 1.34 (m, 6H), 1.29 (m, 12H), 0.88 (t, J=7.0 Hz, 9H).

Compound B18

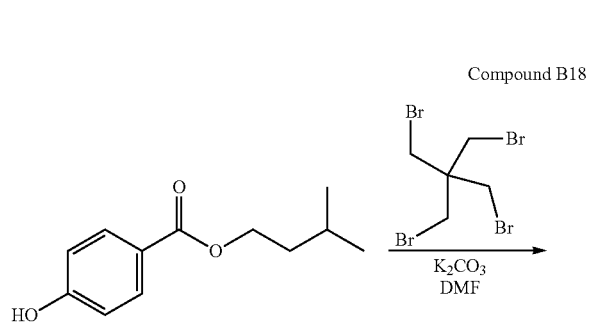

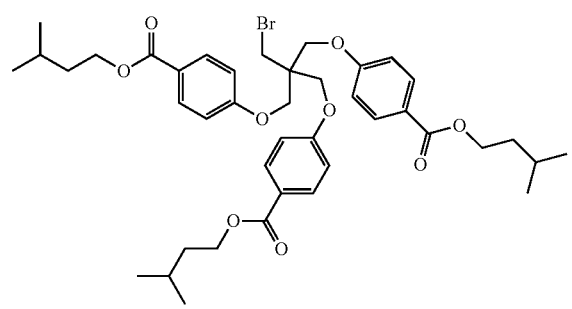

B18

By a procedure analogous to that of Compound B1, reaction of isopentyl 4-hydroxybenzoate (10.41 g, 50 mmol) with pentaerythrityl tetrabromide (6.46 g, 16.66 mmol) gave Compound B18, diisopentyl 4,4'-((2-(bromomethyl)-2-((4-((isopentyloxy)carbonyl)phenoxy)methyl)propane-1,3-diyl)bis(oxy))dibenzoate (6.64 g, 52% yield). $^1$H NMR (400 MHz, CCCl3): δ 7.96 (d, J=8.5 Hz, 6H), 6.92 (d, J=8.5 Hz, 6H), 4.31 (s, 6H), 4.31 (t, J=6.5 Hz, 6H), 3.87 (s, 2H), 1.77 (m, 3H), 1.63 (q, J=7.0 Hz, 6H), 0.95 (d, J=6.6 Hz, 18H).

Compound B19

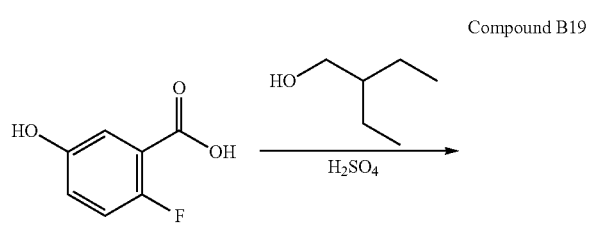

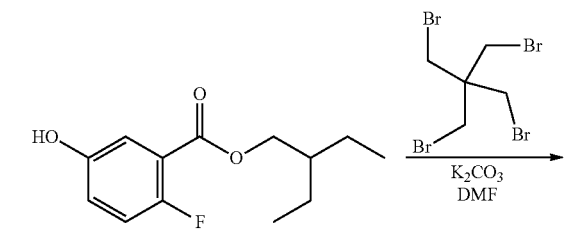

-continued

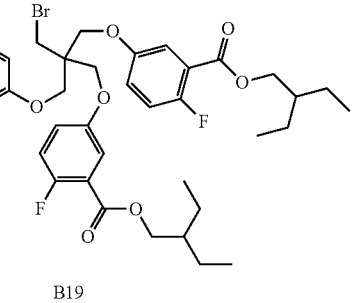

B19

By a procedure analogous to that of Compound B11, reaction of 2-ethylbutyl 2-fluoro-5-hydroxybenzoate (8.00 g, 33 mmol) with pentaerythrityl tetrabromide (4.65 g, 12 mmol) gave Compound B19, bis(2-ethylbutyl) 5,5'-(2-bromomethyl)-2-((3-((2-ethylbutoxy)carbonyl)-4-fluorophenoxy)methyl)propane-1,3-diyl)bis(oxy)bis(2-fluorobenzoate) (4.61 g, 48% yield). $^1$H NMR (400 MHz, CCCl3): δ 7.42 (m, 3H), 7.03 (m, 6H), 4.25 (d, J=5.8 Hz, 6H), 4.22 (s, 6H), 3.82 (s, 2H), 1.64 (m, 3H), 1.43 (quintet, J=7.3 Hz, 12H), 0.92 (t, J=7.5 Hz, 18H).

Compound B20

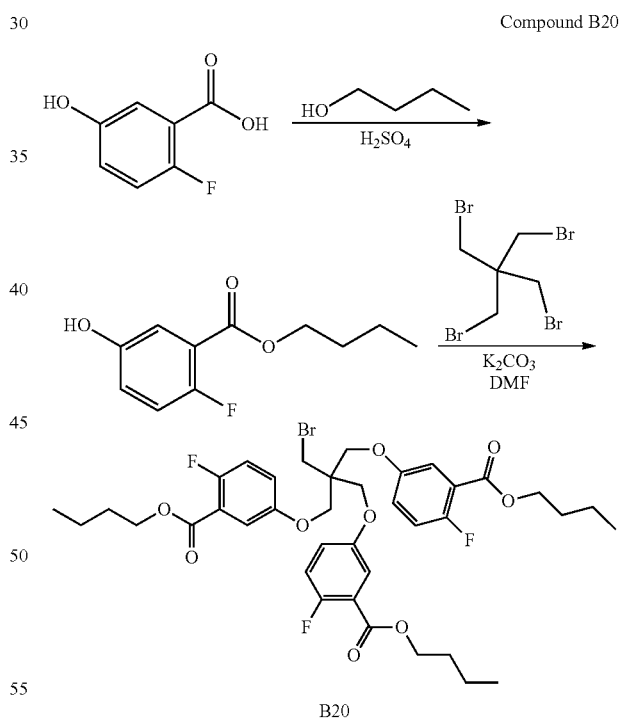

B20

By a procedure analogous to that of B11, reaction of butyl 2-fluoro-5-hydroxybenzoate (6.79 g, 32 mmol) with pentaerythrityl tetrabromide (4.65 g, 12 mmol) gave Compound B20, dibutyl 5,5'-(2-bromomethyl)-2-((3-((2-butoxycarbonyl)-4-fluorophenoxy)methyl)propane-1,3-diyl)bis(oxy)bis(2-fluorobenzoate), (3.13 g, 33% yield). $^1$H NMR (400 MHz, CCCl3): δ 7.41 (m, 3H), 7.03 (m, 6H), 4.33 (t, J=6.6 Hz, 6H), 4.22 (s, 6H), 3.83 (s, 2H) 1.64, 1.72 (quintet, J=8.0 Hz, 6H), 1.47 (sextet, J=7.3 Hz, 6H), 0.96 (t, J=7.3 Hz, 9H).

Compound B21

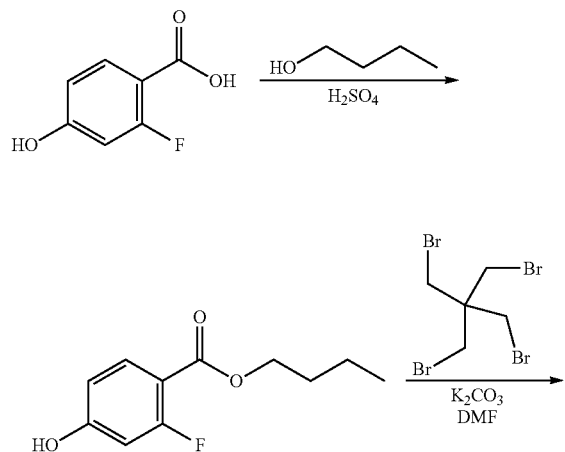

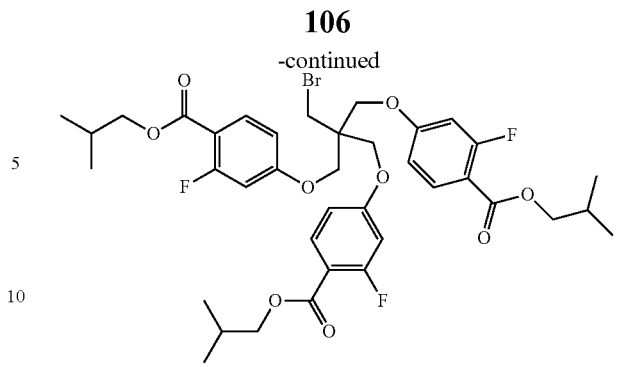

By a procedure analogous to that of Compound B11, reaction of butyl 2-fluoro-4-hydroxybenzoate (6.37 g, 30 mmol) with pentaerythrityl tetrabromide (3.87 g, 10 mmol) gave Compound B21, dibutyl 4,4'-((2-bromomethyl)-2-((4-butoxycarbonyl)-3-fluorophenoxy)methyl)propane-1,3-diyl)bis(oxy)bis(2-fluorobenzoate), (3.24 g, 41% yield). $^1$H NMR (400 MHz, CCCl3): δ 7.88 (t, J=8.60 Hz, 3H), 6.72 (dd, J=8.8 and 2.2 Hz, 3H), 6.65 (dd, J=12.1 and 2.6 Hz, 3H), 4.29 (t, J=7.0 Hz, 6H), 4.26 (s, 6H), 3.81 (s, 2H) 1.72 (quintet, J=8.0 Hz, 6H), 1.46 (sextet, J=7.3 Hz, 6H), 0.95 (t, J=7.3 Hz, 9H).

Compound B22

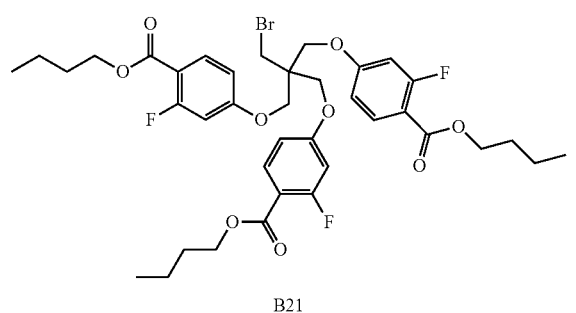

By a procedure analogous to that of Compound B11, reaction of isobutyl 2-fluoro-4-hydroxybenzoate (6.37 g, 30 mmol) with pentaerythrityl tetrabromide (3.87 g, 10 mmol) gave Compound B22, diisobutyl 4,4'-((2-bromomethyl)-2-((3-fluoro-4-isobutoxycarbonyl)phenoxy)methyl)propane-1,3-diyl)bis(oxy)bis(2-fluorobenzoate) (3.10 g, 40% yield). $^1$H NMR (400 MHz, CCCl3): δ 7.90 (t, J=8.6 Hz, 3H), 6.73 (dd, J=0.16 and 2.6 Hz, 3H), 6.65 (dd, J=12.4 and 2.6 Hz, 3H), 4.26 (s, 6H), 4.07 (d, J=6.6 Hz, 6H), 3.81 (s, 2H), 2.04 (nm, 3H), 0.99 (d, J=6.6 Hz, 18H).

Compound B23

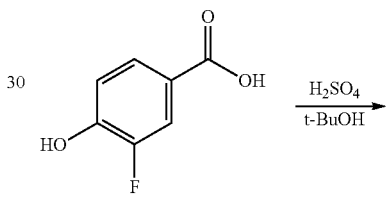

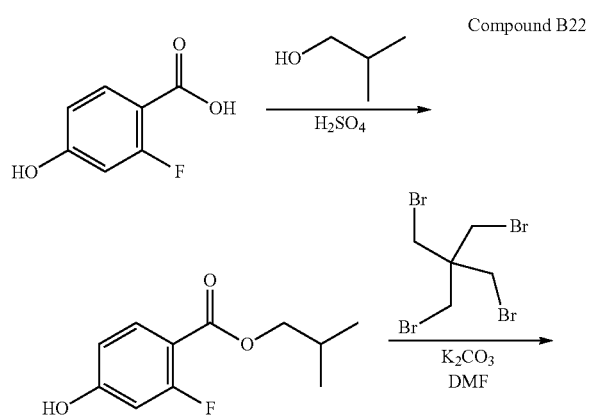

A mixture of 3-fluoro-4-hydroxybenzoic acid (5.00 g, 32 mmol), n-butanol (50 mL) and 20% oleum (0.5 mL) was heated at 110° C. for 16 h. The volatiles were removed under reduced pressure. A solution of the residue in hexane/EA (1:1, 300 mL) was washed with water (2×200 mL), dried over sodium sulfate, and the solvent was removed under reduced pressure to give butyl 3-fluoro-4-hydroxybenzoate (6.50 g, 96% yield).

A solution of the obtained ester and pentaerythrityl tetrabromide (4.65 g, 12 mmol) in DMF (20 mL) was treated with potassium carbonate (6.90 g, 50 mmol), and the obtained mixture was stirred under argon and heated at 110° C. for 6 h. The reaction mixture was poured into ice/water (300 mL), neutralized with 3N HCl and extracted with hexane/toluene/EA (200+200+100 mL). The extract was washed with water (200 mL), dried over magnesium sulfate, and the volatiles were removed under reduced pressure. Column chromatography of the residue (silica gel, hexane/toluene/EA, 45:50:5) gave Compound B23, dibutyl 4,4'-((2-(bromomethyl)-2-((4-(butoxycarbonyl)-2-fluorophenoxy)methyl)propane-1,3-diyl)bis(oxy))bis(3-fluorobenzoate), (3.24 g, 41% yield). $^1$H NMR (400 MHz, CCCl3): δ 7.79 (d, J=8.8 Hz, 3H), 7.71 (m, 3H), 7.03 (t, J=8.6 Hz, 3H), 4.40 (s, 6H), 4.28 (t, J=6.6 Hz, 6H), 3.92 (s, 2H), 1.72 (quintet, J=6.6 Hz, 6H), 1.44 (sextet, J=7.3 Hz, 6H), 0.96 (t, J=7.3 Hz, 9H).

were washed with methanol and dried in a vacuum oven to give pure isobutyl 4'-hydroxy-[1,1'-biphenyl]-4-carboxylate (16.13 g, 80% yield).

A mixture of isobutyl 4'-hydroxy-[1,1'-biphenyl]-4-carboxylate (16.00 g, 59 mmol), pentaerythrityl tetrabromide (9.70 g, 25 mmol), potassium carbonate (13.80 g, 100 mmol), and DMF (50 mL) was stirred under argon and heated at 110° C. for 24 h. After cooling, the mixture was poured into ice/water (300 mL), neutralized with 3N HCl, and extracted with toluene/ethyl acetate (1:1, 500 mL). The extract was washed with water (200 mL), dried over magnesium sulfate, and the volatiles were removed under reduced pressure. The residue was chromatographed (silica gel, hexane/toluene/ethyl acetate, 44:50:6) to give Com-

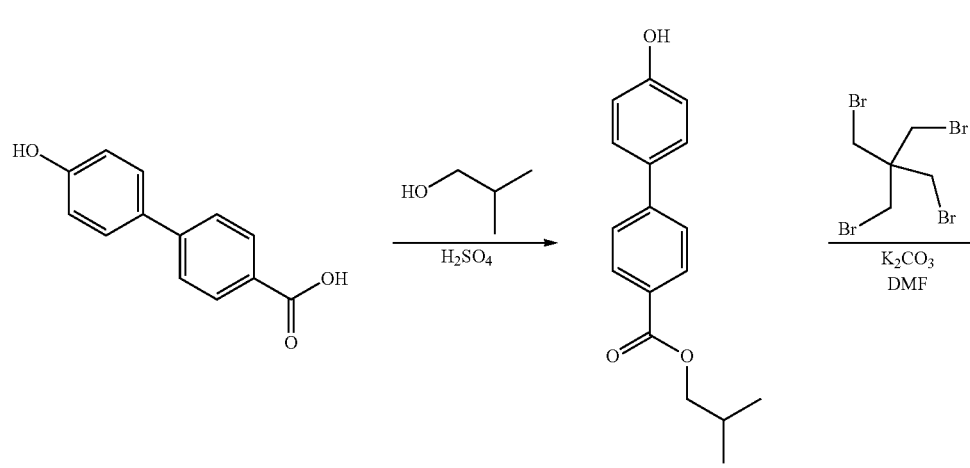

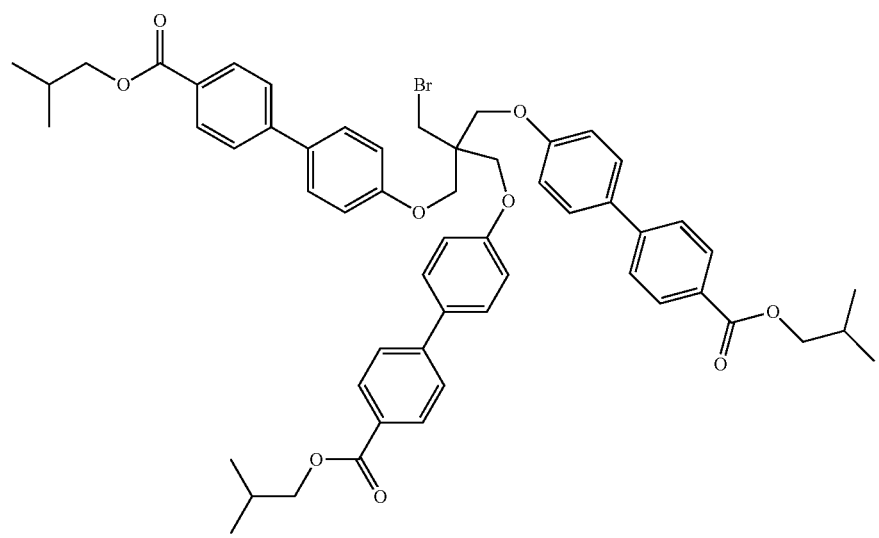

Compound B24

A mixture of 4'-hydroxy-[1,1'-biphenyl]-4-carboxylic acid (16.20 g, 75 mmol), isobutanol (100 mL) and 20% oleum (1.0 mL) was heated at 110° C. for 7 h. After the mixture was set aside at room temperature overnight, the product was separated as colorless crystals. The crystals pound B24 (10.00 g, 42% yield). 1H NMR (400 MHz, CDCl3): δ 8.07 (d, J=8.4 Hz, 6H), 7.59 (d, J=8.4 Hz, 6H), 7.55 (d, J=8.8 Hz, 6H), 7.03 (d, J=8.8 Hz, 6H), 4.34 (s, 6H), 4.11 (d, J=6.6 Hz, 6H), 3.94 (s, 2H), 2.07 (m, 3H), 1.02 (d, J=6.6 Hz, 18H).

Compound C1

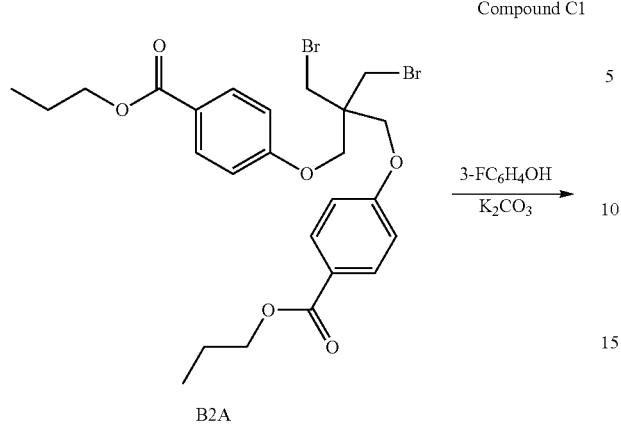

A mixture of Compound B2A (side product from the preparation of Compound B2, 2.40 g, 4.1 mmol), 3-fluorophenol (0.45 mL, 5.0 mmol), potassium carbonate (1.38 g, 10 mmol), and DMF (15 mL) was stirred under argon and heated at 100° C. for 20 h. After cooling, the mixture was poured into ice/water (200 mL) and extracted with toluene/ethyl acetate (1:1, 100 mL). The extract was washed with water (200 mL), dried over magnesium sulfate, and the solvent was removed under reduced pressure to give crude Compound C1, dipropyl 4,4'-((2-(bromomethyl)-2-((3-fluorophenoxy)methyl)propane-1,3-diyl)bis(oxy))dibenzoate, of purity 75% (2.44 g, 74% yield) that was used in the next step without purification.

Compound F1

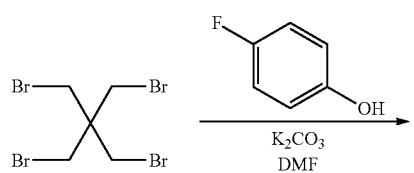

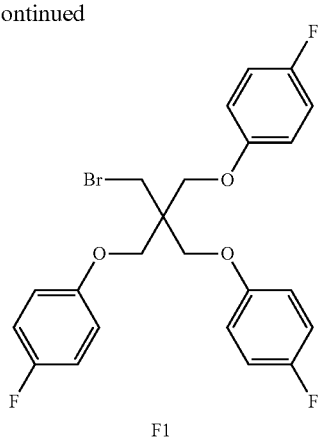

A mixture of pentaerythrityl tetrabromide (7.75 g, 20 mmol), 4-fluorophenol (7.84 g, 70 mmol), potassium carbonate (13.80 g, 100 mmol), and DMF (40 mL) was stirred under argon and heated at 100° C. for 68 h. After aqueous work-up, the reaction mixture was chromatographed (silica gel, hexane/DCM, 3:1) to give Compound F1, 4,4'-((2-(bromomethyl)-2-((4-fluorophenoxy)methyl)propane-1,3-diyl)bis(oxy))bis(fluorobenzene), (3.92 g, 41% yield).

Compound F2

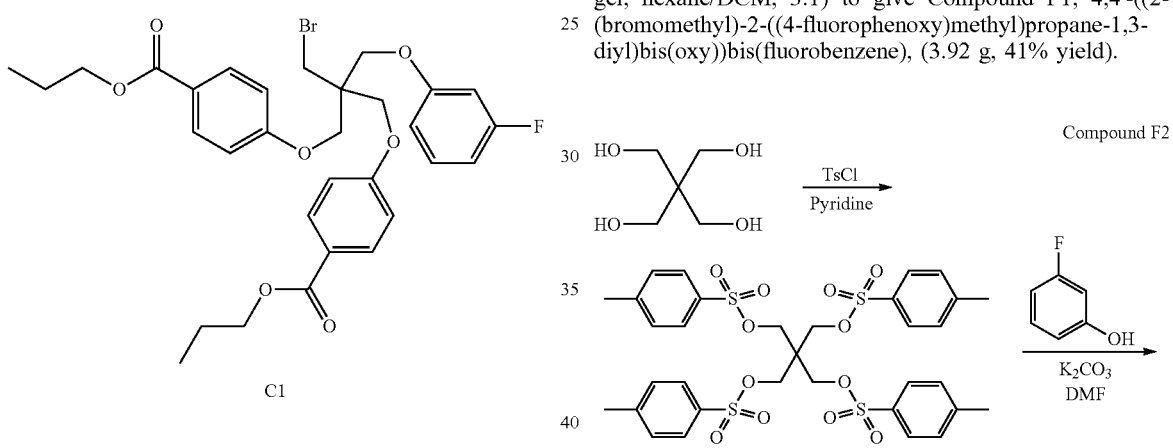

Pentaerythritol (13.6 g, 100 mmol) was reacted with 4-toluenesulfonyl chloride (72.0 g, 0.4 mol) in dry pyridine (100 mL) for 16 h at room temperature. After the reaction was accomplished, 500 mL of ice-cold water was added while the mixture was stirred vigorously. The white precipitate that formed was filtered off and rinsed five times with water to remove pyridine. Drying of the product in a vacuum oven gave pure pentaerythrityl tosylate (PETS, 67.0 g, 89%) as a white solid. $^1$H NMR (400 MHz, CDCl$_3$): δ 7.67 (d, J=8.4 Hz, 8H), 7.35 (d, J=8.04, 8H), 3.80 (s, 8H), 2.46 (s, 12H).

PETS (11.4 g, 15 mmol) was reacted with 3-fluorophenol (5.9 g, 53 mmol, 3.5 eq) in the presence of anhydrous $K_2CO_3$ (10.4 g, 100 mmol, 5 eq.) in dry DMF (25 mL) at 110° C. for 21 h under nitrogen. The reaction was monitored by TLC. After tri-substituted product became the major one in the reaction mixture, it was poured into 200 mL of ice-cold water and neutralized with 1M HCl. Extraction with DCM, washing of the organic layer with water, drying over anhydrous $MgSO_4$, and evaporation of the solvent afforded 11.2 g of the crude product as a yellowish oil. Purification by column chromatography using hexane/ethyl acetate (4:1) as a mobile phase gave Compound F2, 3-(3-fluorophenoxy)-2,2-bis((3-fluorophenoxy)methyl)propyl 4-methylbenzenesulfonate, as the second fraction (5.0 g, 58% yield). $^1$H NMR (400 MHz, $CDCl_3$): δ 7.68 (d, J=6.8 Hz, 2H), 7.15-7.22 (m, 51H), 6.67 (td, J=6.4 and 1.6 Hz, 3H), 6.60 (dd, J=6.4 and 1.6 Hz, 3H), 6.50 (dt, J=8.8 and 1.6 Hz, 3H), 4.38 (s, 2H), 4.11 (s, 6H), 2.36 (s, 3H).

J=6.4 Hz, 2H), 6.82-6.88 (m, 3H), 6.76-6.81 (m, 5H), 4.41 (s, 2H), 4.18 (s, 6H), 2.36 (s, 3H).

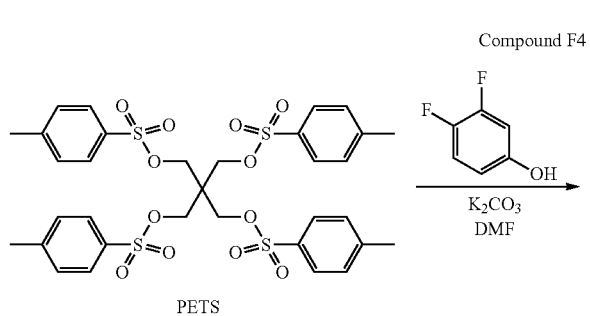

Compound F4

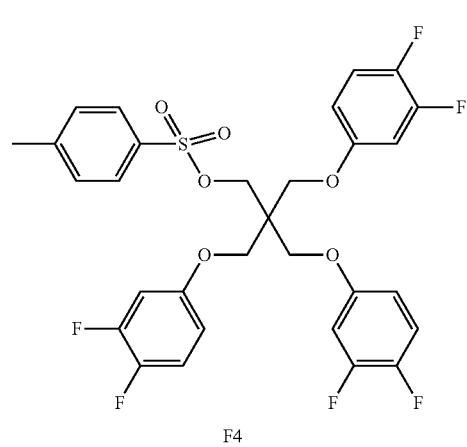

Compound F3

F3

A mixture of PETS (10.3 g, 13.6 mmol), 2,4-difluorophenol (6.2 g, 48 mmol), $K_2CO_3$ (9.4 g, 68 mmol), and dry DMF (25 mL) was heated at 110° C. for 22 h under nitrogen. Work-up similar to that of Compound F2. Purification by column chromatography using hexane/ethyl acetate (5:1) as a mobile phase afforded Compound F3, 3-(2,4-difluorophenoxy)-2,2-bis((2,4-difluorophenoxy)methyl)propyl 4-methylbenzenesulfonate, (3.2 g, 35% yield) as white solid. $^1$H NMR (400 MHz, $CDCl_3$): δ 7.73 (d, J=6.8 Hz, 2H), 7.20 (d, A reaction of PETS with 3,4-difluorophenol under conditions similar to those for Compound F2 and purification of the crude product by column chromatography using hexane/ethyl acetate (5:1) as a mobile phase afforded Compound F4, 3-(3,4-difluorophenoxy)-2,2-bis((3,4-difluorophenoxy)ethyl)propyl 4-methylbenzenesulfonate, (4.0 g, 47% yield) as a white solid. $^1$H NMR (400 MHz, $CDCl_3$): δ 7.69 (d, J=6.8 Hz, 2H), 7.20 (d, J=6.4 Hz, 2H), 7.04 (dd, J=15.2 and 7.2 Hz, 2H), 6.58-6.62 (m, 3H), 6.50-6.53 (m, 3H), 4.34 (s, 2H), 4.18 (s, 6H), 2.36 (s, 3H).

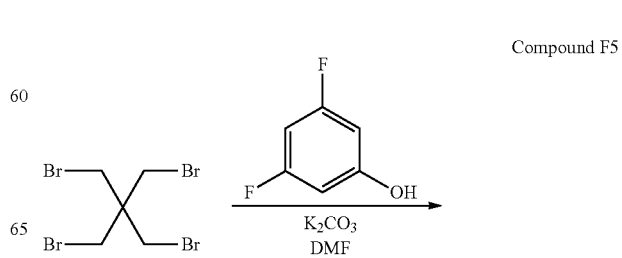

Compound F5

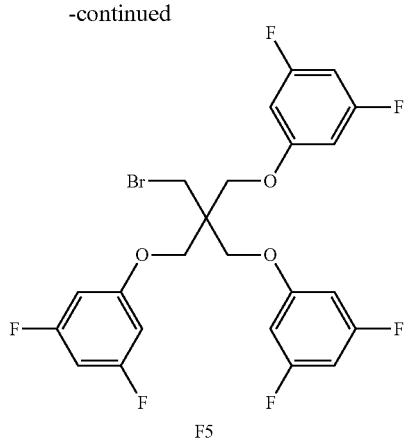

F5

A mixture of pentaerythrityl tetrabromide (7.75 g, 20 mmol), 3,5-difluorophenol (8.45 g, 65 mmol), potassium carbonate (13.80 g, 100 mmol), and DMF (50 mL) was stirred under argon and heated at 100° C. for 16 h. After cooling, the mixture was poured into water (300 mL) and extracted with toluene/ethyl acetate (1:1, 300 mL). The extract was washed with water (300 mL), dried over magnesium sulfate, and the solvent was removed under reduced pressure. Column chromatography of the residue (silica gel, hexane/DCM, 9:1) afforded Compound F5, 3-(3,5-difluorophenoxy)-2,2-bis((3,5-difluorophenoxy)methyl)propyl 4-methylbenzenesulfonate, of purity 80% (5.16 g, 39% yield).

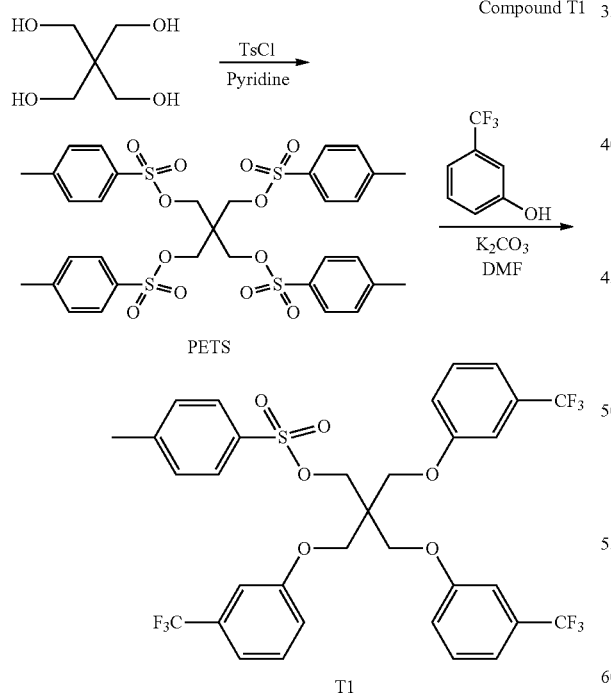

T1

PETS (15.0 g, 20 mmol) was reacted with 3-(trifluoromethyl)phenol (11.3 g, 70 mmol) in the presence of anhydrous $K_2C_3$ (13.8 g, 100 mmol) in dry DMF (25 mL) at 115° C. for 16 h under nitrogen protection. After TLC indicated mainly tris- and bis-substituted products present, the reaction mixture was poured into 200 mL of ice-cold water and neutralized with 1M HCl. Extraction with DCM, washing of the organic layer with water, drying over magnesium sulfate, and evaporation of the solvent afforded 14.7 g of the crude oily product, which soon became almost solid. Purification by column chromatography using hexane/ethyl acetate (6:1) as a mobile phase afforded Compound T1, 3-(3-(Trifluoromethyl)phenoxy)-2,2-bis((3-(trifluoromethyl)phenoxy)methyl)propyl 4-methylbenzenesulfonate, (4.4 g, 30% yield) as a solid. $^1$H NMR (400 MHz, CDCl$_3$): δ 7.68 (d, J=6.8 Hz, 6H), 7.38 (m, 9H), 7.23 (d, J=6.0 Hz, 9H), 7.15 (d, J=6.8 Hz, 6H), 7.03 (s, 9H), 7.00 (d, J=6.8 Hz, 9H), 4.42 (s, 2H), 4.20 (s, 6H), 2.32 (s, 3H).

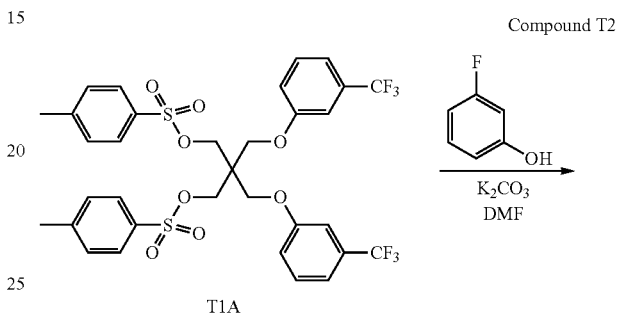

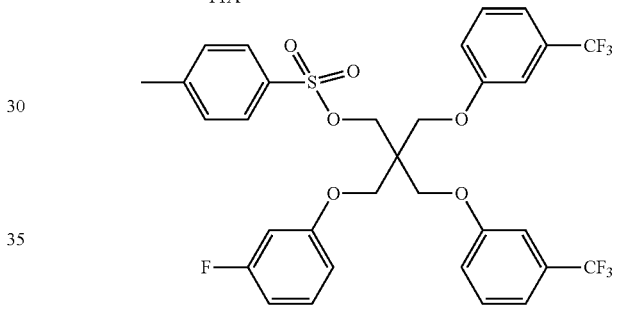

T2

A solution of Compound T1A (a side product from preparation of Compound T1, 1.47 g, 2.0 mmol) was treated with 3-fluorophenol (270 mg, 2.4 mmol) and K$_2$CO$_3$ (560 mg, 4 mmol), and the mixture was heated under nitrogen at 110° C. for 9 h. Work-up with ice cold water and extraction with DCM afforded a crude product that was purified by column chromatography using hexane/ethyl acetate (6:1) to give pure Compound T2, 3-(3-fluorophenoxy)-2,2-bis((3-(trifluoromethyl)phenoxy)methyl)propyl 4-methylbenzenesulfonate, (0.78 g, 58% yield) as colorless oil. $^1$H NMR (400 MHz, CDCl$_3$): δ 7.68 (d, J=6.8 Hz, 2H), 7.38 (t, J=6.4 Hz, 2H), 7.17-7.24 (m, 3H), 7.15 (d, J=6.8 Hz, 2H), 7.03 (s, 21H), 6.99 (d, J=6.8 Hz, 2H), 6.68 (m, 1H), 6.60 (m, 1H), 6.51 (m, 1H), 4.40 (s, 2H), 4.19 (s, 4H), 4.14 (s, 2H), 2.32 (s, 3H).

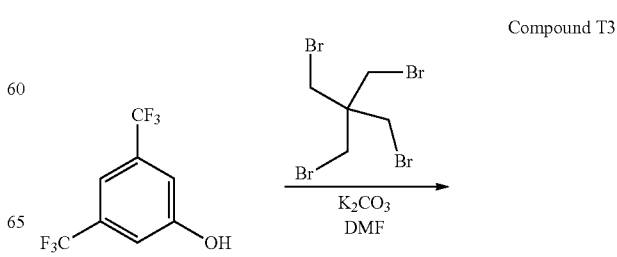

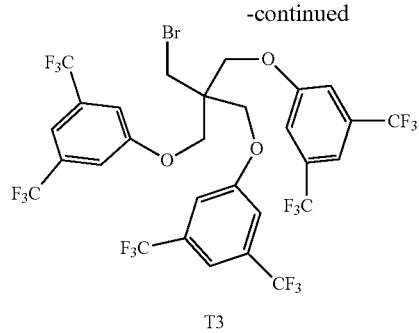

T3

A mixture of 3,5-bis(trifluoromethyl)phenol (15.2 mL, 100 mmol), pentaerythrityl tetrabromide (11.63 g, 30 mmol), potassium carbonate (27.60 g, 200 mmol), and DMF (50 mL) was stirred under argon and heated at 110° C. Progress of the reaction was monitored by NMR. After 3 h, the reaction mixture was poured into ice/water (400 mL), neutralized with 3N HCl, and extracted with EA/toluene/hexane (1:1:1, 300 mL). The extract was washed with water (300 mL), dried over magnesium sulfate, and the volatiles were removed under reduced pressure. The product was purified by recrystallization from toluene/hexane to give Compound T3, 5,5'-((2-((3,5-bis(trifluoromethyl)phenoxy)methyl)-2-(bromomethyl)propane-1,3-diyl)bis(oxy))bis(1,3-bis(trifluoromethyl)benzene) (12.0 g of purity 65%, 48% yield). $^1$H NMR (400 MHz, CDCl$_3$): δ 7.51 (s, 3H), 7.34 (s, 6H), 4.35 (s, 6H), 3.87 (s, 2H).

Compound T4

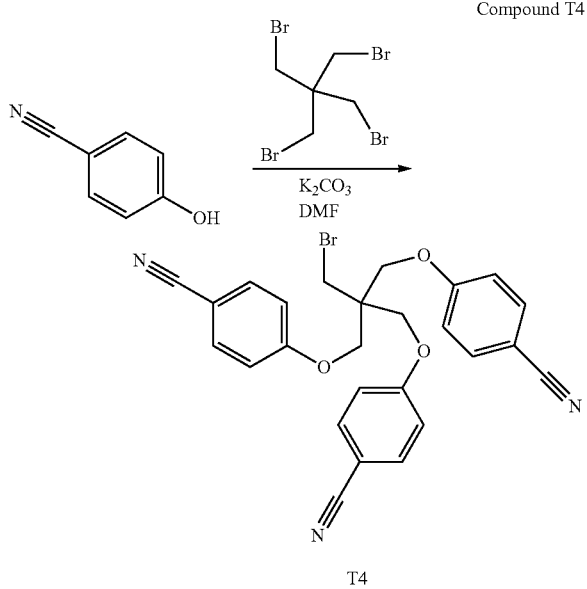

T4

A mixture of 4-hydroxybenzonitrile (15.39 g, 129 mmol), pentaerythrityl tetrabromide (11.63 g, 30 mmol), potassium carbonate (27.60 g, 200 mmol), and DMF (50 mL) was stirred under argon and heated at 110° C. Progress of the reaction was monitored by NMR. After 3 h, the reaction mixture was poured into ice/water (400 mL), acidified with 36% HCl to pH 1, and stirred for 15 min. The precipitate was filtered off, washed with water and dried in air. Column chromatography of the crude product (silica gel, hexane/toluene/ethyl acetate, 30:60:100) gave pure Compound T4, 4,4'-((2-(bromomethyl)-2-((4-cyanophenoxy)methyl)propane-1,3-diyl)bis(oxy))dibenzonitrile. (6.04 g, 40% yield). $^1$H NMR (400 MHz, CDCl3): δ 7.59 (d, J=8.8 Hz, 6H), 6.98 (d, J=9.0 Hz, 6H), 4.29 (s, 6H), 3.84 (s, 2H).

Compound T5

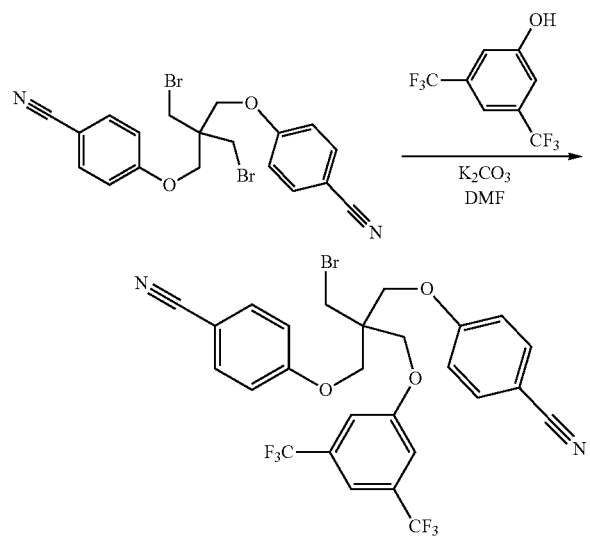

T5

A mixture of 4,4'-((2,2-bis(bromomethyl)propane-1,3-diyl)bis(oxy))dibenzonitrile (2.80 g, 4.7 mmol, a side product from preparation of Compound T4), 3,5-bis(trifluoromethyl)phenol (0.91 mL, 6 mmol), potassium carbonate (1.38 g, 10 mmol), and DMF (20 mL) was stirred under argon and heated at 110° C. for 20 h. The reaction mixture was poured into ice/water (200 mL), neutralized with 3N HCl and extracted with ethyl acetate/toluene (1:1, 300 mL). The extract was washed with water (200 mL), dried over magnesium sulfate and the volatiles were removed off under reduced pressure. The residue was chromatographed (silica gel, hexane/ethyl acetate, 8:2) to give Compound T5, 4,4'-((2-((3,5-bis(trifluoromethyl)phenoxy)methyl)-2-(bromomethyl)-propane-1,3-diyl)bis(oxy)dibenzonitrile, (2.16 g, 75% yield). $^1$H NMR (400 MHz, CDCl3): δ 7.59 (d, J=8.8 Hz, 4H), 7.49 (s, 1H), 7.32 (s, 2H), 6.98 (d, J=8.8 Hz, 4H), 4.34 (s, 2H), 4.30 (s, 4H), 3.85 (s, 2H).

Compound T6

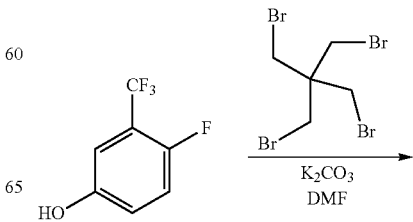

-continued

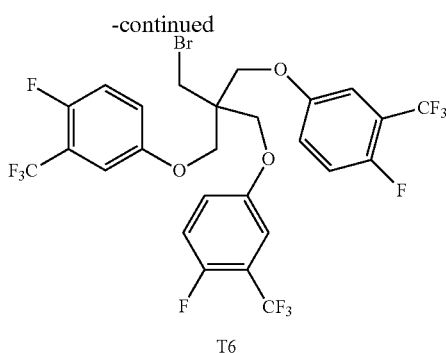

T6

A mixture of 4-fluoro-3-(trifluoromethyl)phenol (9.00 g, 50 mmol), pentaerythrityl tetrabromide (6.46 g, 16.6 mmol), potassium carbonate (13.80 g, 100 mmol), and DMF (40 mL) was stirred under argon and heated at 110° C. for 16 h. The reaction mixture was poured into ice/water (400 mL), acidified with 3N HCl to pH 1 and extracted with EA/toluene/hexane (1:1:1, 300 mL). The extract was washed with water (300 mL), dried over magnesium sulfate, and the solvent was removed under reduced pressure. Chromatography of the residue (silica gel, hexane/EA, 65:33:2) gave Compound T6, 4,4'-((2-Bromomethyl)-2-((4-fluoro-3-(trifluoromethyl)phenoxy)methyl)-propane-1,3-diyl)bis(oxy))bis(1-fluoro-2-(trifluoromethyl)benzene, (4.27 g, 37% yield). $^1$H NMR (400 MHz, CDCl3): δ 7.11 (m, 9H), 4.22 (s, 6H), 3.83 (s, 2H).

A mixture of Compound A (388 mg, 0.6 mmol), Compound B1 (2.20 g, 3.4 mmol), potassium carbonate (690 mg, 5.0 mmol), and anhydrous DMF (6 μmL) was stirred under argon and heated at 90° C. for 16 h. After cooling, the reaction mixture was poured into ice/water (200 mL) and extracted with ethyl acetate/toluene (2:1, 300 mL). The extract was washed with water (200 mL), dried over sodium sulfate and concentrated under reduced pressure. The crude product was purified by column chromatography (silica gel—hexane/DCM/ethyl acetate, 37:60:3) and recrystallization from acetone/methanol to give Compound 1, 4,8-bis(4-(diphenylamino)phenyl)-2,6-bis(3-(3-(ethoxycarbonyl)phenoxy)-2,2-bis((3-(ethoxycarbonyl)phenoxy)methyl)propyl)-2H-benzo[1,2-d:4,5-d']bis([1,2,3]triazole)-6-ium-5-ide, (325 mg, 30% yield). $^1$H NMR (benzene-D$_6$): δ 8.29 (d, J=8.8 Hz, 4H), 7.56 (s, 6H), 7.42 (d, J=7.3 Hz, 6H), 7.12 (m, 8H), 7.02 (d, J=7.7 Hz, 8H), 6.94 (t, J=6.9 Hz, 4H), 6.86 (m, 12H), 6.67 (d, J=9.1 Hz, 4H), 5.11 (s, 4H), 4.06 (m, 24H), 1.05 (t, J=7.6 Hz, 18H). UV-vis spectrum (EVA): $\lambda_{max}$=553 nm. Fluorimetry (EVA): $\lambda_{max}$=634 nm.

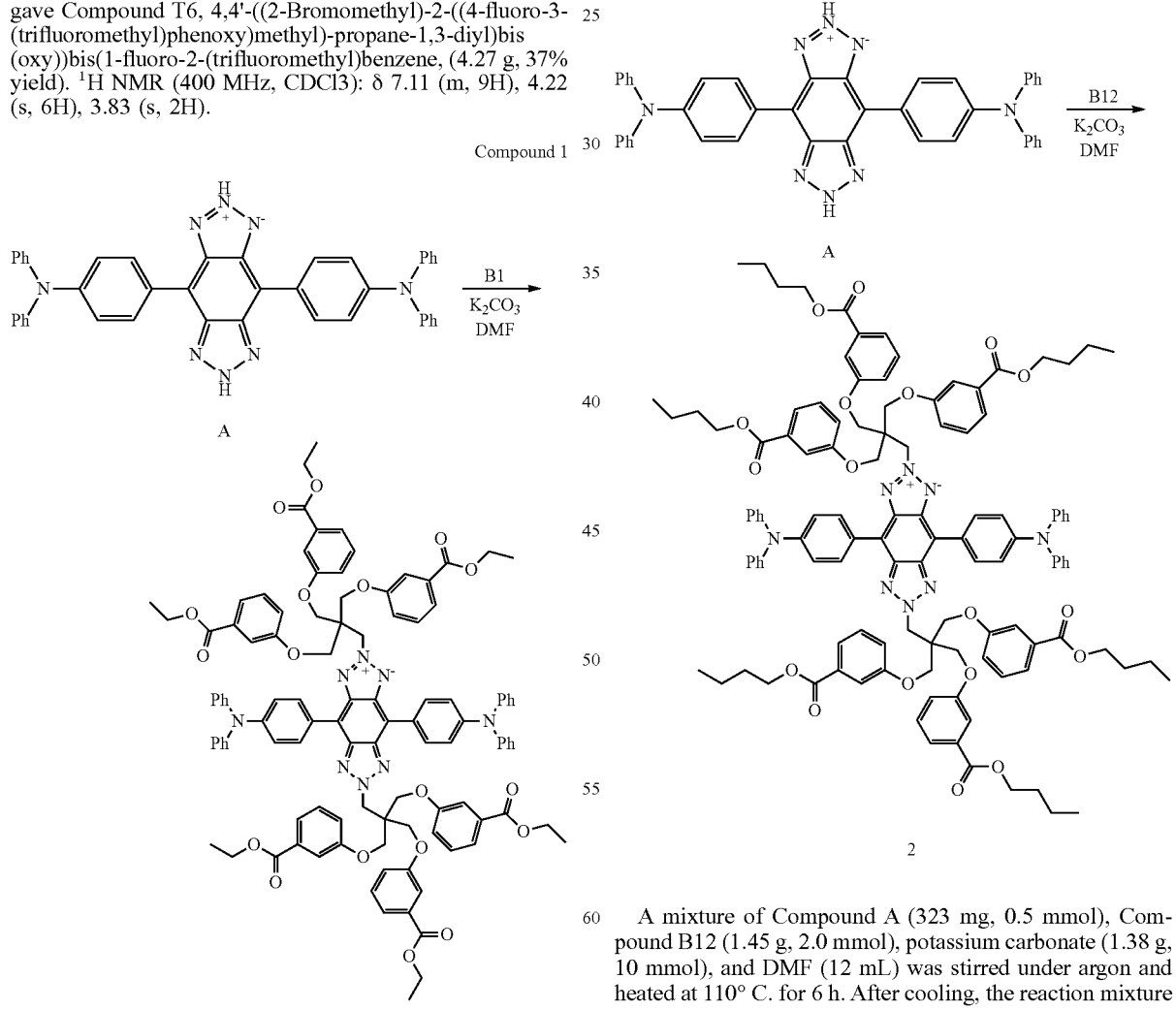

A mixture of Compound A (323 mg, 0.5 mmol), Compound B12 (1.45 g, 2.0 mmol), potassium carbonate (1.38 g, 10 mmol), and DMF (12 mL) was stirred under argon and heated at 110° C. for 6 h. After cooling, the reaction mixture was poured into ice/water (300 mL), neutralized with 1N hydrochloric acid and extracted with ethyl acetate/hexane (1:1, 300 mL). The extract was washed with water (200 mL), dried over magnesium sulfate, and the volatiles were removed under reduced pressure. Column chromatography of the residue (silica gel, hexane/ethyl acetate, 85:15) and recrystallization of the product from acetone/methanol afforded Compound 2, 4,8-bis(4-(diphenylamino)phenyl)-2,6-bis(3-(3-(butoxycarbonyl)phenoxy)-2,2-bis((3-(butoxycarbonyl)phenoxy)methyl)propyl)-2H-benzo[1,2-d:4,5-d']bis([1,2,3]triazole)-6-ium-5-ide, (200 mg, 21% yield). $^1$H NMR (400 MHz, CDCl$_3$): δ 8.14 (d, J=8.8 Hz, 4H), 7.51 (s, 6H), 7.43 (d, J=6.9 Hz, 6H), 7.32 (m, 6H), 7.06 (m, 26H), 6.61 (d, J=8.1 Hz, 4H), 5.41 (s, 4H), 4.38 (s, 12H), 4.22 (t, J=7.0 Hz, 12H), 1.68 (quintet, J=7.5 Hz, 12H), 1.40 (sextet, J=7.7 Hz, 12H), 0.93 (t, J=7.6 Hz, 18H). UV-vis spectrum (EVA): $\lambda_{max}$=551 nm. Fluorimetry (EVA): $\lambda_{max}$=645 nm.

ethyl acetate, 40:50:10) and recrystallization from acetone/methanol afforded Compound 3, 4,8-bis(4-(diphenylamino)phenyl)-2,6-bis(3-(3-(isobutoxycarbonyl)phenoxy)-2,2-bis((3-(isobutoxycarbonyl)phenoxy)methyl)propyl)-2H-benzo[1,2-d:4,5-d']bis([1,2,3]triazole)-6-ium-5-ide, (75 mg, 5% yield). $^1$H NMR (500 MHz, C$_6$D$_6$): δ 8.74 (d, J=9.0 Hz, 4H), 7.90 (s, 6H), 7.70 (d, J=7.5 Hz, 6H), 7.15 (m, 14H), 7.03 (d, J=8.5 Hz, 4H), 6.95 (m, 4H), 6.90 (m, 6H), 6.85 (m, 8H), 5.05 (s, 4H), 4.12 (s, 12H), 3.97 (d, J=6.5 Hz, 12), 1.82 (m, 6H), 0.77 (d, J=6.5 Hz, 36H). UV-vis spectrum (EVA): $\lambda_{max}$=553 nm. Fluorimetry (EVA): $\lambda_{max}$=637 nm.

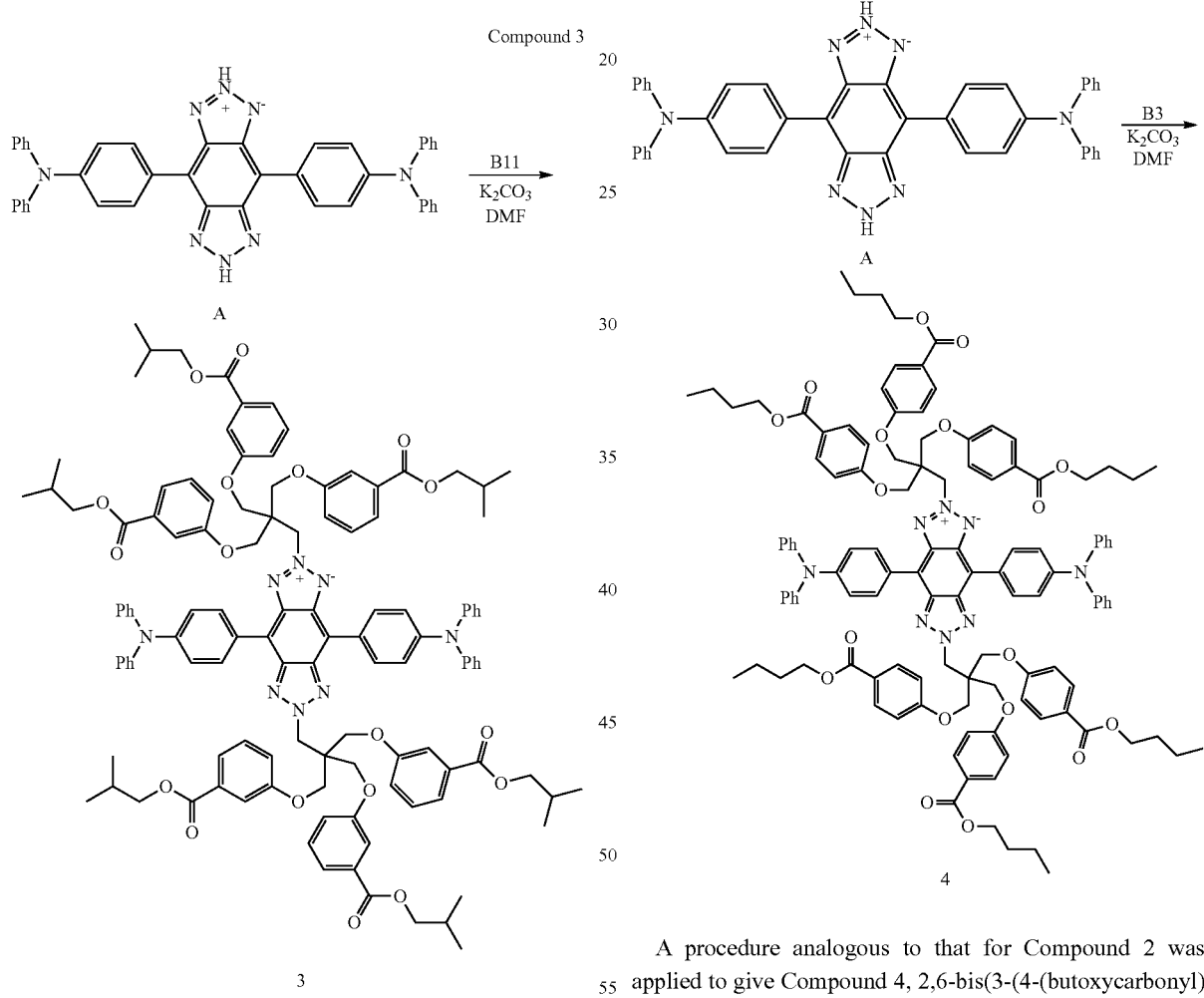

A mixture of Compound A (480 mg, 0.74 mmol), Compound B11 (1.45 g, 2.0 mmol), potassium carbonate (690 mg, 5.0 mmol), and DMF (12 mL) was stirred under argon and heated at 120° C. for 20 h. After cooling, the mixture was poured into ice/water (200 mL) and extracted with hexane/toluene/ethyl acetate (1:1:1, 300 mL). The extract was washed with water (200 mL), dried over magnesium sulfate, and the solvent was removed under reduced pressure. Column chromatography (silica gel, hexane/toluene/

A procedure analogous to that for Compound 2 was applied to give Compound 4, 2,6-bis(3-(4-(butoxycarbonyl)phenoxy)-2,2-bis((4-(butoxycarbonyl)phenoxy)methyl)propyl)-4,8-bis(4-(diphenylamino)phenyl)-2H-benzo[1,2-d:4,5-d']bis([1,2,3]triazole)-6-ium-5-ide, (191 mg, 20% yield). $^1$H NMR (400 MHz, CDCl$_3$): δ 8.29 (d, J=8.8 Hz, 4H), 7.84 (d, J=8.8 Hz, 12H) 7.31 (t, J=7.7 Hz, 8H), 7.15 (d, J=8.0 Hz, 8H), 7.09 (t, J=7.3 Hz, 4H), 6.91 (d, J=8.5 Hz, 4H), 6.84 (d, J=8.8 Hz, 12H), 5.41 (s, 41H), 4.44 (s, 12H), 4.24 (t, J=6.8 Hz, 12H), 1.69 (quintet, J=7.5 Hz, 12H), 1.41 (sextet, J=7.7 Hz, 12H), 0.93 (t, J=7.31 Hz, 18H). UV-vis spectrum (EVA): $\lambda_{max}$=551 nm. Fluorimetry (EVA): $\lambda_{max}$=653 nm.

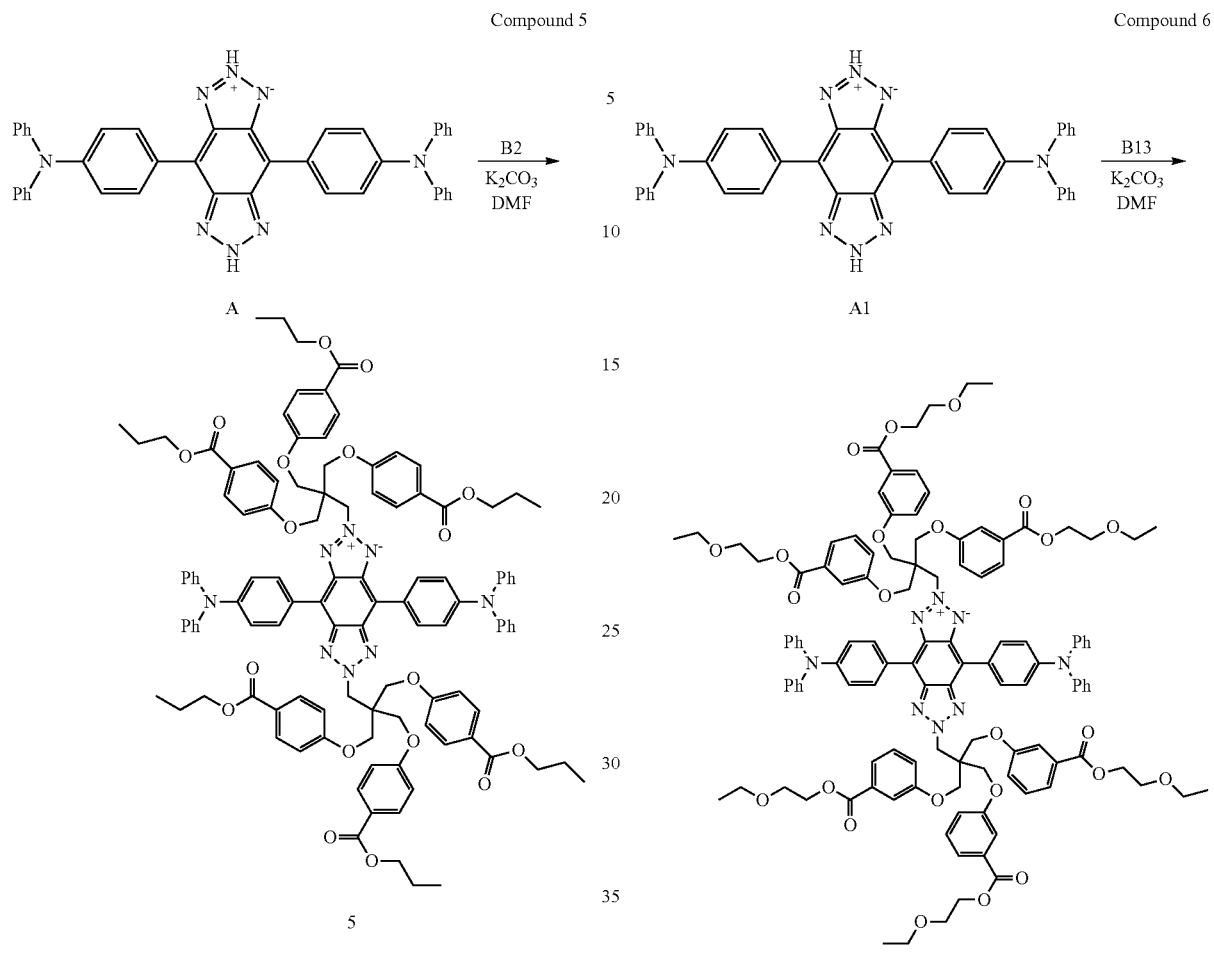

A mixture of Compound A (517 mg, 0.8 mmol), Compound B2 (1.59 g, 2.3 mmol), potassium carbonate (552 mg, 4.0 mmol), and DMF (15 mL) was stirred under argon and heated at 110° C. for 16 h. After cooling, the mixture was poured into ice/water (200 mL) and extracted with toluene/ethyl acetate (1:1, 200 mL). The extract was washed with water (200 mL), dried over magnesium sulfate, and the solvent was removed under reduced pressure. The residue was chromatographed using silica gel and hexane/DCM/ethyl acetate (35:60:5), and the obtained product was crystallized from acetone/methanol to give Compound 5, 4,8-bis(4-(diphenylamino)phenyl)-2,6-bis(3-(4-(propoxycarbonyl)phenoxy)-2,2-bis((4-(propoxycarbonyl)phenoxy)methyl)propyl)-2H-benzo[1,2-d:4,5-d']bis([1,2,3]triazole)-6-ium-5-ide, (220 mg, 15% yield). $^1$H NMR (500 MHz, $C_6D_6$): δ 8.86 (d, J=8.5 Hz, 4H), 8.06 (d, J=8.5 Hz, 12H), 7.25 (d, J=8.5 Hz, 4H), 7.22 (m, 16H), 7.02 (m, 4H), 6.64 (d, J=8.5 Hz, 12H), 5.11 (s, 4H), 4.16 (s, 12H), 4.11 (t, J=7.0 Hz, 12H), 1.50 (sextet, J=7.0 Hz, 12H), 0.77 (t, J=7.5 Hz, 18H). UV-vis spectrum (EVA): $\lambda_{max}$=556 nm. Fluorimetry (EVA): $\lambda_{max}$=643 nm.

A mixture of Compound A (760 mg, 117 mmol), Compound B13 (3.80 g, 4.9 mmol), potassium carbonate (690 mg, 5.0 mmol), and DMF (15 mL) was stirred under argon and heated at 100° C. for 4 h. After cooling, the mixture was poured into ice/water (300 mL) and extracted with hexane/ethyl acetate (1:1, 300 mL). The extract was washed with water (300 mL), dried over magnesium sulfate, and the solvent was removed under reduced pressure. Column chromatography of the residue (silica gel, hexane/ethyl acetate, 1:1) afforded Compound 6, 4,8-bis(4-(diphenylamino)phenyl)-2,6-bis(3-(3-((2-ethoxyethoxy)carbonyl)phenoxy)-2,2-bis((3-((2-ethoxy ethoxy)carbonyl)phenoxy)-methyl)propyl)-2H-benzo[1,2-d:4,5-d']bis([1,2,3]triazole)-6-ium-5-ide, (295 mg, 12% yield). $^1$H NMR (500 MHz, $C_6D_6$): δ 8.74 (d, J=9.0 Hz, 4H), 7.87 (s, 6H), 7.72 (d, J=7.5 Hz, 6H), 7.09 (m 6H), 7.00 (m, 12H), 6.88 (m, 18H), 5.03 (s, 4H), 4.31 (m, 12H), 4.05 (s, 12H), 3.35 (m, 12H), 3.20 (q, J=7.0 Hz, 12H), 1.01 (t, J=7.0 Hz, 18H). UV-vis spectrum (EVA): $\lambda_{max}$=555 nm. Fluorimetry (EVA): $\lambda_{max}$=673 nm.

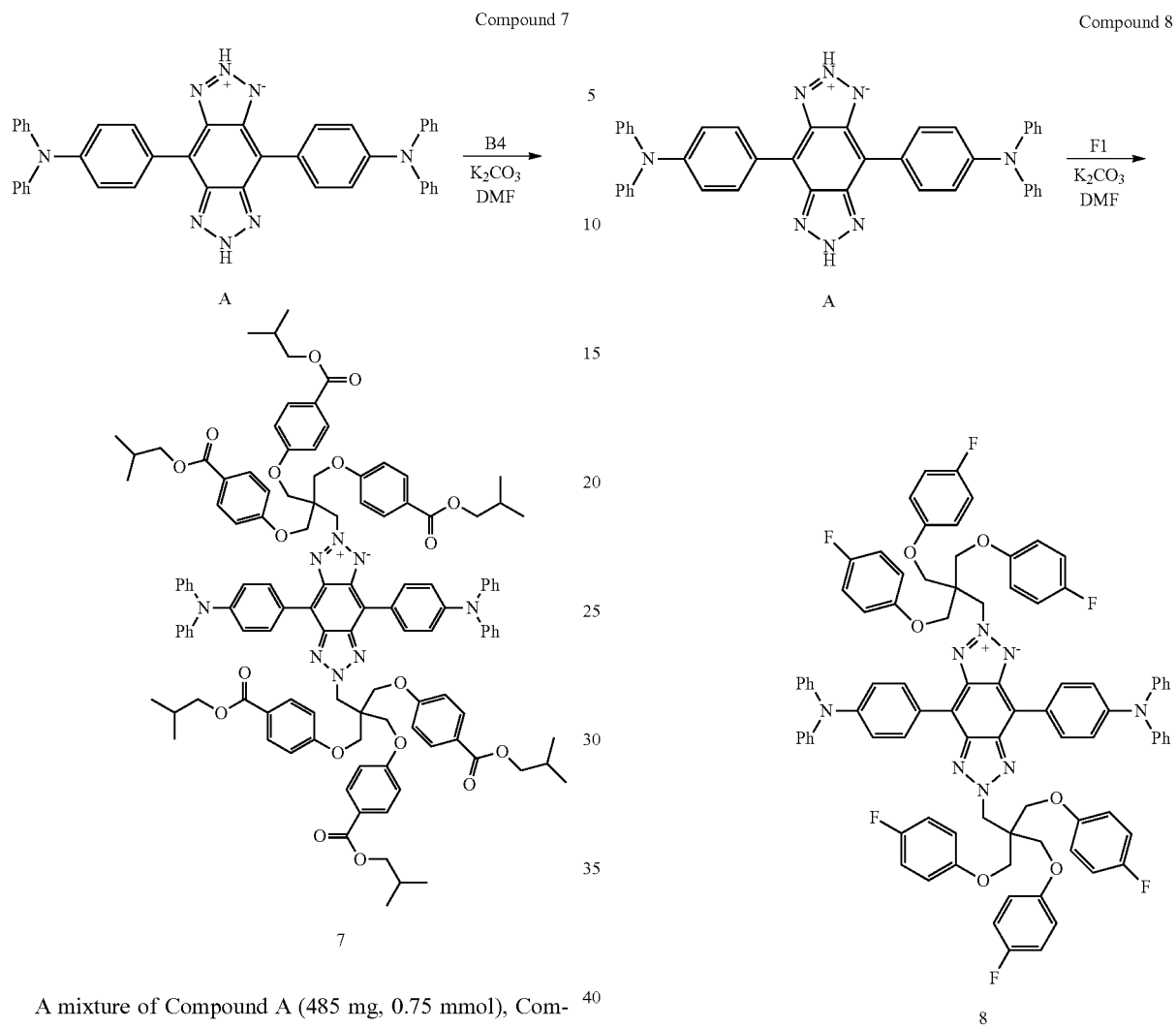

A mixture of Compound A (485 mg, 0.75 mmol), Compound B4 (1.46 g, 2.0 mmol), potassium carbonate (414 mg, 3.0 mmol), and DMF (12 mL) was stirred under argon and heated at 110° C. for 24 h. The reaction mixture was poured into ice/water (300 mL), acidified with 3N HCl to pH 1 and extracted with hexane/toluene/ethyl acetate (1:1:1, 300 mL). The extract was washed with water (200 mL), dried over magnesium sulfate, and the volatiles were removed under reduced pressure. Chromatography of the residue (silica gel, hexane/DCM/ethyl acetate (35:60:5) and crystallization of the separated product from acetone/methanol afforded pure Compound 7, 4,8-bis(4-(diphenylamino)phenyl)-2,6-bis(3-(4-(isobutoxycarbonyl)-phenoxy)-2,2-bis((4-(isobutoxycarbonyl)phenoxy)methyl)propyl)-2H-benzo[1,2-d:4,5-d']bis([1,2,3]triazole)-6-ium-5-ide, (90 mg, 5% yield), $^1$H NMR (benzene-D$_6$): δ 8.46 (d, J=8.8 Hz, 4H), 7.82 (d, J=8.8 Hz, 12H), 6.90-7.20 (m, 24H), 6.62 (d, J=8.8 Hz, 12H), 5.14 (s, 4H), 4.15 (s, 12H), 3.89 (d, J=6.6 Hz, 12H), 1.83 (m, 6H), 0.82 (d, J=7.0 Hz, 36H). UV-vis spectrum (EVA): $\lambda_{max}$=550 nm. Fluorimetry (EVA): $\lambda_{max}$=654 nm.

A mixture of Compound A (323 mg, 0.5 mmol), Compound F1 (962 mg, 2.0 mmol), potassium carbonate (690 mg, 5.0 mmol), and DMF (5 mL) was stirred under argon and heated at 120° C. for 3 h. After cooling, the reaction mixture was poured into water (200 mL) and extracted with petroleum ether/toluene/ethyl acetate (1:1:1, 200 mL). The extract was washed with water (200 mL), and the volatiles were removed under reduced pressure. Column chromatography of the residue (silica gel, hexane/toluene, 1:2) afforded Compound 8, 4,8-bis(4-(diphenylamino)phenyl)-2,6-bis(3-(4-fluorophenoxy)-2,2-bis((4-fluorophenoxy)methyl)propyl)-2H-benzo[1,2-d:4,5-d']bis([1,2,3]triazole)-6-ium-5-ide, (444 mg, 61% yield). $^1$H NMR (benzene-D$_6$): δ 8.86 (d, J=8.8 Hz, 4H), 7.17 (d, J=8.8 Hz, 4H), 7.15 (m, 16H), 6.99 (m, 4H), 6.64 (m, 12H), 6.53 (m, 12H), 5.15 (s, 4H), 4.08 (s, 12H). UV-vis spectrum (EVA): $\lambda_{max}$=558 nm. Fluorimetry (EVA): $\lambda_{max}$=638 nm.

Compound 9

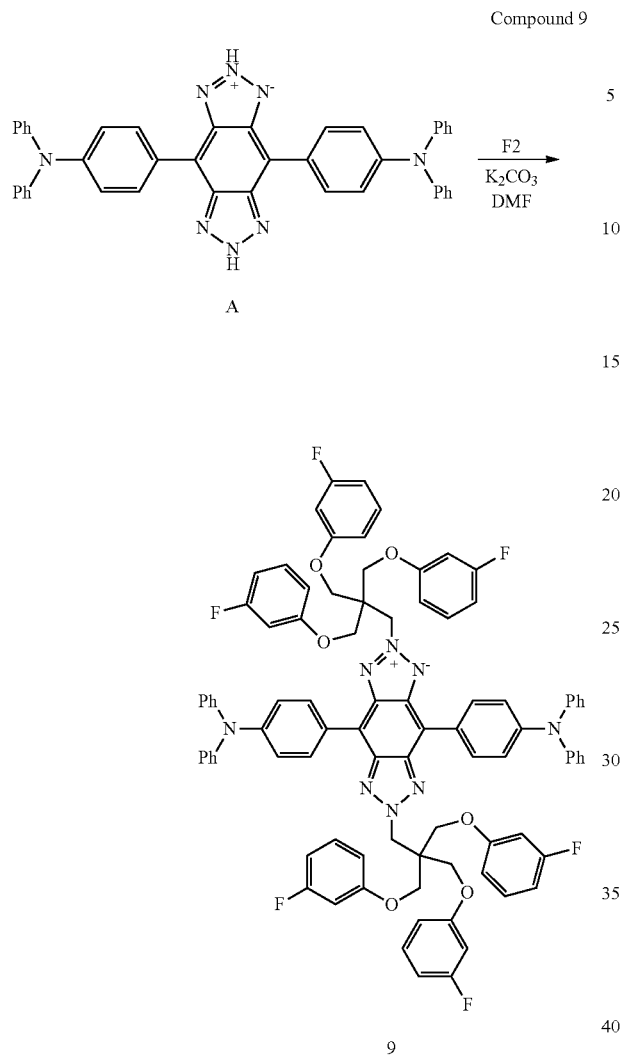

9

Compound 10

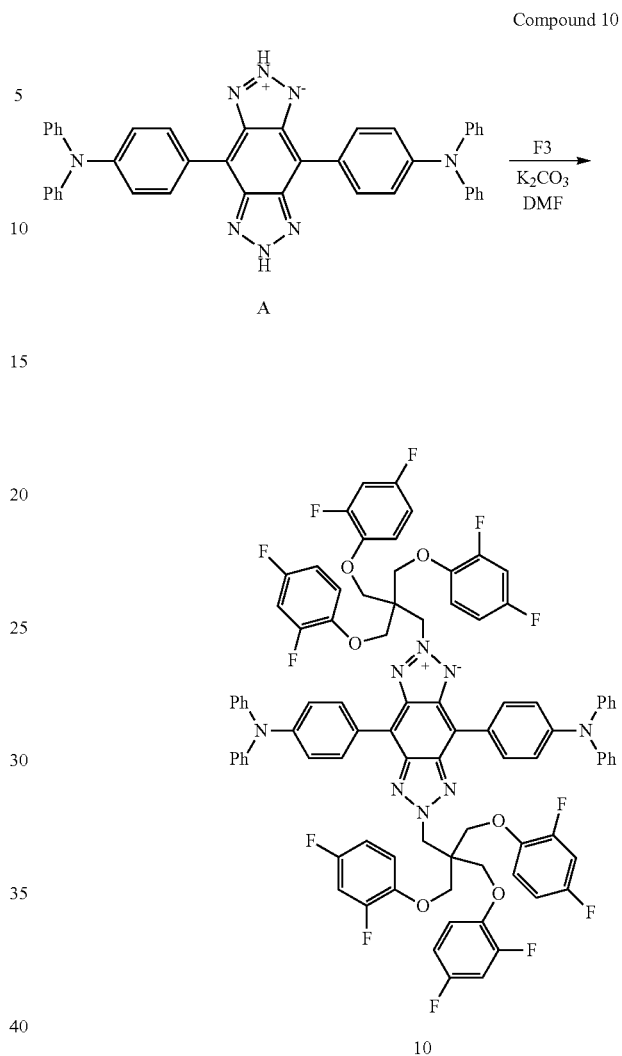

10

A mixture of Compound A (323 mg, 0.5 mmol), Compound F2 (858 mg, 1.5 mmol), potassium carbonate (690 mg, 5.0 mmol), and DMF (10 mL) was stirred under argon and heated at 110° C. for 22 h. After cooling, the reaction mixture was poured into water (100 mL) and extracted with toluene/ethyl acetate (1:1, 100 mL). The extract was washed with water (2×100 mL), and the volatiles were removed under reduced pressure. Column chromatography of the residue (silica gel, DCM/Hexane, 2:3) afforded Compound 9, 4,8-bis(4-(diphenylamino)phenyl)-2,6-bis(3-(3-fluorophenoxy)-2,2-bis((3-fluorophenoxy)methyl)propyl)-2H-benzo[1,2-d:4,5-d']bis([1,2,3]triazole)-6-ium-5-ide, (410 mg, 56% yield). $^1$H NMR (500 MHz, benzene-D$_6$): δ 8.86 (d, J=8.8 Hz, 4H), 7.14 (m, 6H), 7.07 (d, J=8.8 Hz, 4H), 6.95 (m, 4H), 6.74 (m, 6H), 6.52 (m, 6H), 6.47 (m, 6H), 6.42 (m, 6H), 5.05 (s, 4H), 3.98 (s, 12H). UV-vis spectrum (EVA) $\lambda_{max}$=563 nm. Fluorimetry (EVA): $\lambda_{max}$=640 nm.

A mixture of Compound A (323 mg, 0.5 mmol), Compound F3 (940 mg, 1.5 mmol), potassium carbonate (690 mg, 5.0 mmol), and DMF (10 mL) was stirred under argon and heated at 110° C. for 18 h. After cooling, the reaction mixture was poured into water (100 mL) and extracted with toluene/ethyl acetate (1:1, 100 mL). The extract was washed with water (2×100 mL), and the volatiles were removed under reduced pressure. Column chromatography of the residue (silica gel, DCM/Hexane, 1:1) afforded Compound 10, 2,6-bis(3-(2,4-difluorophenoxy)-2,2-bis((2,4-difluorophenoxy)methyl)-propy)-4,8-bis(4-(diphenylamino)phenyl)-2H-benzo[1,2-d:4,5-d']bis([1,2,3]triazole)-6-ium-5-ide, (310 mg, 38% yield). $^1$H NMR (500 MHz, benzene-D$_6$): δ 8.88 (d, J=9.0 Hz, 4H), 7.22 (d, J=9.0 Hz, 4H), 7.15 (m, 16H), 6.97 (m, 4H), 6.46 (m, 12H), 6.32 (m, 6H), 5.20 (s, 4H), 4.16 (s, 12H). UV-vis spectrum (EVA): $\lambda_{max}$=560 nm. Fluorimetry (EVA): $\lambda_{max}$=641 nm.

Compound 11

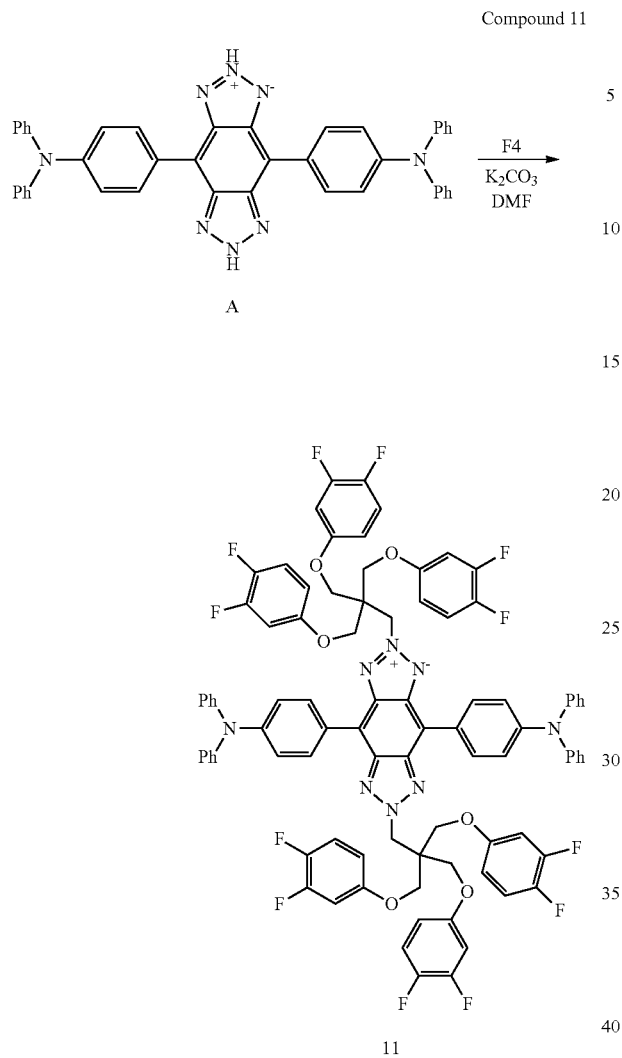

11

A mixture of Compound A (162 mg, 0.25 μmol), Compound F4 (410 mg, 0.65 mmol), potassium carbonate (345 mg, 2.5 mmol), and DMF (5 mL) was stirred under argon and heated at 110° C. for 18 h. After cooling, the reaction mixture was poured into water (50 mL) and extracted with toluene/ethyl acetate (1:1, 2×50 mL). The extract was washed with water (2×50 mL), and the volatiles were removed under reduced pressure. Column chromatography of the residue (silica gel, DCM/Hexane, 1:1) afforded Compound 11, 2,6-bis(3-(3,4-difluorophenoxy)-2,2-bis((3,4-difluorophenoxy)methyl)-propyl)-4,8-bis(4-(diphenylamino)phenyl)-2H-benzo[1,2-d:4,5-d']bis([1,2,3]triazole)-6-ium-5-ide, (120 mg, 30% yield). $^1$H NMR (500 MHz, benzene-D$_6$): δ 8.84 (d, J=8.5 Hz, 4H), 7.16-7.24 (nm, 20H), 6.99 (t, J=7.00 Hz, 4H), 6.55 (m, 6H), 6.40 (m, 6H), 6.18 (d, J=8.0 Hz, 6H), 5.01 (s, 4H), 3.90 (s, 12H). UV-vis spectrum (EVA): $\lambda_{max}$=564 nm. Fluorimetry (EVA): $\lambda_{max}$=639 nm.

Compound 12

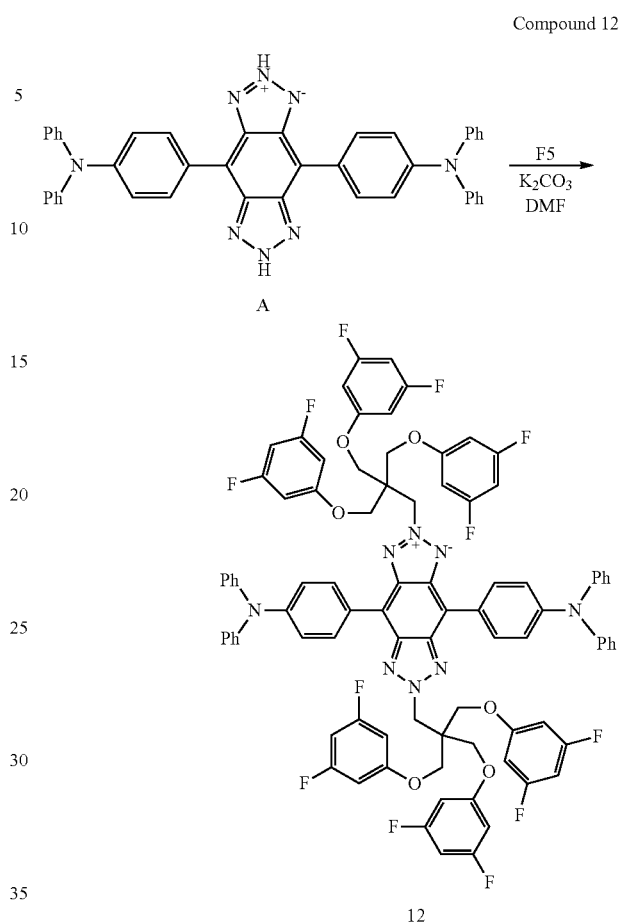

12

A mixture of Compound A (388 mg, 0.6 mmol), Compound F5 (80%, 1.44 g, 2.15 mmol), potassium carbonate (690 mg, 5.0 mmol), and anhydrous DMF (6 mL) was stirred under argon and heated at 90° C. for 18 h. Work-up and purification was similar to those for Compound 8, which gave Compound 12, 2,6-bis(3-(3,5-difluorophenoxy)-2,2-bis((3,5-difluorophenoxy)methyl)-propyl)-4,8-bis(4-(diphenylamino)phenyl)-2H-benzo[1,2-d:4,5-d']bis([1,2,3]triazole)-6-ium-5-ide, (335 mg, 36% yield). UV-vis spectrum (EVA): $\lambda_{max}$=566 nm. Fluorimetry (EVA): $\lambda_{max}$=650 nm.

Compound 13

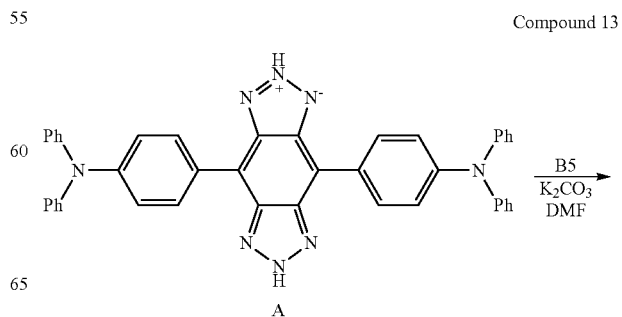

129
-continued

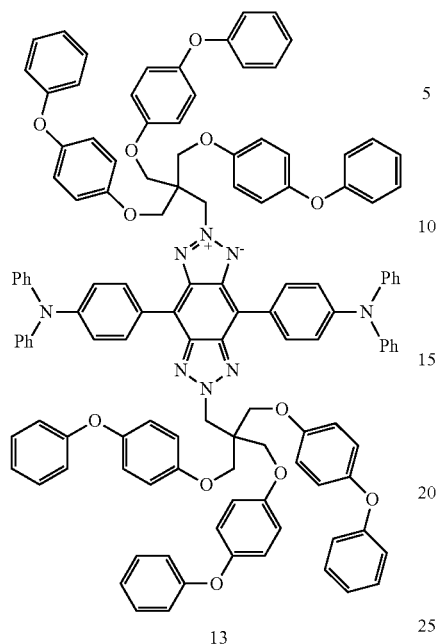

13

A mixture of Compound A (517 mg, 0.8 mmol), Compound B5 (1.65 g, 2.3 mmol), potassium carbonate (690 mg, 5.0 mmol), and DMF (8 mL) was stirred under argon and heated at 120° C. for 4 h. The reaction mixture was poured into water (300 mL) and extracted with toluene/ethyl acetate (2:1, 300 mL). The extract was washed with water (200 mL), and the volatiles were removed under reduced pressure. Chromatography of the residue (silica gel, toluene) followed by crystallization from acetone/methanol gave Compound 13, 4,8-bis(4-(diphenylamino)phenyl)-2,6-bis(3-(4-phenoxyphenoxy)-2,2-bis((4-phenoxyphenoxy)methyl)propyl)-2H-benzo[1,2-d:4,5-d']bis([1,2,3]triazole)-6-ium-5-ide, (524 mg, 34% yield). $^1$H NMR (benzene-D$_6$): δ 8.92 (d, J=8.8 Hz, 4H), 7.30 (d, J=8.8 Hz, 4H), 7.07 (m, 28H), 6.91 (m, 12H), 6.84 (m, 10H), 6.77 (d, J=8.7 Hz, 12H), 6.65 (d, J=8.7 Hz, 12H), 5.20 (s, 4H), 4.23 (s, 12H). UV-vis spectrum (EVA): λ$_{max}$=553 nm. Fluorimetry (EVA): λ$_{max}$=636 nm.

130
-continued

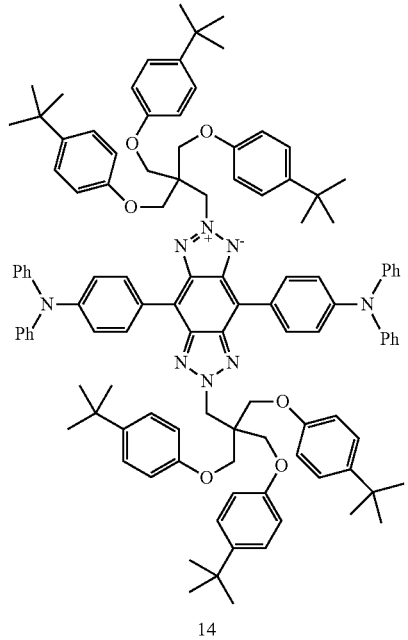

14

A mixture of Compound A (258 mg, 0.4 mmol), Compound B6 (542 mg, 0.91 mmol), potassium carbonate (690 mg, 5 mmol), and DMF (5 mL) was stirred under argon and heated at 120° C. for 4 h. Work-up was similar to Compound 13, column chromatography (silica gel, hexane/toluene, 1:2) and crystallization from acetone/methanol afforded Compound 14, 2,6-bis(3-(4-(tert-butyl)phenoxy)-2,2-bis((4-(tert-butyl)phenoxy)methyl)propyl)-4,8-bis(4-(di phenyl amino) phenyl)-2H-benzo[1,2-d:4,5-d']bis([1,2,3]triazole)-6-ium-5-ide, (88 mg, 13% yield). $^1$H NMR (benzene-D$_6$): δ 8.65 (m, 4H), 7.17 (m, 20H), 7.11 (d, J=8.8 Hz, 12H), 6.94 (m, 4H), 6.82 (d, J=8.8 Hz, 12H), 5.34 (s, 41H), 4.37 (s, 12H), 1.20 (s, 54H). UV-vis spectrum (EVA): λ$_{max}$=536 nm. Fluorimetry (EVA): λ$_{max}$=621 nm.

Compound 14                                   Compound 15

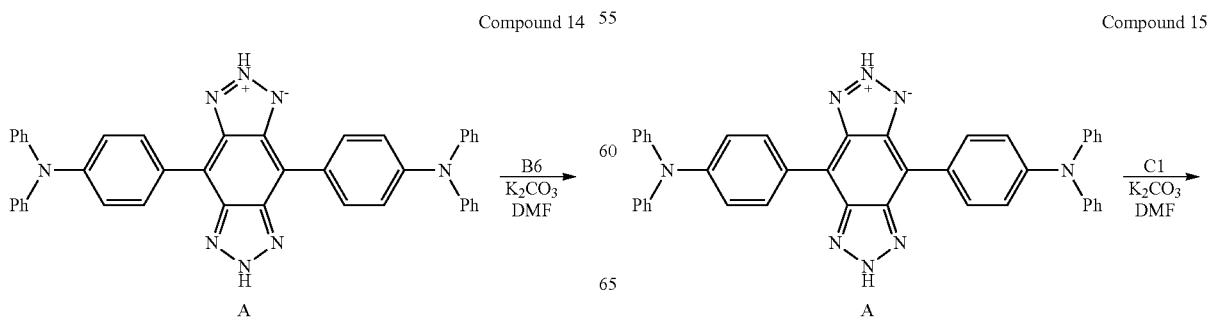

131

-continued

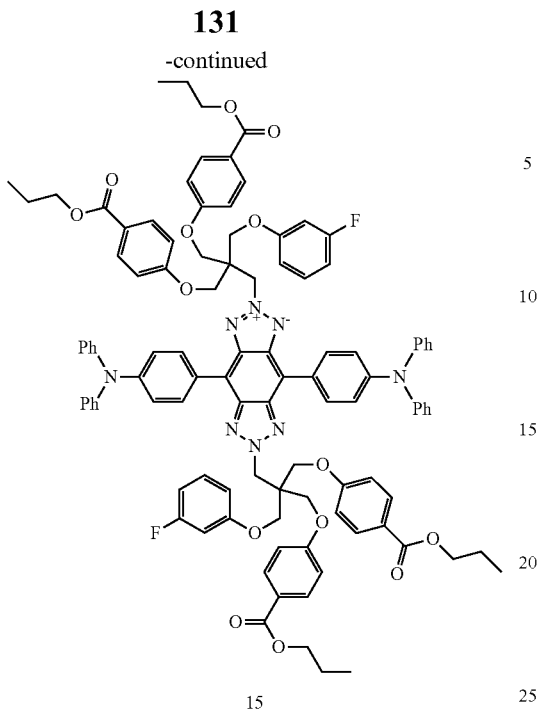

15

A mixture of Compound A (517 mg, 0.8 mmol), Compound C1 (75%, 2.44 mg, 3.0 mmol), potassium carbonate (552 mg, 4.0 mmol), and DMF (12 mL) was stirred under argon and heated at 110° C. for 18 h. After cooling, the mixture was poured into ice/water (200 mL) and extracted with ethyl acetate/toluene (1:1, 400 mL). The extract was washed with water (200 mL), dried over magnesium sulfate, and the solvent was removed under reduced pressure. Column chromatography of the residue (silica gel, hexane/DCM/ethyl acetate, 48:50:2) and recrystallization from acetone afforded Compound 15, 2,6-bis(3-(3-chlorophenoxy)-2,2-bis((4-(propoxycarbonyl)phenoxy)-methyl)propyl)-4,8-bis(4-(diphenylamino)phenyl)-2H-benzo[1,2-d:4,5-d']bis([1,2,3]triazole)-6-ium-5-ide, (235 mg, 17% yield). UV-vis spectrum (EVA): $\lambda_{max}$=558 nm. Fluorimetry (EVA): $\lambda_{max}$=641 nm.

Compound 16

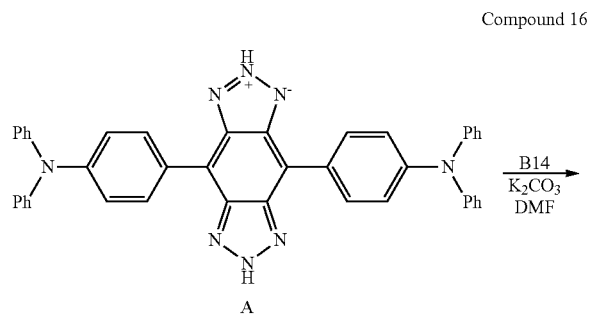

132

-continued

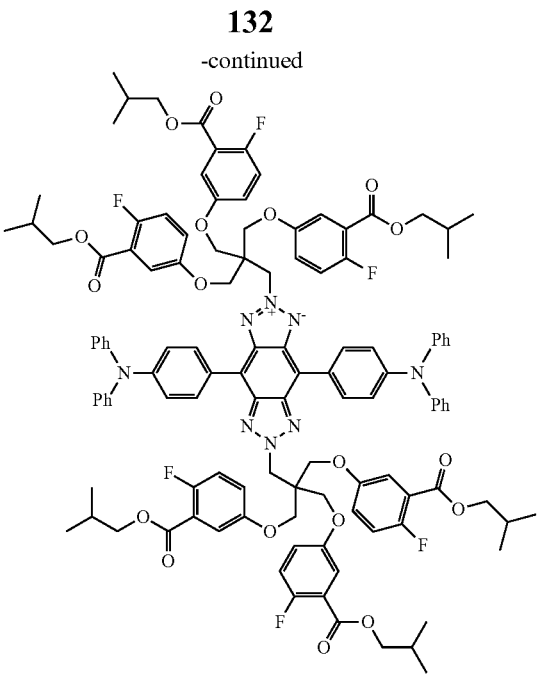

16

A mixture of Compound A (485 mg, 0.75 mmol), Compound B14 (1.50 g, 1.9 mmol), potassium carbonate (414 mg, 3.0 mmol), and DMF (12 mL) was stirred under argon and heated at 110° C. for 24 h. The reaction mixture was poured into ice/water (300 mL), acidified with 3N HCl to pH 1 and extracted with hexane/toluene/ethyl acetate (1:1:1, 300 mL). The extract was washed with water (200 mL), dried over magnesium sulfate, and the volatiles were removed under reduced pressure. Chromatography of the residue (silica gel, hexane/DCM/ethyl acetate, 48:50:2) and crystallization of the separated product from acetone/methanol afforded pure Compound 16, 4,8-bis(4-(diphenylamino)phenyl)-2,6-bis(3-(4-fluoro-3-(isobutoxycarbonyl)phenoxy)-2,2-bis((4-fluoro-3-(isobutoxycarbonyl)phenoxy)-methyl)propyl)-2H-benzo[1,2-d:4,5-d']bis([1,2,3]triazole)-6-ium-5-ide, (331 mg, 22% yield). $^1$H NMR (benzene-D$_6$): δ 8.37 (d, J=8.8 Hz, 4H), 7.34 (dd, J=3.3 and 5.2 Hz, 6H), 7.00-7.20 (m, 16H), 6.92 (m, 8H), 6.65 (dt, J=9.0 and 3.3 Hz, 6H), 6.55 (t, J=9.3 Hz, 6H), 5.08 (s, 4H), 4.04 (s, 12H), 3.88 (d, J=6.6 Hz, 12H), 1.81 (m, 6H), 0.78 (d, J=6.6 Hz, 36H). UV-vis spectrum (EVA): $\lambda_{max}$=550 nm. Fluorimetry (EVA): $\lambda_{max}$=651 nm.

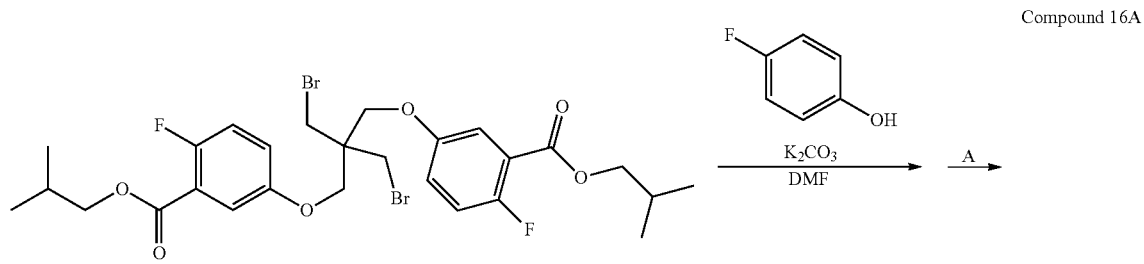

Compound 16A

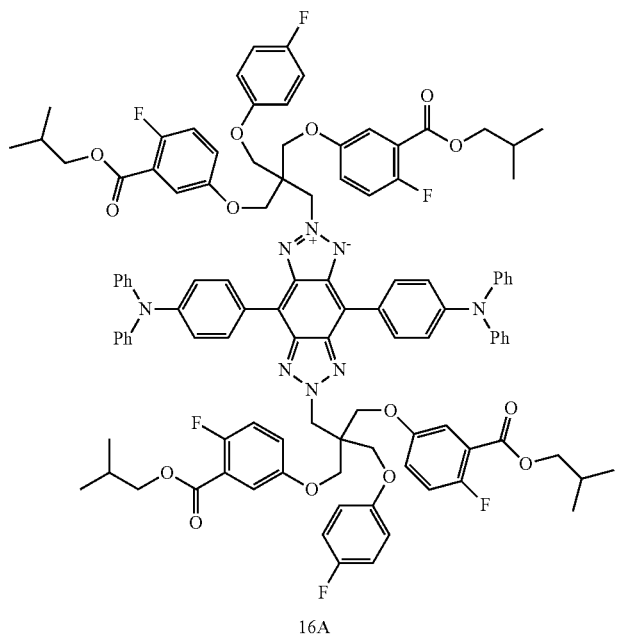

16A

A mixture of diisobutyl 5,5'-((2,2-bis(bromomethyl)propane-1,3-diyl)bis(oxy))bis(2-fluorobenzoate) (a side product from preparation of Compound B14, 0.98 g, 1.50 mmol), 4-fluorophenol (196 mg, 1.75 mmol), potassium carbonate (414 mg, 3.0 mmol), and DMF (5 mL) was stirred under argon and heated at 100° C. for 16 h, and then at 110° C. for additional 8 h.

Compound A (323 mg, 0.5 µmol), potassium carbonate (414 mg, 3.0 mmol) and DMF (5 mL) were added to the reaction mixture, and the whole was stirred and heated at 110° C. for 16 h. The mixture was poured into ice/water (200 mL), acidified to pH 3 with IN HCl and extracted with toluene/EA (1:1, 200 mL). The extract was washed with water (100 mL), dried over magnesium sulfate, and the solvent was removed under reduced pressure. The residue was chromatographed (silica gel/hexane/toluene/EA, 45:50:5) to afford Compound 16A, 4,8-bis(4-(diphenylamino)phenyl)-2,6-bis(3-(4-fluoro-3-(isobutoxycarbonyl)phenoxy)-2-((4-fluoro-3-(isobutoxycarbonyl)phenoxy)methyl)-2-((4-fluorophenoxy)methyl)propyl)-2H-benzo[1,2-d:4,5-d']bis([1,2,3]triazole)-6-ium-5-ide, (250 mg, 18% yield) as a glassy material. $^1$H NMR (benzene-D6): δ 8.85 (m, 4H), 7.34 (m, 4H), 7.00-7.20 (m, 16H), 6.92 (m, 8H), 6.65 (m, 8H), 6.55 (m, 8H), 5.06 (s, 4H) 4.04 (s, 8H), 3.97 (d, J=6.6 Hz, 8H), 1.83 (m, 4H), 0.80 (d, J=6.6 Hz, 24H). UV-vis spectrum (PVB): $λ_{max}$=550 nm. Fluorimetry (PVB): $λ_{max}$=641 nm.

Compound 16B

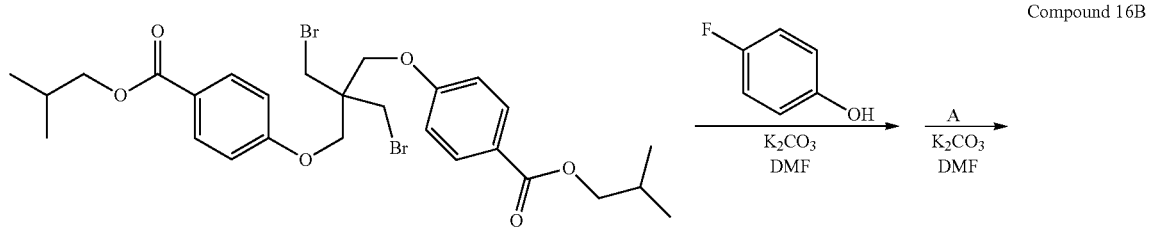

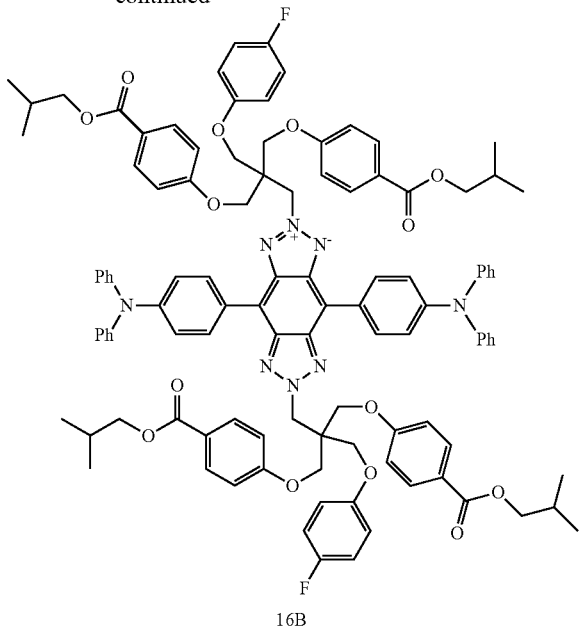

16B

Following a procedure from Compound 16A, diisobutyl 4,4'-((2,2-bis(bromomethyl)propane-1,3-diyl)bis(oxy)) dibenzoate (2.00 g, 3.25 mmol) was treated consecutively with 4-fluorophenol (448 mg, 4.0 mmol) and Compound A (485 mg, 0.75 mmol). The crude product was purified by column chromatography (silica gel, hexane/toluene/EA, 35:50:15) to give Compound 16B, 4,8-bis(4-(diphenylamino)phenyl)-2,6-bis(3-(4-fluorophenoxy)-2,2-bis((4-(isobutoxycarbonyl)phenoxy)methyl)propyl)-2H-benzo[1,2-d:4,5-d']bis([1,2,3]triazole)-6-ium-5-ide, (472 mg, 16% yield). $^1$H NMR (benzene-D6): δ 8.66 (d, J=8.4 Hz, 4H), 8.06 (d, J=8.8 Hz, 4H), 7.92 (d, J=8.8 Hz, 8H), 6.90-7.20 (m, 24H), 6.50-6.80 (m, 12H), 5.13 (s, 4H), 4.15 (s, 12H), 3.90-4.20 (m, 20H), 1.83 (m, 4H), 0.81 (d, J=7.0 Hz, 24H). UV-vis spectrum (PVB): $\lambda_{max}$=551 nm. Fluorimetry (PVB): $\lambda_{max}$=651 nm.

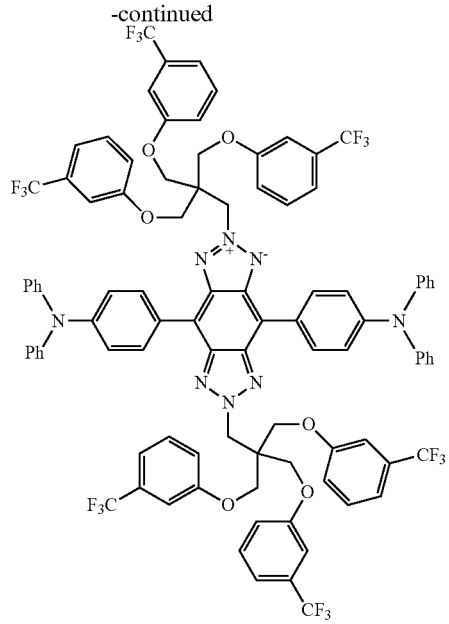

17

Compound 17

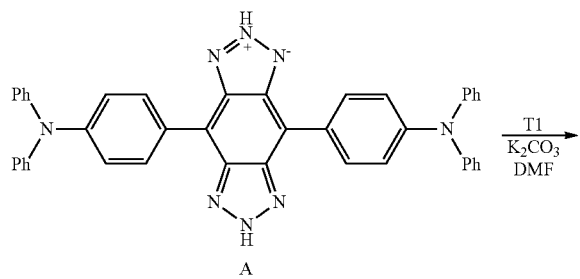

A solution of Compound A (325 mg, 0.5 mmol) in dry DMF (15 mL) was treated with Compound 17 (1.10 g, 1.5 mmol) and K$_2$CO$_3$ (560 mg, 4 mmol), and the reaction mixture was stirred under nitrogen and heated at 125° C. for 16 h. Work-up with ice-cold water, neutralization with 1M HCl, extraction with ethyl acetate (100 mL) containing small amount of THF (5 mL), washing the organic layer with water and drying with MgSO$_4$ afforded 1.3 g of a glassy material, which was subjected to column chromatography using DCM/Hex (1:1-3:2) as a mobile phase. The separated product was crystallized from acetone/methanol to give Compound 17, 4,8-bis(4-(diphenylamino)phenyl)-2,6-bis(3-(3-(trifluoromethyl)phenoxy)-2,2-bis((3-(trifluoromethyl)

phenoxy)methyl)propyl)-2H-benzo[1,2-d:4,5-d']bis([1,2,3]triazole)-6-ium-5-ide, as purple crystals (247 mg, 28% yield). $^1$H NMR (500 MHz, C$_6$H$_6$): δ 8.67 (d, J=9.0 Hz, 4H), 7.16-7.12 (m, 22H), 6.95-6.92 (m, 14H), 6.79 (m, 6H), 6.71 (d, J=8.0 Hz, 6H), 5.04 (s, 4H), 4.00 (s, 12H). UV-vis spectrum (EVA): $λ_{max}$=562 nm. Fluorimetry (EVA): $λ_{max}$=650 nm.

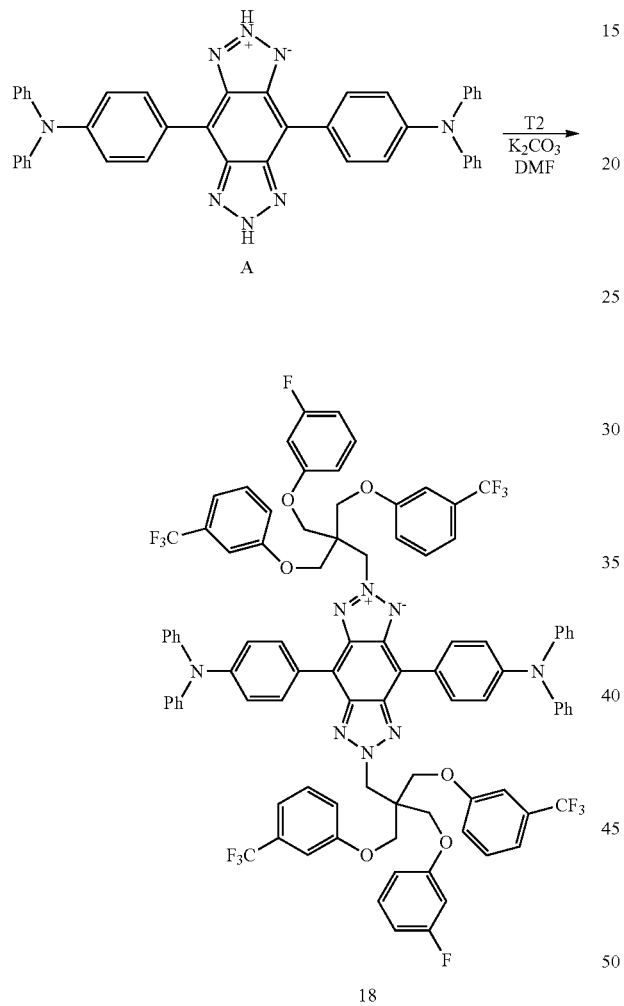

Starting from Compound T2 and applying conditions similar to those for Compound 17, Compound 18, 4,8-bis(4-(diphenylamino)phenyl)-2,6-bis(3-(3-fluorophenoxy)-2,2-bis((3-(trifluoromethyl)phenoxy)methyl)propyl)-2H-benzo[1,2-d:4,5-d']bis([1,2,3]triazole)-6-ium-5-ide, was obtained. $^1$H NMR (400 MHz, C$_6$H$_6$): δ 8.69 (d, J=8.0 Hz, 4H), 7.96 (m, 12H), 7.12-7.35 (m, 20H), 6.74-6.79 (m, 6H), 6.66-6.68 (m, 4H), 6.40-6.55 (m, 6H), 5.03 (s, 4H), 3.98 (s, 8H), 3.96 (s, 4H). UV-vis spectrum (EVA): $λ_{max}$=560 nm. Fluorimetry (EVA): $λ_{max}$=650 nm.

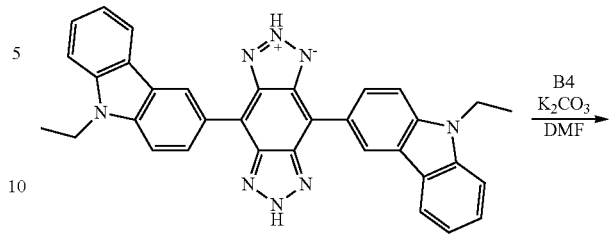

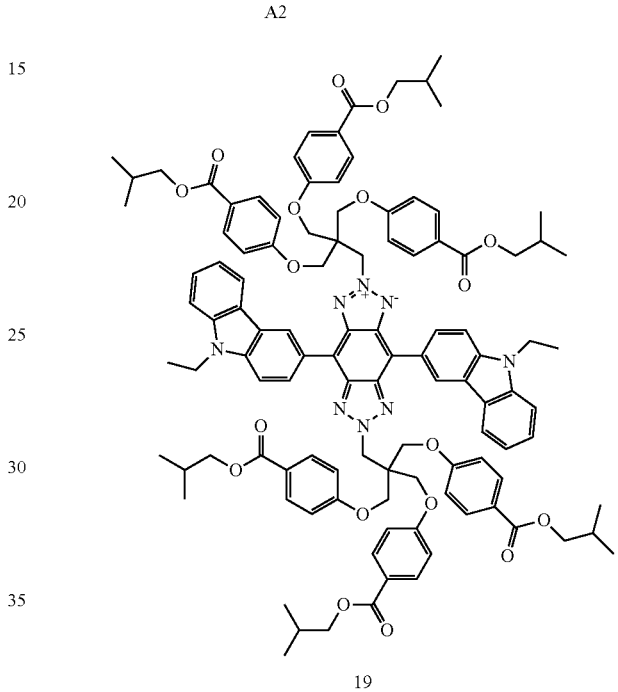

Compound A2 (280 mg, 0.5 mmol) in 20 mL of dry DMF was treated with Compound B4 (1.15 g, 3 eq.) and potassium carbonate (700 mg, 5.0 mmol) under nitrogen protection at 110° C. for 18 hours. Work-up with water and ethyl acetate. After drying of the extract over magnesium sulfate, the solvent was removed, and the residue was subjected to column chromatography using first DCM and later 2.5% ethyl acetate in DCM. Recrystallization of the obtained product from acetone/MeOH provided pure Compound 19, 4,8-bis(9-ethyl-9H-carbazol-3-yl)-2,6-bis(3-(4-(isobutoxycarbonyl)-phenoxy)-2,2-bis((4-(isobutoxycarbonyl)phenoxy)methyl)propyl)-2H-benzo[1,2-d:4,5-d']bis([1,2,3]triazole)-6-ium-5-ide, of purple color (355 mg, 38% yield). $^1$H NMR (benzene-D$_6$): δ 9.8 (s, 2H), 8.97 (m, 2H), 8.18 (m, 2H), 8.05 (m, 14H), 8.18 (m, 2H), 7.44 (m, 2H), 7.32 (m, 2H), 6.80 (d, J=8.8 Hz, 2H), 6.71 (m, 12H), 5.20 (bs, 4H), 4.21 (m, 12H), 4.0 (m, 12H), 1.80-1.87 (m, 6H), 1.20-1.26 (m, 6H), 0.79 (m, 36H). UV-vis spectrum (EVA): $λ_{max}$=535 nm. Fluorimetry (EVA): $λ_{max}$=631 nm.

Compound 20

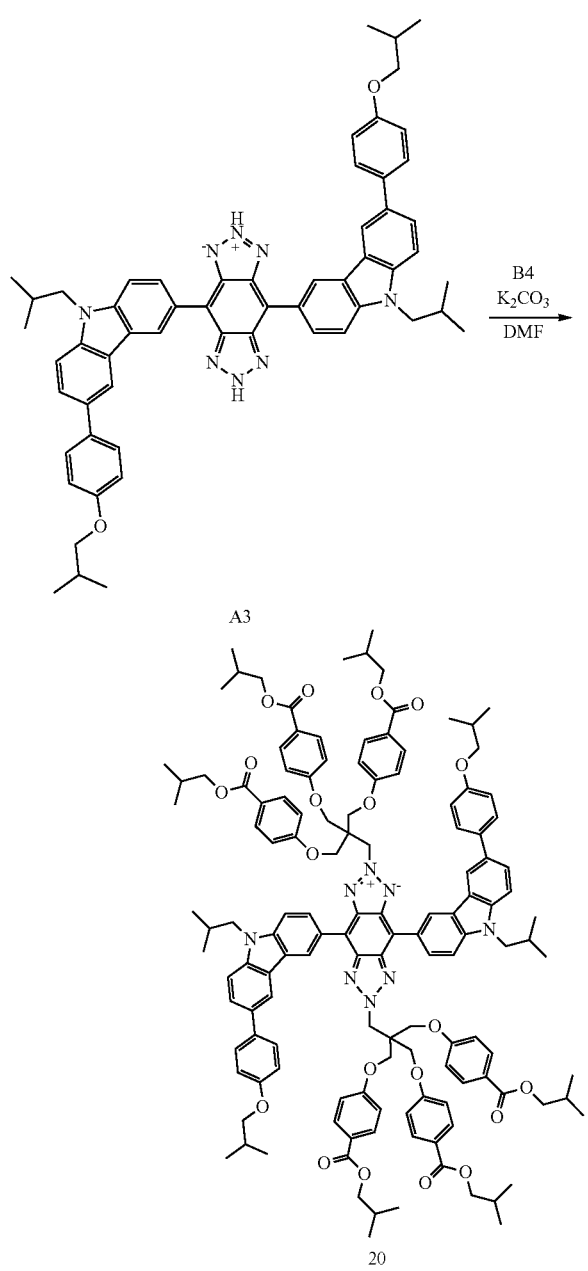

20

A solution of Compound A3 (330 mg, 0.36 mmol) in DMF (10 mL) was treated with Compound B4 (916 mg, 1.28 mmol) and potassium carbonate (500 mg, 3.6 mmol) and heated for 14 h at 110° C. The reaction mixture was poured into water (100 mL). The precipitate was filtered off, washed with water, followed by MeOH, and dried in a vacuum oven. Column chromatography of the crude product using a mixture of hexane/DCM/ethyl acetate (37:60:3) provided pure Compound 20 as a purple solid (92 mg, 12% yield). $^1$H NMR (400 MHz, CDCl$_3$): δ 9.24 (s, 2H), 8.39 (d, J=8.5 Hz, 2H), 8.21 (s, 2H), 7.99 (d, J=9.0 Hz, 12H), 7.81 (d, J=9.0 Hz, 4H), 7.57 (d, J=8.5 Hz, 2H), 7.46 (d, J=8.5 Hz, 2H), 7.12 (d, J=9.0 Hz, 2H), 6.97 (d, J=8.5 Hz, 12H), 6.92 (d, J=9.0 Hz, 4H), 5.53 (s, 4H), 4.51 (s, 10H), 4.32 (s, 8H), 4.13 (d, J=8.5 Hz, 4H), 4.07 (d, J=7.0 Hz, 8H), 4.01 (d, J=7.0 Hz, 12H), 3.78 (d, J=6.5 Hz, 4H), 2.43 (m, 2H), 1.98-2.09 (m, 8H), 1.04 (d, J=7.0 Hz, 6H), 1.00 (d, J=6.5 Hz, 6H), 0.96 (d, J=6.5 Hz, 36H).

Compound 21

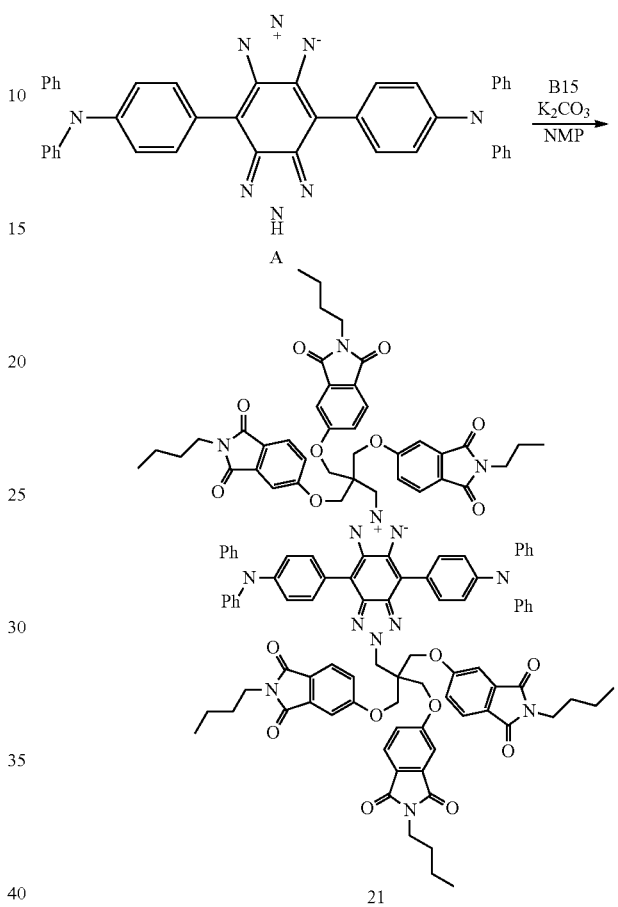

21

A mixture of Compound A (400 mg, 0.62 mmol), Compound B15 (1.96 g, 24 mmol), potassium carbonate (552 mg, 4.0 mmol), and NMP (12 mL) was stirred under argon and heated at 110° C. for 5 h. The reaction mixture was poured into ice/water (300 mL) and extracted with toluene/ethyl acetate (1:2, 300 mL). The extract was washed with water (200 mL), dried over magnesium sulfate, and the volatiles were removed under reduced pressure. Chromatography of the residue (silica gel, hexane/ethyl acetate, 2:1) afforded Compound 21, 2-(3-((2-butyl-1,3-dioxoisoindolin-5-yl)oxy)-2,2-bis(((2-butyl-1,3-dioxoisoindolin-5-yl)oxy)methyl)propyl)-6-(3-((2-butyl-1,3-dioxoisoindolin-5-yl)oxy)-2-(((2-butyl-1,3-dioxoisoindolin-5-yl)oxy)methyl)-2-(((1,3-dioxo-2-propylisoindolin-5-yl)oxy)methyl)propyl)-4,8-bis(4-(diphenylamino)phenyl)-2H-benzo[1,2-d:4,5-d']bis([1,2,3]triazole)-6-ium-5-ide, (120 mg, 9% yield). $^1$H NMR (benzene-D$_6$): δ 8.49 (d, J=8.1 Hz, 4H), 7.31 (d, J=8.0 Hz, 6H), 6.90-7.20 (m, 30H), 6.67 (m, 6H), 5.03 (s, 4H), 4.12 (s, 12H), 3.43 (t, J=7.0 Hz, 12H), 1.46 (quintet, J=7.3 Hz, 12H), 1.14 (sextet, J=7.3 Hz, 12H), 0.76 (t, J=7.3 Hz, 18H). UV-vis spectrum (EVA): λ$_{max}$=550 nm. Fluorimetry (EVA): λ$_{max}$=657 nm.

Comparative Example Compound 22

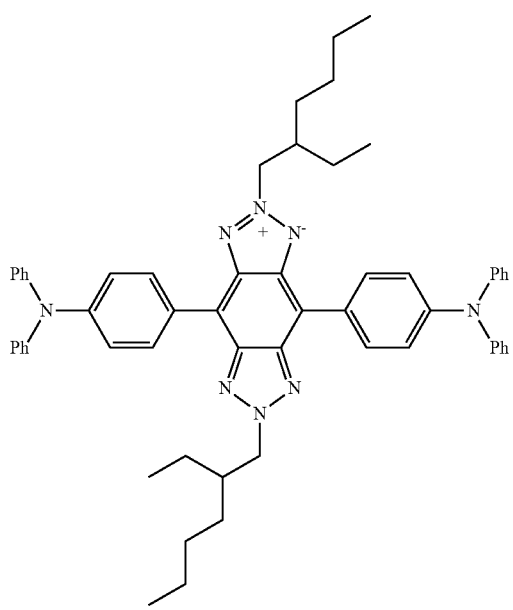

CE-22

Comparative Example Compound 22 (CE-22) was prepared using similar methods to those described in International Patent Application PCT/US2014/010226, which is hereby incorporated by reference in its entirety.

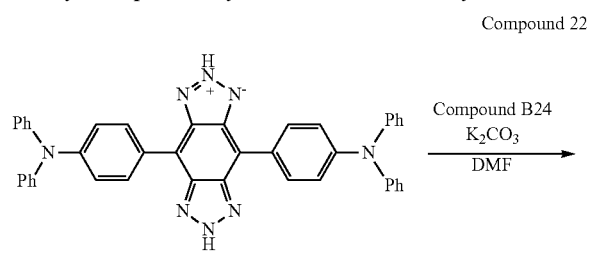

Compound 22

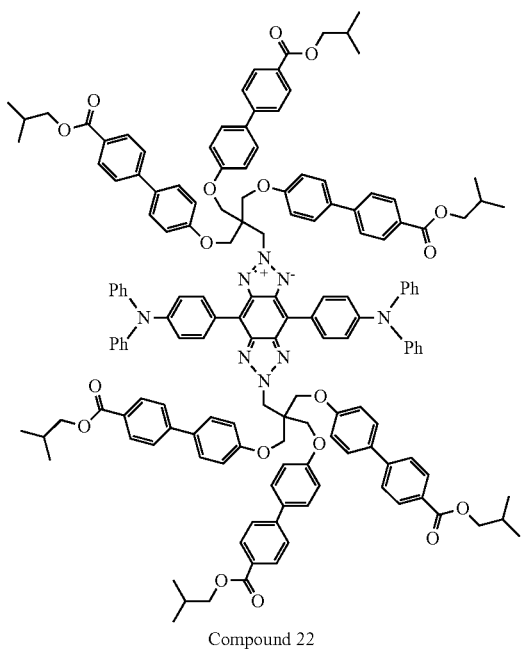

Compound 22

In a procedure analogous to the above, 4,8-bis(4-(diphenylamino)phenyl)-2H-benzo[1,2-d:4,5-d']bis([1,2,3]triazole)-6-ium-5-ide (647 mg, 1.0 mmol) reacted with Compound B24 (1.90 g, 2 mmol) and potassium carbonate (552 mg, 4.0 mmol) to give Compound 22 (1.20 g, 50% yield) $^1$H NMR (400 MHz, CDCl3): δ 8.20 (d, J=8.8 Hz, 4H), 8.01 (d, J=8.4 Hz, 12H), 7.45 (d, J=8.4 Hz, 12H), 7.37 (d, J=8.8 Hz, 12H), 7.15 (t, J=7.3 Hz, 8H), 6.99 (m, 12H), 6.96 (d, J=8.8 Hz, 12H), 6.84 (d, J=8.8 Hz, 4H), 5.47 (s, 4H), 4.45 (s, 12H), 4.11 (d, J=6.6 Hz, 12H), 2.09 (m, 6H), 1.02 (d, J=6.6 Hz, 36H). UV-vis spectrum (PVB): $\lambda_{max}$=554 nm. Fluorimetry (PVB): $\lambda_{max}$=659 nm.

Compound 23

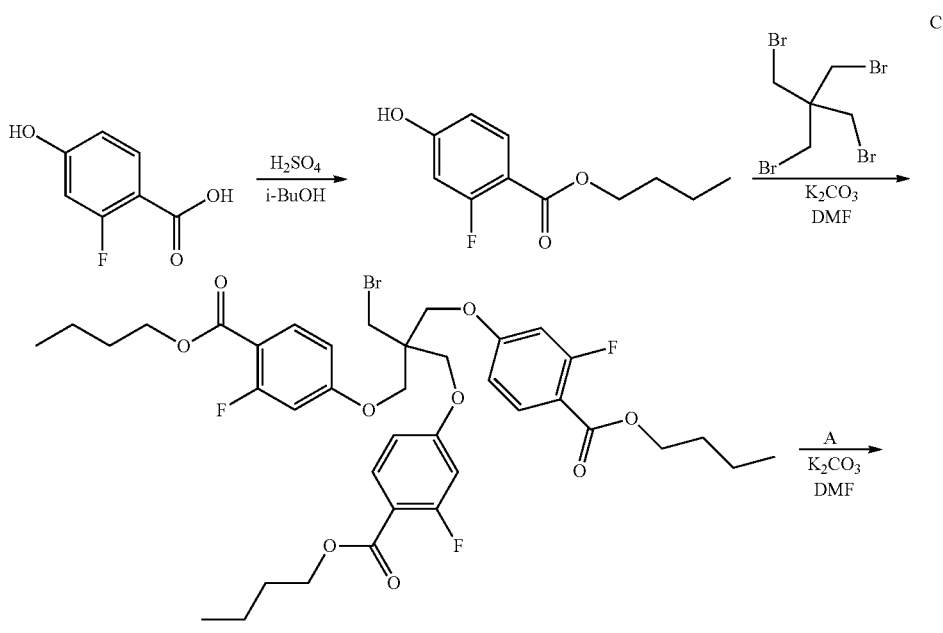

B22

-continued

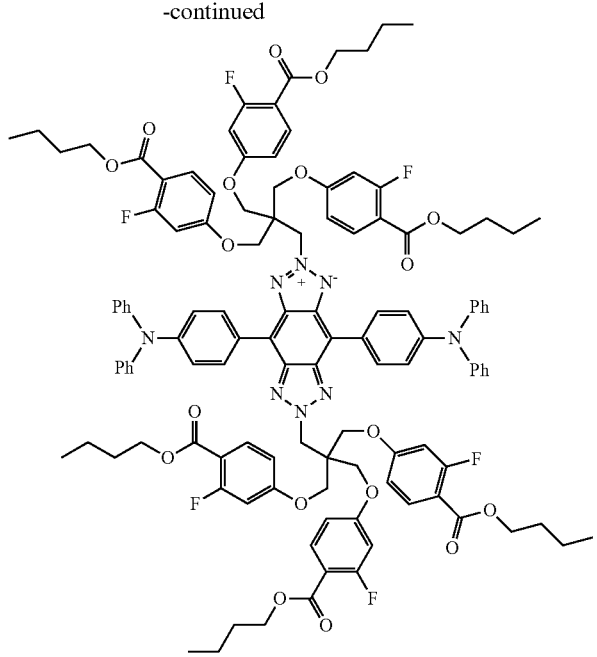

A mixture of 2-fluoro-4-hydroxybenzoic acid (10.00 g, 64 mmol), n-butanol (80 mL) and 20% oleum (1 mL) was heated at 100° C. for 20 h. The mixture was diluted with toluene (100 mL), and the volatiles were removed under reduced pressure. A solution of the residue in ethyl acetate (200 mL) was washed with brine (2×100 mL), dried over magnesium sulfate, and the solvent was removed under reduced pressure to give pure n-butyl 2-fluoro-4-hydroxybenzoate (13.02 g, 96% yield).

A mixture of n-butyl 2-fluoro-4-hydroxybenzoate (6.37 g, 30 mmol), pentaerythrityl tetrabromide (3.87 g, 10 mmol), potassium carbonate (7.68 g, 60 mmol), and DMF (20 mL) was stirred under argon and heated at 100° C. for 16 h. The reaction mixture was poured into ice/water (300 mL), acidified to pH 2 with 3N HCl and extracted with ethyl acetate/hexane (200+100 mL). The extract was washed with water (200 mL), dried over magnesium sulfate, and the volatiles were removed under reduced pressure. Column chromatography of the residue (silica gel, hexane/ethyl acetate, 80:20) afforded pure Compound B22 (3.24 g, 41% yield).

A mixture of Compound A (485 mg, 0.75 mmol), Compound B22 (1.56 g, 2.0 mmol), potassium carbonate (690 mg, 5 mmol), and DMF (5 mL) was stirred under argon and heated at 100° C. for 20 h. After cooling, the reaction mixture was poured into ice/water (200 mL), acidified to pH 1 with 3N HCl, and extracted with hexane/ethyl acetate (1:2, 300 mL). The extract was washed with water (200 mL), dried over magnesium sulfate, and the volatiles were removed under reduced pressure. The residue was subjected to column chromatography (silica gel, hexane/ethyl acetate, 2:1) to give crude product Compound 23 that was further purified by recrystallization from acetone/methanol to afford pure Compound 23 (115 mg, 7% yield). $^1$H NMR (400 MHz, benzene-$d_6$): δ 8.61 (d, J=8.8 Hz, 4H), 7.77 (t, J=8.8 Hz, 6H), 6.90-7.20 (m, 20H), 6.34 (m, 16H), 4.96 (s, 4H), 4.14 (t, J=6.6 Hz, 18H), 3.90 (s, 12H), 1.50 (quintet, J=6.6 Hz, 12H), 1.25 (sextet, J=7.3 Hz, 12H), 0.78 (t, J=7.3 Hz, 18H). UV-vis spectrum (EVA): $\lambda_{max}$=554 nm. Fluorimetry (EVA): $\lambda_{max}$=668 nm.

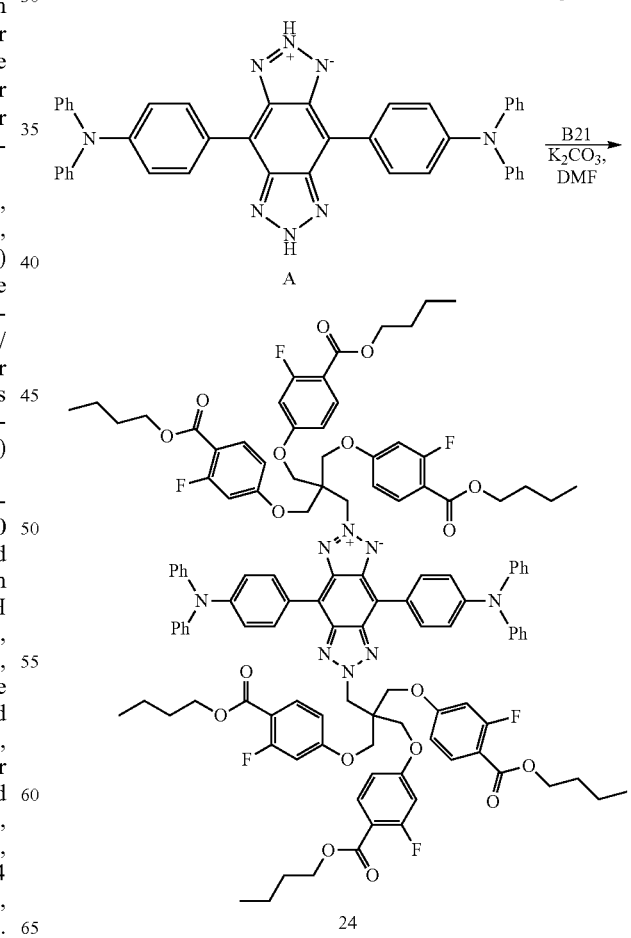

Compound 24

A mixture of Compound A (485 mg, 0.75 mmol), Compound B21 (1.56 g, 2.0 mmol), potassium carbonate (690 mg, 5.0 mmol), and DMF (5 mL) was stirred under argon and heated at 100° C. for 20 h. The reaction mixture was poured into ice/water (200 mL), acidified to pH 1 with 3N HCl and extracted with hexane/EA (1:2, 300 mL). The extract was washed with water (200 mL), dried over magnesium sulfate, and the solvent was removed under reduced pressure. The crude product was purified by column chromatography (silica gel, hexane/EA, 2:1) and recrystallization from acetone/methanol to afford pure Compound 24, 2,6-bis(3-(4-(butoxycarbonyl)-3-fluorophenoxy)-2,2-bis((4-(butoxycarbonyl)-3-fluorophenoxy)methyl)propyl)-4,8-bis(4-(diphenylamino)phenyl)-2H-benzo[1,2-d:4,5-d']bis([1,2,3]triazole)-6-ium-5-ide (200 mg, 13% yield). $^1$H NMR (500 MHz, C6D6): δ 8.61 (d, J=8.8 Hz, 4H), 7.76 (m, 6H), 7.16 (m, 20H), 6.98 (m, 4H), 6.34 (m, 12H), 4.96 (s, 4H), 4.13 (t, J=7.0 Hz, 12H), 3.99 (s, 12H), 1.48 (sextet, J=7.0 Hz, 12H), 1.26 (m, 12H), 0.79 (t, J=7.5 Hz, 18H). UV-vis spectrum (PVB): $\lambda_{max}$=554 nm. Fluorimetry (PVB): $\lambda_{max}$=668 nm.

A mixture of Compound A (647 mg, 1.0 mmol), Compound B20 (2.34 g, 3.0 mmol), potassium carbonate (690 mg, 5.0 μmmol), and DMF (15 mL) was stirred under argon and heated at 110° C. for 20 h. The reaction mixture was poured into ice/water (300 mL), acidified to pH 1 with 3N HCl and extracted with hexane/EA (1:1, 500 mL). The extract was washed with water (300 mL), dried over magnesium sulfate, and the solvent was removed under reduced pressure. The crude product was purified by column chromatography (silica gel, hexane/toluene/EA, 45:50:5) and recrystallization from toluene/hexane to afford pure Compound 25, 2,6-Bis(3-(3-(butoxycarbonyl)-4-fluorophenoxy)-2,2-bis((3-(butoxycarbonyl)-4-fluorophenoxy)methyl)propyl)-4,8-bis(4-(diphenylamino)phenyl)-2H-benzo[1,2-d:4,5-d']bis([1,2,3]triazole)-6-ium-5-ide, (252 mg, 12% yield). $^1$H NMR (benzene-D6): δ 8.25 (d, J=8.8 Hz, 4H), 7.35 (m, 14H), 7.16 (m, 8H), 7.13 (t, J=7.4 Hz, 4H), 6.95 (dt, J=9.0 and 3.3 Hz, 6H), 6.87 (d, J=8.8 Hz, 4H), 6.79 (t, J=9.3 Hz, 6H), 5.36 (s, 4H), 4.34 (s, 12H), 4.23 (t, J=6.6 Hz, 12H), 1.67 (quintet, J=6.6 Hz, 12H), 1.40 (sextet, J=7.3 Hz, 12H), 0.92 (t, J=7.3 Hz, 18H). UV-vis spectrum (PVB): $\lambda_{max}$=550 nm. Fluorimetry (PVB): $\lambda_{max}$=660 nm.

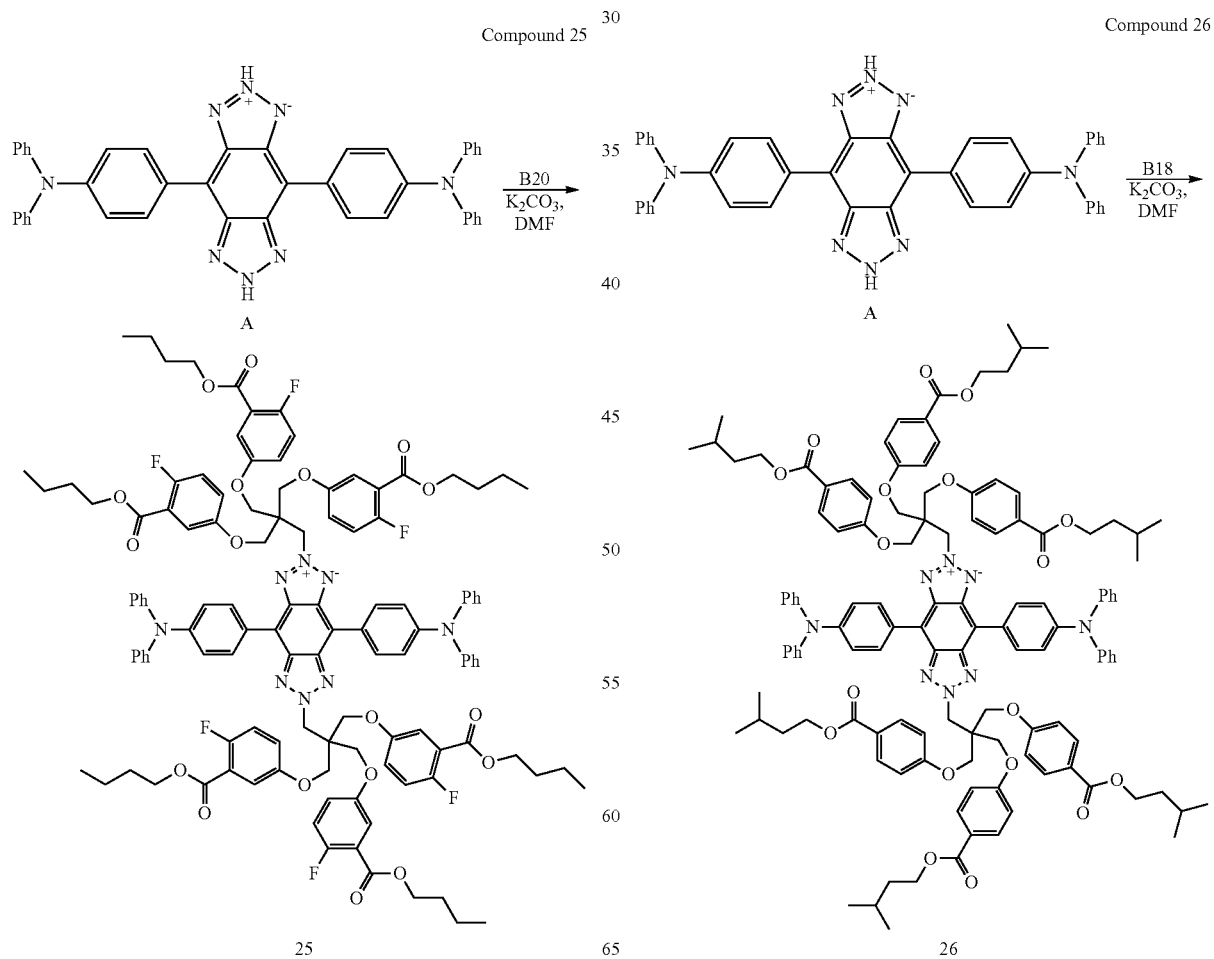

A mixture of Compound A (452 m g, 0.7 mmol), Compound B18 (2.37 g, 3.1 mmol), potassium carbonate (1.38 g, 10 mmol), and DMF (20 mL) was stirred under argon and heated at 110° C. for 20 h. After cooling, the reaction mixture was poured into ice/water (300 mL), acidified to pH 1 with 3N HCl and extracted with hexane/toluene/EA (1:1:1, 300 mL). The extract was washed with water (300 mL), dried over magnesium sulfate, and the solvent was removed under reduced pressure. The crude product was purified by column chromatography (silica gel, hexane/toluene/EA, 40:50:10) and recrystallization from toluene/hexane to afford pure Compound 26, 4,8-bis(4-(diphenylamino)phenyl)-2,6-bis(3-(4-fluoro-3-((isopentyloxy)-carbonyl)phenoxy)-2,2-bis((4-fluoro-3-((isopentyloxy)carbonyl)phenoxy)methyl)propyl)-2H-benzo[1,2-d:4,5-d']bis([1,2,3]triazole)-6-ium-5-ide, (504 mg, 25% yield). $^1$H NMR (400 MHz, CDCl3): δ 8.29 (d, J=8.8 Hz, 4H), 7.84 (d, J 8.8 Hz, 12H), 7.31 (t, J=7.7 Hz, 8H), 7.15 (d, J=8.0 Hz, 8H), 7.09 (t, J=7.3 Hz, 4H), 6.91 (d, J=8.5 Hz, 4H) 6.84 (d, J=8.8 Hz, 12H), 5.41 (s, 4H) 4.43 (s, 12H), 4.26 (t, J=6.8 Hz, 12H), 1.74 (m, 6H), 1.60 (q, J=7.0 Hz, 12H), 0.93 (d, J=6.6 Hz, 36H). UV-vis spectrum (PVB): $\lambda_{max}$=557 nm. Fluorimetry (PVB): $\lambda_{max}$=663 nm.

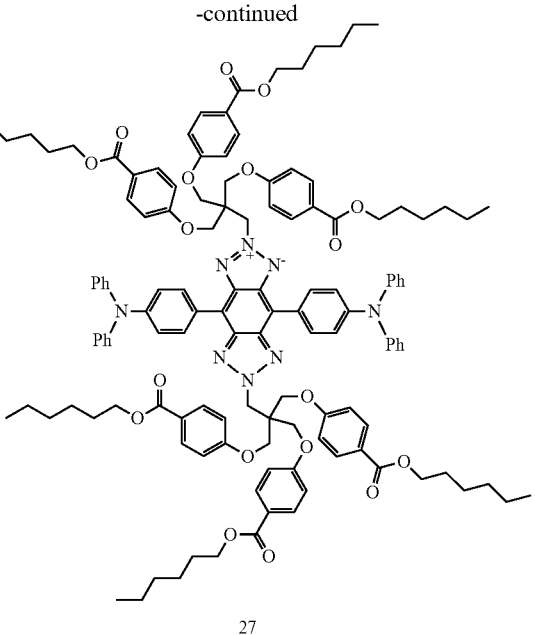

27

A mixture of Compound A (452 mg, 0.7 mmol), Compound B16 (2.36 g, 2.9 mmol), potassium carbonate (1.38 g, 10 mmol), and DMF (20 mL) was stirred under argon and heated at 110° C. for 20 h. After cooling, the reaction mixture was poured into ice/water (300 mL), acidified to pH 1 with 3N HCl and extracted with hexane/toluene/EA (1:1:1, 300 mL). The extract was washed with water (300 mL), dried over magnesium sulfate, and the solvent was removed under reduced pressure. The crude product was purified by column chromatography (silica gel, hexane/toluene/EA, 44:50:6) and recrystallization from toluene/hexane to afford pure Compound 27, 4,8-bis(4-(diphenylamino)phenyl)-2,6-bis(3-(4-((hexyloxy)carbonyl)phenoxy)-2,2-bis((4-((hexyloxy)carbonyl)phenoxy)methyl)propyl)-2H-benzo[1,2-d:4,5-d']bis([1,2,3]triazole)-6-ium-5-ide, (639 mg, 31% yield)). $^1$H NMR (400 MHz, CDCl3): δ 8.29 (d, J=8.8 Hz, 4H), 7.84 (d, J=8.8 Hz, 12H), 7.30 (t, J=7.7 Hz, 8H), 7.15 (d, J=8.0 Hz, 8H), 7.09 (t, J=7.3 Hz, 4H), 6.91 (d, J=8.5 Hz, 4H), 6.84 (d, J=8.8 Hz, 12H), 5.41 (s, 4H), 4.44 (s, 12H), 4.24 (t, J=6.8 Hz, 12H), 1.70 (quintet, J=7.5 Hz, 12H), 1.39 (m, 12H), 1.29 (m, 24H), 0.88 (t, J=7.2 Hz, 18H). UV-vis spectrum (PVB): $\lambda_{max}$=560 nm. Fluorimetry (PVB): $\lambda_{max}$=666 nm.

Compound 27

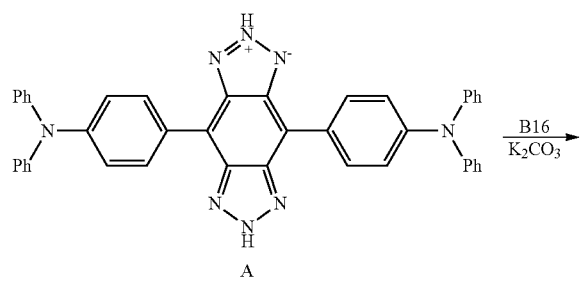

Compound 28

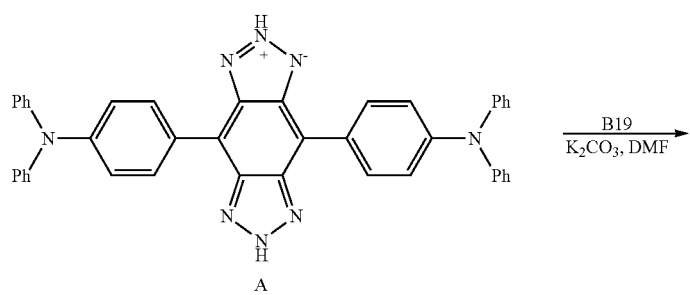

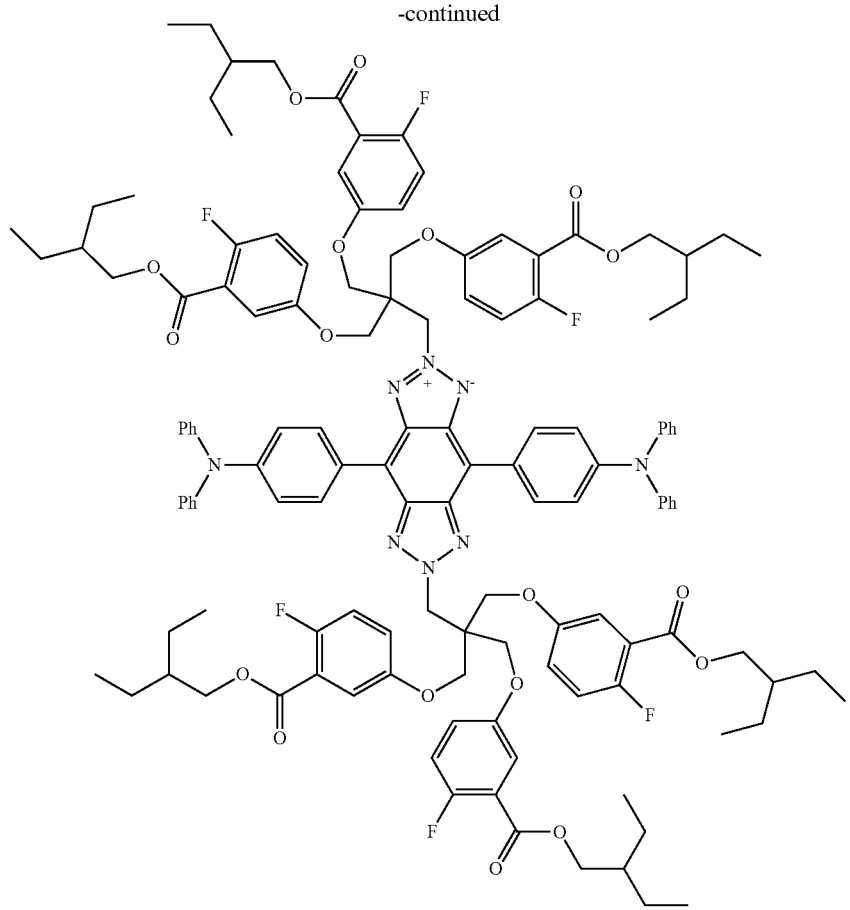

28

A mixture of Compound A (452 mg, 0.7 mmol), Compound B19 (2.30 g, 2.6 mmol), potassium carbonate (1.38 g, 10 mmol), and DMF (20 mL) was stirred under argon and heated at 110° C. for 16 h. After cooling, the reaction mixture was poured into ice/water (300 mL), acidified to pH 1 with 3N HCl and extracted with hexane/toluene/EA (1:1:1, 300 mL). The extract was washed with water (300 mL), dried over magnesium sulfate, and the solvent was removed under reduced pressure. The crude product was purified by column chromatography (silica gel, hexane/toluene/EA, 44:50:6) and recrystallization from EA/hexane to afford pure Compound 28 (605 mg, 39% yield). $^1$H NMR (CDCl3): δ 8.24 (d, J=8.8 Hz, 4H), 7.3 (m, 14H), 7.16 (m, 8H), 7.11 (t, J=7.4 Hz, 4H), 6.95 (dt, J=9.0 and 3.3 Hz, 6H), 6.87 (d, J=8.8 Hz, 4H), 6.78 (t, J=9.3 Hz, 6H), 5.36 (s, 4H), 4.34 (s, 12H), 4.17 (t, J=6.6 Hz, 12H), 1.58 (m, 6H), 1.38 (quintet, J=7.3 Hz, 12H), 0.88 (t, J=7.0 Hz, 18H). UV-vis spectrum (PVB): $\lambda_{max}$=555 nm. Fluorimetry (PVB): $\lambda_{max}$=661 nm.

Compound 29

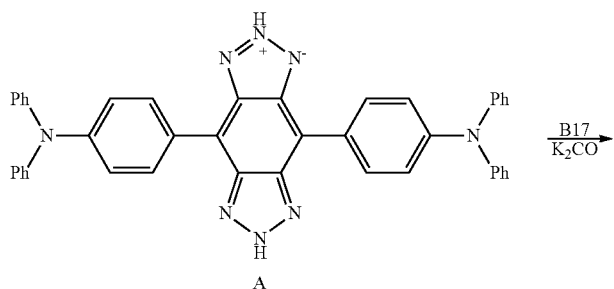

A

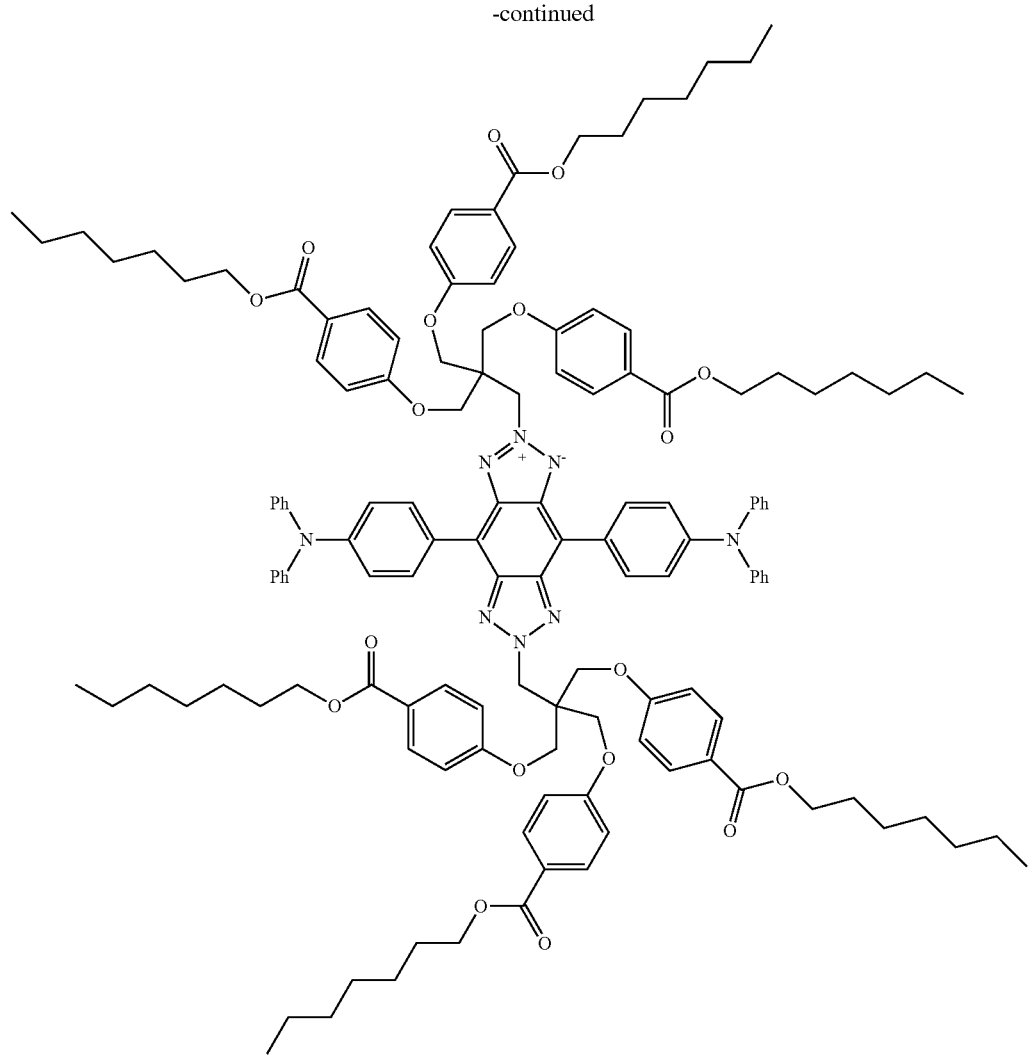

29

A mixture of Compound A (452 mg, 0.7 mmol), Compound B17 (1.70 g, 2.0 μmol), potassium carbonate (690 mg, 5 mmol), and DMF (20 mL) was stirred under argon and heated at 110° C. for 6 h. After cooling, the reaction mixture was poured into ice/water (300 mL), acidified to pH 1 with 3N HCl and extracted with hexane/toluene/EA (1:1:1, 300 mL). The extract was washed with water (300 mL), dried over magnesium sulfate, and the solvent was removed under reduced pressure. The crude product was purified by column chromatography (silica gel, hexane/toluene/EA, 44:50:6) and recrystallization from toluene/hexane to afford pure Compound 29, 4,8-bis(4-(diphenylamino)phenyl)-2,6-bis(3-(4-((heptyloxy)carbonyl)-phenoxy)-2,2-bis((4-((heptyloxy)carbonyl)phenoxy)methyl)propyl)-2H-benzo[1,2-d:4,5-d']bis([1,2,3]triazole)-6-ium-5-ide, (405 mg, 260% yield). $^1$H NMR (400 MHz, CDCl3): δ 8.29 (d, J=8.8 Hz, 4H), 7.84 (d, J=8.8 Hz, 12H), 7.30 (t, J=7.7 Hz, 8H), 7.15 (d, J=8.0 Hz, 8H), 7.09 (t, J=7.3 Hz, 4H), 6.91 (d, J=8.5 Hz, 4H), 6.84 (d, J=8.8 Hz, 12H), 5.41 (s, 4H), 4.44 (s, 12H), 4.22 (t, J=6.8 Hz, 12H), 1.70 (quintet, J=7.5 Hz, 12H), 1.27 (m, 48H), 0.87 (t, J=7.2 Hz, 18H). UV-vis spectrum (PVB): $\lambda_{max}$=560 nm. Fluorimetry (PVB): $\lambda_{max}$=666 nm.

Compound 30

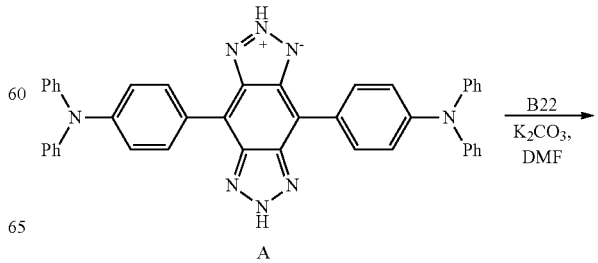

153

-continued

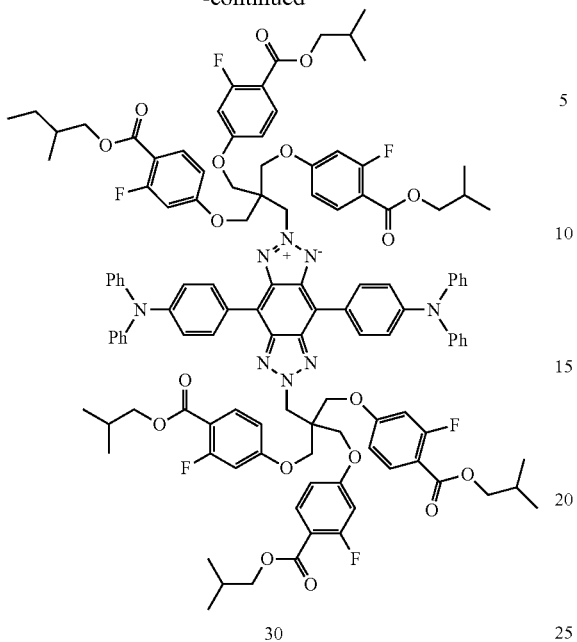

30

154

-continued

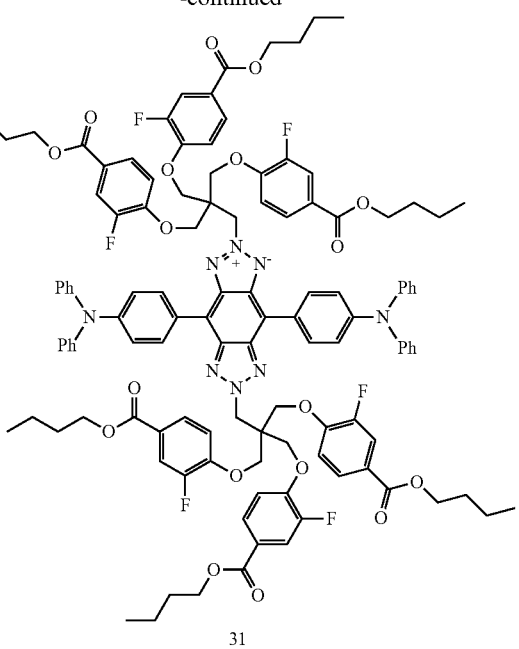

31

A mixture of Compound A (485 mg, 0.75 mmol), Compound B22 (1.56 g, 2.0 mmol), potassium carbonate (690 mg, 5.0 mmol), and DMF (5 mL) was stirred under argon and heated at 100° C. for 30 h. The reaction mixture was poured into ice/water (200 mL), acidified to pH 1 with 3N HCl and extracted with hexane/EA (1:2, 300 mL). The extract was washed with water (200 mL), dried over magnesium sulfate, and the solvent was removed under reduced pressure. The crude product was purified by column chromatography (silica gel, hexane/EA, 2:1) and recrystallization from acetone/methanol to afford pure Compound 30, 4,8-bis(4-(diphenylamino)phenyl)-2,6-bis(3-(3-fluoro-4-(isobutoxy-carbonyl)phenoxy)-2,2-bis((3-fluoro-4-(isobutoxycarbonyl)phenoxy)methyl)propyl)-2H-benzo[1,2-d:4,5-d']bis([1,2,3]triazole)-6-ium-5-ide, (36 rug, 2% yield). $^1$H NMR (500 MHz, C6D6): δ 8.60 (d, J=8.8 Hz, 4H), 7.77 (m, 6H), 7.16 (m, 20H), 6.98 (m, 4H), 6.34 (m, 12H), 4.97 (s, 4H), 3.99 (s, 12H), 3.95 (d, J=6.6 Hz, 12H), 1.84 (m, 6H), 0.82 (d, J=8.6 Hz, 36H). UV-vis spectrum (PVB): $\lambda_{max}$=555 nm. Fluorimetry (PVB): $\lambda_{max}$=662 nm.

Compound 31

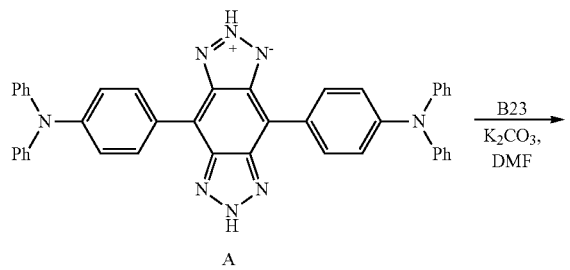

A mixture of Compound A (452 mg, 0.7 mmol), Compound B23 (1.82 g, 2.3 mmol), potassium carbonate (1.38 g, 10 mmol), and DMF (20 mL) was stirred under argon and heated at 100° C. for 7 h. After cooling, the reaction mixture was poured into ice/water (300 mL), acidified to pH 1 with 3N HCl and extracted with hexane/toluene EA (1:1:1, 300 mL). The extract was washed with water (200 mL), dried over magnesium sulfate, and the solvent was removed under reduced pressure. The crude product was purified by column chromatography (silica gel, hexane/toluene/EA, 42:50:8) and recrystallization from toluene hexane to afford pure Compound 31, 2,6-bis(3-(4-(butoxycarbonyl)-2-fluorophenoxy)-2,2-bis((4-(butoxycarbonyl)-2-fluorophenoxy)methyl)propyl)-4, 8-bis(4-(diphenylamino)phenyl)-2H-benzo[1,2-d:4,5-d']bis([1,2,3]triazole)-6-ium-5-ide, (225 mg, 16% yield). $^1$H NMR (400 MHz, CDCl3): δ 8.34 (d, J=8.8 Hz, 4H), 7.63 (m, 12H), 7.31 (t, J=8.1 Hz, 8H), 7.16 (d, J=7.7 Hz, 8H), 7.09 (t, J=7.3 Hz, 4H), 6.96 (m, 10H), 5.45 (s, 4H), 4.52 (s, 12) 4.25 (t, J=6.4 Hz, 12H), 1.67 (m, 12H), 1.43 (m, 12H), 0.94 (t, J=7.4 Hz, 18H). UV-vis spectrum (PVB): $\lambda_{max}$=564 nm. Fluorimetry (PVB): $\lambda_{max}$=672 nm.

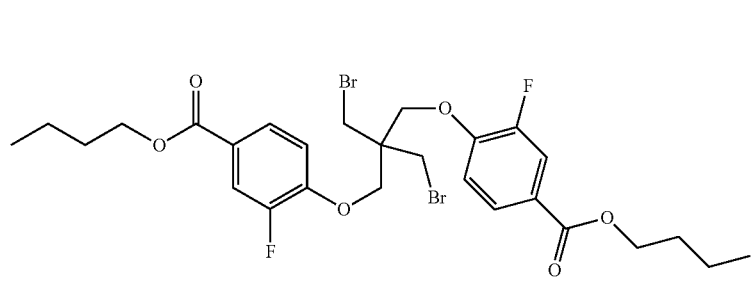
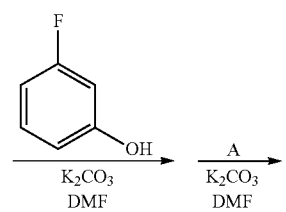

Compound 32

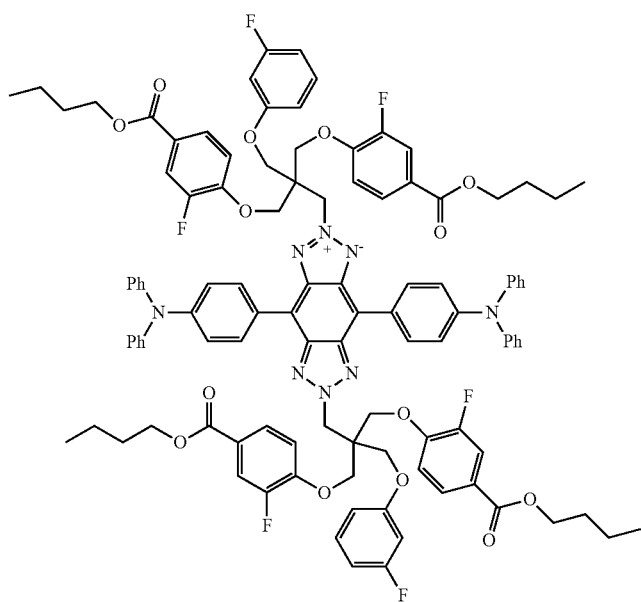

32

A mixture of dibutyl 4,4'-((2,2-bis(bromomethyl)propane-1,3-diyl)bis(oxy))bis(3-fluorobenzoate) (a side products from preparation of Compound B23, 2.10 g, 3.2 mmol), 3-fluorophenol (0.45 mL, 5.0 mmol), potassium carbonate (1.38 g, 10 mmol), and DMF (20 mL) was stirred under argon and heated at 110° C. for 5 h. The reaction mixture was poured into ice/water (300 mL), acidified to pH 1 with 3N HCl and extracted with hexane/toluene/EA (1:1:1, 300 mL) The extract was washed with water (200 mL), dried over magnesium sulfate, and the solvent was removed under reduced pressure. The crude product was treated with Compound A (452 mg, 0.7 mmol), potassium carbonate (276 mg, 2.0 mmol) and DMF (12 mL), and the mixture was stirred under argon and heated at 110° C. for 16 h. Aqueous work-up (as above) gave crude Compound 32 that was purified by column chromatography (silica gel, hexane/toluene/EA, 42:50:8) and crystallization from EA/methanol to afford pure Compound 32, 2,6-bis(3-(4-(butoxy carbonyl)-2-fluorophenoxy)-2-((4-(butoxy carbonyl)-2-fluorophenoxy)methyl)-2-((3-fluorophenoxy)methyl)propyl)-4,8-bis(4-(diphenylamino)phenyl)-2H-benzo[1,2-d:4,5-d']bis([1,2,3]triazole)-6-ium-5-ide, (145 mg, 11% yield). $^1$H NMR (400 MHz, CDCl3): δ 8.28 (d, J=8.8 Hz, 4H), 7.63 (m, 8H), 7.32 (t, J=8.1 Hz, 8H), 7.16 (d, J=7.7 Hz, 8H), 7.11 (t, J=7.3 Hz, 4H), 6.96 (t, J=8.4 Hz, 8H), 6.85 (d, J=9.2 Hz, 4H), 6.64 (m, 2H), 6.57 (m, 2H), 6.42 (m, 2H), 5.43 (s, 4H), 4.50 (m, 8H), 4.34 (s, 4H), 4.25 (t, J=6.4 Hz, 12H), 1.67 (m, 12H), 1.43 (m, 12H), 0.94 (t, J=7.4 Hz, 18H). UV-vis spectrum (PVB): $\lambda_{max}$=564 nm. Fluorimetry (PVB): $\lambda_{max}$=667 nm.

Compound 33

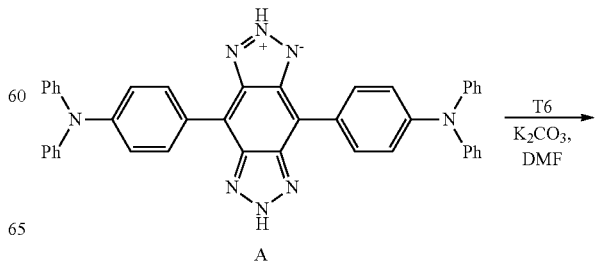

A

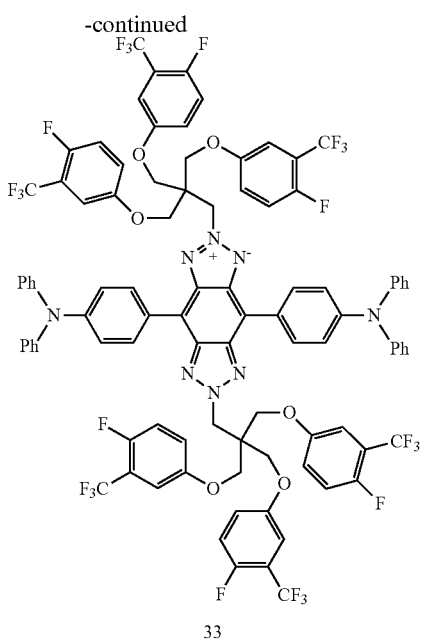

33

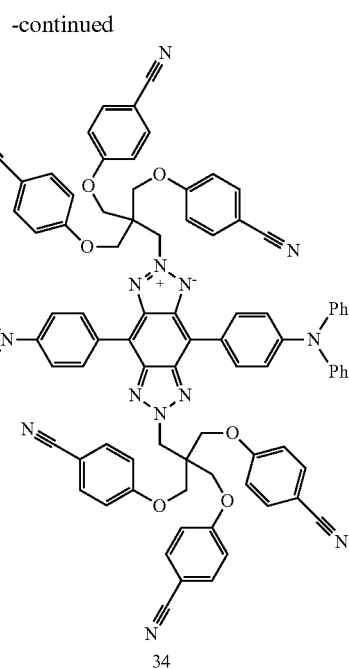

34

A mixture of Compound A (452 mg, 0.7 mmol), Compound T6 (2.10 g, 3.1 mmol), potassium carbonate (1.38 g, 10 mmol), and DMF (20 ma) was stirred under argon and heated at 110° C. for 16 h. After cooling, the reaction mixture was poured into ice/water (300 mL), acidified to pH 1 with 3N HCl and extracted with hexane/toluene/EA (1:1:1, 300 mL). The extract was washed with water (300 mL), dried over magnesium sulfate, and the solvent was removed under reduced pressure. The crude product was purified by column chromatography (silica gel, hexane/toluene/EA, 44:50:6) and recrystallization from methanol to afford pure Compound 33, 4,8-bis(4-(diphenylamino)phenyl)-2,6-bis(3-(4-fluoro-3-(trifluoromethyl)phenoxy)-2,2-bis((4-fluoro-3-(trifluoromethyl)phenoxy)methyl)propyl)-2H-benzo[1,2-d:4,5-d']bis([1,2,3]triazole)-6-ium-5-ide, (680 mg, 52% yield). $^1$H NMR (CDCl3): δ 8.25 (d, J=8.8 Hz, 4H), 7.3 (t, J=8.04 Hz, 8H), 7.16 (d, J=7.7 Hz, 8H), 7.13 (t, J=7.4 Hz, 4H), 6.95 (m, 12H), 6.90 (t, J=9.2 Hz, 6H), 6.84 (d, J=8.8 Hz, 4H), 5.35 (s, 4H), 4.35 (s, 12H). UV-vis spectrum (PVB): $\lambda_{max}$=561 nm. Fluorimetry (PVB): $\lambda_{max}$=665 nm.

A mixture of Compound T4 (1.54 g, 3.06 mmol), Compound A (0.54 g, 0.83 mmol), potassium carbonate (1.38 g, 10 mmol) and DMF (20 mL) was stirred under argon and heated at 110° C. for 6 h. After cooling to room temperature, the mixture was poured into ice/water (300 mL), neutralized with 3N HCl and extracted with EA/toluene/THF (200+200+100 mL). The extract was washed with water (200 mL), dried over magnesium sulfate, and the volatiles were removed under reduced pressure. The crude product was purified by column chromatography (silica gel, toluene/EA, 88:12) and crystallization from toluene/hexane to afford pure Compound 34, 2,6-bis(3-(4-cyanophenoxy)-2,2-bis((4-cyanophenoxy)methyl)propyl)-4,8-bis(4-(diphenylamino)phenyl)-2H-benzo[1,2-d:4,5-d']bis([1,2,3]triazole)-6-ium-5-ide, (370 mg, 30% yield). $^1$H NMR (400 MHz, CDCl3): δ 8.18 (d, J=8.8 Hz, 4H), 7.40 (m, 20H), 7.22 (m, 12H), 6.87 (d, J=9.2 Hz, 12H), 6.81 (d, J=8.8 Hz, 4H) 5.37 (s, 4H), 4.43 (s, 12H) UV-vis spectrum (PVB): $\lambda_{max}$=573 nm. Fluorimetry (PVB) $\lambda_{max}$=676 nm.

Compound 34

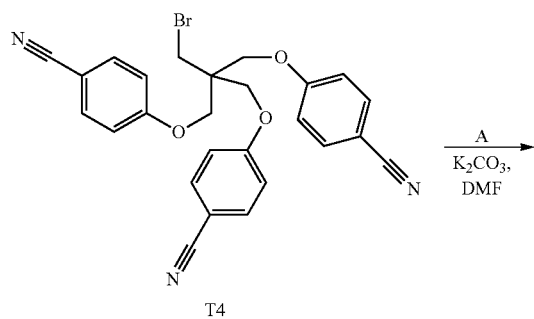

T4

Compound 35

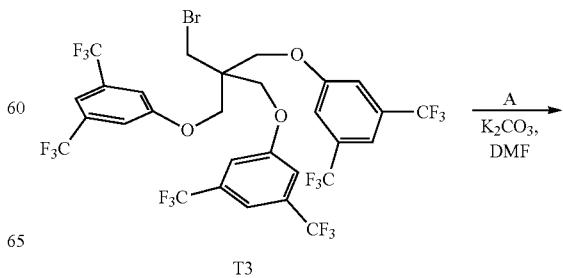

T3

-continued

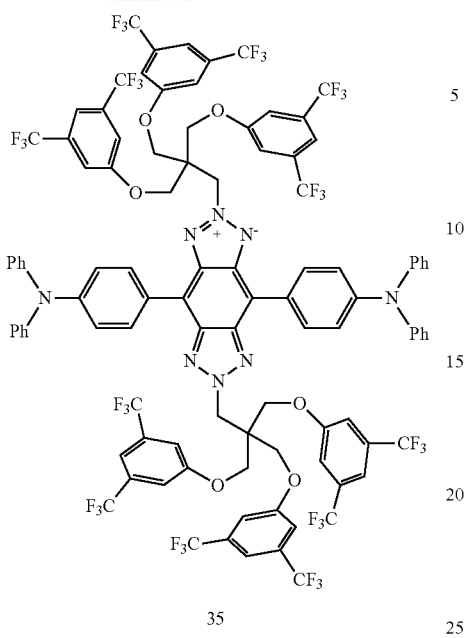

35

A mixture of crude Compound T3 (3.0 g, purity 50%, 1.8 mmol), Compound A (0.48 g, 0.74 mmol), potassium carbonate (0.67 g, 5.0 mmol), and DMF (20 mL) was stirred under argon and heated at 110° C. for 48 h. The reaction mixture was poured into ice/water (300 mL), neutralized with 3N HCl and extracted with EA/toluene/THF (200+200+100 mL). The extract was washed with water (200 mL), dried over magnesium sulfate, and the volatiles were removed under reduced pressure. The crude product was purified by column chromatography (silica gel, hexane/toluene, 1:1) and crystallization from toluene/hexane to afford pure Compound 35, 2,6-bis(3-(3,5-bis(trifluoromethyl)phenoxy)-2,2-bis((3,5-bis(trifluoromethyl)phenoxy)methyl)propyl)-4,8-bis(4-(diphenylamino)phenyl)-2H-benzo[1,2-d:4,5-d']bis([1,2,3]triazole)-6-ium-5-ide (105 mg, 7% yield). $^1$H NMR (400 MHz, CDCl3): δ 7.97 (d, J=8.4 Hz, 4H), 7.30 (m, 26H), 7.10 (m, 12H), 6.48 (d, J=8.8 Hz, 4H), 5.40 (s, 4H), 4.44 (s, 12H). UV-vis spectrum (PVB): $\lambda_{max}$=566 nm. Fluorimetry (PVB): $\lambda_{max}$=667 nm.

Compound 36

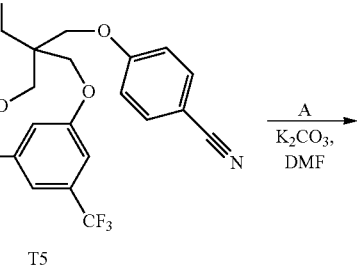

-continued

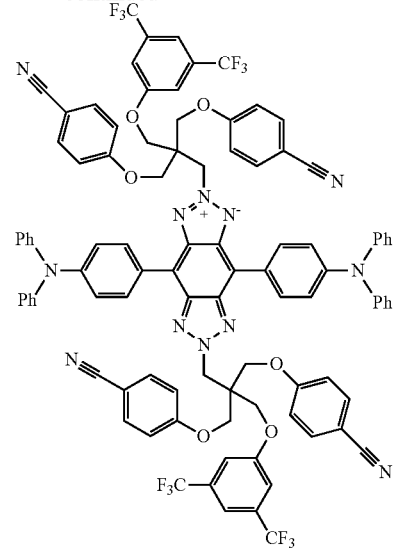

36

A mixture of Compound T5 (90%, 1.40 g, 2.0 mmol), Compound A (0.50 g, 0.77 mmol), potassium carbonate (1.38 g, 10 mmol), and DMF (20 mL) was stirred under argon and heated at 110° C. for 24 h. After cooling to room temperature, the mixture was poured into ice/water (300 μmL), neutralized with 3N HCl and extracted with EA/toluene/THF (200+200+100 mL). The extract was washed with water (200 mL), dried over magnesium sulfate, and the volatiles were removed under reduced pressure. The crude product was purified by column chromatography (silica gel, toluene/EA, 95:5) and crystallization from acetone/methanol to afford pure Compound 36, 2,6-bis(3-(3,5-bis(trifluoromethyl)phenoxy)-2,2-bis((4-cyanophenoxy)methyl)propyl)-4,8-bis(4-(diphenylamino)phenyl)-2H-benzo[1,2-d:4,5-d']bis([1,2,3]triazole)-6-ium-5-ide, (150 mg, 11% yield). $^1$H NMR (400 MHz, CDCl3): δ 8.15 (d, J=8.8 Hz, 4H), 7.38 (m, 18H), 7.30 (bs, 2H), 7.18 (m, 16H), 6.90 (d, J=8.8 Hz, 8H), 6.74 (d, J=8.8 Hz, 4H), 5.37 (s, 4H), 4.43 (s, 12H). UV-vis spectrum (PVB): $\lambda_{max}$=566 nm. Fluorimetry (PVB): $\lambda_{max}$=667 nm.

Compound 37

Other compounds can be made by analogous methods to those detailed above.

Comparative Example 1—Preparation of Wavelength Conversion Films

In an embodiment, a wavelength conversion film which comprises a chromophore, and an optically transparent polymer matrix, is fabricated by (i) preparing a 15 wt %

Ethyl-methyl methacrylate (EMMA) (from Sigma Aldrich, St. Louis, Mo.; and used as received) polymer solution with dissolved polymer powder in cyclopentanone; (ii) preparing a chromophore containing an EMMA matrix by mixing the EMMA polymer solution with the synthesized CE-22 at a weight ratio (CE-22/EMMA) of 0.3 wt %, to obtain a chromophore-containing polymer solution; (iii) stirring the solution for approximately 30 min; (iv) then forming the chromophore/polymer film by directly drop casting the dye-containing polymer solution onto a substrate, then allowing the film to dry at room temperature over night followed by heat treating the film at 60° C. under vacuum for 10 min, to completely remove the remaining solvent, and (v) hot pressing the dry composition under vacuum to form a bubble free film with film thickness of approximately 200 □m.

Measurement of the Photostability

The Comparative Example 1 wavelength conversion film, was exposed to continuous one sun (AM1.5 G) irradiation at ambient temperature. The absorption peak of the wavelength conversion film was measured using a UV-Vis spectrometer prior to exposure, and then again after 100 h. The initial UV-Vis absorption data was normalized to its absorption peak maximum so that at 0 hours, the peak intensity is 100%. The UV-Vis measurements after exposure to one sun are then normalized to the initial 0 hour data, and the absorption peak intensity is reported as the photostability. Easily degraded films typically show a drastic decay of the absorption peak within a few hours of one sun irradiation. Films with excellent photostability will maintain the peak absorption over a long time period of exposure to one sun irradiation. Table 1 shows the photostability of the wavelength conversion films that were fabricated, where the data is normalized to the Comparative Example 1 film.

Example 2

A wavelength conversion film was prepared in the same manner as in Comparative Example 1 except that Compound 10 was used instead of CE-22. The measured photostability of the wavelength conversion film was 5.3× higher than the Comparative Example 1 film.

Example 3

A wavelength conversion film was prepared in the same manner as in Comparative Example 1 except that Compound 3 was used instead of CE-22. The measured photostability of the wavelength conversion film was 12.4× higher than the Comparative Example 1 film.

TABLE 1

Photostability of the example wavelength conversion films normalized to the Comparative Example 1 data.

| Example | Chromphore | Stability in EMMA |
|---|---|---|
| Comparative Example 1 | 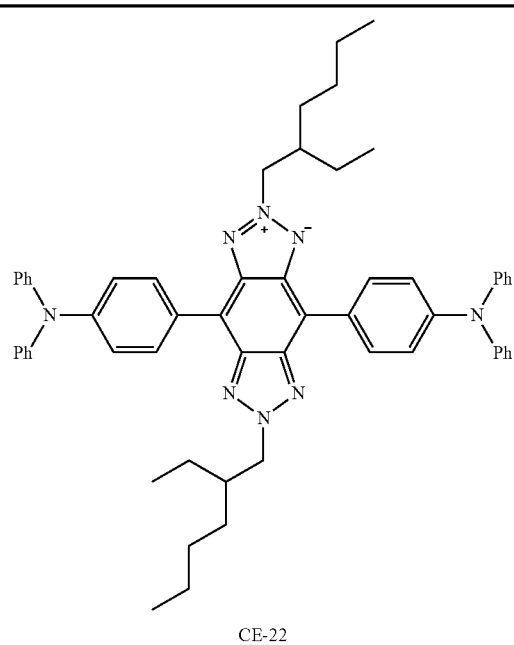 CE-22 | 1 |

TABLE 1-continued

Photostability of the example wavelength conversion films normalized to the Comparative Example 1 data.

| Example | Chromphore | Stability in EMMA |
|---|---|---|
| Example 2 | 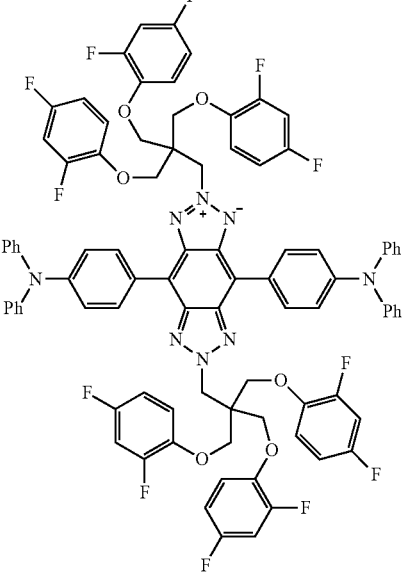<br>Compound 10 | 5.3 |
| Example 3 | 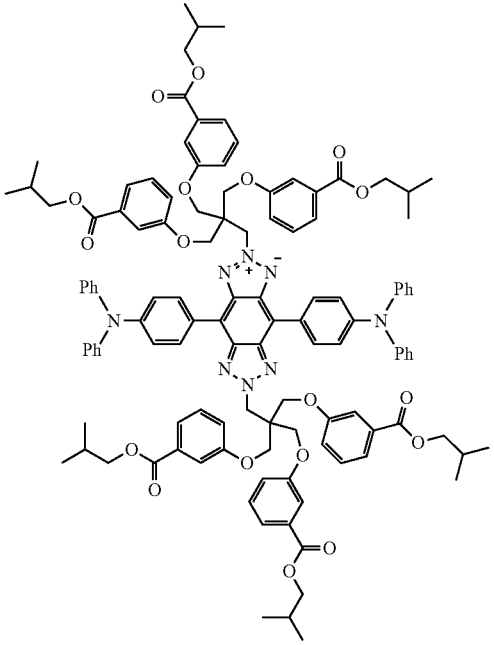<br>Compound 3 | 12.4 |

It has been discovered that the chromophore derivatives, as disclosed herein, can be combined with a polymer matrix to form an organic down-shifting luminescent medium, which is significantly higher photostability compared to previously reported chomophores. Surprisingly, the unique combination of pentaerythritol and phenol substituents increase the photostability greater than 2×, greater than 5×, or greater than 10×. This allows these chromophores to be utilized in applications requiring long lifetimes.

Although the foregoing description has shown, described, and pointed out the fundamental novel features of the present teachings, it will be understood that various omissions, substitutions, and changes in the form of the detail of the invention as illustrated, as well as the uses thereof, may be made by those skilled in the art, without departing from

189
-continued
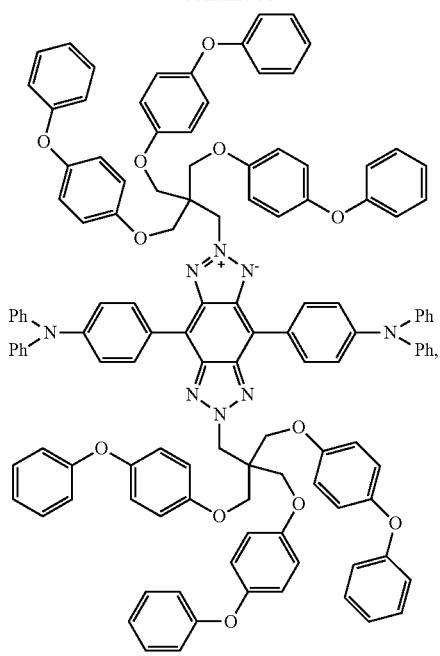
190
-continued
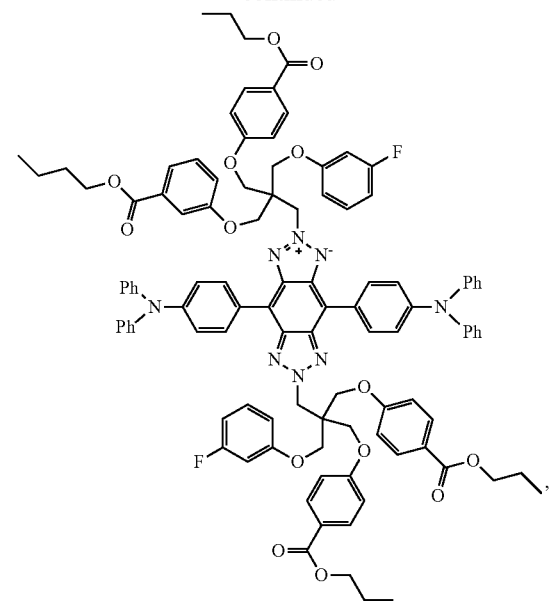
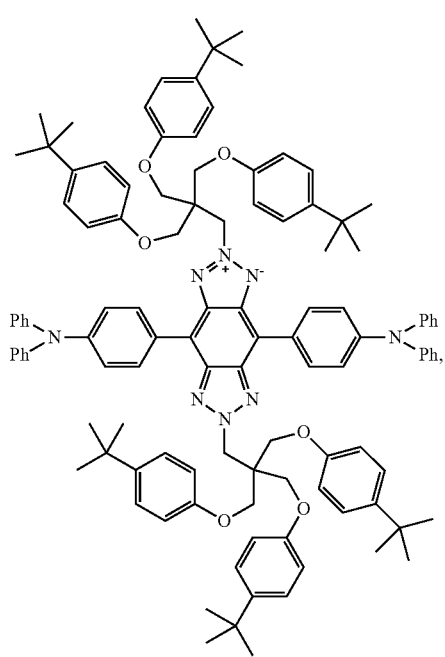
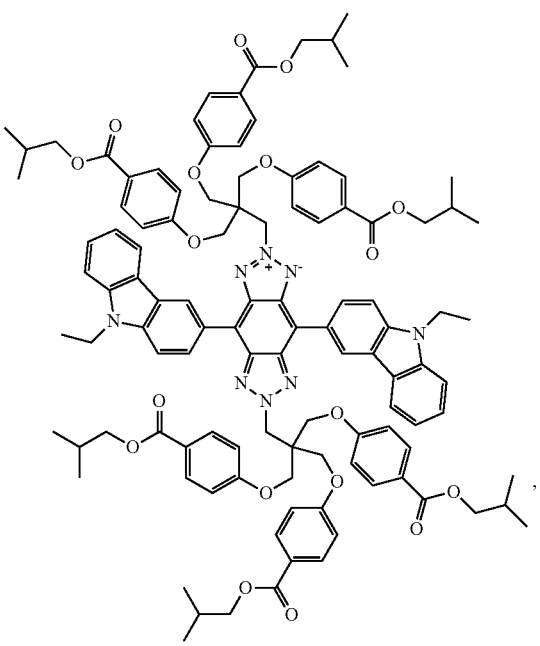

191
-continued
192
-continued
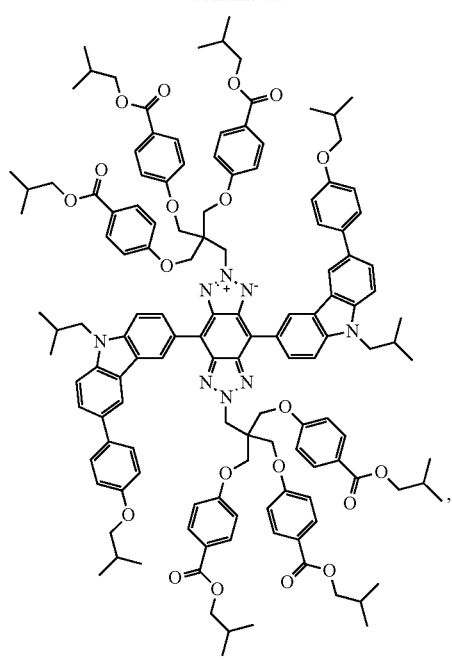
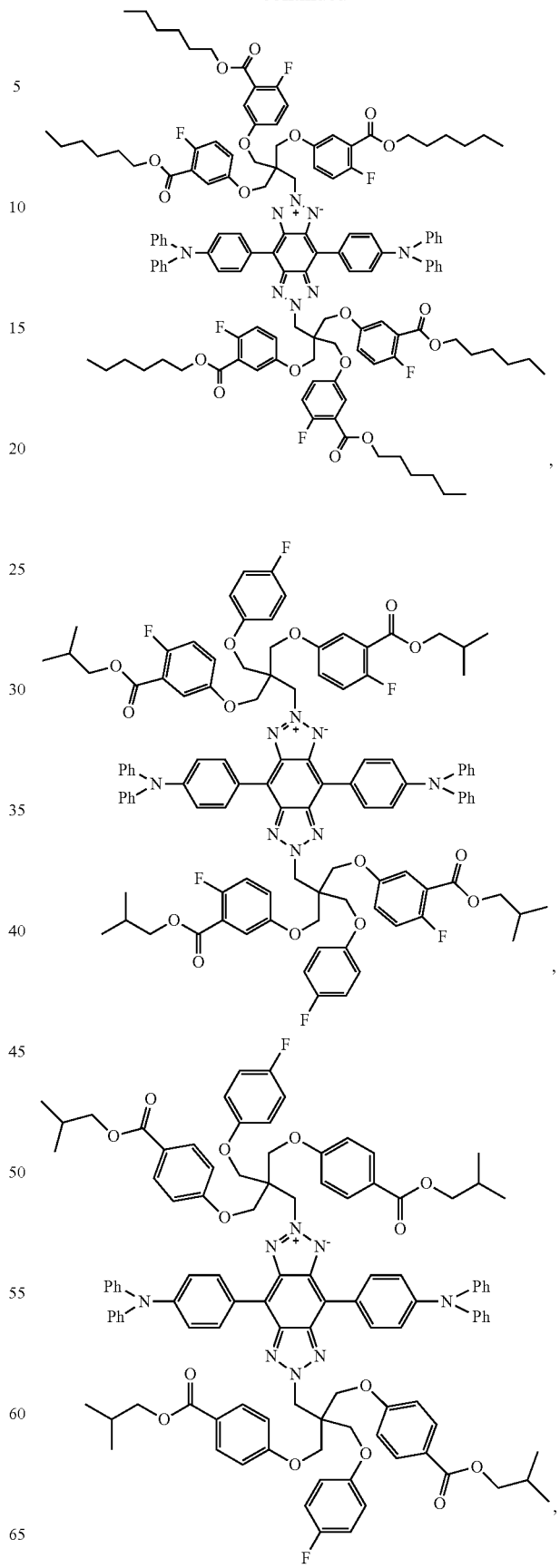

193
-continued
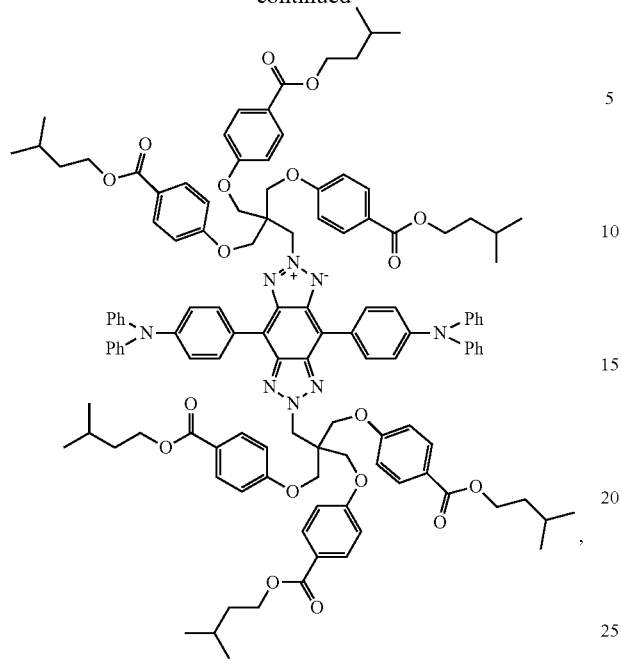
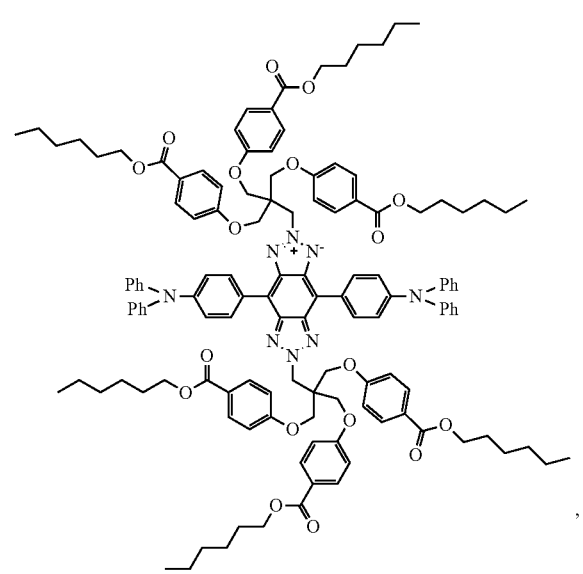
194
-continued
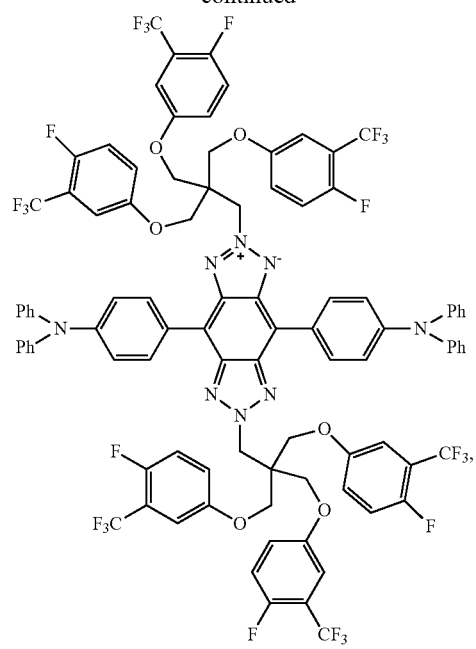
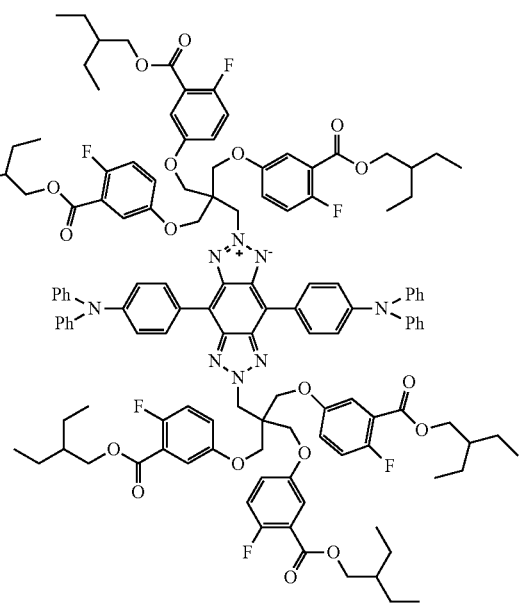

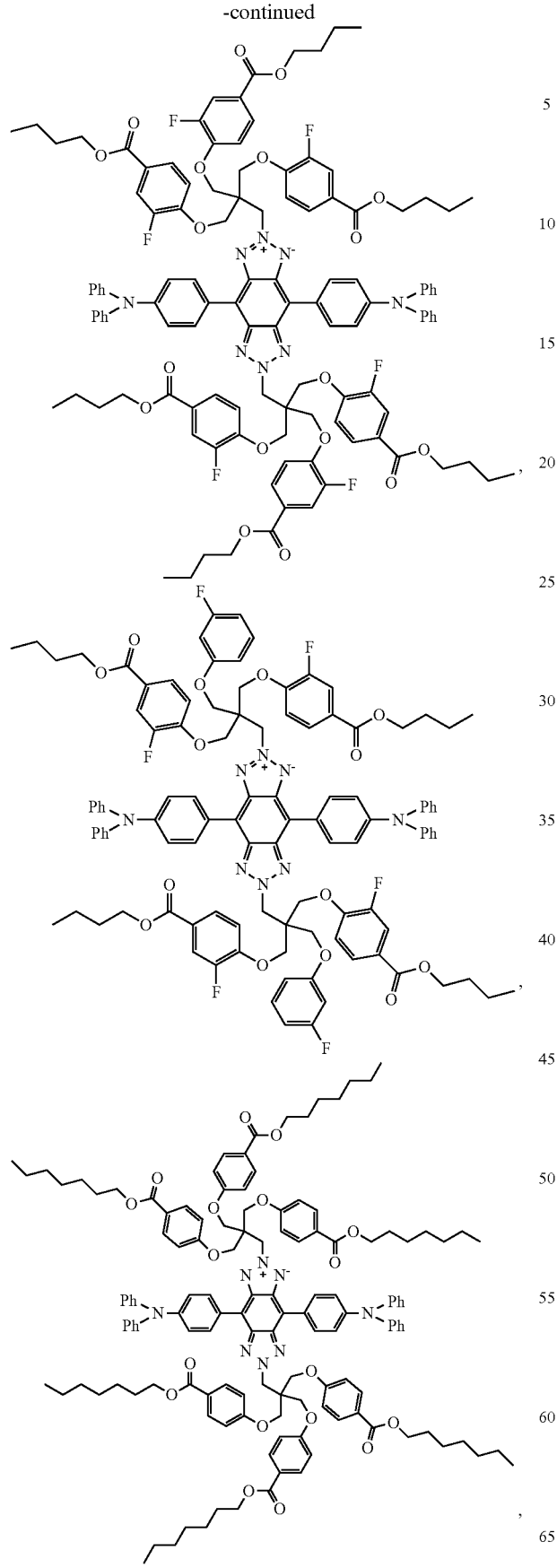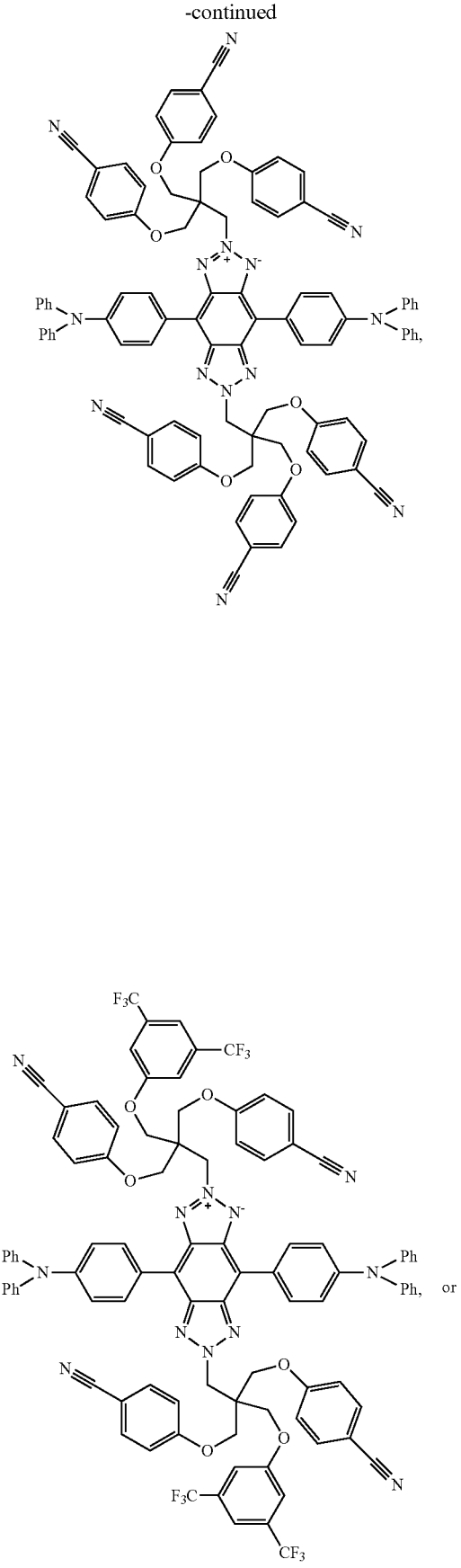

-continued
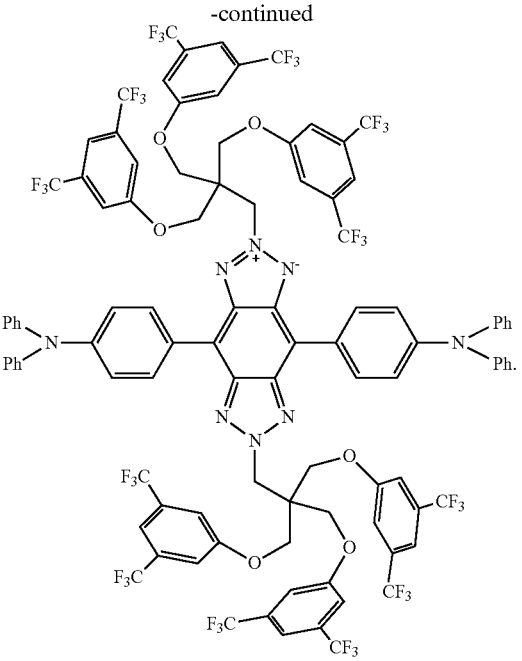

The invention claimed is:

1. A compound represented by formula I:

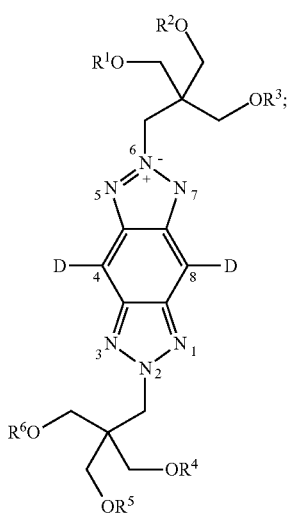

(I)

wherein:
D is optionally substituted phenyl or optionally substituted heteroaryl; and
$R^1$, $R^2$, $R^3$, $R^4$, $R^5$, and $R^6$ are independently optionally substituted phenyl, optionally substituted naphthyl, or optionally substituted heterocyclyl.

2. The compound of claim 1, wherein each substituent of D, $R^1$, $R^2$, $R^3$, $R^4$, $R^5$, and $R^6$, if present, has a molecular weight of 15 Da to 500 Da and is represented by a formula $C_{0-20}H_{0-41}N_{0-5}O_{0-10}S_{0-5}P_{0-3}F_{0-10}Cl_{0-5}Br_{0-3}$, provided that at least 1 non-hydrogen atom is present in each substituent.

3. The compound of claim 1, wherein D is optionally substituted phenyl.

4. The compound of claim 3, wherein the D is optionally substituted 4-(diphenylamino)phenyl.

5. The compound of claim 3, wherein $R^1$ or $R^2$ is optionally substituted carbazolyl.

6. The compound of claim 1, wherein D is optionally substituted 9H-carbazol-2-yl.

7. The compound of claim 5, wherein the carbazolyl has 1, 2, or 3 substituents, wherein each substituent is independently $C_{1-6}$ alkyl, $C_{1-6}$—O-alkyl, or phenyl optionally substituted with $C_{1-6}$ alkyl or $C_{1-6}$—O-alkyl.

8. The compound of claim 1, wherein $R^1$ and $R^4$ are independently optionally substituted phenyl.

9. The compound of claim 8, wherein $R^2$ and $R^5$ are independently optionally substituted phenyl.

10. The compound of claim 9, wherein $R^3$ and $R^6$ are independently optionally substituted phenyl.

11. The compound of claim 1, wherein $R^1$ and $R^4$ are independently optionally substituted 1,3-dioxoisoindolin-5-yl.

12. The compound of claim 11, wherein $R^2$ and $R^5$ are independently optionally substituted 1,3-dioxoisoindolin-5-yl.

13. The compound of claim 12, wherein $R^3$ and $R^6$ are independently optionally substituted 1,3-dioxoisoindolin-5-yl.

14. The compound of claim 8, wherein each phenyl has 1, 2, or 3 substituents, wherein each substituent is independently $R^a$, —$OR^a$, —$CO_2$—$R^a$, —$CO_2$—$CH_2CH_2O$—$R^a$, F, $CF_3$, —CN, phenyl, -phenyl-$R^a$, -phenyl-$OR^a$, or -phenyl-$CO_2$—$R^a$, wherein $R^a$ is $C_{1-12}$ alkyl.

15. The compound of claim 11, wherein each 1,3-dioxoisoindolin-5-yl has 1, 2, or 3 substituents, wherein each substituent is independently $R^a$, —$OR^a$, —$CO_2$—$R^a$, —$CO_2$—$CH_2CH_2O$—$R^a$, F, $CF_3$, —CN, phenyl, -phenyl-$R^a$, -phenyl-$OR^a$, or -phenyl-$CO_2$—$R^a$, wherein $R^a$ is $C_{1-12}$ alkyl.

16. The compound of claim 15, wherein each 1,3-dioxoisoindolin-5-yl has 1, 2, or 3 substituents, wherein each substituent is independently $R^a$, or —$OR^a$.

17. The compound of claim 14, wherein each phenyl has 1, 2, or 3 substituents, wherein each substituent is independently $R^a$, —$OR^a$, —$CO_2$—$R^a$, —$CO_2$—$CH_2CH_2O$—$R^a$, F, $CF_3$, —CN, phenyl, -phenyl-$R^a$, -phenyl-$OR^a$, or -phenyl-$CO_2$—$R^a$, wherein $R^a$ is $C_{1-12}$ alkyl.

18. The compound of claim 10, wherein $R^3$ and $R^6$ are independently phenyl having 1, 2, or 3 substituents, wherein each substituent is independently $R^a$, —$OR^a$, —$CO_2$—$R^a$, —$CO_2$—$C_2H_4O$—$R^a$, F, $CF_3$, —CN, or phenyl, wherein $R^a$ is $C_{1-12}$ alkyl.

19. The compound of claim 10, wherein $R^3$ and $R^6$ are independently phenyl having 1, 2, or 3 substituents, wherein each substituent is independently F or $CF_3$.

20. A compound represented by a formula:

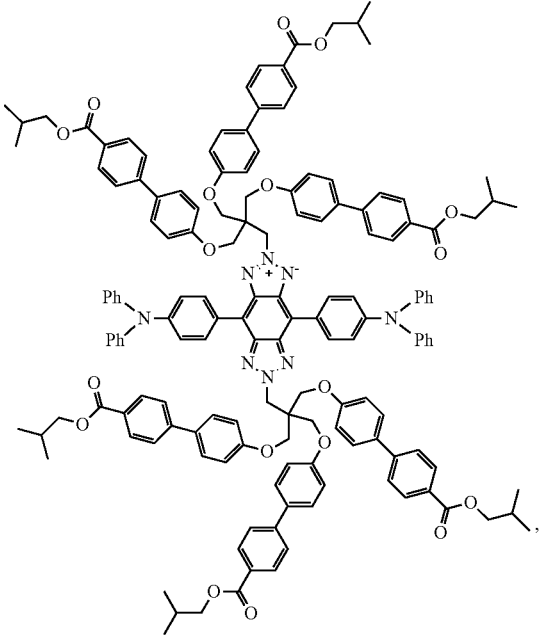

167
-continued
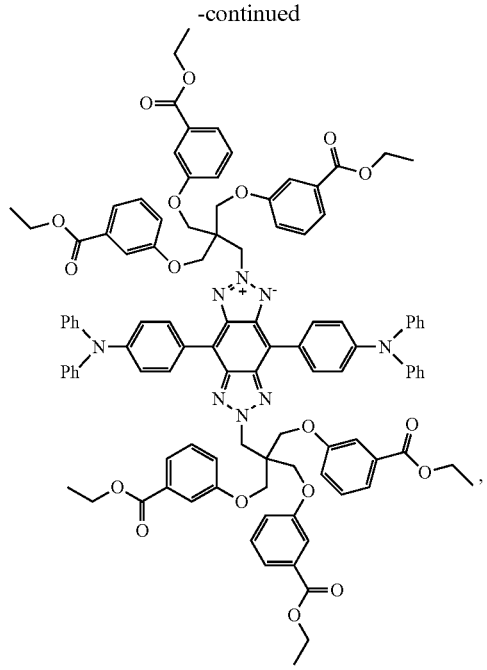
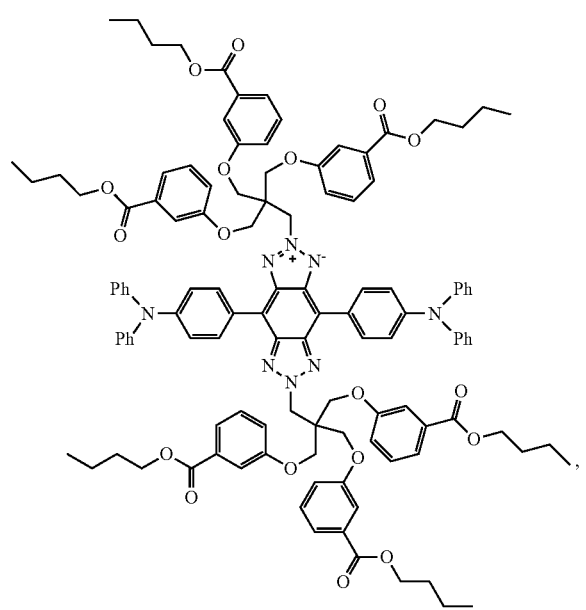
168
-continued
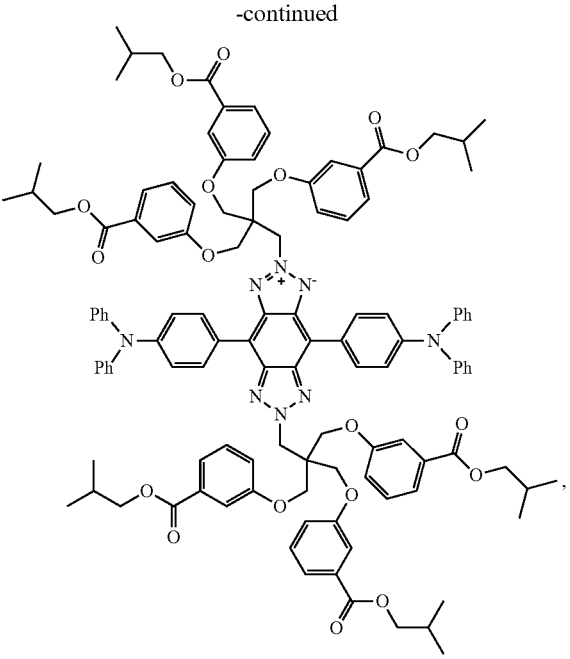

169
-continued
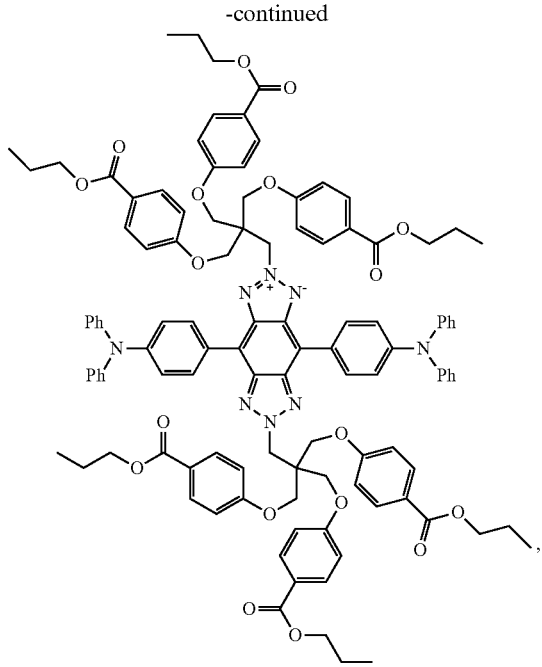
170
-continued
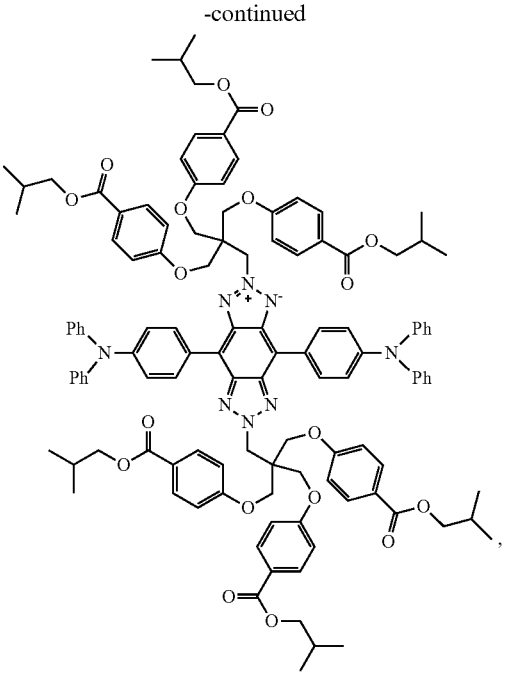
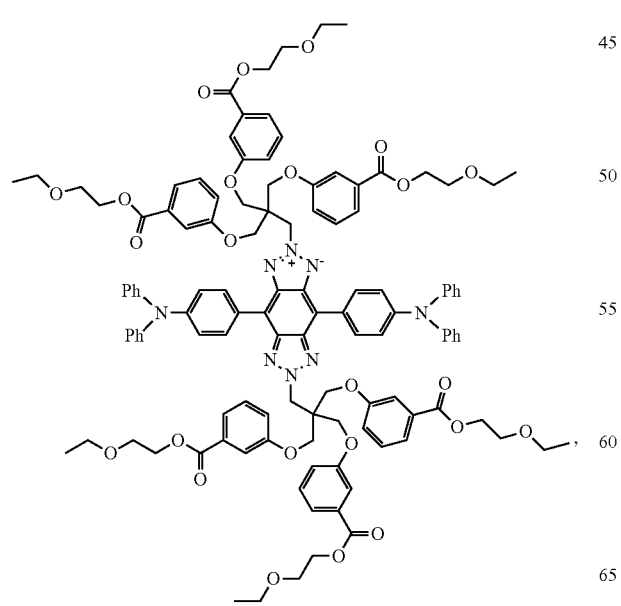
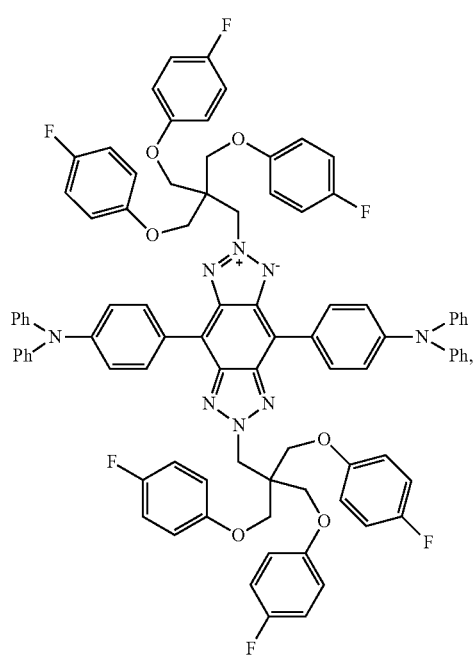

171
-continued
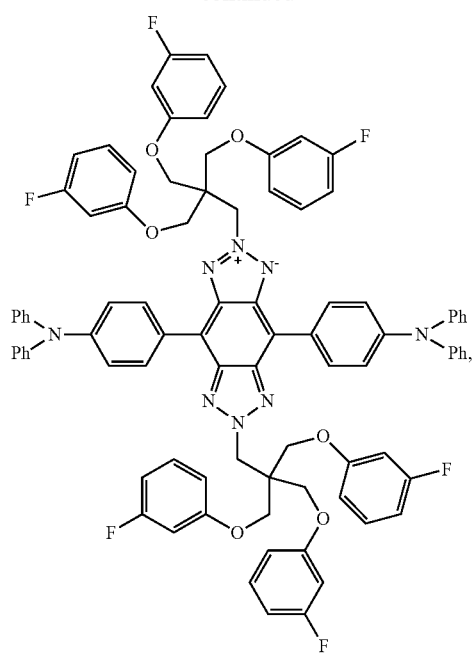
172
-continued
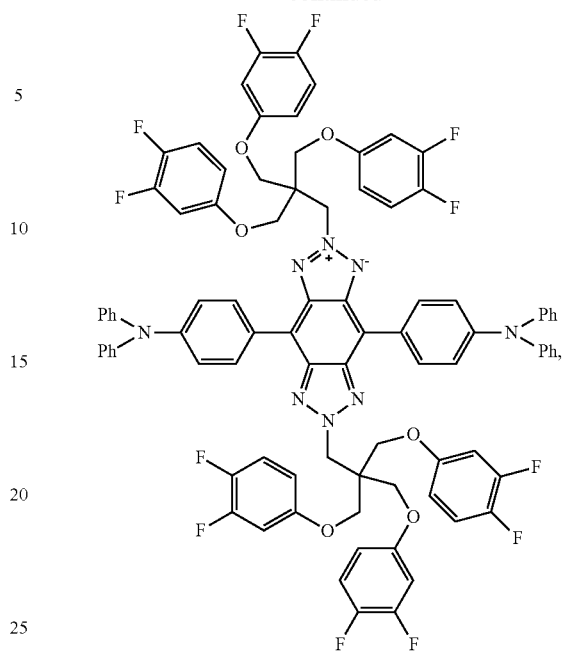
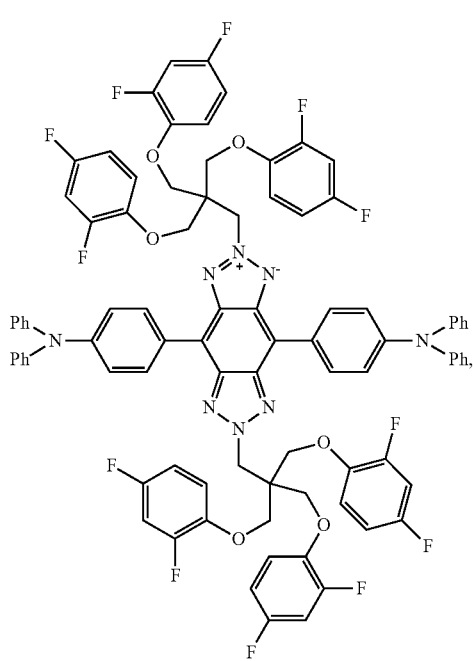
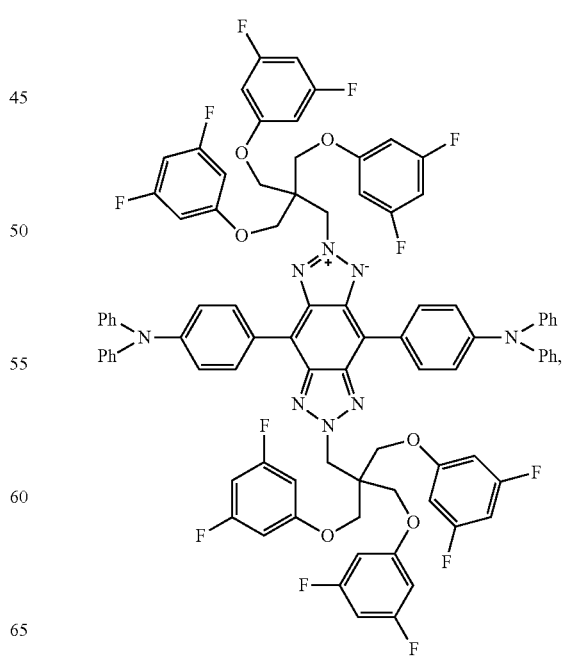

173
-continued
174
-continued
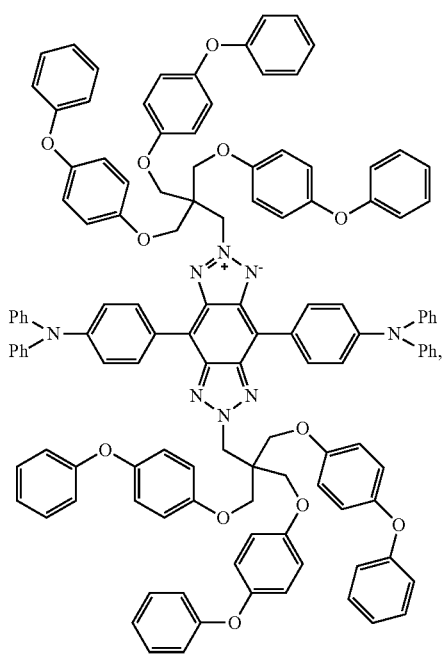
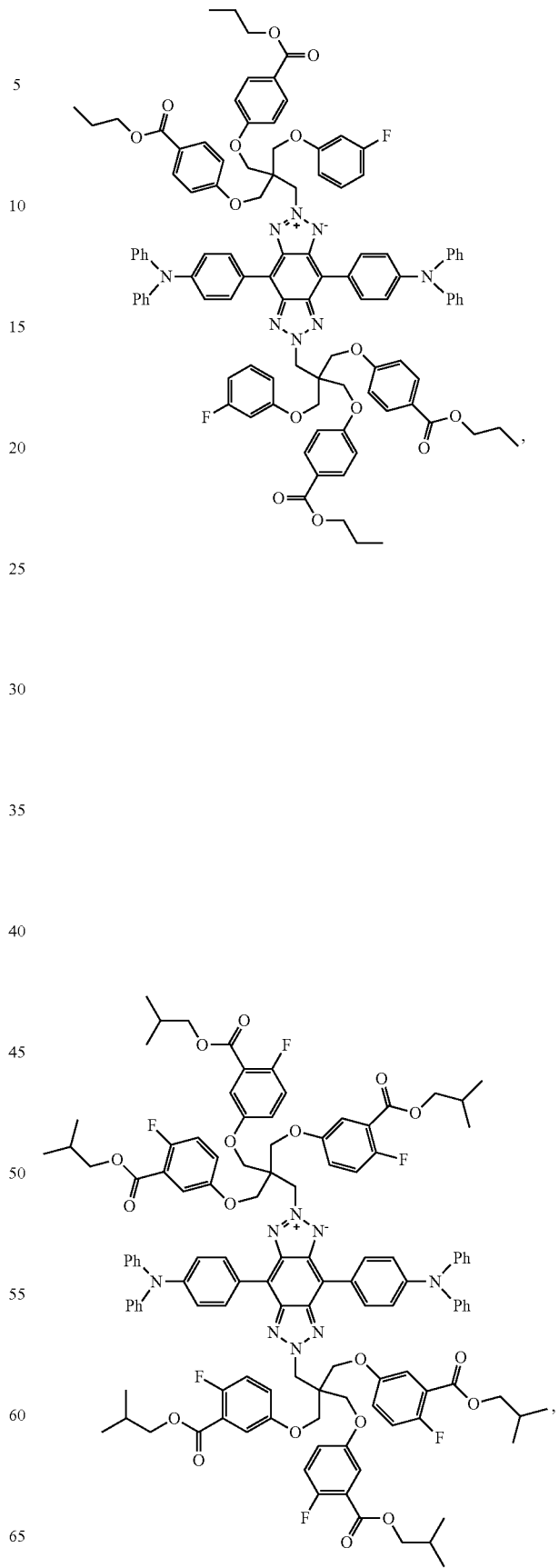

175
-continued
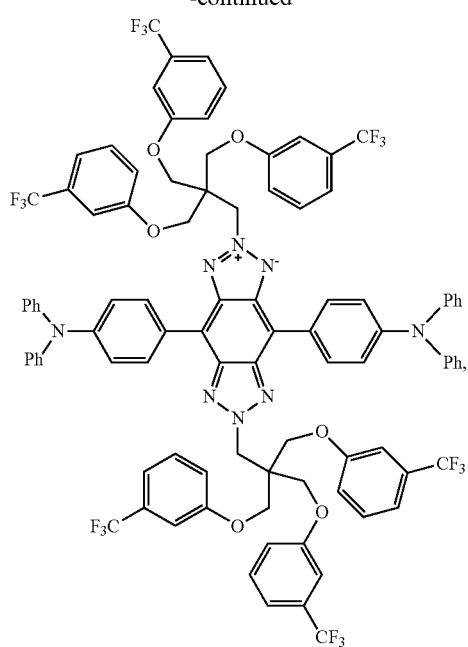
176
-continued
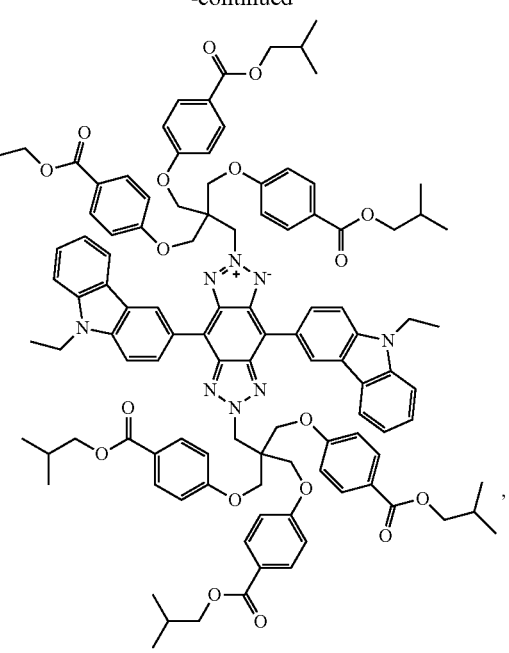
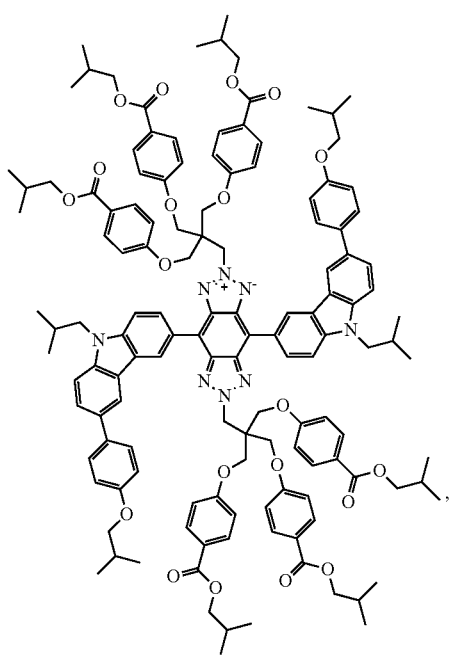

177
-continued
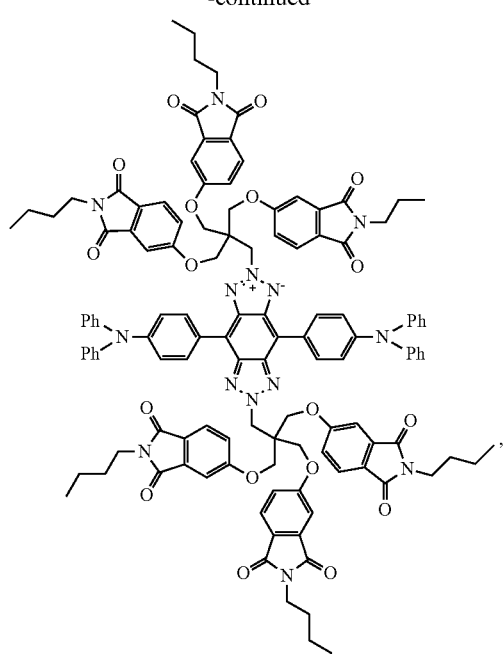
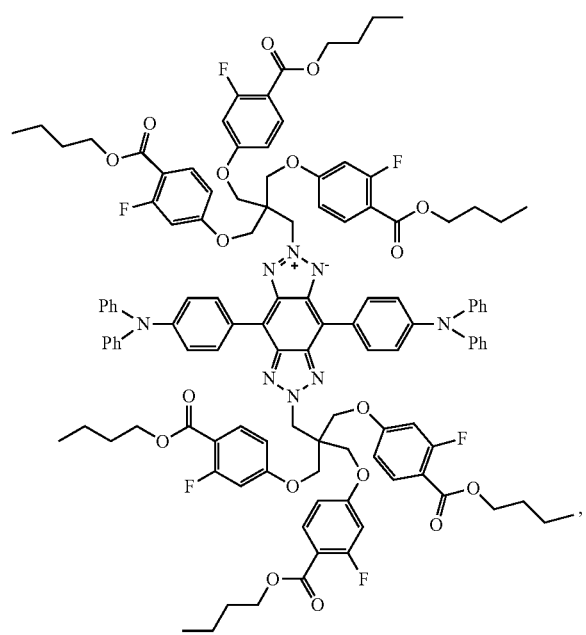
178
-continued
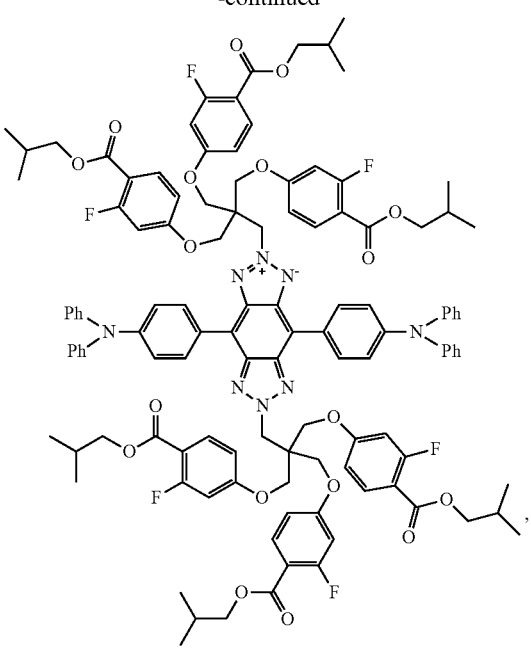
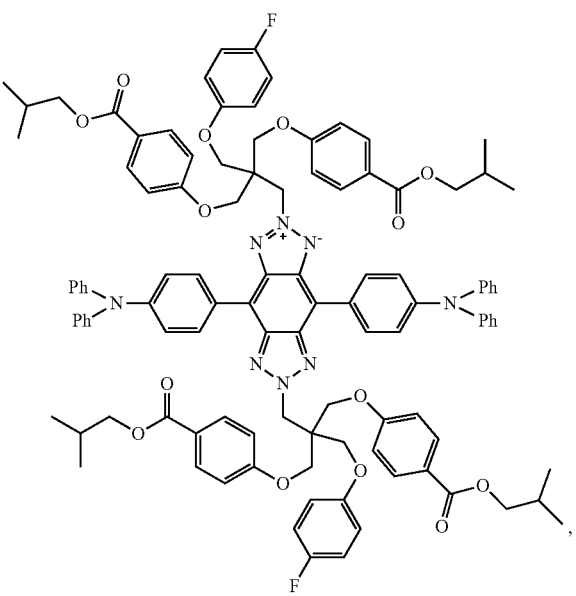

179
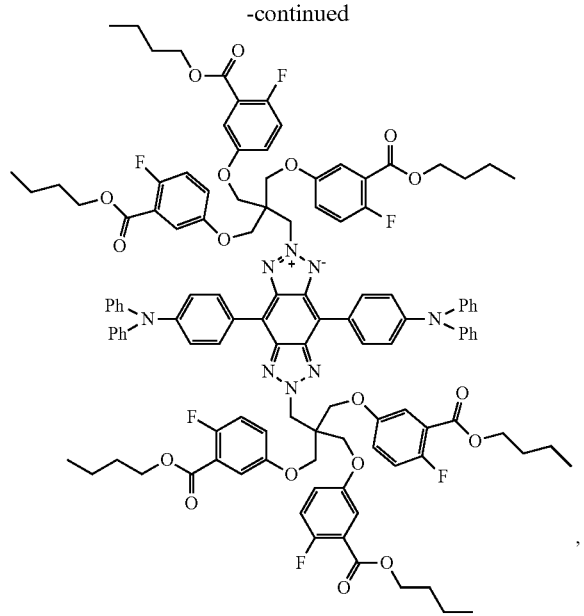
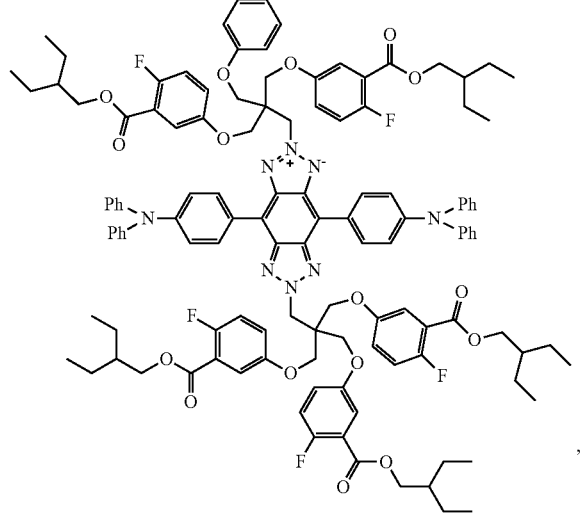
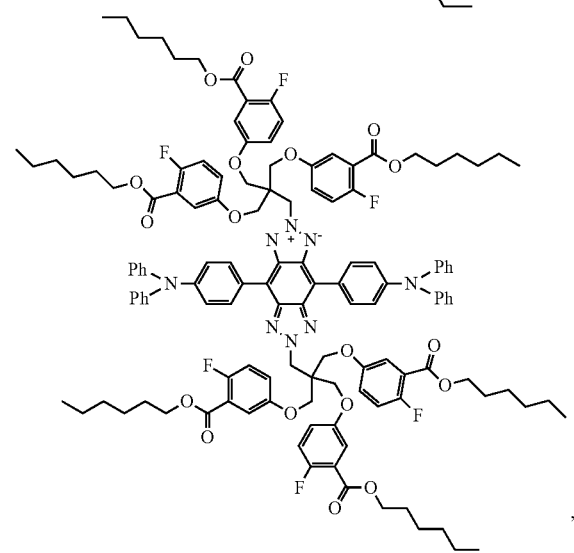
180
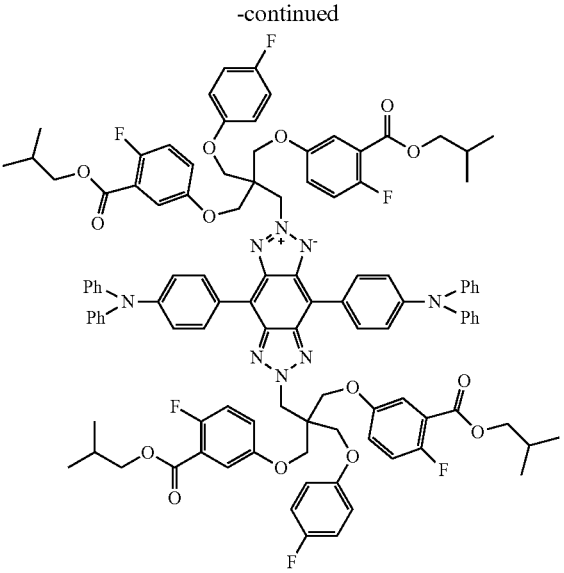
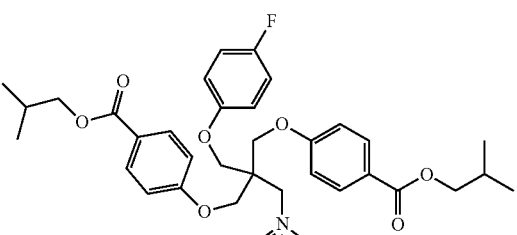
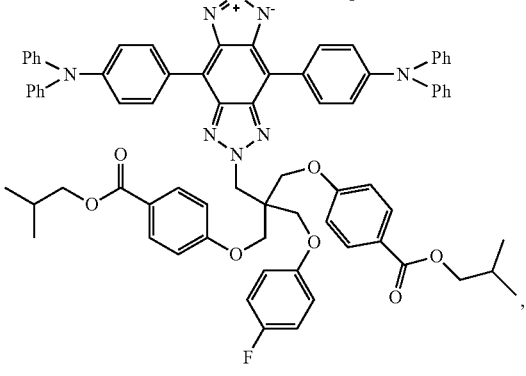

181
-continued
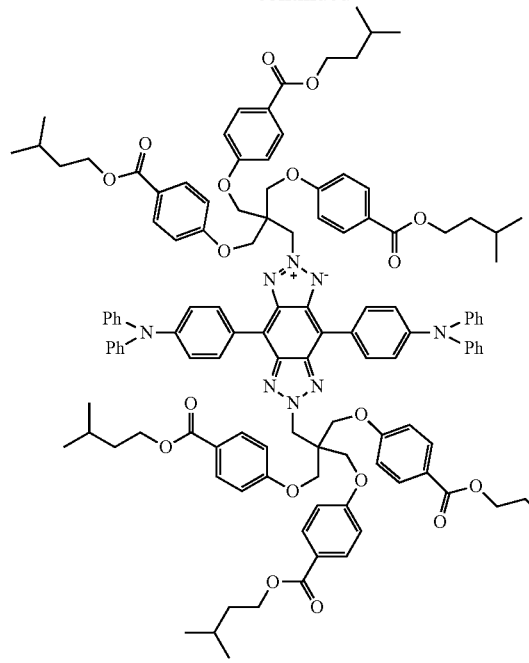
182
-continued
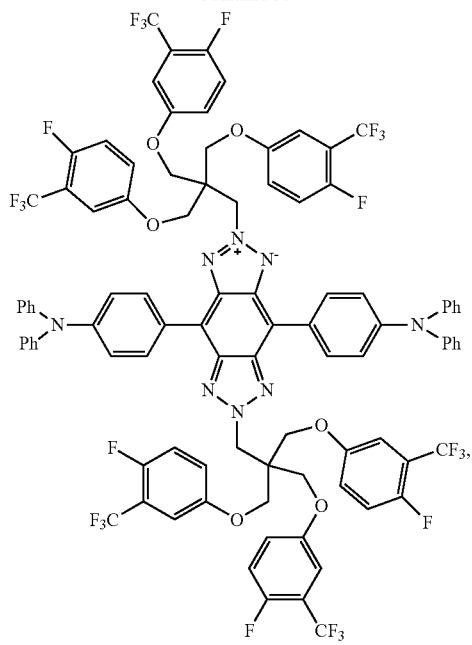
,
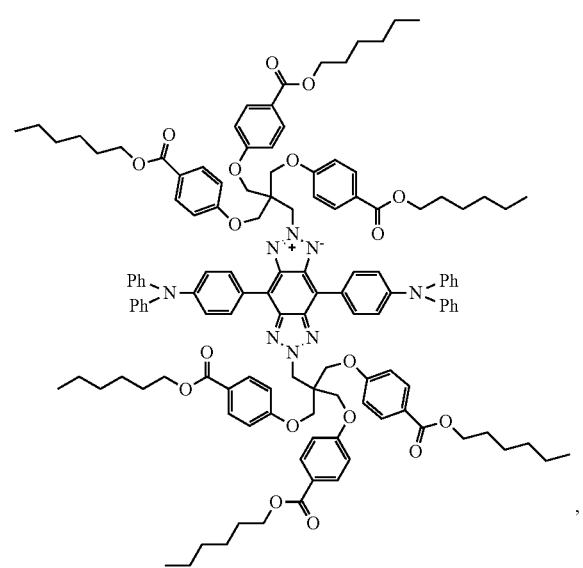
,
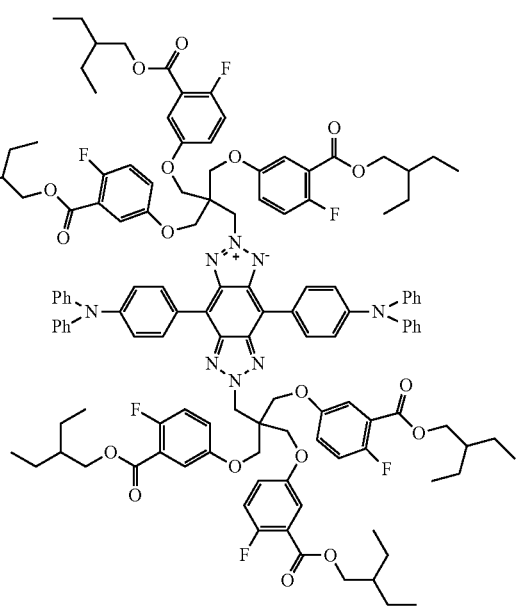
, 183
-continued
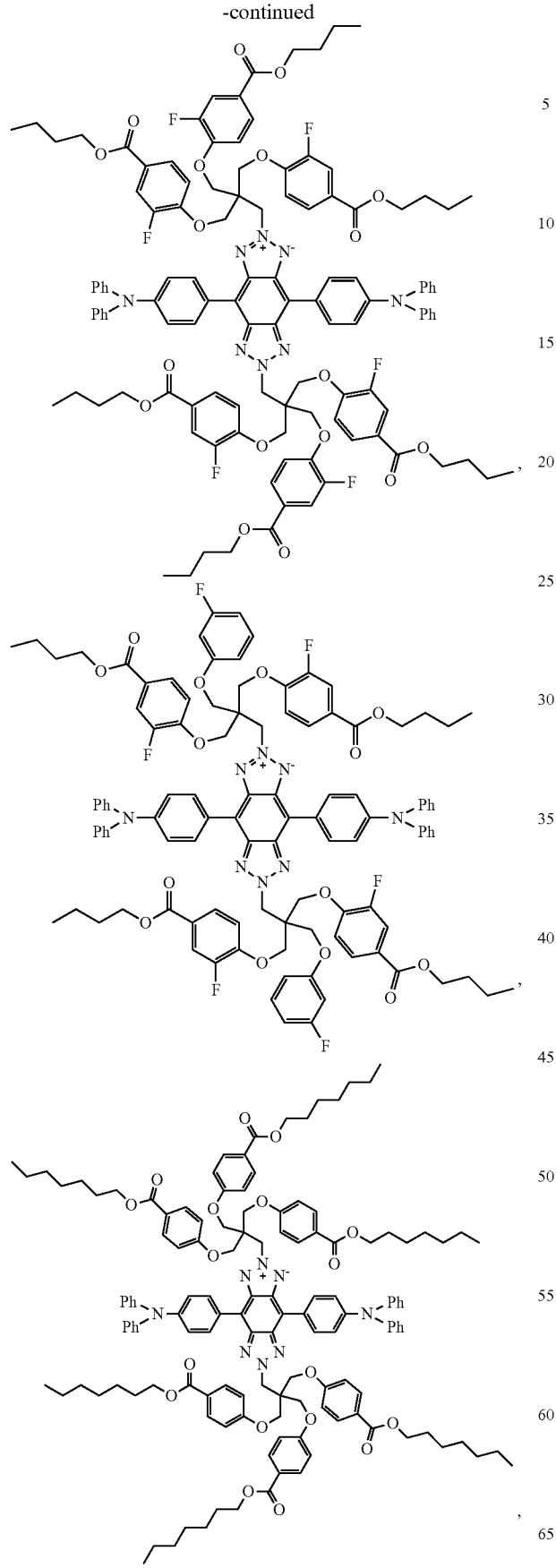
184
-continued
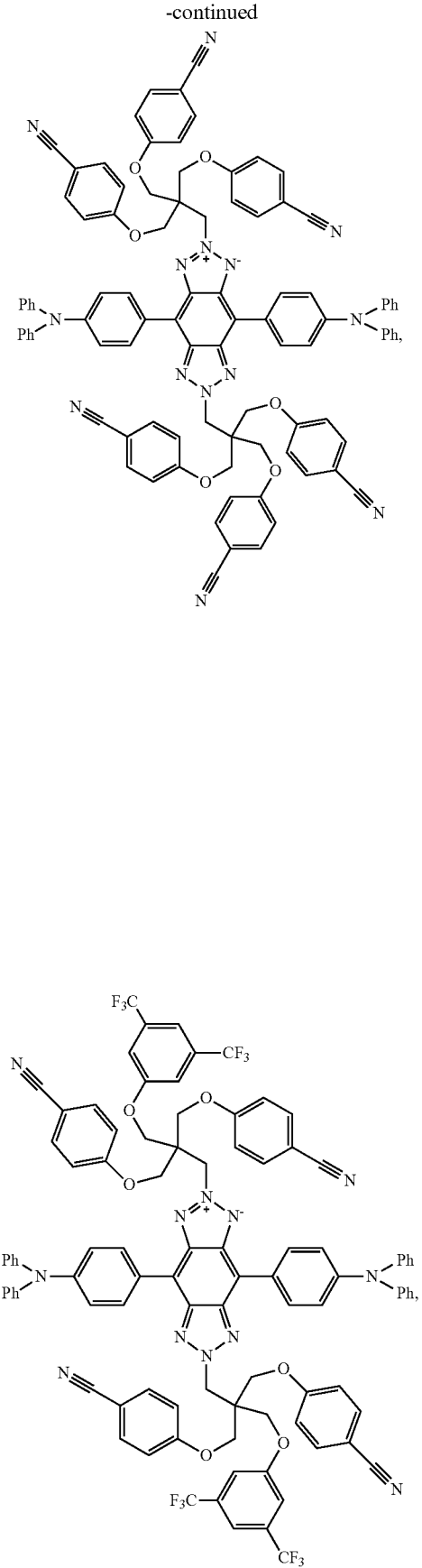

185
-continued
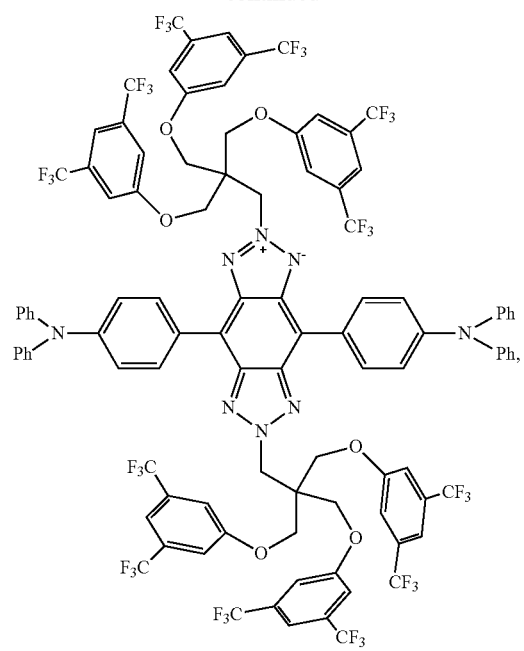 [SMILES: FC(F)(F)c1cc(OCC(COc2cc(C(F)(F)F)cc(C(F)(F)F)c2)(COc2cc(C(F)(F)F)cc(C(F)(F)F)c2)Cn2nc3c(-c4ccc(N(c5ccccc5)c5ccccc5)cc4)c4n[n+](CC(COc5cc(C(F)(F)F)cc(C(F)(F)F)c5)(COc5cc(C(F)(F)F)cc(C(F)(F)F)c5)COc5cc(C(F)(F)F)cc(C(F)(F)F)c5)[n-]c4c(-c4ccc(N(c5ccccc5)c5ccccc5)cc4)c3n2)cc(C(F)(F)F)c1]
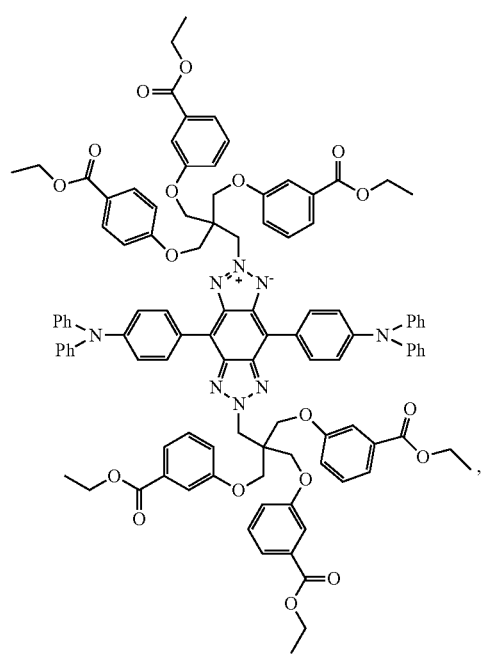
186
-continued
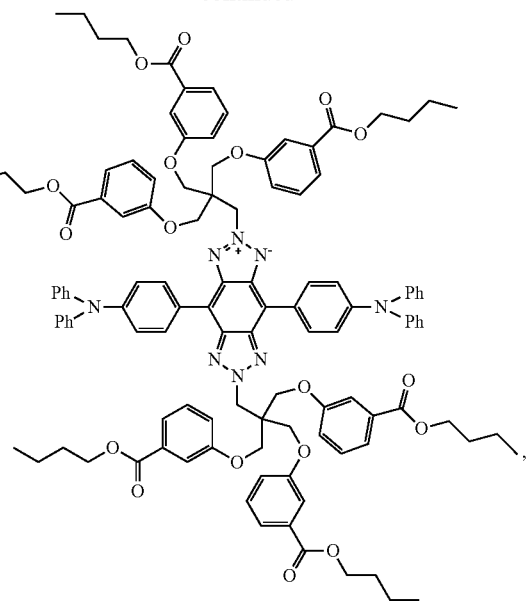
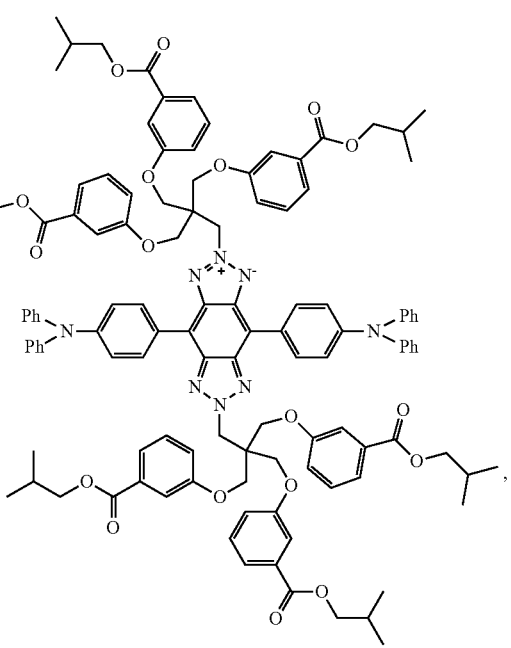

187
-continued
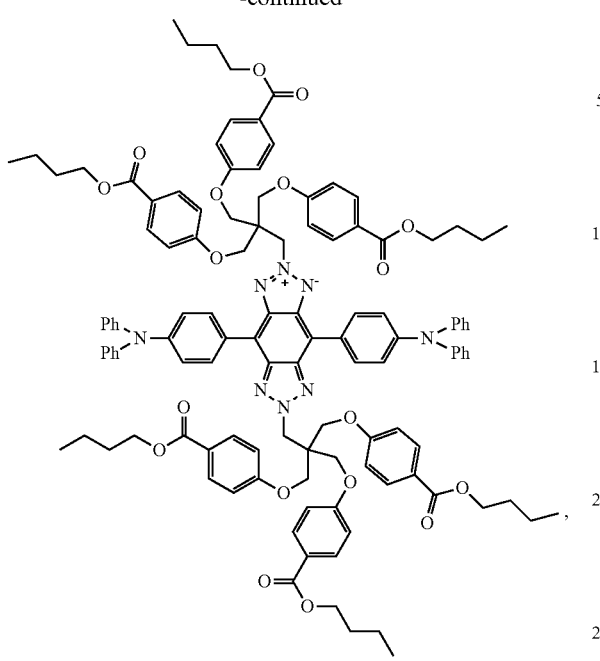
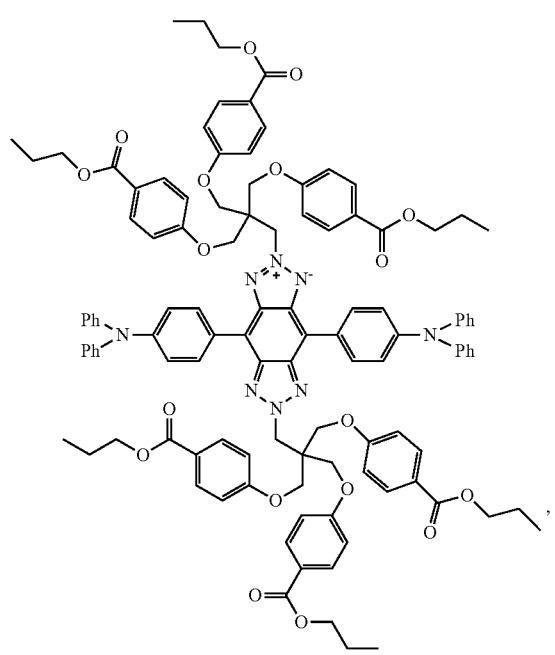
188
-continued
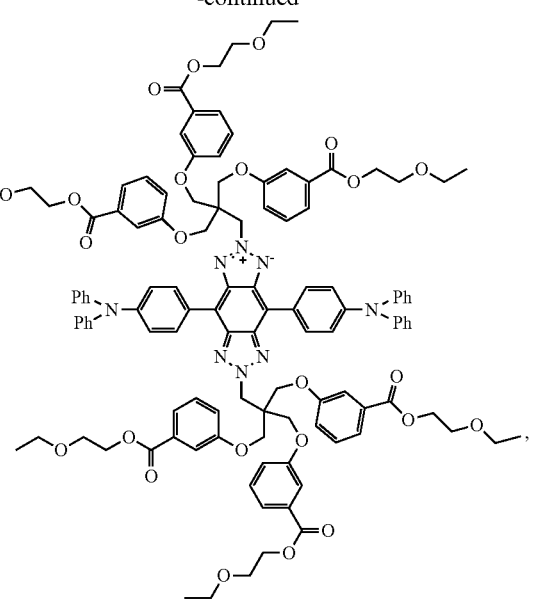,
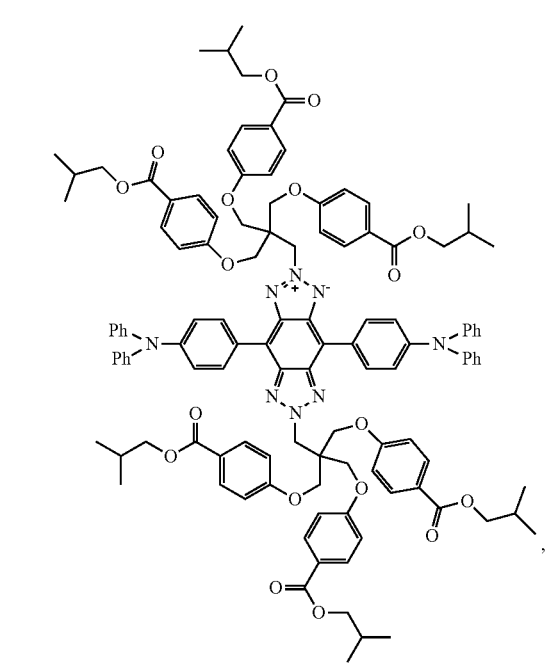,